US011306298B1

(12) United States Patent
Kim et al.

(10) Patent No.: US 11,306,298 B1
(45) Date of Patent: Apr. 19, 2022

(54) MAD NUCLEASES

(71) Applicant: Inscripta, Inc., Boulder, CO (US)

(72) Inventors: Juhan Kim, Boulder, CO (US); Benjamin Mijts, Boulder, CO (US); Aamir Mir, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

(21) Appl. No.: 17/463,498

(22) Filed: Aug. 31, 2021

Related U.S. Application Data

(60) Provisional application No. 63/133,502, filed on Jan. 4, 2021.

(51) Int. Cl.
*C12N 9/16* (2006.01)
*C12N 9/22* (2006.01)

(52) U.S. Cl.
CPC .................................... *C12N 9/22* (2013.01)

(58) Field of Classification Search
CPC ....................................................... C12N 9/22
See application file for complete search history.

(56) References Cited

U.S. PATENT DOCUMENTS

| | | | |
|---|---|---|---|
| 6,391,582 B2 | 5/2002 | Ying et al. |
| 6,837,995 B1 | 1/2005 | Vassarotti et al. |
| 7,166,443 B2 | 1/2007 | Walker et al. |
| 8,332,160 B1 | 12/2012 | Platt et al. |
| 8,697,359 B1 | 4/2014 | Zhang et al. |
| 8,926,977 B2 | 1/2015 | Miller et al. |
| 9,260,505 B2 | 2/2016 | Weir et al. |
| 9,361,427 B2 | 6/2016 | Hillson |
| 9,499,855 B2 | 11/2016 | Hyde et al. |
| 9,776,138 B2 | 10/2017 | Innings et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 9,988,624 B2 | 6/2018 | Serber et al. |
| 10,011,849 B1 | 7/2018 | Gill et al. |
| 10,017,760 B2 | 7/2018 | Gill et al. |
| 10,227,576 B1 | 3/2019 | Cameron et al. |
| 10,266,851 B2 | 4/2019 | Chen |
| 10,704,033 B1 | 7/2020 | Kim et al. |
| 10,724,021 B1 | 7/2020 | Kim et al. |
| 10,745,678 B1 | 8/2020 | Kim et al. |
| 10,767,169 B1 | 9/2020 | Kim et al. |
| 10,837,021 B1 | 11/2020 | Tian et al. |
| 10,883,095 B1 * | 1/2021 | Mijts ........................ C12N 9/22 |
| 10,927,385 B2 | 2/2021 | Kannan et al. |
| 11,053,485 B2 * | 7/2021 | Mijts .................... C12N 15/111 |
| 11,085,030 B2 * | 8/2021 | Mijts ........................ C12N 9/22 |
| 11,174,471 B2 * | 11/2021 | Mijts .................... C12N 15/113 |
| 11,193,115 B2 * | 12/2021 | Mijts .................... C12N 15/111 |
| 2002/0139741 A1 | 10/2002 | Kopf |
| 2004/0110253 A1 | 6/2004 | Kappler et al. |
| 2006/0014137 A1 | 1/2006 | Ghosh et al. |
| 2007/0020761 A1 | 1/2007 | Yu et al. |
| 2010/0076057 A1 | 3/2010 | Sontheimer et al. |
| 2011/0294217 A1 | 12/2011 | Mcconnell-Smith et al. |
| 2013/0236970 A1 | 9/2013 | Anneren et al. |
| 2014/0068797 A1 | 3/2014 | Doudna et al. |
| 2014/0199767 A1 | 7/2014 | Barrangou et al. |
| 2014/0242033 A1 | 8/2014 | Gruber et al. |
| 2014/0273226 A1 | 9/2014 | Wu et al. |
| 2015/0024464 A1 | 1/2015 | Lippow et al. |
| 2015/0071898 A1 | 3/2015 | Liu et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0191719 A1 | 7/2015 | Hudson et al. |
| 2015/0225732 A1 | 8/2015 | Williams et al. |
| 2015/0344549 A1 | 12/2015 | Muir et al. |
| 2016/0024529 A1 | 1/2016 | Carstens et al. |
| 2016/0053272 A1 | 2/2016 | Wurzel et al. |
| 2016/0053304 A1 | 2/2016 | Wurzel et al. |
| 2016/0076093 A1 | 3/2016 | Shendure et al. |
| 2016/0102322 A1 | 4/2016 | Ravinder et al. |
| 2016/0130608 A1 | 5/2016 | Doudna et al. |
| 2016/0168592 A1 | 6/2016 | Church et al. |
| 2016/0264981 A1 | 9/2016 | Yang et al. |
| 2016/0281053 A1 | 9/2016 | Sorek et al. |
| 2016/0289673 A1 | 10/2016 | Huang et al. |
| 2016/0298134 A1 | 10/2016 | Chen et al. |
| 2016/0354487 A1 | 12/2016 | Zhang et al. |
| 2017/0002339 A1 | 1/2017 | Barrngou et al. |
| 2017/0022499 A1 | 1/2017 | Lu et al. |
| 2017/0044525 A1 | 2/2017 | Kaper et al. |
| 2017/0051310 A1 | 2/2017 | Doudna et al. |

(Continued)

FOREIGN PATENT DOCUMENTS

| | | |
|---|---|---|
| EP | 2395087 | 12/2011 |
| EP | 3199632 | 8/2017 |

(Continued)

OTHER PUBLICATIONS

Studer. Residue mutations and their impact on protein structure and function: detecting beneficial and pathogenic changes. Biochem. J. (2013) 449, 581-594.*
International Search Report and Written Opinion for International Application No. PCT/US21/48566, dated Dec. 10, 2021, p. 1-10.
UniProtKB/TrEMBL, "A0A1G4WF58_9FIRM", Nov. 22, 2017, rerieved from Internet: https://www.uniprot.org/uniprot/A0A_1G4WF58.txt, pp. 1-3.
International Search Report and Written Opinion for International Application No. PCT/US20/19379, dated Jul. 22, 2020, p. 1-10.
International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.
Arnak, et al., "Yeast Artificial Chromosomes", John Wiley & Sons, Ltd., doi:10.1002/9780470015902.a0000379.pub3, pp. 1-10 (2012).
Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).

(Continued)

*Primary Examiner* — Yong D Pak
(74) *Attorney, Agent, or Firm* — Sarah Brashears

(57) ABSTRACT

The present disclosure provides new RNA-guided nuclease systems and engineered nickases for making rational, direct edits to nucleic acids in live cells.

6 Claims, 7 Drawing Sheets

Specification includes a Sequence Listing.

(56) References Cited

U.S. PATENT DOCUMENTS

| | | |
|---|---|---|
| 2017/0073705 A1 | 3/2017 | Chen et al. |
| 2017/0191123 A1 | 7/2017 | Kim et al. |
| 2017/0211078 A1 | 7/2017 | Kamineni et al. |
| 2017/0240922 A1 | 8/2017 | Gill et al. |
| 2017/0369870 A1 | 12/2017 | Gill et al. |
| 2018/0028567 A1 | 2/2018 | Li et al. |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0187149 A1 | 7/2018 | Ma et al. |
| 2018/0200342 A1 | 7/2018 | Bikard et al. |
| 2018/0230460 A1 | 8/2018 | Gill et al. |
| 2018/0230461 A1 | 8/2018 | Gill et al. |
| 2018/0284125 A1 | 10/2018 | Gordon et al. |
| 2019/0017072 A1 | 1/2019 | Ditommaso et al. |
| 2019/0085324 A1 | 3/2019 | Regev et al. |
| 2019/0136230 A1 | 5/2019 | Sather et al. |
| 2019/0169605 A1 | 6/2019 | Masquelier et al. |
| 2019/0194650 A1 | 6/2019 | Gill et al. |
| 2019/0225928 A1 | 7/2019 | Masquelier et al. |
| 2019/0270987 A1 | 9/2019 | Masquelier et al. |
| 2020/0071660 A1 | 3/2020 | Spindler et al. |
| 2020/0095533 A1 | 3/2020 | Garst et al. |
| 2020/0216794 A1 | 7/2020 | Belgrader et al. |
| 2020/0263197 A1 | 8/2020 | Cheng et al. |
| 2020/0270632 A1 | 8/2020 | Roy et al. |

FOREIGN PATENT DOCUMENTS

| | | |
|---|---|---|
| WO | WO2002/010183 | 2/2002 |
| WO | WO 2003/087341 | 10/2003 |
| WO | WO 2010/079430 | 7/2010 |
| WO | WO 2011/072246 | 6/2011 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO2014/143381 | 9/2014 |
| WO | WO 2014/144495 | 9/2014 |
| WO | WO 2016/110453 | 7/2016 |
| WO | WO2016/110453 | 7/2016 |
| WO | WO 2017/053902 | 3/2017 |
| WO | WO2017/075265 | 5/2017 |
| WO | WO 2017/078631 | 5/2017 |
| WO | WO 2017/083722 | 5/2017 |
| WO | WO 2017/106414 | 6/2017 |
| WO | WO2017/106414 | 6/2017 |
| WO | WO 2017/161371 | 9/2017 |
| WO | WO 2017/174329 | 10/2017 |
| WO | WO 2017/186718 | 11/2017 |
| WO | WO2017/212400 | 12/2017 |
| WO | WO2017/216392 | 12/2017 |
| WO | WO 2017/216392 | 12/2017 |
| WO | WO 2017/223330 | 12/2017 |
| WO | WO2017/223330 | 12/2017 |
| WO | WO 2018/031950 | 2/2018 |
| WO | WO 2018/071672 | 4/2018 |
| WO | WO 2018/083339 | 5/2018 |
| WO | WO2018/152325 | 8/2018 |
| WO | WO2018/172556 | 9/2018 |
| WO | WO 2018/172556 | 9/2018 |
| WO | WO 2018/191715 | 10/2018 |
| WO | WO2019/006436 | 1/2019 |
| WO | WO2019/055878 | 3/2019 |
| WO | WO2019/200004 | 10/2019 |
| WO | WO2019/209926 | 10/2019 |
| WO | WO2020/005383 | 1/2020 |
| WO | WO2020/021045 | 1/2020 |
| WO | WO2020/074906 | 4/2020 |

OTHER PUBLICATIONS

International Search Report and Written Opinion for International Application No. PCT/US2021/012868, dated Mar. 26, 2021, p. 1-15.

Anzalone et al., "Search-and-replace genome editing without doubles-strand breaks or donor DNA," Nature, Oct. 21, 2019, vol. 576, No. 7785, pp. 149-157.

Alvarez, et al., "In vivo diversification of target genomic sites using processive T7 RNA polymerase-base deaminase fusions blocked by RNA-guided dCas9", Dept.of Microbial Biotechnology and Systems Biology Program, Madrid, Spain, Jan. 1, 2019, p. 1-33.

International Search Report and Written Opinion for International Application No. PCT/US20/65168, dated Mar. 17, 2021, p. 1-15.

International Search Report and Written Opinion for International Application No. PCT/US2020/038345, dated Nov. 23, 2020, p. 1-13.

International Search Report and Written Opinion for International Application No. PCT/US21/12867, dated May 12, 2021, p. 1-17.

International Search Report and Written Opinion for International Application No. PCT/US2020/064727, dated Apr. 28, 2021, p. 1-13.

International Search Report and Written Opinion for International Application No. PCT/US21/29008, dated Aug. 24, 2021, p. 1-19.

International Search Report and Written Opinion for International Application No. PCT/US21/29011, dated Aug. 24, 2021, p. 1-20.

Bauer, et al., "Cell-microcarrier Adhesion to Gas-Liquid Interfaces and Foam", Biotechnol. Prog. 2000, 16, 125-132, Oct. 19, 1999.

Datlinger, et al., "Pooled CRISPR screening with single-cell transcriptome readout", Nature Methods, Jan. 10, 2017; p. 1-10, doi:10.1038/nmeth.4177.

Dixit, et al., "Perturb-Seq: Dissecting Molecular Circuits with Scalable Single-Cell RNA Profiling of Pooled Genetic Screens", Cell 167, p. 1853-1866, Dec. 15, 2016.

GE Healthcare Life Sciences, "Microcarrier Cell Culture Principles and Methods", 18-1140-62 AC, p. 1-23, Nov. 2013.

Jacobi, et al., "Simplified CRISPR tools for efficient genome editing and streamlined protocols for their delivery into mammalian cells and mouse zygotes", Methods 121-122, p. 16-28, Mar. 23, 2017.

Jaitin, et al., "Dissecting Immune Circuits by Linking CRISPR-Pooled Screens with Single-Cell RNA-Seq", Cell 167, p. 1883-1896, Dec. 15, 2016.

Kim, et al., "Formation of Thermoresponsive Poly(N-isopropylacrylamide)/Dextran Particles by Atom Transfer Radical Polymerization", Macromol. Rapid Commun., 24, p. 517-521, 2003.

Kimple, et al., "Overview of Affinity Tags for Protein Purification", Curr Protoc Protein Sci.; 73: Unit-9-9. Doi:10.1002/0471140864. ps0909s73, p. 1-26, Aug. 6, 2015.

Nienow, et al., "A potentially scalable method for the harvesting of hMSCs from microcarriers", Biochemical Engineering Journal 85, p. 79-88, Feb. 4, 2014.

Replogle, et al., "Direct capture of CRISPR guides enables scalable, multiplexed, and multi-omic Perturb-Seg", bioRxiv; doi:http://dx.doi.org/10.1101/503367, p. 1-26, Dec. 21, 2018.

Sivalingam, et al., "Superior Red Blood Cell Generation from Human Pluripotent Stem Cells Through a Novel Microcarrier-Based Embryoid Body Platform", Tissue Engineering: Part C, vol. 22, No. 8, p. 765-780, Jun. 9, 2016.

International Search Report and Written Opinion for International Application No. PCT/US21/35807, dated Nov. 24, 2021, p. 1-21.

International Search Report and Written Opinion for International Application No. PCT/US21/50338, dated Dec. 10, 2021, p. 1-17.

International Search Report and Written Opinion for International Application No. PCT/US21/43097, dated Nov. 19, 2021, p. 1-12.

International Search Report and Written Opinion for International Application No. PCT/US21/39872, dated Oct. 27, 2021, p. 1-14.

Filsinger, et al., "Characterizing the portability of RecT-mediated oligonucleotide recombination", bioRxiv, Apr. 15, 2020, doi:org/10.1101/2020.04.14.041095, p. 1-25.

Nelson, et al., "Engineered pegRNAs improve prime editing efficiency", Nature Biotechnology, Jul. 25, 2021, doi.org/10.1038/s41587-021-01039-7, p. 1-14.

(56) References Cited

OTHER PUBLICATIONS

Yu, et al., "Improved delivery of Cas9 protein/gRNA complexes using lipofectamine CRISPRMAX", Biotechnol Ltt, Feb. 18, 2016, doi 10.1007/sl0529-016-2064-9, p. 919-929.
Bengali, et al., "Gene Delivery Through Cell Culture Substrate Adsorbed DNA Complexes", Biotechnol Bioeng., May 5, 2005, doi:10.1002/bit.20393, p. 1-23.
Segura, et al., "Substrate-mediated DNA delivery: role of the cationic polymer structure and extent of modification", Journal of Controlled Release, Aug. 9, 2003, doi:10.1016/j.jconrel.2003.08.003, p. 69-84.
Takahashi, et al., "Integration of CpG-free DNA induces de novo methylation of CpG islands in pluripotent stem cells," Science, May 5, 2017, vol. 356, No. 6337, pp. 1-7.
Chen, et al., "Human Pluripotent Stem Cell Culture: Considerations for Maintenance, Expansion, and Therapeutics", Cell Stem Cell, Jan. 2, 2014, doi.org/10.1016/j.stem.2013.12.005, p. 13-26.
Fayazpour, F., "Exploring New Applications for Photophysically Encoded Mircrocarriers", Ghent University Faculty of Pharmaceutical Sciences, Thesis Submission, Sep. 2008, 169 pages.
Chueng, et al., "Unlinking the methylome pattern from nucleotide sequence, revealed by large-scale in vivo genome engineering and methylome editing in medaka fish," PLoS Genetics, Dec. 21, 2017, vol. 13, No. 12, pp. 1-25.
Elvin, et al., "Modified bacteriophage lambda promoter vectors for overproduction of proteins in *Escherichia coli*", Gene, 87, Sep. 15, 1989, p. 123-126.
Segall-Shapiro, et al., "Engineered promoters enable constant gene expression at any copy number in bacteria", Nature Biotechology, vol. 36, No. 4, Mar. 19, 2018, p. 352-363.
Xing, et al., "A CRISPR/Cas9 toolkit for multiplex genome editing in plants", BMC Plant Biology, 2014, p. 1-12.
Sun, et al., "A Single Multiplex crRNA Array for FnCpf1-Mediated Human Genome Editing," Molecular Therapy, Aug. 1, 2018, vol. 26, No. 8, pp. 2070-2076.
Kurata, et al., "Highly multiplexed genome engineering using CRISPR/Cas9 gRNA arrays," PLoS ONE, Sep. 17, 2018, vol. 13, No. 9, pp. 1-17.
Hubmann, et al., "Natural and Modified Promoters for Tailored Metabolic Engineering of the Yeast *Saccharomyces cerevisiae*", Methods in Molecular Biology, vol. 1152, doi10.1007/978-1-4939-0563-8_2, p. 17-42.
Unciti-Broceta, et al., "Combining Nebulization—Mediated Transfection and Polymer Microarrays for the Rapid Determination of Optimal Transfection Substrates", Journal of Combinatorial Chemistry, vol. 10, No. 2, Feb. 5, 2008, p. 179-184.
Fayazpour, et al., "Evaluation of Digitally Encoded Layer-by-layer Coated Microparticles as Cell Carriers", Advanced Functional Materials, Sep. 1, 2008, p. 2716-2723.
UniProtKB/TrEMBL, "A0A1G4WF58_9FIRM", Nov. 22, 2017, rerieved from Internet: https://www.uniprot.org/uniprot/A0A_164WF58.txt, pp. 1-3.
Natsume, et al., "Conditional Degrons for Controlling Protein Expression at the Protein Level", Annual Review of Genetics, vol. 51, 2017, doi.org/10.1146/annurev-genet-120116-024656, p. 83-104.
Chen, et al., "Enhancing the copy number of episomal plasmids in *Saccharomyces cerevisiae* for improved protein production", FEMS Yeast Research, Apr. 25, 2012, doi:10.1111/j.1567-1364.2012.00809.x; p. 598-607.
Price, et al., "Expanding and understanding the CRISPR toolbox for Bacillus subtilis with MAD7 and dMAD7", Biotechnology and Bioengineering, Feb. 19, 2020, doi:10.1002/bit.27312 p. 1805-1816.
International Search Report and Written Opinion for International Application No. PCT/US21/43534, dated Nov. 10, 2021, p. 1-16.
International Search Report and Written Opinion for International Application No. PCT/US20/26095, dated Jul. 17, 2020, p. 1-10.
Bao, et al., "Genome-scale engineering of *Saccharomyces cerevisiae* with single-nucleotide precision", Nature Biotechnology, doi:10.1038/nbt.4132, pp. 1-6 (May 7, 2018).
Dicarlo, et al., "Genome engineering in *Saccharomyces cervisiae* using CRISPR-Case systems", Nucleic Acids Research, 41(7):4336-43 (2013).
Garst, et al., "Genome-wide mapping of mutations at single-nucleotide resolution for protein, metabolic and genome engineering", Nature Biotechnology, 35(1):48-59 (2017).
Hsu, et al., "DNA targeting specificity of RNA-guided Cas9 nucleases", Nature Biotechnology, 31(9):827-32 (2013).
Jiang, et al., "RNA-guided editing of bacterial genomes using CRISPR-Cas systems", Nature Biotechnology, 31(3):233-41 (2013).
Jinek, et al., "A Programmable Dual-RNA-Guided DNA Endonuclease in Adaptive Bacterial Immunity", Science, 337:816-20 (2012).
Verwaal, et al., "CRISPR/Cpfl enables fast and simple genome editing of *Saccharamyces cerevisiae*", Yeast, 35:201-11 (2018).
Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).
Roy, et cl., "Multiplexed precision genome editing with trackable genomic barcodes in yeast", Nature Biotechnolgy, doi:10.1038/nbt.4137, pp. 1-16 (2018).
Dong, "Establishment of a highly efficient virus-inducible CRISPR/Cas9 system in insect cells," Antiviral Res., 130:50-7(2016).
Epinat et al., "A novel engineered meganuclease induces homologous recombination in eukaryotic cells, e.g., yeast and mammalian cells", Nucleic Acids Research, 31(11): 2952-2962.
Farasat et al., "A Biophysical Model of CRISPR/Cas9 Activity for Rational Design of Genome Editing and Gene Regulation," PLoS Comput Biol., 29:12(1):e1004724 (2016).
Liu et al., "A chemical-inducible CRISPR-Cas9 system for rapid control of genome editing", Nature Chemical Biology, 12:980-987(2016).
Eklund, et al., "Altered target site specificity variants of the I-Ppol His-Cys bis homing endonuclease" Nucleic Acids Research, 35(17):5839-50 (2007).
Boles, et al., "Digital-to-biological converter for on-demand production of biologies", Nature Biotechnology, doi:10.1038/nbt.3859 (May 29, 2017).
Pines, et al., "Codon Compression Algorithms for Saturation Mutagenesis", ACS Synthetic Biology, 4:604-14 (2015).
Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Du Rai et al., "Zinc finger nucleases: custom-designed molecular scissors for genome engineering of plant and mammalian cells", Nucleic Acids Res., 33(18):5978-90 (2005).
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20(1): 81-9 (2009).
Miller et al., "A TALE nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).

(56) References Cited

OTHER PUBLICATIONS

International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Sep. 26, 2018, p. 1-12.
International Search Report and Written Opinion for International Application No. PCT/US2018/040519, dated Sep. 26, 2018, p. 1-8.
International Search Report and Written Opinion for International Application No. PCT/US2019/026836, dated Jul. 2, 2019, p. 1-10.
International Search Report and Written Opinion for International Application No. PCT/US2019/023342, dated Jun. 6, 2019, p. 1-34.
International Search Report and Written Opinion for International Application No. PCT/US2019/030085, dated Jul. 23, 2019, p. 1-14.
International Search Report and Written Opinion for International Application No. PCT/US20/24341, dated Jun. 19, 2020, p. 1-9.
NonFinal Office Action for U.S. Appl. No. 16/399,988, dated Jul. 31, 2019, p. 1-20.
First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication Preinterview for U.S. Appl. No. 16/454,865 dated Aug. 16, 2019, p. 1-36.
Yoshioka, et al., "Development of a mono-promoter-driven CRISPR/Cas9 system in mammalian cells", Scientific Reports, Jul. 3, 2015, p. 1-8.
Remaut, et al., "Plasmid vectors for high-efficiency expression controlled by the PL promoter of coliphage lambda," Laboratory of Molecular Biology, Apr. 15, 1981, p. 81-93.
International Search Report and Written Opinion for International Application No. PCT/US2019/028821, dated Aug. 2, 2019, p. 1-14.
International Search Report and Written Opinion for International Application No. PCT/US2019/028883, dated Aug. 16, 2019, p. 1-12.
International Search Report and Written Opinion for International Application No. PCT/US2019/46526, dated Dec. 18, 2019, p. 1-17.
International Search Report and Written Opinion for International Application No. PCT/US2018/34779, dated Nov. 26, 2018, p. 1-39.
International Search Report and Written Opinion for International Application No. PCT/US19/57250, dated Feb. 25, 2020, p. 1-16.
International Search Report and Written Opinion for International Application No. PCT/US19/47135, dated Jun. 11, 2020, p. 1-15.

\* cited by examiner

11 New active Type II MADzymes are found with diverse profiles

| Name | Cluster | AA length | nt length (bp) | Active | Pam (IUPAC) | PAM logo | In vitro activity | Possible advantage | In vitro test candidate |
|---|---|---|---|---|---|---|---|---|---|
| MAD2015 | Cluster_59 | 1339 | 4017 | inactive | inactive | | None | | |
| MAD2016 | Cluster_59 | 1337 | 4011 | active | NGG | | Medium | CFE compatible | Yes |
| MAD2017 | Cluster_59 | 1375 | 4125 | active | NGG | | High | CFE compatible | Yes |
| MAD2019 | Cluster_59 | 1367 | 4101 | active | NGG | | High | CFE compatible | Yes |
| MAD2020 | Cluster_55 | 1393 | 4179 | active | NRTATT | | Medium | | |
| MAD2022 | Cluster_57 | 1364 | 4092 | active | NNNAAA | | | | |
| MAD2025 | Cluster_56 | 1384 | 4152 | active | NNNCC | | Medium | | |
| MAD2027 | Cluster_65 | 1370 | 4110 | inactive | inactive | | None | | |
| MAD2029 | Cluster_66 | 1360 | 4080 | active | GGSGC | | Medium | Small | Yes |
| MAD2032 | Cluster_141 | 1087 | 3261 | active | NNNNCMNA | | | | |
| MAD2033 | Cluster_141 | 1084 | 3252 | active | GGGGCNNA | | | | |
| MAD2034 | Cluster_141 | 1084 | 3252 | active | NNRGRYAA | | | | |
| MAD2039 | Cluster_141 | 1095 | 3285 | active | NNNNCNNC | | High | Small, broader PAM | Yes |

40% sequence identity between clusters

SEQUENCE LISTING

<160> NUMBER OF SEQ ID NOS: 182

<210> SEQ ID NO 1
<211> LENGTH: 1339
<212> TYPE: PRT
<213> ORGANISM: Vagococcus fluvialis

<400> SEQUENCE: 1

Met Gly Lys Asn Tyr Thr Ile Gly Leu Asp Ile Gly Thr Asn Ser Val
1               5                   10                  15

Gly Trp Ser Val Val Thr Glu Asn Gln Gln Leu Val Lys Lys Arg Met
            20                  25                  30

Lys Ile Arg Gly Asp Ser Glu Lys Gln Val Lys Lys Asn Phe Trp
        35                  40                  45

Gly Val Arg Leu Phe Asp Glu Gly Glu Thr Ala Glu Ala Thr Arg Leu
    50                  55                  60

Lys Arg Thr Thr Arg Arg Arg Tyr Thr Arg Arg Asn Arg Val Val
65                  70                  75                  80

Asp Leu Gln Asn Ile Phe Lys Asp Glu Ile Asn Gln Lys Asp Ser Asn
                85                  90                  95

Phe Phe Asn Arg Leu Asn Glu Ser Phe Leu Val Val Glu Asp Lys Lys
            100                 105                 110

Gln Pro Lys Gln Met Ile Phe Gly Thr Val Glu Glu Ala Ser Tyr
        115                 120                 125

His Glu Ser Phe Pro Thr Ile Tyr His Leu Arg Lys Glu Leu Val Asp
    130                 135                 140

Asn Lys Asp Gln Ala Asp Ile Arg Leu Val Tyr Leu Ala Met Ala His
145                 150                 155                 160

Met Ile Lys Tyr Arg Gly His Phe Leu Ile Glu Gly Gln Leu Ser Thr
                165                 170                 175

Glu Asn Thr Ser Val Glu Glu Lys Phe His Leu Phe Leu Lys Glu Tyr
            180                 185                 190

Asn Ser Thr Phe Cys Lys Gln Glu Asp Gly Ser Leu Val Asn Pro Val
        195                 200                 205

Asn Glu Asp Ile Asn Gly Glu Glu Ile Leu Met Gly Thr Leu Ser Arg
    210                 215                 220

Ser Lys Lys Ala Glu Gln Ile Met Lys Ser Phe Gly Glu Lys Ser
225                 230                 235                 240

Asn Gly Val Phe Ser Gln Phe Leu Lys Met Ile Val Gly Asn Gln Gly
                245                 250                 255

Asn Phe Lys Lys Ala Phe Asn Leu Glu Glu Asp Ala Lys Ile Gln Phe
            260                 265                 270

Ala Lys Glu Glu Tyr Asp Glu Asp Leu Thr Thr Leu Leu Ser Asn Ile
        275                 280                 285

Gly Asp Glu Tyr Ala Asn Val Phe Ser Leu Ala Lys Thr Tyr Glu
    290                 295                 300

Ala Ile Glu Leu Ser Gly Ile Leu Ser Thr Lys Asp Lys Glu Thr Tyr
305                 310                 315                 320

Ala Lys Leu Ser Ser Ser Met Thr Glu Arg Tyr Glu Asp His Glu Lys
                325                 330                 335

Asp Leu Ala Ser Leu Lys Ser Phe Phe Arg Glu His Leu Pro Glu Lys
            340                 345                 350

Tyr Ala Val Met Phe Lys Asp Val Ser Lys Asn Gly Tyr Ala Gly Tyr
        355                 360                 365

-continued

```
Ile Glu Asn Ser Asn Lys Ile Ser Gln Glu Glu Phe Tyr Lys Tyr Thr
    370             375                 380
Lys Lys Leu Ile Gly Gln Ile Glu Gly Ala Asp Tyr Phe Ile Lys Lys
385                 390                 395                 400
Met Glu Gln Glu Ala Phe Leu Arg Lys Gln Arg Thr Tyr Asp Asn Gly
                405                 410                 415
Val Ile Pro Tyr Gln Val His Leu Ser Glu Leu Thr His Ile Ile Asn
            420                 425                 430
Asn Gln Lys Lys Tyr Tyr Pro Phe Leu Leu Glu Lys Glu Glu Ile
        435                 440                 445
Lys Ser Ile Leu Thr Phe Lys Ile Pro Tyr Tyr Ile Gly Pro Leu Ala
450                 455                 460
Lys Gly Asn Ser Asp Phe Ala Trp Leu Ile Arg Asn Ser Asn Asp Lys
465                 470                 475                 480
Ile Thr Pro Ser Asn Phe Asn Glu Val Leu Asp Ile Glu Asn Ser Ala
                485                 490                 495
Ser Gln Phe Ile Glu Arg Met Thr Asn Asn Asp Val Tyr Leu Pro Glu
            500                 505                 510
Glu Lys Val Leu Pro Lys Asn Ser Met Leu Tyr Gln Lys Tyr Ile Val
        515                 520                 525
Phe Asn Glu Leu Thr Lys Val Arg Tyr Ile Asn Asp Arg Gly Thr Glu
530                 535                 540
Cys Asn Phe Ser Gly Glu Glu Lys Leu Gln Ile Phe Glu Arg Phe Phe
545                 550                 555                 560
Lys Asp Ser Ser Thr Lys Val Lys Lys Val Ser Leu Glu Asn Tyr Leu
                565                 570                 575
Asn Lys Glu Tyr Met Ile Glu Ser Pro Thr Ile Lys Gly Ile Glu Asp
            580                 585                 590
Asp Phe Asn Ala Ser Phe Arg Thr Tyr His Asp Phe Ile Lys Leu Gly
        595                 600                 605
Val Ser Arg Glu Met Leu Asp Asp Ile Asp Asn Glu Glu Met Phe Glu
610                 615                 620
Asp Ile Val Lys Ile Leu Thr Ile Phe Glu Asp Arg Gln Met Ile Lys
625                 630                 635                 640
Lys Gln Leu Glu Lys Tyr Lys Asp Val Phe Asp Ser Asp Ile Leu Lys
                645                 650                 655
Lys Met Val Arg Arg His Tyr Thr Gly Trp Gly Arg Leu Ser Lys Lys
            660                 665                 670
Leu Leu His Glu Met Lys Asp Asp Asn Ser Gly Lys Thr Ile Leu Asp
        675                 680                 685
Tyr Leu Ile Glu Asp Asp Arg Leu Pro Lys His Ile Asn Arg Asn Phe
690                 695                 700
Met Gln Leu Ile Asn Asp Ser Asn Leu Ser Phe Lys Glu Lys Ile Glu
705                 710                 715                 720
Lys Ala Gln Leu Thr Asp Gly Thr Glu Asp Ile Asp Ser Val Val Lys
                725                 730                 735
Asn Leu Ile Gly Ser Pro Ala Ile Lys Lys Gly Ile Ser Gln Ser Leu
            740                 745                 750
Lys Ile Val Glu Glu Leu Val Ser Ile Met Gly Tyr Gln Pro Thr Ser
        755                 760                 765
Ile Val Val Glu Met Ala Arg Glu Asn Gln Thr Thr Ser Lys Gly Lys
770                 775                 780
Arg Gln Ser Ile Gln Arg Tyr Lys Arg Leu Glu Ala Ala Ile Asn Glu
```

-continued

```
                785                 790                 795                 800
Leu Gly Ser Asp Leu Leu Lys Val Cys Pro Thr Asp Asn His Ala Leu
                805                 810                 815
Lys Asp Asp Arg Leu Tyr Leu Tyr Tyr Leu Gln Asn Gly Arg Asp Met
                820                 825                 830
Tyr Thr Gly Leu Glu Leu Asp Ile His Asn Leu Ser Gln Tyr Asp Ile
                835                 840                 845
Asp His Ile Val Pro Arg Ser Phe Ile Thr Asp Asn Ser Ile Asp Asn
                850                 855                 860
Arg Val Leu Val Ser Ser Lys Lys Asn Arg Gly Lys Leu Asp Asn Val
865                 870                 875                 880
Pro Ser Lys Glu Ile Val Gln Lys Asn Lys Leu Leu Trp Met Asn Leu
                885                 890                 895
Lys Lys Ser Lys Leu Met Ser Glu Lys Lys Tyr Ala Asn Leu Ile Lys
                900                 905                 910
Gly Glu Thr Gly Gly Leu Thr Glu Asp Asp Lys Ala Lys Phe Leu Asn
                915                 920                 925
Arg Gln Leu Val Glu Thr Arg Gln Ile Thr Lys Asn Val Ala Gln Ile
                930                 935                 940
Leu Asp Gln Arg Phe Asn Thr Gln Lys Asp Glu Lys Gly Asn Ile Ile
945                 950                 955                 960
Arg Glu Val Lys Val Ile Thr Leu Lys Ser Ala Leu Val Ser Gln Phe
                965                 970                 975
Arg Gln Asn Phe Glu Phe Tyr Lys Val Arg Glu Val Asn Asp Phe His
                980                 985                 990
His Ala His Asp Ala Tyr Leu Asn Ala Val Val Ala Asn Thr Leu Leu
                995                 1000                1005
Lys Val Tyr Pro Lys Leu Thr Pro Asp Phe Val Tyr Gly Glu Tyr
                1010                1015                1020
Arg Lys Gly Asn Pro Phe Lys Asn Thr Lys Ala Thr Ala Lys Lys
                1025                1030                1035
His Tyr Tyr Ser Asn Ile Met Glu Asn Leu Cys His Glu Thr Thr
                1040                1045                1050
Ile Ile Asp Asp Glu Thr Gly Glu Ile Leu Trp Asp Lys Lys Cys
                1055                1060                1065
Ile Gly Thr Ile Lys Gln Val Leu Asn Tyr His Gln Val Asn Val
                1070                1075                1080
Val Lys Lys Val Glu Thr Gln Thr Gly Arg Phe Ser Glu Glu Thr
                1085                1090                1095
Leu Val Pro Arg Gly Ser Thr Lys Asn Pro Ile Ala Leu Lys Ser
                1100                1105                1110
His Leu Asp Pro Gln Lys Tyr Gly Gly Phe Lys Ser Pro Thr Ile
                1115                1120                1125
Ala Tyr Thr Ile Val Ile Glu Tyr Lys Lys Gly Lys Lys Asp Ile
                1130                1135                1140
Leu Ile Lys Glu Leu Leu Gly Ile Ser Ile Met Asn Arg Gly Ala
                1145                1150                1155
Phe Glu Lys Asn Asn Lys Glu Tyr Leu Glu Lys Leu Asn Tyr Lys
                1160                1165                1170
Glu Pro Arg Val Leu Met Val Leu Pro Lys Tyr Ser Leu Phe Glu
                1175                1180                1185
Leu Glu Asn Gly Arg Arg Arg Leu Leu Ala Ser Asp Lys Glu Ser
                1190                1195                1200
```

```
Gln Lys Gly Asn Gln Met Ala Val Pro Ser Tyr Leu Asn Asn Leu
    1205                1210                1215

Leu Tyr His Thr Asn Lys Ser Leu Ser Lys Asn Ala Lys Ser Leu
    1220                1225                1230

Glu Tyr Val Asn Glu His Arg Gln Gln Phe Glu Glu Leu Leu Glu
    1235                1240                1245

Glu Ile Ile Asp Phe Ala Asn Gln Phe Thr Leu Ala Glu Lys Asn
    1250                1255                1260

Thr Leu Leu Ile Ala Asp Leu Tyr Glu Ser Asn Lys Glu Ala Asp
    1265                1270                1275

Ile Glu Leu Leu Ala Ser Ser Phe Ile Asn Leu Leu Arg Phe Asn
    1280                1285                1290

Gln Met Gly Ala Pro Ala Glu Phe Ser Phe Phe Glu Lys Pro Ile
    1295                1300                1305

Pro Arg Lys Arg Tyr Ser Ser Thr Phe Glu Leu Leu Lys Gly Lys
    1310                1315                1320

Val Ile His Gln Ser Ile Thr Gly Leu Tyr Glu Thr His Gln Lys
    1325                1330                1335

Val

<210> SEQ ID NO 2
<211> LENGTH: 36
<212> TYPE: DNA
<213> ORGANISM: Artificial Sequence
<220> FEATURE:
<223> OTHER INFORMATION: CRrNA

<400> SEQUENCE: 2
gttttagagc tatgctgttt tgaatgcttc caaaac                                36

<210> SEQ ID NO 3
<211> LENGTH: 80
<212> TYPE: DNA
<213> ORGANISM: Artificial Sequence
<220> FEATURE:
<223> OTHER INFORMATION: TRACR RNA

<400> SEQUENCE: 3
tgttggtagc attcaaaaca acatagcaag ttaaaataag gctttgtccg ttctcaactt      60
ttagtgacgc tgtttcggcg                                                 80

<210> SEQ ID NO 4
<211> LENGTH: 1337
<212> TYPE: PRT
<213> ORGANISM: Enterococcus faecalis

<400> SEQUENCE: 4

Met Lys Lys Asp Tyr Val Ile Gly Leu Asp Ile Gly Thr Asn Ser Val
1               5                   10                  15

Gly Trp Ala Val Met Thr Glu Asp Tyr Gln Leu Val Lys Lys Lys Met
                20                  25                  30

Pro Ile Tyr Gly Asn Thr Glu Lys Lys Ile Lys Lys Asn Phe Trp
        35                  40                  45

Gly Val Arg Leu Phe Glu Glu Gly His Thr Ala Glu Asp Arg Arg Leu
    50                  55                  60

Lys Arg Thr Ala Arg Arg Ile Ile Ser Arg Arg Arg Asn Arg Leu Arg
65                  70                  75                  80
```

```
Tyr Leu Gln Ala Phe Phe Glu Glu Ala Met Thr Asp Leu Asp Glu Asn
             85                  90                  95

Phe Phe Ala Arg Leu Gln Glu Ser Phe Leu Val Pro Glu Asp Lys Lys
            100                 105                 110

Trp His Arg His Pro Ile Phe Ala Lys Leu Glu Asp Glu Val Ala Tyr
            115                 120                 125

His Glu Thr Tyr Pro Thr Ile Tyr His Leu Arg Lys Lys Leu Ala Asp
        130                 135                 140

Ser Ser Glu Gln Ala Asp Leu Arg Leu Ile Tyr Leu Ala Leu Ala His
145                 150                 155                 160

Ile Val Lys Tyr Arg Gly His Phe Leu Ile Glu Gly Lys Leu Ser Thr
                165                 170                 175

Glu Asn Ile Ser Val Lys Glu Gln Phe Gln Gln Phe Met Ile Ile Tyr
            180                 185                 190

Asn Gln Thr Phe Val Asn Gly Glu Ser Arg Leu Val Ser Ala Pro Leu
        195                 200                 205

Pro Glu Ser Val Leu Ile Glu Glu Leu Thr Glu Lys Ala Ser Arg
210                 215                 220

Thr Lys Lys Ser Glu Lys Val Leu Gln Gln Phe Pro Gln Glu Lys Ala
225                 230                 235                 240

Asn Gly Leu Phe Gly Gln Phe Leu Lys Leu Met Val Gly Asn Lys Ala
                245                 250                 255

Asp Phe Lys Lys Val Phe Gly Leu Glu Glu Ala Lys Ile Thr Tyr
            260                 265                 270

Ala Ser Glu Ser Tyr Glu Glu Asp Leu Glu Gly Ile Leu Ala Lys Val
        275                 280                 285

Gly Asp Glu Tyr Ser Asp Val Phe Leu Ala Ala Lys Asn Val Tyr Asp
290                 295                 300

Ala Val Glu Leu Ser Thr Ile Leu Ala Asp Ser Asp Lys Lys Ser His
305                 310                 315                 320

Ala Lys Leu Ser Ser Ser Met Ile Val Arg Phe Thr Glu His Gln Glu
                325                 330                 335

Asp Leu Lys Lys Phe Lys Arg Phe Ile Arg Glu Asn Cys Pro Asp Glu
            340                 345                 350

Tyr Asp Asn Leu Phe Lys Asn Glu Gln Lys Asp Gly Tyr Ala Gly Tyr
        355                 360                 365

Ile Ala His Ala Gly Lys Val Ser Gln Leu Lys Phe Tyr Gln Tyr Val
        370                 375                 380

Lys Lys Ile Ile Gln Asp Ile Ala Gly Ala Glu Tyr Phe Leu Glu Lys
385                 390                 395                 400

Ile Ala Gln Glu Asn Phe Leu Arg Lys Gln Arg Thr Phe Asp Asn Gly
            405                 410                 415

Val Ile Pro His Gln Ile His Leu Ala Glu Leu Gln Ala Ile Ile His
        420                 425                 430

Arg Gln Ala Ala Tyr Tyr Pro Phe Leu Lys Glu Asn Gln Glu Lys Ile
        435                 440                 445

Glu Gln Leu Val Thr Phe Arg Ile Pro Tyr Tyr Val Gly Pro Leu Ser
    450                 455                 460

Lys Gly Asp Ala Ser Thr Phe Ala Trp Leu Lys Arg Gln Ser Glu Glu
465                 470                 475                 480

Pro Ile Arg Pro Trp Asn Leu Gln Glu Thr Val Asp Leu Asp Gln Ser
            485                 490                 495

Ala Thr Ala Phe Ile Glu Arg Met Thr Asn Phe Asp Thr Tyr Leu Pro
```

-continued

```
               500                 505                 510
Ser Glu Lys Val Leu Pro Lys His Ser Leu Leu Tyr Glu Lys Phe Met
            515                 520                 525
Val Phe Asn Glu Leu Thr Lys Ile Ser Tyr Thr Asp Asp Arg Gly Ile
            530                 535                 540
Lys Ala Asn Phe Ser Gly Lys Glu Lys Glu Lys Ile Phe Asp Tyr Leu
545                 550                 555                 560
Phe Lys Thr Arg Arg Lys Val Lys Lys Asp Ile Ile Gln Phe Tyr
                565                 570                 575
Arg Asn Glu Tyr Asn Thr Glu Ile Val Thr Leu Ser Gly Leu Glu Glu
            580                 585                 590
Asp Gln Phe Asn Ala Ser Phe Ser Thr Tyr Gln Asp Leu Leu Lys Cys
            595                 600                 605
Gly Leu Thr Arg Ala Glu Leu Asp His Pro Asp Asn Ala Glu Lys Leu
            610                 615                 620
Glu Asp Ile Ile Lys Ile Leu Thr Ile Phe Glu Asp Arg Gln Arg Ile
625                 630                 635                 640
Arg Thr Gln Leu Ser Thr Phe Lys Gly Gln Phe Ser Ala Glu Val Leu
                645                 650                 655
Lys Lys Leu Glu Arg Lys His Tyr Thr Gly Trp Gly Arg Leu Ser Lys
            660                 665                 670
Lys Leu Ile Asn Gly Ile Tyr Asp Lys Glu Ser Gly Lys Thr Ile Leu
            675                 680                 685
Gly Tyr Leu Ile Lys Asp Asp Gly Val Ser Lys His Tyr Asn Arg Asn
            690                 695                 700
Phe Met Gln Leu Ile Asn Asp Ser Gln Leu Ser Phe Lys Asn Ala Ile
705                 710                 715                 720
Gln Lys Ala Gln Ser Ser Glu His Glu Glu Thr Leu Ser Glu Thr Val
                725                 730                 735
Asn Glu Leu Ala Gly Ser Pro Ala Ile Lys Lys Gly Ile Tyr Gln Ser
            740                 745                 750
Leu Lys Ile Val Asp Glu Leu Val Ala Ile Met Gly Tyr Ala Pro Lys
            755                 760                 765
Arg Ile Val Val Glu Met Ala Arg Glu Asn Gln Thr Thr Ser Thr Gly
            770                 775                 780
Lys Arg Arg Ser Ile Gln Arg Leu Lys Ile Val Glu Lys Ala Met Ala
785                 790                 795                 800
Glu Ile Gly Ser Asn Leu Leu Lys Glu Gln Pro Thr Thr Asn Glu Gln
                805                 810                 815
Leu Arg Asp Thr Arg Leu Phe Leu Tyr Tyr Met Gln Asn Gly Lys Asp
            820                 825                 830
Met Tyr Thr Gly Asp Glu Leu Ser Leu His Arg Leu Ser His Tyr Asp
            835                 840                 845
Ile Asp His Ile Ile Pro Gln Ser Phe Met Lys Asp Asp Ser Leu Asp
            850                 855                 860
Asn Leu Val Leu Val Gly Ser Thr Glu Asn Arg Gly Lys Ser Asp Asp
865                 870                 875                 880
Val Pro Ser Lys Glu Val Val Lys Asp Met Lys Ala Tyr Trp Glu Lys
                885                 890                 895
Leu Tyr Ala Ala Gly Leu Ile Ser Gln Arg Lys Phe Gln Arg Leu Thr
            900                 905                 910
Lys Gly Glu Gln Gly Gly Leu Thr Leu Glu Asp Lys Ala His Phe Ile
            915                 920                 925
```

```
Gln Arg Gln Leu Val Glu Thr Arg Gln Ile Thr Lys Asn Val Ala Gly
    930                 935                 940

Ile Leu Asp Gln Arg Tyr Asn Ala Asn Ser Lys Glu Lys Val Gln
945                 950                 955                 960

Ile Ile Thr Leu Lys Ala Ser Leu Thr Ser Gln Phe Arg Ser Ile Phe
                965                 970                 975

Gly Leu Tyr Lys Val Arg Glu Val Asn Asp Tyr His His Gly Gln Asp
            980                 985                 990

Ala Tyr Leu Asn Cys Val Val Ala Thr Thr Leu Leu Lys Val Tyr Pro
        995                 1000                1005

Asn Leu Ala Pro Glu Phe Val Tyr Gly Glu Tyr Pro Lys Phe Gln
    1010                1015                1020

Thr Phe Lys Glu Asn Lys Ala Thr Ala Lys Ala Ile Ile Tyr Thr
    1025                1030                1035

Asn Leu Leu Arg Phe Phe Thr Glu Asp Glu Pro Arg Phe Thr Lys
    1040                1045                1050

Asp Gly Glu Ile Leu Trp Ser Asn Ser Tyr Leu Lys Thr Ile Lys
    1055                1060                1065

Lys Glu Leu Asn Tyr His Gln Met Asn Ile Val Lys Lys Val Glu
    1070                1075                1080

Val Gln Lys Gly Gly Phe Ser Lys Glu Ser Ile Lys Pro Lys Gly
    1085                1090                1095

Pro Ser Asn Lys Leu Ile Pro Val Lys Asn Gly Leu Asp Pro Gln
    1100                1105                1110

Lys Tyr Gly Gly Phe Asp Ser Pro Ile Val Ala Tyr Thr Val Leu
    1115                1120                1125

Phe Thr His Glu Lys Gly Lys Lys Pro Leu Ile Lys Gln Glu Ile
    1130                1135                1140

Leu Gly Ile Thr Ile Met Glu Lys Thr Arg Phe Glu Gln Asn Pro
    1145                1150                1155

Ile Leu Phe Leu Glu Glu Lys Gly Phe Leu Arg Pro Arg Val Leu
    1160                1165                1170

Met Lys Leu Pro Lys Tyr Thr Leu Tyr Glu Phe Pro Glu Gly Arg
    1175                1180                1185

Arg Arg Leu Leu Ala Ser Ala Lys Glu Ala Gln Lys Gly Asn Gln
    1190                1195                1200

Met Val Leu Pro Glu His Leu Leu Thr Leu Leu Tyr His Ala Lys
    1205                1210                1215

Gln Cys Leu Leu Pro Asn Gln Ser Glu Ser Leu Thr Tyr Val Glu
    1220                1225                1230

Gln His Gln Pro Glu Phe Gln Glu Ile Leu Glu Arg Val Val Asp
    1235                1240                1245

Phe Ala Glu Val His Thr Leu Ala Lys Ser Lys Val Gln Gln Ile
    1250                1255                1260

Val Lys Leu Phe Glu Ala Asn Gln Thr Ala Asp Val Lys Glu Ile
    1265                1270                1275

Ala Ala Ser Phe Ile Gln Leu Met Gln Phe Asn Ala Met Gly Ala
    1280                1285                1290

Pro Ser Thr Phe Lys Phe Phe Gln Lys Asp Ile Glu Arg Ala Arg
    1295                1300                1305

Tyr Thr Ser Ile Lys Glu Ile Phe Asp Ala Thr Ile Ile Tyr Gln
    1310                1315                1320
```

```
Ser Thr Thr Gly Leu Tyr Glu  Thr Arg Arg Lys Val  Val Asp
    1325                1330                 1335
```

<210> SEQ ID NO 5
<211> LENGTH: 36
<212> TYPE: DNA
<213> ORGANISM: Artificial Sequence
<220> FEATURE:
<223> OTHER INFORMATION: CR REPEAT

<400> SEQUENCE: 5

```
gttttagagt catgttgttt agaatggtac caaaac                                    36
```

<210> SEQ ID NO 6
<211> LENGTH: 84
<212> TYPE: DNA
<213> ORGANISM: Artificial Sequence
<220> FEATURE:
<223> OTHER INFORMATION: TRACR RNA

<400> SEQUENCE: 6

```
tcttttggga ctattctaaa caacatagca agttaaaata aggttttaac cgtaatcaac          60
tgtaaagtgg cgctgtttcg gcgc                                                 84
```

<210> SEQ ID NO 7
<211> LENGTH: 1375
<212> TYPE: PRT
<213> ORGANISM: Streptococcus acidominimus

<400> SEQUENCE: 7

```
Met Lys Lys Pro Tyr Ser Ile Gly Leu Asp Ile Gly Thr Asn Ser Val
1               5                   10                  15

Gly Trp Ala Val Ile Thr Asp Asp Tyr Lys Val Pro Ala Lys Lys Met
            20                  25                  30

Lys Val Leu Gly Asn Thr Asp Lys Lys Tyr Ile Lys Lys Asn Leu Leu
        35                  40                  45

Gly Ala Leu Leu Phe Asp Ser Gly Glu Thr Ala Glu Val Thr Arg Leu
    50                  55                  60

Lys Arg Thr Ala Arg Arg Arg Tyr Thr Arg Arg Lys Asn Arg Leu Arg
65                  70                  75                  80

Tyr Leu Gln Glu Ile Phe Ala Lys Glu Met Thr Lys Val Asp Glu Ser
                85                  90                  95

Phe Phe Gln Arg Leu Glu Glu Ser Phe Leu Thr Asp Asp Lys Thr
            100                 105                 110

Phe Asp Ser His Pro Ile Phe Gly Asn Lys Ala Glu Asp Ala Tyr
        115                 120                 125

His Gln Lys Phe Pro Thr Ile Tyr His Leu Arg Lys Tyr Leu Ala Asp
    130                 135                 140

Ser Gln Glu Lys Ala Asp Leu Arg Leu Val Tyr Leu Ala Leu His
145                 150                 155                 160

Met Ile Lys Tyr Arg Gly His Phe Leu Ile Glu Gly Glu Leu Asn Ala
                165                 170                 175

Glu Asn Thr Asp Val Gln Lys Leu Phe Asn Val Phe Val Glu Thr Tyr
            180                 185                 190

Asp Lys Ile Val Asp Glu Ser His Leu Ser Glu Ile Glu Val Asp Ala
        195                 200                 205

Ser Ser Ile Leu Thr Glu Lys Val Ser Lys Ser Arg Arg Leu Glu Asn
    210                 215                 220
```

```
Leu Ile Lys Gln Tyr Pro Thr Glu Lys Lys Asn Thr Leu Phe Gly Asn
225                 230                 235                 240

Leu Ile Ala Leu Ala Leu Gly Leu Gln Pro Asn Phe Lys Thr Asn Phe
            245                 250                 255

Lys Leu Ser Glu Asp Ala Lys Leu Gln Phe Ser Lys Asp Thr Tyr Glu
            260                 265                 270

Glu Asp Leu Glu Glu Leu Leu Gly Lys Val Gly Asp Asp Tyr Ala Asp
            275                 280                 285

Leu Phe Ile Ser Ala Lys Asn Leu Tyr Asp Ala Ile Leu Leu Ser Gly
            290                 295                 300

Ile Leu Thr Val Asp Asp Asn Ser Thr Lys Ala Pro Leu Ser Ala Ser
305                 310                 315                 320

Met Ile Lys Arg Tyr Val Glu His His Glu Asp Leu Glu Lys Leu Lys
                325                 330                 335

Glu Phe Ile Lys Ile Asn Lys Leu Lys Leu Tyr His Asp Ile Phe Lys
                340                 345                 350

Asp Lys Thr Lys Asn Gly Tyr Ala Gly Tyr Ile Asp Asn Gly Val Lys
            355                 360                 365

Gln Asp Glu Phe Tyr Lys Tyr Leu Lys Thr Ile Leu Thr Lys Ile Asp
370                 375                 380

Asp Ser Asp Tyr Phe Leu Asp Lys Ile Glu Arg Asp Asp Phe Leu Arg
385                 390                 395                 400

Lys Gln Arg Thr Phe Asp Asn Gly Ser Ile Pro His Gln Ile His Leu
                405                 410                 415

Gln Glu Met His Ser Ile Leu Arg Arg Gln Gly Glu Tyr Tyr Pro Phe
                420                 425                 430

Leu Lys Glu Asn Gln Ala Lys Ile Glu Lys Ile Leu Thr Phe Arg Ile
            435                 440                 445

Pro Tyr Tyr Val Gly Pro Leu Ala Arg Lys Asp Ser Arg Phe Ala Trp
            450                 455                 460

Ala Asn Tyr His Ser Asp Glu Pro Ile Thr Pro Trp Asn Phe Asp Glu
465                 470                 475                 480

Val Val Asp Lys Glu Lys Ser Ala Glu Lys Phe Ile Thr Arg Met Thr
                485                 490                 495

Leu Asn Asp Leu Tyr Leu Pro Glu Glu Lys Val Leu Pro Lys His Ser
                500                 505                 510

His Val Tyr Glu Thr Phe Thr Val Tyr Asn Glu Leu Thr Lys Ile Lys
            515                 520                 525

Tyr Val Asn Glu Gln Gly Glu Ser Phe Phe Asp Ala Asn Met Lys
530                 535                 540

Gln Glu Ile Phe Asp His Val Phe Lys Glu Asn Arg Lys Val Thr Lys
545                 550                 555                 560

Ala Lys Leu Leu Ser Tyr Leu Asn Asn Glu Phe Glu Glu Phe Arg Ile
                565                 570                 575

Asn Asp Leu Ile Gly Leu Asp Lys Asp Ser Lys Ser Phe Asn Ala Ser
            580                 585                 590

Leu Gly Thr Tyr His Asp Leu Lys Lys Ile Leu Asp Lys Ser Phe Leu
            595                 600                 605

Asp Asp Lys Thr Asn Glu Gln Ile Ile Glu Asp Ile Val Leu Thr Leu
            610                 615                 620

Thr Leu Phe Glu Asp Arg Asp Met Ile His Glu Arg Leu Gln Lys Tyr
625                 630                 635                 640

Ser Asp Phe Phe Thr Ser Gln Gln Leu Lys Lys Leu Glu Arg Arg His
```

```
                  645                 650                 655
Tyr Thr Gly Trp Gly Arg Leu Ser Tyr Lys Leu Ile Asn Gly Ile Arg
                660                 665                 670

Asn Lys Glu Asn Asn Lys Thr Ile Leu Asp Phe Leu Ile Asp Asp Gly
            675                 680                 685

His Ala Asn Arg Asn Phe Met Gln Leu Ile Asn Asp Glu Ser Leu Ser
        690                 695                 700

Phe Lys Thr Ile Ile Gln Glu Ala Gln Val Val Gly Asp Val Asp Asp
705                 710                 715                 720

Ile Glu Ala Val Val His Asp Leu Pro Gly Ser Pro Ala Ile Lys Lys
                725                 730                 735

Gly Ile Leu Gln Ser Val Lys Ile Val Asp Glu Leu Val Lys Val Met
                740                 745                 750

Gly Asp Asn Pro Asp Asn Ile Val Ile Glu Met Ala Arg Glu Asn Gln
            755                 760                 765

Thr Thr Gly Tyr Gly Arg Asn Lys Ser Asn Gln Arg Leu Lys Arg Leu
        770                 775                 780

Gln Asp Ser Leu Lys Glu Phe Gly Ser Asp Ile Leu Ser Lys Lys Lys
785                 790                 795                 800

Pro Ser Tyr Val Asp Ser Lys Val Glu Asn Ser His Leu Gln Asn Asp
                805                 810                 815

Arg Leu Phe Leu Tyr Tyr Ile Gln Asn Gly Lys Asp Met Tyr Thr Gly
                820                 825                 830

Glu Glu Leu Asp Ile Asp Arg Leu Ser Asp Tyr Asp Ile Asp His Ile
            835                 840                 845

Ile Pro Gln Ala Phe Ile Lys Asp Asn Ser Ile Asp Asn Lys Val Leu
        850                 855                 860

Thr Ser Ser Ala Lys Asn Arg Gly Lys Ser Asp Asp Val Pro Ser Ile
865                 870                 875                 880

Glu Ile Val Arg Asn Arg Arg Ser Tyr Trp Tyr Lys Leu Tyr Lys Ser
                885                 890                 895

Gly Leu Ile Ser Lys Arg Lys Phe Asp Asn Leu Thr Lys Ala Glu Arg
                900                 905                 910

Gly Gly Leu Thr Glu Ala Asp Lys Ala Gly Phe Ile Lys Arg Gln Leu
            915                 920                 925

Val Glu Thr Arg Gln Ile Thr Lys His Val Ala Gln Ile Leu Asp Ala
        930                 935                 940

Arg Phe Asn Thr Lys Arg Asp Glu Asn Asp Lys Val Ile Arg Asp Val
945                 950                 955                 960

Lys Val Ile Thr Leu Lys Ser Asn Leu Val Ser Gln Phe Arg Lys Glu
                965                 970                 975

Phe Lys Phe Tyr Lys Val Arg Glu Ile Asn Asp Tyr His His Ala His
                980                 985                 990

Asp Ala Tyr Leu Asn Ala Val Val Gly Thr Ala Leu Leu Lys Lys Tyr
            995                 1000                1005

Pro Lys Leu Thr Pro Glu Phe Val Tyr Gly Glu Tyr Lys Lys Tyr
        1010                1015                1020

Asp Val Arg Lys Leu Ile Ala Lys Ser Glu Asp Tyr Ser Glu
        1025                1030                1035

Met Gly Lys Ala Thr Ala Lys Tyr Phe Phe Tyr Ser Asn Leu Met
        1040                1045                1050

Asn Phe Phe Lys Thr Glu Val Lys Tyr Ala Asp Gly Arg Val Phe
        1055                1060                1065
```

-continued

```
Glu Arg Pro Asp Ile Glu Thr Asn Ala Asp Gly Glu Val Val Trp
    1070                1075                1080
Asn Lys Gln Lys Asp Phe Asp Ile Val Arg Lys Val Leu Ser Tyr
    1085                1090                1095
Pro Gln Val Asn Ile Val Lys Lys Val Glu Ala Gln Thr Gly Gly
    1100                1105                1110
Phe Ser Lys Glu Ser Ile Leu Ser Lys Gly Asp Ser Asp Lys Leu
    1115                1120                1125
Ile Pro Arg Lys Thr Lys Lys Val Tyr Trp Asn Thr Lys Lys Tyr
    1130                1135                1140
Gly Gly Phe Asp Ser Pro Thr Val Ala Tyr Ser Val Leu Val Val
    1145                1150                1155
Ala Asp Ile Glu Lys Gly Lys Ala Lys Lys Leu Lys Thr Val Lys
    1160                1165                1170
Glu Leu Val Gly Ile Ser Ile Met Glu Arg Ser Phe Phe Glu Glu
    1175                1180                1185
Asn Pro Val Ser Phe Leu Glu Lys Lys Gly Tyr His Asn Val Gln
    1190                1195                1200
Glu Asp Lys Leu Ile Lys Leu Pro Lys Tyr Ser Leu Phe Glu Phe
    1205                1210                1215
Glu Gly Gly Arg Arg Arg Leu Leu Ala Ser Ala Thr Glu Leu Gln
    1220                1225                1230
Lys Gly Asn Glu Val Met Leu Pro Ala His Leu Val Glu Leu Leu
    1235                1240                1245
Tyr His Ala His Arg Ile Asp Ser Phe Asn Ser Thr Glu His Leu
    1250                1255                1260
Lys Tyr Val Ser Glu His Lys Lys Glu Phe Glu Lys Val Leu Ser
    1265                1270                1275
Cys Val Glu Asn Phe Ser Asn Leu Tyr Val Asp Val Glu Lys Asn
    1280                1285                1290
Leu Ser Lys Val Arg Ala Ala Ala Glu Ser Met Thr Asn Phe Ser
    1295                1300                1305
Leu Glu Glu Ile Ser Ala Ser Phe Ile Asn Leu Leu Thr Leu Thr
    1310                1315                1320
Ala Leu Gly Ala Pro Ala Asp Phe Asn Phe Leu Gly Glu Lys Ile
    1325                1330                1335
Pro Arg Lys Arg Tyr Thr Ser Thr Lys Glu Cys Leu Ser Ala Thr
    1340                1345                1350
Leu Ile His Gln Ser Val Thr Gly Leu Tyr Glu Thr Arg Ile Asp
    1355                1360                1365
Leu Ser Lys Leu Gly Glu Glu
    1370                1375
```

<210> SEQ ID NO 8
<211> LENGTH: 36
<212> TYPE: DNA
<213> ORGANISM: Artificial Sequence
<220> FEATURE:
<223> OTHER INFORMATION: CR RNA

<400> SEQUENCE: 8
gttttagagc tgtgctgttt cgaatggttc caaaac                          36

<210> SEQ ID NO 9
<211> LENGTH: 87

```
<212> TYPE: DNA
<213> ORGANISM: Artificial Sequence
<220> FEATURE:
<223> OTHER INFORMATION: TRACR RNA

<400> SEQUENCE: 9
tgttggaact attcgaaaca acacagcgag ttaaaataag gctttgtccg tacacaactt    60
gtaaaagggg cacccgattc gggtgca                                       87

<210> SEQ ID NO 10
<211> LENGTH: 1367
<212> TYPE: PRT
<213> ORGANISM: Streptococcus acidominimus

<400> SEQUENCE: 10
```

| Met | Thr | Lys | Pro | Tyr | Ser | Ile | Gly | Leu | Asp | Ile | Gly | Thr | Asn | Ser | Val |
|---|---|---|---|---|---|---|---|---|---|---|---|---|---|---|---|
| 1 | | | | 5 | | | | | 10 | | | | | 15 | |

| Gly | Trp | Ala | Val | Ile | Thr | Asp | Asp | Tyr | Lys | Val | Pro | Ser | Lys | Lys | Met |
|---|---|---|---|---|---|---|---|---|---|---|---|---|---|---|---|
| | | | 20 | | | | | 25 | | | | | 30 | | |

| Lys | Val | Leu | Gly | Asn | Thr | Ser | Lys | Lys | Tyr | Ile | Lys | Lys | Asn | Leu | Leu |
|---|---|---|---|---|---|---|---|---|---|---|---|---|---|---|---|
| | | 35 | | | | | 40 | | | | | 45 | | | |

| Gly | Ala | Leu | Leu | Phe | Asp | Ser | Gly | Ile | Thr | Ala | Glu | Gly | Arg | Arg | Leu |
|---|---|---|---|---|---|---|---|---|---|---|---|---|---|---|---|
| 50 | | | | | 55 | | | | | 60 | | | | | |

| Lys | Arg | Thr | Ala | Arg | Arg | Tyr | Thr | Arg | Arg | Asn | Arg | Ile | Leu |
|---|---|---|---|---|---|---|---|---|---|---|---|---|---|
| 65 | | | | 70 | | | | | 75 | | | | 80 |

| Tyr | Leu | Gln | Glu | Ile | Phe | Ser | Thr | Glu | Met | Ala | Thr | Leu | Asp | Asp | Ala |
|---|---|---|---|---|---|---|---|---|---|---|---|---|---|---|---|
| | | | | 85 | | | | | 90 | | | | | 95 | |

| Phe | Phe | Gln | Arg | Leu | Asp | Asp | Ser | Phe | Leu | Val | Pro | Asp | Asp | Lys | Arg |
|---|---|---|---|---|---|---|---|---|---|---|---|---|---|---|---|
| | | | 100 | | | | | 105 | | | | | 110 | | |

| Asp | Ser | Lys | Tyr | Pro | Ile | Phe | Gly | Asn | Leu | Val | Glu | Glu | Lys | Ala | Tyr |
|---|---|---|---|---|---|---|---|---|---|---|---|---|---|---|---|
| | | 115 | | | | | 120 | | | | | 125 | | | |

| His | Asp | Glu | Phe | Pro | Thr | Ile | Tyr | His | Leu | Arg | Lys | Tyr | Leu | Ala | Asp |
|---|---|---|---|---|---|---|---|---|---|---|---|---|---|---|---|
| | 130 | | | | | 135 | | | | | 140 | | | | |

| Ser | Thr | Lys | Lys | Ala | Asp | Leu | Arg | Leu | Val | Tyr | Leu | Ala | Leu | Ala | His |
|---|---|---|---|---|---|---|---|---|---|---|---|---|---|---|---|
| 145 | | | | | 150 | | | | | 155 | | | | | 160 |

| Met | Ile | Lys | Tyr | Arg | Gly | His | Phe | Leu | Ile | Glu | Gly | Glu | Phe | Asn | Ser |
|---|---|---|---|---|---|---|---|---|---|---|---|---|---|---|---|
| | | | | 165 | | | | | 170 | | | | | 175 | |

| Lys | Asn | Asn | Asp | Ile | Gln | Lys | Asn | Phe | Gln | Asp | Phe | Leu | Asp | Thr | Tyr |
|---|---|---|---|---|---|---|---|---|---|---|---|---|---|---|---|
| | | | 180 | | | | | 185 | | | | | 190 | | |

| Asn | Ala | Ile | Phe | Glu | Ser | Asp | Leu | Ser | Leu | Glu | Asn | Ser | Lys | Gln | Leu |
|---|---|---|---|---|---|---|---|---|---|---|---|---|---|---|---|
| | | 195 | | | | | 200 | | | | | 205 | | | |

| Glu | Glu | Ile | Val | Lys | Asp | Lys | Ile | Ser | Lys | Leu | Glu | Lys | Lys | Asp | Arg |
|---|---|---|---|---|---|---|---|---|---|---|---|---|---|---|---|
| | 210 | | | | | 215 | | | | | 220 | | | | |

| Ile | Leu | Lys | Leu | Phe | Pro | Gly | Glu | Lys | Asn | Ser | Gly | Ile | Phe | Ser | Glu |
|---|---|---|---|---|---|---|---|---|---|---|---|---|---|---|---|
| 225 | | | | | 230 | | | | | 235 | | | | | 240 |

| Phe | Leu | Lys | Leu | Ile | Val | Gly | Asn | Gln | Ala | Asp | Phe | Lys | Lys | Tyr | Phe |
|---|---|---|---|---|---|---|---|---|---|---|---|---|---|---|---|
| | | | | 245 | | | | | 250 | | | | | 255 | |

| Asn | Leu | Asp | Glu | Lys | Ala | Ser | Leu | His | Phe | Ser | Lys | Glu | Ser | Tyr | Asp |
|---|---|---|---|---|---|---|---|---|---|---|---|---|---|---|---|
| | | | 260 | | | | | 265 | | | | | 270 | | |

| Glu | Asp | Leu | Glu | Thr | Leu | Leu | Gly | Tyr | Ile | Gly | Asp | Asp | Tyr | Ser | Asp |
|---|---|---|---|---|---|---|---|---|---|---|---|---|---|---|---|
| | | 275 | | | | | 280 | | | | | 285 | | | |

| Val | Phe | Leu | Lys | Ala | Lys | Lys | Leu | Tyr | Asp | Ala | Ile | Leu | Leu | Ser | Gly |
|---|---|---|---|---|---|---|---|---|---|---|---|---|---|---|---|
| | 290 | | | | | 295 | | | | | 300 | | | | |

| Ile | Leu | Thr | Val | Thr | Asp | Asn | Gly | Thr | Glu | Thr | Pro | Leu | Ser | Ser | Ala |
|---|---|---|---|---|---|---|---|---|---|---|---|---|---|---|---|
| 305 | | | | | 310 | | | | | 315 | | | | | 320 |

```
Met Ile Met Arg Tyr Lys Glu His Glu Glu Asp Leu Gly Leu Leu Lys
            325                 330                 335

Ala Tyr Ile Arg Asn Ile Ser Leu Lys Thr Tyr Asn Glu Val Phe Asn
            340                 345                 350

Asp Asp Thr Lys Asn Gly Tyr Ala Gly Tyr Ile Asp Gly Lys Thr Asn
            355                 360                 365

Gln Glu Asp Phe Tyr Val Tyr Leu Lys Lys Leu Leu Ala Lys Phe Glu
            370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
            405                 410                 415

Gln Glu Met Arg Ala Ile Leu Asp Lys Gln Ala Lys Phe Tyr Pro Phe
            420                 425                 430

Leu Ala Lys Asn Lys Glu Arg Ile Glu Lys Ile Leu Thr Phe Arg Ile
            435                 440                 445

Pro Tyr Tyr Val Gly Pro Leu Ala Arg Gly Asn Ser Asp Phe Ala Trp
            450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
            485                 490                 495

Ser Phe Asp Leu Tyr Leu Pro Glu Glu Lys Val Leu Pro Lys His Ser
            500                 505                 510

Leu Leu Tyr Glu Thr Phe Thr Val Tyr Asn Glu Leu Thr Lys Val Arg
            515                 520                 525

Phe Ile Ala Glu Gly Met Ser Asp Tyr Gln Phe Leu Asp Ser Lys Gln
            530                 535                 540

Lys Lys Asp Ile Val Arg Leu Tyr Phe Lys Gly Lys Arg Lys Val Lys
545                 550                 555                 560

Val Thr Asp Lys Asp Ile Ile Glu Tyr Leu His Ala Ile Asp Gly Tyr
            565                 570                 575

Asp Gly Ile Glu Leu Lys Gly Ile Glu Lys Gln Phe Asn Ser Ser Leu
            580                 585                 590

Ser Thr Tyr His Asp Leu Leu Asn Ile Ile Asn Asp Lys Glu Phe Leu
            595                 600                 605

Asp Asp Ser Ser Asn Glu Ala Ile Ile Glu Glu Ile Ile His Thr Leu
            610                 615                 620

Thr Ile Phe Glu Asp Arg Glu Met Ile Lys Gln Arg Leu Ser Lys Phe
625                 630                 635                 640

Glu Asn Ile Phe Asp Lys Ser Val Leu Lys Lys Leu Ser Arg Arg His
            645                 650                 655

Tyr Thr Gly Trp Gly Lys Leu Ser Ala Lys Leu Ile Asn Gly Ile Arg
            660                 665                 670

Asp Glu Lys Ser Gly Asn Thr Ile Leu Asp Tyr Leu Ile Asp Asp Gly
            675                 680                 685

Ile Ser Asn Arg Asn Phe Met Gln Leu Ile His Asp Asp Ala Leu Ser
            690                 695                 700

Phe Lys Lys Lys Ile Gln Lys Ala Gln Ile Ile Gly Asp Lys Asp Lys
705                 710                 715                 720

Asp Asn Ile Lys Glu Val Val Lys Ser Leu Pro Gly Ser Pro Ala Ile
            725                 730                 735

Lys Lys Gly Ile Leu Gln Ser Ile Lys Ile Val Asp Glu Leu Val Lys
```

```
                740              745                750
    Val Met Gly Arg Lys Pro Glu Ser Ile Val Glu Met Ala Arg Glu
                    755              760                765
    Asn Gln Tyr Thr Asn Gln Gly Lys Ser Asn Ser Gln Gln Arg Leu Lys
                    770              775                780
    Arg Leu Glu Glu Ser Leu Glu Leu Gly Ser Lys Ile Leu Lys Glu
    785              790              795                800
    Asn Ile Pro Ala Lys Leu Ser Lys Ile Asp Asn Asn Ser Leu Gln Asn
                    805              810                815
    Asp Arg Leu Tyr Leu Tyr Tyr Leu Gln Asn Gly Lys Asp Met Tyr Thr
                    820              825                830
    Gly Asp Asp Leu Asp Ile Asp Arg Leu Ser Asn Tyr Asp Ile Asp His
                    835              840                845
    Ile Ile Pro Gln Ala Phe Leu Lys Asp Asn Ser Ile Asp Asn Lys Val
                    850              855                860
    Leu Val Ser Ser Ala Ser Asn Arg Gly Lys Ser Asp Asp Val Pro Ser
    865              870              875                880
    Leu Glu Val Val Lys Lys Arg Lys Thr Leu Trp Tyr Gln Leu Leu Lys
                    885              890                895
    Ser Lys Leu Ile Ser Gln Arg Lys Phe Asp Asn Leu Thr Lys Ala Glu
                    900              905                910
    Arg Gly Gly Leu Ser Pro Glu Asp Lys Ala Gly Phe Ile Gln Arg Gln
                    915              920                925
    Leu Val Glu Thr Arg Gln Ile Thr Lys His Val Ala Arg Leu Leu Asp
                    930              935                940
    Glu Lys Phe Asn Asn Lys Lys Asp Glu Asn Asn Arg Ala Val Arg Thr
    945              950              955                960
    Val Lys Ile Ile Thr Leu Lys Ser Thr Leu Val Ser Gln Phe Arg Lys
                    965              970                975
    Asp Phe Glu Leu Tyr Lys Val Arg Glu Ile Asn Asp Phe His His Ala
                    980              985                990
    His Asp Ala Tyr Leu Asn Ala Val  Val Ala Ser Ala Leu Leu Lys Lys
                    995              1000               1005
    Tyr Pro Lys Leu Glu Pro Glu  Phe Val Tyr Gly Asp  Tyr Pro Lys
        1010             1015                1020
    Tyr Asn Ser Phe Arg Glu Arg  Lys Ser Ala Thr Glu  Lys Val Tyr
        1025             1030                1035
    Phe Tyr Ser Asn Ile Met Asn  Ile Phe Lys Lys Ser  Ile Ser Leu
        1040             1045                1050
    Ala Asp Gly Arg Val Ile Glu  Arg Pro Leu Ile Glu  Val Asn Glu
        1055             1060                1065
    Glu Thr Gly Glu Ser Val Trp  Asn Lys Glu Ser Asp  Leu Ala Thr
        1070             1075                1080
    Val Arg Arg Val Leu Ser Tyr  Pro Gln Val Asn Val  Val Lys Lys
        1085             1090                1095
    Val Glu Val Gln Ser Gly Gly  Phe Ser Lys Glu Leu  Val Gln Pro
        1100             1105                1110
    His Gly Asn Ser Asp Lys Leu  Ile Pro Arg Lys Thr  Lys Lys Met
        1115             1120                1125
    Ile Trp Asp Thr Lys Lys Tyr  Gly Gly Phe Asp Ser  Pro Ile Val
        1130             1135                1140
    Ala Tyr Ser Val Leu Val Met  Ala Glu Arg Glu Lys  Gly Lys Ser
        1145             1150                1155
```

| Lys | Lys | Leu | Lys | Pro | Val | Lys | Glu | Leu | Val | Arg | Ile | Thr | Ile | Met |
|---|---|---|---|---|---|---|---|---|---|---|---|---|---|---|
| 1160 | | | | | 1165 | | | | | 1170 | | | | |

| Glu | Lys | Glu | Ser | Phe | Lys | Glu | Asn | Thr | Ile | Asp | Phe | Leu | Glu | Arg |
|---|---|---|---|---|---|---|---|---|---|---|---|---|---|---|
| 1175 | | | | | 1180 | | | | | 1185 | | | | |

| Arg | Gly | Leu | Arg | Asn | Ile | Gln | Asp | Glu | Asn | Ile | Ile | Leu | Leu | Pro |
|---|---|---|---|---|---|---|---|---|---|---|---|---|---|---|
| 1190 | | | | | 1195 | | | | | 1200 | | | | |

| Lys | Phe | Ser | Leu | Phe | Glu | Leu | Glu | Asn | Gly | Arg | Arg | Leu | Leu |
|---|---|---|---|---|---|---|---|---|---|---|---|---|---|
| 1205 | | | | | 1210 | | | | | 1215 | | | | |

| Ala | Ser | Ala | Lys | Glu | Leu | Gln | Lys | Gly | Asn | Glu | Phe | Ile | Leu | Pro |
|---|---|---|---|---|---|---|---|---|---|---|---|---|---|---|
| 1220 | | | | | 1225 | | | | | 1230 | | | | |

| Asn | Lys | Leu | Val | Lys | Leu | Leu | Tyr | His | Ala | Lys | Asn | Ile | His | Asn |
|---|---|---|---|---|---|---|---|---|---|---|---|---|---|---|
| 1235 | | | | | 1240 | | | | | 1245 | | | | |

| Thr | Leu | Glu | Pro | Glu | His | Leu | Glu | Tyr | Val | Glu | Ser | His | Arg | Ala |
|---|---|---|---|---|---|---|---|---|---|---|---|---|---|---|
| 1250 | | | | | 1255 | | | | | 1260 | | | | |

| Asp | Phe | Gly | Lys | Ile | Leu | Asp | Val | Val | Ser | Val | Phe | Ser | Glu | Lys |
|---|---|---|---|---|---|---|---|---|---|---|---|---|---|---|
| 1265 | | | | | 1270 | | | | | 1275 | | | | |

| Tyr | Ile | Leu | Ala | Glu | Ala | Lys | Leu | Glu | Lys | Ile | Lys | Glu | Ile | Tyr |
|---|---|---|---|---|---|---|---|---|---|---|---|---|---|---|
| 1280 | | | | | 1285 | | | | | 1290 | | | | |

| Arg | Lys | Asn | Met | Asn | Thr | Glu | Ile | His | Glu | Met | Ala | Thr | Ala | Phe |
|---|---|---|---|---|---|---|---|---|---|---|---|---|---|---|
| 1295 | | | | | 1300 | | | | | 1305 | | | | |

| Ile | Asn | Leu | Leu | Thr | Phe | Thr | Ser | Ile | Gly | Ala | Pro | Ala | Thr | Phe |
|---|---|---|---|---|---|---|---|---|---|---|---|---|---|---|
| 1310 | | | | | 1315 | | | | | 1320 | | | | |

| Lys | Phe | Phe | Gly | His | Asn | Ile | Glu | Arg | Lys | Arg | Tyr | Ser | Ser | Val |
|---|---|---|---|---|---|---|---|---|---|---|---|---|---|---|
| 1325 | | | | | 1330 | | | | | 1335 | | | | |

| Ala | Glu | Ile | Leu | Asn | Ala | Thr | Leu | Ile | His | Gln | Ser | Val | Thr | Gly |
|---|---|---|---|---|---|---|---|---|---|---|---|---|---|---|
| 1340 | | | | | 1345 | | | | | 1350 | | | | |

| Leu | Tyr | Glu | Thr | Arg | Ile | Asp | Leu | Gly | Lys | Leu | Gly | Glu | Asp |
|---|---|---|---|---|---|---|---|---|---|---|---|---|---|
| 1355 | | | | | 1360 | | | | | 1365 | | | | |

<210> SEQ ID NO 11
<211> LENGTH: 36
<212> TYPE: DNA
<213> ORGANISM: Artificial Sequence
<220> FEATURE:
<223> OTHER INFORMATION: CR RNA

<400> SEQUENCE: 11
gttttagagc tgtgttgttt cgaatggttc caaaac        36

<210> SEQ ID NO 12
<211> LENGTH: 87
<212> TYPE: DNA
<213> ORGANISM: Artificial Sequence
<220> FEATURE:
<223> OTHER INFORMATION: TRACR RNA

<400> SEQUENCE: 12
ggtttgaaac cattcgaaac aatacagcaa agttaaaata aggctagtcc gtatacaacg        60
tgaaaacacg tggcaccgat tcggtgc        87

<210> SEQ ID NO 13
<211> LENGTH: 1393
<212> TYPE: PRT
<213> ORGANISM: Artificial Sequence
<220> FEATURE:
<223> OTHER INFORMATION: Acholeplasmatales

<400> SEQUENCE: 13

Met Lys Asn Asn Glu Glu Thr Leu Lys Lys Leu Arg Leu Gly Leu Asp
1               5                   10                  15

Ile Gly Thr Asn Ser Val Gly Tyr Ala Leu Leu Asp Glu Asn Asn Lys
            20                  25                  30

Leu Ile Lys Lys Asn Gly His Thr Phe Trp Gly Val Arg Met Phe Asp
        35                  40                  45

Glu Ala Glu Thr Ala Lys Asp Arg Gly Ser Tyr Arg Lys Ser Arg Arg
50                  55                  60

Arg Leu Leu Arg Arg Lys Glu Arg Met Glu Ile Leu Arg Ser Phe Phe
65                  70                  75                  80

Thr Lys Glu Ile Cys Asp Ile Asp Pro Thr Phe Phe Glu Arg Leu Asp
                85                  90                  95

Asp Ser Phe Tyr Tyr Lys Glu Asp Lys Lys Asn Lys Asn Thr Tyr Asn
                100                 105                 110

Leu Phe Thr Ser Glu Tyr Thr Asp Lys Asp Phe Tyr Leu Glu Tyr Pro
            115                 120                 125

Thr Ile Tyr His Leu Arg Lys Ala Met Gln Glu Glu Asp Lys Lys Phe
        130                 135                 140

Asp Ile Arg Met Val Tyr Leu Ala Ile Ala His Ile Ile Lys Tyr Arg
145                 150                 155                 160

Gly Asn Phe Leu Tyr Pro Gly Glu Glu Phe Ser Thr Ser Glu Tyr Thr
                165                 170                 175

Ser Ile Lys Gln Phe Phe Leu Asp Phe Asn Asp Ile Leu Asp Glu Leu
                180                 185                 190

Ser Asn Glu Leu Glu Asp Asn Glu Asp Tyr Ser Ala Glu Tyr Phe Asp
            195                 200                 205

Lys Ile Glu Asn Ile Asn Asp Asp Phe Leu Glu Lys Leu Lys Val Ile
        210                 215                 220

Leu Met Glu Ile Lys Gly Ile Ser Asn Lys Lys Glu Leu Leu Asp
225                 230                 235                 240

Leu Phe Asn Val Asn Lys Lys Ser Ile Tyr Asn Glu Leu Val Ile Pro
                245                 250                 255

Phe Ile Ser Gly Ser Ala Lys Val Asn Ile Ser Ser Leu Ser Val Ile
                260                 265                 270

Lys Asn Ser Lys Tyr Pro Lys Thr Glu Ile Ser Leu Gly Ser Glu Glu
        275                 280                 285

Leu Glu Gly Gln Val Glu Glu Ala Ile Ser Val Ala Pro Glu Ile Lys
        290                 295                 300

Ser Val Leu Glu Met Ile Ile Lys Ile Lys Glu Ile Ser Asp Phe Tyr
305                 310                 315                 320

Phe Ile Asn Lys Ile Leu Ser Asp Ser Lys Thr Ile Ser Glu Ser Met
            325                 330                 335

Val Lys Met Tyr Asp Glu His Asn Glu Asp Leu Lys Lys Leu Lys Gly
                340                 345                 350

Phe Phe Lys Lys Tyr Ala Glu Asp Gln Tyr Asn Glu Ile Phe Lys Ile
            355                 360                 365

Arg Asp Glu Lys Leu Ala Asn Tyr Val Ala Tyr Val Gly Phe Asn Lys
        370                 375                 380

Leu Arg Lys Asn Lys Val Glu Arg Phe Lys His Ala Ser Arg Glu Glu
385                 390                 395                 400

Phe Tyr Gly Tyr Leu Lys Gln Lys Leu Asn Asn Ile Lys Tyr Ala Glu
                405                 410                 415

Ala Gln Glu Glu Ile Lys Tyr Phe Ile Asp Lys Ile Asp Asn Asn Glu

-continued

```
            420                 425                 430
Phe Leu Leu Lys Gln Asn Ser Asn Gln Asn Gly Ala Phe Pro Met Gln
            435                 440                 445
Leu His Leu Lys Glu Leu Lys Thr Ile Leu Asn Asn Gln Glu Lys Tyr
            450                 455                 460
Tyr Pro Phe Leu Ser Glu Gly Asn Asp Gly Tyr Ser Ile Lys Glu Lys
465                 470                 475                 480
Ile Ile Leu Thr Phe Lys Tyr Lys Ile Pro Tyr Tyr Val Gly Pro Leu
                485                 490                 495
Asn Lys Glu Ser Lys Tyr Ser Trp Val Val Arg Glu Asp Glu Lys Ile
                500                 505                 510
Tyr Pro Trp Asn Phe Asp Lys Val Val Lys Leu Asp Glu Thr Ala Glu
            515                 520                 525
Lys Phe Ile Leu Arg Met Gln Asn Lys Cys Thr Tyr Leu Lys Gly Asp
            530                 535                 540
Asn Asp Tyr Cys Leu Pro Lys Asn Ser Leu Ile Phe Ser Glu Tyr Ser
545                 550                 555                 560
Cys Leu Ser Tyr Leu Asn Lys Leu Ser Ile Asn Gly Lys Pro Ile Asp
                565                 570                 575
Pro Ile Met Lys Ser Lys Ile Phe Asn Glu Val Phe Leu Ile Lys Lys
                580                 585                 590
Gln Pro Thr Lys Lys Asp Ile Ile Glu Phe Ile Lys Thr Asn Tyr Asn
            595                 600                 605
Ala Asp Ala Leu Thr Thr Thr Glu Lys Glu Leu Pro Glu Ala Thr Cys
            610                 615                 620
Asn Met Ala Ser Tyr Ile Lys Met Lys Glu Ile Phe Gly Lys Asp Phe
625                 630                 635                 640
Asn Asp Asn Lys Glu Met Ile Glu Asn Ile Ile Lys Asp Ile Thr Ile
                645                 650                 655
Phe Glu Asp Lys Ser Ile Leu Gly Asn Arg Leu Lys Glu Leu Tyr Lys
                660                 665                 670
Leu Asn Asn Asp Arg Ile Lys Gln Ile Lys Gly Leu Asn Tyr Lys Gly
            675                 680                 685
Tyr Ser Arg Leu Ser Lys Asn Leu Leu Val Gly Leu Gln Ile Val Asp
            690                 695                 700
Asn Gln Thr Gly Glu Ile Lys Gly Asn Val Ile Glu Val Met Arg Lys
705                 710                 715                 720
Thr Asn Leu Asn Leu Gln Glu Ile Leu Tyr Leu Asp Gly Tyr Arg Leu
                725                 730                 735
Ile Asp Ala Ile Asp Glu Tyr Asn Arg Lys Asn Ser Leu Asn Asp Ser
                740                 745                 750
Tyr Leu Cys Ala Arg Asp Tyr Ile Ala Glu Asn Leu Val Ile Ser Pro
            755                 760                 765
Ser Phe Lys Arg Ala Leu Ile Gln Thr Cys Ser Ile Ile Gln Glu Ile
            770                 775                 780
Glu Arg Ile Phe His Lys Ile Asp Glu Phe Tyr Val Glu Val Thr
785                 790                 795                 800
Arg Thr Asn Lys Asp Lys Asn Lys Gly Lys Thr Thr Ser Ser Arg Tyr
                805                 810                 815
Asp Lys Ile Lys Lys Ile Tyr Ser Ser Cys Gln Glu Leu Ala Met Ala
            820                 825                 830
Tyr Asn Phe Asp Met Lys Arg Leu Lys Asn Glu Leu Glu Ser Asn Lys
            835                 840                 845
```

-continued

Asp Asn Leu Lys Ser Asp Ile Leu Tyr Phe Tyr Phe Thr Gln Leu Gly
        850                 855                 860

Lys Cys Met Tyr Ser Leu Glu Asp Ile Asp Ile Ser Asp Leu Thr Asn
865                 870                 875                 880

Asn Tyr His Tyr Asp Ile Asp His Ile Tyr Pro Gln Ser Ile Ile Lys
                885                 890                 895

Asp Asp Ser Leu Ser Asn Arg Val Leu Val Asp Lys Lys Asn Ala
        900                 905                 910

Ala Lys Thr Asp Lys Phe Leu Phe Glu Ala Lys Val Leu Asn Pro Lys
        915                 920                 925

Ala Gln Gln Phe Tyr Lys Leu Leu Ser Leu Glu Leu Ile Ser Lys
        930                 935                 940

Glu Lys Tyr Arg Arg Leu Thr Gln Lys Glu Ile Ser Lys Asp Glu Leu
945                 950                 955                 960

Glu Gly Phe Val Asn Arg Gln Leu Val Ser Thr Asn Gln Ser Val Met
                965                 970                 975

Gly Leu Ile Lys Leu Leu Lys Glu Tyr Tyr Lys Val Asp Glu Lys Asn
                980                 985                 990

Ile Ile Tyr Ser Lys Gly Glu Asn Val Ser Asp Phe Arg His Thr Phe
        995                 1000                1005

Asp Leu Val Lys Ser Arg Thr Ala Asn Asn Phe His His Ala His
        1010                1015                1020

Asp Ala Tyr Leu Asn Val Val Val Gly Gly Ile Leu Asn Lys Tyr
        1025                1030                1035

Tyr Thr Ser Arg Arg Phe Tyr Gln Phe Ser Asp Ile Ala Arg Ile
        1040                1045                1050

Glu Asn Glu Gly Glu Ser Leu Asn Pro Ser Arg Ile Phe Thr Lys
        1055                1060                1065

Arg Asp Ile Leu Lys Ala Asn Gly Lys Val Ile Trp Asp Lys Lys
        1070                1075                1080

Glu Asp Ile Lys Arg Ile Glu Lys Asp Leu Tyr His Arg Phe Asp
        1085                1090                1095

Ile Thr Glu Thr Ile Arg Thr Tyr Asn Pro Asn Lys Met Tyr Ser
        1100                1105                1110

Lys Val Thr Ile Leu Pro Lys Gly Glu Gly Glu Ser Ala Val Pro
        1115                1120                1125

Phe Gln Thr Thr Thr Pro Arg Val Asp Val Glu Lys Tyr Gly Gly
        1130                1135                1140

Ile Thr Ser Asn Lys Phe Ser Arg Tyr Val Ile Ile Glu Ala His
        1145                1150                1155

Gly Lys Lys Gly Leu Asp Thr Ile Leu Glu Ala Ile Pro Lys Thr
        1160                1165                1170

Ala Cys Gly Asp Asn Asn Lys Ile Glu Lys Asp Ile Asp Asn Tyr
        1175                1180                1185

Ile Ala Ser Leu Asp Glu Tyr Gln Lys Tyr Thr Ser Tyr Lys Val
        1190                1195                1200

Val Asn Tyr Asn Ile Lys Ala Asn Val Val Ile Gln Glu Gly Ser
        1205                1210                1215

Phe Lys Tyr Ile Ile Thr Gly Lys Ser Gly Asn Gln Tyr Val Leu
        1220                1225                1230

Gln Asn Val Gln Asp Arg Phe Phe Ser Lys Ala Met Ile Thr
        1235                1240                1245

-continued

```
Ile Lys Asn Ile Asp Lys Tyr Leu Asn Asn Lys Leu Gly Ile
    1250                1255                1260

Ile Met Ala Lys Asp Asn Glu Lys Ile Ile Val Ser Pro Ala Arg
    1265                1270                1275

Gly Lys Asn Asn Glu Glu Ile Phe Phe Glu Lys Thr Glu Leu Val
    1280                1285                1290

Asn Leu Leu Lys Glu Ile Lys Thr Met Tyr Ser Lys Asp Ile Tyr
    1295                1300                1305

Ser Phe Ser Ala Ile Gln Asn Ile Val Asn Asn Ile Asp Cys Ser
    1310                1315                1320

Ile Asp Tyr Ser Ile Asp Asp Phe Ile Ile Ile Cys Asn Asn Leu
    1325                1330                1335

Leu Gln Ile Leu Lys Thr Asn Glu Arg Lys Asn Ala Asp Leu Arg
    1340                1345                1350

Leu Ile His Leu Ser Gly Asn Ser Gly Thr Leu Tyr Leu Gly Lys
    1355                1360                1365

Lys Leu Lys Ser Gly Met Lys Phe Ile Trp Gln Ser Ile Thr Gly
    1370                1375                1380

Tyr Tyr Glu Glu Ile Leu Tyr Glu Val Lys
    1385                1390
```

<210> SEQ ID NO 14
<211> LENGTH: 36
<212> TYPE: DNA
<213> ORGANISM: Artificial Sequence
<220> FEATURE:
<223> OTHER INFORMATION: CR RNA

<400> SEQUENCE: 14
gtttgctagt tatgttattt atagtattaa gcaaac     36

<210> SEQ ID NO 15
<211> LENGTH: 82
<212> TYPE: DNA
<213> ORGANISM: Artificial Sequence
<220> FEATURE:
<223> OTHER INFORMATION: TRACR RNA

<400> SEQUENCE: 15
tgtaaataac ataacgagtg caaataagcg tttcgcgaaa atttacagtg gccctgctgt     60
ggggcctttt ttatttatca aa     82

<210> SEQ ID NO 16
<211> LENGTH: 1392
<212> TYPE: PRT
<213> ORGANISM: Artificial Sequence
<220> FEATURE:
<223> OTHER INFORMATION: Lachnospiraceae

<400> SEQUENCE: 16

```
Met Ser Glu Lys Tyr Phe Val Gly Leu Asp Met Gly Thr Ser Ser Val
1               5                   10                  15

Gly Trp Ala Val Thr Asp Glu His Tyr His Leu Leu Arg Arg Lys Gly
            20                  25                  30

Lys Asp Leu Trp Gly Ala Arg Leu Phe Asp Glu Ala Thr Ala Ala
            35                  40                  45

Gly Arg Arg Thr Asn Arg Val Ser Arg Arg Leu Ala Arg Gln Arg
        50                  55                  60

Ala Arg Ile Gly Trp Leu Lys Glu Leu Phe Arg Pro Tyr Leu Glu Glu
```

```
                65                  70                  75                  80
Lys Asp Ala Gly Phe Leu Gln Arg Leu Glu Glu Ser Arg Phe Phe Leu
                        85                  90                  95
Glu Asp Lys Thr Val Lys Gln Pro Tyr Ala Leu Phe Ser Asp Lys Glu
                        100                 105                 110
Phe Thr Asp Lys Asp Tyr Tyr Gln Lys Tyr Pro Thr Ile Phe His Leu
                        115                 120                 125
Arg Lys Glu Leu Leu Glu Ser Lys Ala Pro His Asp Val Arg Leu Val
                130                 135                 140
Phe Leu Ala Val Leu Asn Met Tyr Ala His Arg Gly His Phe Leu Asn
145                 150                 155                 160
Pro Glu Leu Gln Glu Gly Thr Leu Gly Asp Ile His Asp Leu Leu Ser
                        165                 170                 175
Arg Leu Asp Ala Tyr Ile Gln Asp Leu Phe Glu Asp Gln Gly Trp Ser
                        180                 185                 190
Ile Leu Glu Asn Val Glu Glu Gln Lys Val Leu Ala Glu Lys Asn
                        195                 200                 205
Ile Ser Asn Thr Val Arg Leu Glu Lys Ile Leu Ser Ala Ile Gly Thr
                210                 215                 220
Ser Pro Lys Asp Lys Glu Lys Lys Pro Leu Ile Glu Ile Tyr Lys Leu
225                 230                 235                 240
Ile Cys Gly Leu Lys Gly Ser Leu Ser Leu Ala Phe Ser Gly Val Glu
                        245                 250                 255
Met Asn Glu Thr Asp Ala Gln Met Lys Phe Ser Phe Ser Asp Ser Asn
                        260                 265                 270
Leu Glu Glu Asn Glu Pro Glu Ile Glu Arg Ile Leu Gly Glu Arg Tyr
                275                 280                 285
Phe Glu Met Tyr Ser Ile Leu Lys Glu Ile His Ala Trp Gly Leu Leu
                290                 295                 300
Ser Glu Ile Met Ser Asp Asp Ser Gly Lys Thr Tyr Pro Tyr Ile Ser
305                 310                 315                 320
Tyr Ala Lys Val Asp Leu Tyr Gln Lys His His Glu Gln Leu Arg Met
                        325                 330                 335
Leu Lys Lys Ile Ile Arg Thr Tyr Ala Pro Asp Glu Tyr His Arg Met
                        340                 345                 350
Phe Arg Ser Met Glu Asp Asn Thr Tyr Ser Ala Tyr Val Gly Ser Val
                        355                 360                 365
Asn Ser Lys Asn Lys Gln Arg Arg Gly Ala Lys Ser Thr Asp Phe
                370                 375                 380
Phe Lys Glu Val Lys Arg Ile Ile Glu Lys Ile Glu Lys Glu His Gly
385                 390                 395                 400
Glu Leu Pro Glu Cys Glu Glu Ile Leu Asp Leu Ile Ala Arg Asp Ser
                        405                 410                 415
Phe Leu Pro Lys Gln Leu Thr Thr Ala Asn Gly Val Ile Pro Asn Gln
                        420                 425                 430
Val Tyr Ala Thr Glu Leu Arg Gln Ile Val Thr Asn Ala Ala Ala Tyr
                        435                 440                 445
Leu Pro Phe Leu Asn Asp Lys Asp Asp Thr Gly Leu Thr Asn Ala Glu
                        450                 455                 460
Lys Ile Val Glu Met Phe Lys Phe His Ile Pro Tyr Tyr Ile Gly Pro
465                 470                 475                 480
Leu Lys Asn Asp Gly Asn Gly Thr Ala Trp Val Val Arg Lys Gln Gln
                        485                 490                 495
```

```
Gly Thr Val Tyr Pro Trp Asn Ile Asp Glu Lys Val Asp Met Ala Lys
            500                 505                 510

Thr Arg Asp Gln Phe Ile Leu Asn Leu Val Arg Lys Cys Ser Tyr Leu
        515                 520                 525

Asn Asp Glu Thr Val Leu Pro Ala Ser Ser Leu Leu Tyr Glu Lys Phe
            530                 535                 540

Lys Val Leu Asn Glu Leu Asn Asn Leu Thr Ile Asn Gly Gln Lys Ile
545                 550                 555                 560

Ser Val Glu Leu Lys Gln Asp Ile Phe Arg Asp Leu Phe Arg Ala Thr
                565                 570                 575

Gly Lys Arg Val Thr Thr Arg Lys Leu Met Gly Tyr Leu Arg Arg Lys
            580                 585                 590

Ala Val Ile Asp Ala Asp Ala Asp Glu Thr Cys Leu Glu Gly Phe Asp
            595                 600                 605

Lys Thr Gln Gly Gly Phe Val Ser Thr Leu Ser Ser Tyr His Lys Phe
            610                 615                 620

Met Glu Ile Phe Ser Thr Asp Val Leu Thr Asp Arg Gln Arg Glu Ile
625                 630                 635                 640

Ala Glu Gly Ala Ile Tyr Phe Ala Thr Val Tyr Gly Glu Asp Lys Ser
                645                 650                 655

Phe Leu Lys Lys Val Leu Arg Asp Lys Phe Ser Pro Ala Glu Leu Ser
            660                 665                 670

Gln Ala Gln Ile Asp Arg Leu Ser Gly Ile Arg Phe Lys Asp Trp Ser
            675                 680                 685

His Leu Ser Arg Glu Phe Leu Leu Glu Glu Ala Asp His Ser Thr
            690                 695                 700

Gly Glu Ile Met Thr Ile Ile Asp Arg Leu Trp Asn Thr Asn Glu Asn
705                 710                 715                 720

Leu Met Gln Ile Ile His Ser Asp Glu Tyr Thr Tyr Lys Gln Ala Ile
                725                 730                 735

Glu Glu Arg Thr Ala Arg Leu Glu Lys Ser Leu Ser Glu Val Ser Phe
            740                 745                 750

Glu Asp Ile Glu Asp Ser Tyr Met Ser Ala Pro Val Arg Arg Met Val
            755                 760                 765

Trp Gln Thr Ile Arg Ile Leu Gln Glu Ile Glu Glu Val Met Gly Ser
            770                 775                 780

Glu Pro Ala Arg Val Phe Val Glu Met Thr Arg Ser Glu Gly Glu Lys
785                 790                 795                 800

Gly Asp Lys Gly Arg Lys Asp Ser Arg Lys Lys Leu Lys Glu Leu
                805                 810                 815

Tyr Lys Lys Cys Lys Asp Asp Gln Gly Leu Leu Ser Asp Ile Glu
                820                 825                 830

Gly Arg Asp Glu Arg Asp Phe Arg Ile Arg Lys Leu Tyr Leu Tyr Tyr
            835                 840                 845

Met Gln Lys Gly Leu Cys Met Tyr Ser Gly His Pro Ile Asp Phe Gly
            850                 855                 860

Lys Leu Phe Asp Asp Ser Tyr Tyr Asp Ile Asp His Ile Tyr Pro Arg
865                 870                 875                 880

His Tyr Val Lys Asp Asp Ser Ile Glu Asn Asn Leu Val Leu Val Glu
                885                 890                 895

Ser Lys Leu Asn Arg Asp Lys Lys Asp Thr Leu Leu Cys Pro Asp Ile
            900                 905                 910
```

-continued

Gln Glu Arg Met His Pro Val Trp Glu Met Leu His Arg Gln Gly Phe
                915                 920                 925
Met Asn Asp Glu Lys Phe Lys Arg Leu Met Arg Lys Glu Pro Phe Ser
        930                 935                 940
Glu Glu Glu Phe Ala His Phe Ile Glu Arg Gln Leu Val Glu Thr Gly
945                 950                 955                 960
Gln Gly Thr Lys Glu Ile Ala Arg Ile Leu Asn Asp Val Leu Gly Asn
                965                 970                 975
Lys Asp Glu Asn Asn Lys Val Ile Tyr Val Lys Ala Gly Asn Val Ser
        980                 985                 990
Ser Phe Arg Asn Asp Asn Lys Lys Asn Pro Glu Phe Val Lys Cys Arg
        995                 1000                1005
Val Ile Asn Asp His His His Ala Lys Asp Ala Tyr Leu Asn Ile
        1010                1015                1020
Val Val Gly Asn Thr Tyr Tyr Thr Lys Phe Thr Leu His Pro Ala
        1025                1030                1035
Asn Phe Ile Arg Glu Leu Arg Asn Lys Ser His Pro Thr Leu Glu
        1040                1045                1050
Asp Gln Tyr Asn Met Asp Lys Leu Phe Ala Arg Arg Val Glu Arg
        1055                1060                1065
Asn Gly Tyr Thr Ala Trp Asn Pro Asp Thr Asp Phe Gln Thr Val
        1070                1075                1080
Lys Gln Val Leu Arg Lys Asn Ser Val Leu Ile Ser Arg Arg Ser
        1085                1090                1095
Phe Ile Glu His Gly Gln Ile Ala Asp Leu Gln Leu Val Ser Gly
        1100                1105                1110
Arg Lys Ile Ser Glu Val Asn Gly Lys Gly Tyr Leu Pro Ile Lys
        1115                1120                1125
Ala Ser Asp Ile Arg Leu Ser Gly Pro Ser Gly Thr Met Lys Tyr
        1130                1135                1140
Gly Gly Tyr Asn Lys Ala Ser Gly Ala Tyr Phe Phe Leu Val Glu
        1145                1150                1155
His Glu Leu Lys Gly Lys Leu Val Arg Thr Ile Glu Pro Val Tyr
        1160                1165                1170
Val Tyr Met Met Ala Ser Ile His Gly Lys Glu Asp Leu Glu Lys
        1175                1180                1185
Tyr Cys Gln Glu Glu Leu Gly Tyr Ile His Pro Arg Ile Cys Leu
        1190                1195                1200
Lys Lys Ile Pro Met Tyr Ser His Ile Arg Ile Asn Gly Phe Asp
        1205                1210                1215
Tyr Tyr Leu Thr Gly Arg Ser Asn Asp Arg Leu Phe Ile Cys Asn
        1220                1225                1230
Ala Val Gln Leu Thr Leu Ser Ser Glu Trp Ser Ala Tyr Ile Lys
        1235                1240                1245
Ala Leu Ser Lys Ala Val Asp Glu Lys Trp Asp Ala Ala Tyr Ile
        1250                1255                1260
Glu Gln Gln Ala Ser Arg Ile Gln Asp Ser Leu Lys Ser Glu Glu
        1265                1270                1275
Val Phe Ile Ser Lys Glu Arg Asn Asp Gln Leu Tyr Lys Val Leu
        1280                1285                1290
Leu Gln Lys His Leu Glu Gly Phe Phe Asn Asn Arg Ile Asn Ser
        1295                1300                1305
Ile Gly Thr Ile Met Lys Glu Gly Tyr Asp Ser Phe Arg Ala Leu

```
            1310                1315                1320

Pro Val Asn Glu Gln Ala Glu Thr Leu Met Glu Ile Leu Lys Ile
        1325                1330                1335

Ser Gln Leu Val Asn Ile Gly Ala Asn Leu Val Ser Ile Gly Gly
        1340                1345                1350

Lys Ser Arg Ser Gly Val Ala Thr Val Ser Lys Ile Ser Asp
        1355                1360                1365

Ser Lys Ser Phe Gln Leu Ile Ser Asp Ser Val Thr Gly Ile Phe
        1370                1375                1380

Gln Arg Ala Thr Asp Leu Leu Thr Ile
        1385                1390

<210> SEQ ID NO 17
<211> LENGTH: 36
<212> TYPE: DNA
<213> ORGANISM: Artificial Sequence
<220> FEATURE:
<223> OTHER INFORMATION: CR RNA

<400> SEQUENCE: 17
gtttgagagc cttgtaaaac cgtatatctc tcaagc                              36

<210> SEQ ID NO 18
<211> LENGTH: 97
<212> TYPE: DNA
<213> ORGANISM: Artificial Sequence
<220> FEATURE:
<223> OTHER INFORMATION: TRACR RNA

<400> SEQUENCE: 18
gataatgttt tacaaggcga gttcaaataa ggatttatcc gaaatcgctt gcgtgcattg    60
gcaccatcta tcttttaaga ctttctttga aagtctt                             97

<210> SEQ ID NO 19
<211> LENGTH: 1364
<212> TYPE: PRT
<213> ORGANISM: Artificial Sequence
<220> FEATURE:
<223> OTHER INFORMATION: Lachnospiraceae

<400> SEQUENCE: 19

Met Glu Lys Glu Tyr Tyr Leu Gly Leu Asp Met Gly Thr Ser Ser Val
1               5                   10                  15

Gly Trp Ala Val Thr Asp Lys Glu Tyr Arg Leu Leu Arg Ala Lys Gly
            20                  25                  30

Lys Asp Met Trp Gly Ile Arg Glu Phe Glu Glu Ala Gln Thr Ala Val
        35                  40                  45

Glu Arg Arg Thr His Arg Leu Ser Lys Arg Arg Ala Arg Gln Leu
    50                  55                  60

Val Arg Ile Gly Leu Leu Lys Asp Tyr Phe His Asp Glu Ile Met Lys
65                  70                  75                  80

Ile Asp Pro Asn Phe Tyr Ile Arg Leu Glu Asn Ser Lys Tyr Tyr Leu
                85                  90                  95

Glu Asp Lys Asp Val Arg Leu Ala Ser Ser Asn Gly Ile Phe Asp Asp
            100                 105                 110

Lys Asn Tyr Thr Asp Lys Asp Tyr Tyr Glu Gln Tyr Lys Thr Ile Phe
        115                 120                 125

His Leu Arg Ser Glu Leu Ile Asn Ser Gln Lys His Asp Val Arg
    130                 135                 140
```

```
Leu Val Tyr Leu Ala Leu Leu Asn Met Phe Lys His Arg Gly His Phe
145                 150                 155                 160

Leu Phe Glu Gly Asp Ala Tyr Val Gln Gly Asn Ile Gly Asp Ile Tyr
                165                 170                 175

Lys Glu Phe Ile Gln Leu Leu Lys Asn Glu Tyr Tyr Glu Asp Glu Asn
            180                 185                 190

Val Lys Leu Thr Asp Gln Ile Asp Tyr Phe Lys Leu Lys Glu Ile Leu
        195                 200                 205

Ser Asn Ser Glu Phe Ser Arg Thr Ala Lys Ala Glu Lys Ile Asn Ser
    210                 215                 220

Leu Val His Ile Asp Lys Lys Asn Lys Leu Glu Asn Thr Tyr Ile Arg
225                 230                 235                 240

Leu Leu Cys Gly Leu Glu Ile Glu Leu Lys Ile Leu Phe Pro Glu Ile
                245                 250                 255

Asp Glu Lys Ile Lys Ile Cys Phe Ala Lys Gly Tyr Asp Glu Lys Leu
            260                 265                 270

Val Glu Ile Thr Glu Ile Leu Thr Asp Asn Gln Leu Gln Ile Leu Glu
        275                 280                 285

Asn Leu Lys Lys Ile His Asp Ile Ala Ala Leu Asp Lys Ile Arg Lys
    290                 295                 300

Gly Lys Glu Tyr Leu Ser Asp Ala Arg Val Ala Glu Tyr Glu Lys His
305                 310                 315                 320

Arg Glu Asp Leu Ala Leu Leu Lys Lys Ile Tyr Arg Glu Tyr Met Thr
                325                 330                 335

Lys Gln Asp Tyr Asp Arg Met Phe Arg Glu Gly Glu Asp Gly Ser Tyr
            340                 345                 350

Ser Ala Tyr Val Asn Ser Tyr Asn Thr Ser Lys Lys Gln Arg Arg Asn
        355                 360                 365

Met Lys His Arg Lys Ile Asp Glu Phe Tyr Gly Thr Ile Arg Lys Asp
    370                 375                 380

Leu Lys Leu Leu Leu Lys Gln Gly Ile Gln Asp Asp Asn Ile Glu Arg
385                 390                 395                 400

Ile Leu Glu Glu Ile Asp Gly Asn Asn Asp Asn Lys Phe Met Pro Lys
                405                 410                 415

Gln Leu Ser Phe Ala Asn Gly Val Ile Pro Asn Ser Leu His Lys Ala
            420                 425                 430

Glu Met Lys Ala Ile Leu Arg Asn Ala Glu Thr Tyr Leu Pro Phe Leu
        435                 440                 445

Leu Glu Thr Asp Glu Ser Gly Leu Thr Val Ser Glu Arg Ile Leu Gln
    450                 455                 460

Leu Phe Ser Phe His Ile Pro Tyr Tyr Ile Gly Pro Val Ser Val Asn
465                 470                 475                 480

Ser Glu Lys Asn Asn Gly Asn Gly Trp Val Val Arg Arg Glu Asp Gly
                485                 490                 495

Glu Val Leu Pro Trp Asn Ile Glu Gln Lys Ile Asp Tyr Gly Glu Thr
            500                 505                 510

Ser Lys Arg Phe Ile Glu Lys Met Val Arg Arg Cys Thr Tyr Ile Ser
        515                 520                 525

Gly Glu Gln Val Leu Pro Lys Asn Ser Phe Ile Tyr Glu Lys Tyr Cys
    530                 535                 540

Val Leu Asn Glu Ile Asn Asn Ile Lys Ile Asp Gly Glu Arg Ile Thr
545                 550                 555                 560
```

```
Val Glu Leu Lys Gln Asn Ile Tyr Asn Asp Leu Tyr Leu His Gly Lys
                565                 570                 575

Arg Val Thr Lys Lys Gln Leu Ile Asn Tyr Leu Asn Asn Arg Gly Met
            580                 585                 590

Ile Glu Asp Glu Asn Gln Val Ser Gly Ile Asp Ile Asn Leu Asn Asn
        595                 600                 605

Tyr Leu Gly Ser Tyr Gly Lys Phe Leu Pro Ile Phe Glu Glu Lys Leu
    610                 615                 620

Lys Glu Asp Asn Tyr Ile Lys Ile Ala Glu Asp Ile Ile Tyr Leu Ala
625                 630                 635                 640

Ser Ile Tyr Gly Asp Ser Lys Lys Met Leu Lys Ser Gln Ile Lys Ser
                645                 650                 655

Lys Tyr Gly Asp Ile Leu Asp Asp Lys Gln Ile Lys Arg Ile Leu Gly
            660                 665                 670

Leu Lys Phe Lys Asp Trp Gly Arg Ile Ser Arg Arg Phe Leu Glu Leu
        675                 680                 685

Glu Gly Leu Asp Lys Glu Thr Gly Glu Ile Thr Thr Ile Ile Lys Ala
    690                 695                 700

Met Trp Asp Tyr Asn Leu Asn Phe Met Glu Ile Ile His Ser Asp Ala
705                 710                 715                 720

Phe Asp Phe Lys Asp Lys Ile Glu Glu Leu His Ala Asn Ser Ile Lys
                725                 730                 735

Pro Leu Ala Glu Ile Glu Val Glu Asp Leu Asp Asp Met Tyr Phe Ser
            740                 745                 750

Ala Pro Val Lys Arg Met Ile Trp Gln Thr Phe Lys Val Ile Lys Glu
        755                 760                 765

Ile Glu Lys Val Met Gly Cys Pro Lys Lys Val Phe Ile Glu Met
    770                 775                 780

Thr Arg Ile Asn Asp Lys Lys Ser Lys Gly Lys Arg Thr Asn Ser Arg
785                 790                 795                 800

Lys Glu Lys Phe Leu Ser Leu Tyr Lys Asn Ile His Asp Glu Leu Val
                805                 810                 815

Asp Trp Lys Gln Leu Ile Ile Ser Ser Asp Glu Ser Gly Lys Leu Asn
            820                 825                 830

Ser Lys Lys Met Tyr Leu Tyr Leu Thr Gln Gln Gly Ile Cys Met Tyr
        835                 840                 845

Thr Gly Arg Arg Ile Asn Leu Glu Glu Leu Phe Asp Asp Asn Lys Tyr
    850                 855                 860

Asp Ile Asp His Ile Tyr Pro Arg His Phe Val Lys Asp Asn Leu
865                 870                 875                 880

Glu Asn Asn Leu Val Leu Val Glu Lys Gln Ser Asn Ser Arg Lys Ser
                885                 890                 895

Asp Thr Tyr Pro Ile Asp Lys Ser Ile Arg Asn Asn Ser Gln Val Tyr
            900                 905                 910

Lys His Trp Lys Ser Leu Arg Glu Gly Asn Phe Ile Ser Lys Glu Lys
        915                 920                 925

Tyr Asp Arg Leu Thr Gly Lys Asn Glu Phe Thr Asp Glu Gln Lys Ala
    930                 935                 940

Gly Phe Ile Ala Arg Gln Met Val Glu Thr Ser Gln Gly Thr Lys Gly
945                 950                 955                 960

Val Ala Asp Ile Ile Lys Gln Ala Leu Pro Gln Ser Arg Ile Ile Tyr
                965                 970                 975

Ser Lys Ala Ser Asn Val Ser Glu Phe Arg Arg Lys Tyr Asp Ile Leu
```

-continued

```
                  980               985               990
Lys Ser Arg Thr Val Asn Glu Phe His His Ala His Asp Ala Tyr Leu
            995               1000              1005
Asn Ile Val Val Gly Asn Val Tyr Asp Thr Lys Phe Thr Ser Asn
        1010              1015              1020
Pro Leu Asn Phe Ile Lys Lys Gln Tyr Asn Val Asp Arg Lys Ala
        1025              1030              1035
Asn Asn Tyr Asn Leu Asp Lys Met Phe Val Tyr Asp Val Lys Arg
        1040              1045              1050
Gly Asn Glu Ile Ala Trp Ile Gly Trp Asn Pro Lys Lys Ser Glu
        1055              1060              1065
Asp Ser Ser Glu Met Ser Lys Arg Gly Thr Ile Val Thr Val Lys
        1070              1075              1080
Lys Met Leu Ser Lys Asn Thr Pro Leu Met Thr Arg Met Ser Phe
        1085              1090              1095
Val Gly His Gly Gly Ile Ala Glu Asp Asn Leu Ser Ser His Phe
        1100              1105              1110
Val Ala Lys Asn Lys Gly Tyr Met Pro Asn Gly Lys Glu Ser Asp
        1115              1120              1125
Val Thr Lys Tyr Gly Gly Tyr Lys Lys Ala Lys Thr Ala Tyr Phe
        1130              1135              1140
Phe Val Val Glu His Gly Gln Thr Asn Asn Arg Ile Arg Thr Ile
        1145              1150              1155
Glu Thr Leu Pro Ile Tyr Arg Arg Arg Glu Val Glu Lys Tyr Glu
        1160              1165              1170
Asp Gly Leu Ile Lys Tyr Cys Glu Gln Ser Leu Ser Leu Leu Asn
        1175              1180              1185
Pro Ile Ile Ile Tyr Lys Lys Ile Lys Ile Gln Ser Leu Met Lys
        1190              1195              1200
Ile Asn Gly Tyr Tyr Ala Tyr Ile Ser Gly Lys Ser Asn Glu Val
        1205              1210              1215
Tyr Thr Phe Arg Asn Gly Val Asn Met Cys Leu Ser Gln Glu Trp
        1220              1225              1230
Ile Asn Tyr Val Lys Lys Leu Glu Asn Tyr Ile Glu Lys Asp Arg
        1235              1240              1245
Gln Asp Arg Met Ile Thr Tyr Glu Lys Asn Ile Glu Leu Tyr Glu
        1250              1255              1260
Ile Ile Leu Arg Lys Tyr Ser Thr Thr Ile Leu Asn Lys Arg Leu
        1265              1270              1275
Ser Lys Met Asp Lys Lys Leu Ile Asn Ala Lys Asp Arg Phe Cys
        1280              1285              1290
Ile Leu Asn Val Lys Glu Gln Ser Gln Val Leu Ile Asn Val Phe
        1295              1300              1305
Val Leu Ser Arg Ile Gly Asp Asn Gln Thr Asp Leu Ser Lys Ile
        1310              1315              1320
Gly Ile Gly Lys Gln Ser Gly Gln Ile Thr Gln Asn Lys Lys Ile
        1325              1330              1335
Thr Gly Cys Lys Glu Phe Lys Leu Val Asn Gln Ser Val Thr Gly
        1340              1345              1350
Leu Tyr Glu Asn Glu Ile Asp Leu Leu Thr Val
        1355              1360
```

<210> SEQ ID NO 20

```
<211> LENGTH: 36
<212> TYPE: DNA
<213> ORGANISM: Artificial Sequence
<220> FEATURE:
<223> OTHER INFORMATION: CR RNA

<400> SEQUENCE: 20
gtttgagagt cttgttaatt cttaaaggtg taaaac                                36

<210> SEQ ID NO 21
<211> LENGTH: 100
<212> TYPE: DNA
<213> ORGANISM: Artificial Sequence
<220> FEATURE:
<223> OTHER INFORMATION: TRACR RNA

<400> SEQUENCE: 21
gagaattaac aagacgagtg caaataaggt ttatccggaa tcgtcaatat gacctgcatt       60
gtgcagaatc tttaaaatca tatgatttca tatggtttta                           100

<210> SEQ ID NO 22
<211> LENGTH: 1357
<212> TYPE: PRT
<213> ORGANISM: Artificial Sequence
<220> FEATURE:
<223> OTHER INFORMATION: ELEPHANT FECES

<400> SEQUENCE: 22
```

Met Glu Lys Asn Asn Tyr Leu Leu Gly Leu Asp Ile Gly Thr Asp Ser
1               5                   10                  15

Val Gly Tyr Ala Val Thr Asn Asp Lys Tyr Asp Ile Leu Lys Phe His
            20                  25                  30

Gly Glu Pro Ala Trp Gly Val Thr Ile Phe Asp Glu Ala Ser Leu Ser
        35                  40                  45

Thr Glu Lys Arg Ser Phe Arg Val Ser Arg Arg Leu Asp Arg Arg
    50                  55                  60

Gln Gln Arg Val Leu Leu Val Gln Glu Leu Phe Ala Ser Glu Val Ala
65                  70                  75                  80

Lys Val Asp Lys Asp Phe Phe Lys Arg Ile Gln Glu Ser Asn Leu Tyr
                85                  90                  95

Arg Ser Asp Ala Glu Asn Gln Ala Gly Leu Phe Ile Gly Glu Asp Tyr
            100                 105                 110

Cys Asp Arg Glu Tyr Tyr Gly Gln Tyr Pro Thr Ile His His Leu Ile
        115                 120                 125

Ser Asp Leu Met Asn Gly Thr Ser Pro His Asp Val Arg Leu Val Tyr
    130                 135                 140

Leu Ala Cys Ala Trp Leu Val Ala His Arg Gly His Phe Leu Ser Asn
145                 150                 155                 160

Ile Asp Lys Asp Asn Leu Ser Gly Leu Lys Asp Phe Ser Ser Val Tyr
                165                 170                 175

Glu Gly Leu Met Gln Tyr Phe Ser Asp Asn Gly Tyr Glu Arg Pro Trp
            180                 185                 190

Asn Ala Asn Val Asp Val Lys Ala Leu Gly Asp Ala Leu Lys Lys Lys
        195                 200                 205

Gln Gly Val Thr Ala Lys Thr Lys Glu Leu Leu Ala Leu Leu Leu Asp
    210                 215                 220

Ser Ala Lys Ala Glu Lys Leu Pro Arg Glu Glu Phe Pro Phe Ser Gln
225                 230                 235                 240

```
Asp Gly Ile Ile Lys Leu Leu Ala Gly Gly Thr Tyr Lys Leu Ser Glu
            245                 250                 255
Leu Phe Gly Asn Glu Glu Tyr Lys Asp Phe Gly Ser Val Lys Leu Ser
        260                 265                 270
Met Asp Asp Glu Lys Leu Gly Glu Ile Met Ser Asn Ile Gly Glu Asp
    275                 280                 285
Tyr Glu Leu Ile Ala Ser Leu Arg Ile Val Ser Asp Trp Ala Val Leu
290                 295                 300
Val Asp Val Leu Gly Glu Ser Ala Thr Ile Ser Glu Ala Lys Val Gly
305                 310                 315                 320
Ile Tyr Asn Gln His Lys Ala Asp Leu Glu Val Leu Lys Lys Ile Ile
                325                 330                 335
Arg Lys Tyr Thr Gly Lys Glu Gly Tyr Lys Lys Val Phe Arg Gln Val
            340                 345                 350
Asp Ser Lys Glu Asn Tyr Val Ala Tyr Ser Gln His Glu Ser Asp Gly
        355                 360                 365
Lys Ala Pro Lys Glu Lys Gly Ile Asp Ile Ala Thr Phe Ser Lys Phe
    370                 375                 380
Ile Leu Asn Ile Val Arg Leu Leu Asp Val Glu Pro Glu Asp Lys Glu
385                 390                 395                 400
Val Tyr Glu Asp Met Val Ala Arg Leu Glu Leu Asn Ser Phe Leu Pro
                405                 410                 415
Lys Gln Val Asn Thr Asp Asn Arg Val Ile Pro Tyr Gln Leu Tyr Trp
            420                 425                 430
Phe Glu Leu His Lys Ile Leu Glu Asn Ala Ser Ile Tyr Leu Pro Met
        435                 440                 445
Leu Thr Glu Lys Asp Ser Asn Gly Ile Ser Val Met Glu Lys Leu Glu
    450                 455                 460
Ser Val Phe Met Phe Arg Ile Pro Tyr Phe Val Gly Pro Leu Asn Lys
465                 470                 475                 480
His Ser Lys Tyr Ala Trp Leu Glu Arg Lys Glu Gly Lys Ile Tyr Pro
                485                 490                 495
Trp Asn Phe Glu Asn Met Val Asp Leu Asp Ala Ser Glu Ala Asn Phe
            500                 505                 510
Ile Lys Arg Met Thr Asn Thr Cys Thr Tyr Leu Pro Gly Gln Asn Val
        515                 520                 525
Leu Pro Lys Asp Ser Leu Arg Tyr His Arg Phe Met Val Leu Asn Glu
    530                 535                 540
Ile Asn Asn Leu Arg Ile Asn Asn Glu Arg Ile Ser Val Glu Leu Lys
545                 550                 555                 560
Gln Lys Ile Tyr Ser Glu Leu Phe Leu Asn Val Lys Lys Val Thr Arg
                565                 570                 575
Lys Arg Leu Val Asp Phe Leu Ile Ser Asn Gly Glu Leu Arg Lys Gly
            580                 585                 590
Glu Glu Ser Ser Leu Thr Gly Ile Asp Val Glu Ile Lys Ala Asn Leu
        595                 600                 605
Ala Pro Gln Ile Ala Phe Lys Lys Leu Met Glu Ser Gly Gln Leu Thr
    610                 615                 620
Glu Glu Asp Val Glu Ser Ile Ile Glu Arg Ala Ser Tyr Ala Glu Asp
625                 630                 635                 640
Lys Ala Arg Leu Ala His Trp Leu Glu Ala Lys Tyr Ser Lys Leu Ser
                645                 650                 655
Glu Ile Asp Arg Lys Tyr Ile Cys Gly Ile Lys Ile Lys Asp Phe Gly
```

```
                660               665               670
Arg Leu Ser Lys Met Phe Leu Ser Glu Leu Glu Gly Val Asp Lys Thr
            675               680               685

Thr Gly Glu Met Thr Thr Ile Leu Gly Ala Met Trp Asn Ser Gln Leu
690               695               700

Asn Leu Met Glu Leu Ile Asn Ser Glu Leu Tyr Ser Phe Arg Glu Ala
705               710               715               720

Ile Cys Ala Tyr Gln Thr Asp Tyr Tyr Ser Thr His Ser Ser Ser Leu
            725               730               735

Glu Glu Arg Met Asn Glu Met Tyr Leu Ser Asn Ala Val Lys Arg Pro
                740               745               750

Val Tyr Arg Thr Leu Asp Ile Val Lys Asp Val Lys Lys Ala Phe Gly
            755               760               765

Glu Pro Lys Lys Ile Phe Val Glu Met Thr Arg Gly Ala Ser Glu Glu
            770               775               780

Gln Lys Gly Lys Arg Thr Lys Ser Arg Lys Glu Gln Ile Leu Glu Leu
785               790               795               800

Tyr Lys Gln Cys Lys Asp Glu Asp Val Arg Ile Leu Gln Gln Gln Leu
                805               810               815

Glu Glu Met Gly Asp Leu Ala Asp Asn Lys Leu Gln Gly Asp Lys Leu
            820               825               830

Phe Leu Tyr Tyr Met Gln Lys Gly Lys Cys Met Tyr Thr Gly Thr Pro
            835               840               845

Ile Val Leu Glu Gln Leu Gly Ser Lys Ala Tyr Asp Ile Asp His Ile
850               855               860

Tyr Pro Gln Ala Tyr Val Lys Asp Asp Ser Ile Leu Asn Asn Arg Val
865               870               875               880

Leu Val Leu Ser Glu Ala Asn Gly Lys Lys Lys Asp Ile Tyr Pro Ile
                885               890               895

Glu Lys Glu Thr Arg Asp Lys Met His Gly Phe Trp Thr Tyr Leu Asn
                900               905               910

Asp Lys Gly Met Ile Thr Glu Glu Lys Tyr Lys Arg Leu Thr Arg Thr
            915               920               925

Thr Gly Phe Thr Glu Glu Lys Trp Ser Phe Ile Asn Arg Gln Leu
930               935               940

Thr Glu Thr Ser Gln Ala Thr Lys Ala Val Ala Thr Leu Leu Gly Glu
945               950               955               960

Leu Phe Pro Asn Ala Glu Ile Val Tyr Ser Lys Ala Arg Leu Thr Ser
            965               970               975

Glu Phe Arg Gln Glu Phe Asn Leu Leu Lys Cys Arg Ser Tyr Asn Asp
            980               985               990

Leu His His Ala Val Asp Ala Tyr Leu Asn Ile Val Cys Gly Asn Val
            995               1000              1005

Tyr Asn Met Lys Phe Thr Lys Arg Trp Phe Asn Ile Asn Lys Asp
            1010              1015              1020

Tyr Ser Ile Lys Thr Lys Thr Val Phe Thr His Pro Val Val Cys
            1025              1030              1035

Gly Gly Gln Val Val Trp Asp Gly Gln Glu Met Leu Asn Lys Val
            1040              1045              1050

Ile Arg Asn Ala Lys Lys Asn Thr Ala His Phe Thr Lys Tyr Ala
            1055              1060              1065

Tyr Ile Arg Lys Gly Gly Phe Phe Asp Gln Met Pro Val Lys Ala
            1070              1075              1080
```

```
Ala Glu Gly Leu Thr Pro Leu Lys Lys Asp Met Pro Thr Ala Val
    1085                1090                1095

Tyr Gly Gly Tyr Asn Lys Pro Ser Val Ala Phe Leu Ile Pro Thr
    1100                1105                1110

Arg Tyr Lys Ala Gly Lys Lys Thr Glu Ile Ile Ile Leu Ser Val
    1115                1120                1125

Glu His Leu Phe Gly Glu Arg Phe Leu Arg Asp Glu Ala Tyr Ala
    1130                1135                1140

Lys Glu Tyr Ala Ala Glu Arg Leu Lys Lys Ile Leu Gly Lys Gln
    1145                1150                1155

Val Asp Glu Val Ser Phe Pro Met Gly Met Arg Pro Trp Lys Ile
    1160                1165                1170

Asn Thr Val Leu Ser Leu Asp Gly Phe Leu Ile Cys Ile Ser Gly
    1175                1180                1185

Ile Gly Ser Gly Gly Lys Cys Leu Arg Ala Gln Ser Ile Met Gln
    1190                1195                1200

Phe Ser Ser Asp Tyr Arg Trp Thr Ile Tyr Leu Lys Arg Leu Glu
    1205                1210                1215

Arg Leu Val Glu Lys Ile Thr Val Asn Ala Lys Tyr Val Tyr Ser
    1220                1225                1230

Glu Glu Phe Asp Lys Val Ser Thr Ile Glu Asn Ile Glu Leu Tyr
    1235                1240                1245

Asp Leu Tyr Ile Glu Lys Tyr Lys Ala Thr Ile Phe Ser Lys Arg
    1250                1255                1260

Val Asn Ser Pro Glu Glu Ile Ile Glu Ser Gly Arg Asp Lys Phe
    1265                1270                1275

Val Lys Leu Asp Val Leu Ser Gln Ala Arg Ala Leu Leu Cys Ile
    1280                1285                1290

His Gln Thr Phe Gly Arg Ile Val Gly Gly Cys Asp Leu Gly Leu
    1295                1300                1305

Ile Gly Gly Lys Lys Asn Ser Ala Ala Thr Gly Asn Phe Ser Ser
    1310                1315                1320

Thr Ile Ser Asn Trp Ala Lys Tyr Tyr Lys Asp Val Arg Ile Ile
    1325                1330                1335

Asp Gln Ser Thr Ser Gly Leu Trp Val Arg Lys Ser Glu Asn Leu
    1340                1345                1350

Leu Glu Leu Val
    1355

<210> SEQ ID NO 23
<211> LENGTH: 36
<212> TYPE: DNA
<213> ORGANISM: Artificial Sequence
<220> FEATURE:
<223> OTHER INFORMATION: CRRNA

<400> SEQUENCE: 23
gtttgagagt agtgtaaatc catagggtc tcaaac                                    36

<210> SEQ ID NO 24
<211> LENGTH: 102
<212> TYPE: DNA
<213> ORGANISM: Artificial Sequence
<220> FEATURE:
<223> OTHER INFORMATION: TRACR RNA

<400> SEQUENCE: 24
```

```
agacccctat ggatttacat tgcgagttca aataaaagtt tactcaaatc gttggcttga    60
ccaaccgcac agcgtgtgct taaagatctc ttcagtgagg tc                      102
```

<210> SEQ ID NO 25
<211> LENGTH: 1368
<212> TYPE: PRT
<213> ORGANISM: Artificial Sequence
<220> FEATURE:
<223> OTHER INFORMATION: Lachnospiraceae bacterium

<400> SEQUENCE: 25

```
Met Asn Phe Asp Gly Glu Tyr Phe Leu Gly Leu Asp Ile Gly Thr Asp
1               5                   10                  15

Ser Val Gly Tyr Ala Val Thr Asp Gln Arg Tyr Asn Leu Val Lys Phe
                20                  25                  30

Lys Gly Glu Pro Met Trp Gly Ser His Leu Phe Asp Ala Ala Asn Gln
            35                  40                  45

Cys Ala Glu Arg Arg Gly Phe Arg Thr Ala Arg Arg Leu Asp Arg
        50                  55                  60

Arg Gln Gln Arg Val Lys Leu Val Asp Glu Ile Phe Ala Pro Glu Val
65                  70                  75                  80

Ala Lys Val Asp Pro Asn Phe Tyr Ile Arg Lys Met Glu Ser Ala Leu
                85                  90                  95

Tyr Pro Glu Asp Lys Ser Asn Lys Gly Asp Leu Tyr Leu Tyr Phe Asn
            100                 105                 110

Lys Gln Glu Tyr Asp Glu Lys His Tyr Tyr Lys Asp Tyr Pro Thr Ile
        115                 120                 125

His His Leu Ile Cys Ala Leu Met Asn Asp Glu Lys Thr Lys Phe Asp
    130                 135                 140

Ile Arg Leu Ile Asn Ile Ala Ile Asp Trp Leu Val Ala His Arg Gly
145                 150                 155                 160

His Phe Leu Ser Glu Val Gly Thr Asp Ser Val Asp Lys Val Leu Asp
                165                 170                 175

Phe Arg Lys Ile Tyr Asp Glu Phe Met Ala Leu Phe Ser Asp Glu Asp
            180                 185                 190

Asp Ala Val Ser Ser Lys Pro Trp Glu Asn Ile Asn Pro Asp Glu Leu
        195                 200                 205

Gly Lys Val Leu Lys Ile His Gly Lys Asn Ala Lys Arg Asn Glu Leu
    210                 215                 220

Lys Lys Leu Leu Tyr Gly Gly Lys Ile Pro Thr Asp Glu Asp Ser Phe
225                 230                 235                 240

Ile Asp Arg Lys Leu Leu Ile Asp Phe Ile Ala Gly Thr Ser Val Gln
                245                 250                 255

Cys Asn Lys Leu Phe Arg Asn Ser Glu Tyr Glu Asp Asp Leu Lys Ile
            260                 265                 270

Thr Ile Ser Asn Ser Asp Glu Arg Glu Val Val Leu Pro Gln Leu Glu
        275                 280                 285

Asp Phe His Ala Asp Ile Ile Ala Lys Leu Ser Ser Met Tyr Asp Trp
    290                 295                 300

Ser Val Leu Ser Asp Ile Leu Ser Gly Ser Thr Tyr Ile Ser Glu Ser
305                 310                 315                 320

Lys Val Lys Val Tyr Glu Gln His Lys Lys Asp Leu Lys Glu Leu Lys
                325                 330                 335

Glu Phe Val Arg Lys Tyr Ala Pro Glu Lys Tyr Asn Asp Ile Phe Arg
```

-continued

```
                340             345             350
Leu Ala Ser Lys Glu Thr Tyr Asn Tyr Thr Ala Tyr Ser Tyr Asn Leu
            355                 360             365

Lys Ser Val Lys Asp Glu Lys Asp Leu Pro Lys Gly Lys Ala Ser Lys
        370                 375             380

Glu Asp Phe Tyr Ser Tyr Leu Lys Lys Thr Leu Lys Leu Asp Lys Ala
385                     390             395                 400

Glu Asn Tyr Asn Phe Val Asn Asp Ala Asp Thr Arg Phe Phe Asp Asp
                    405             410                 415

Met Val Glu Arg Ile Ser Ser Gly Thr Phe Leu Pro Lys Gln Val Asn
                420              425             430

Ser Asp Asn Arg Val Ile Pro Tyr Gln Val Tyr Tyr Ile Glu Leu Lys
            435                 440             445

Lys Ile Leu Glu Asn Ala Lys Lys His Tyr Ala Phe Phe Glu Glu Lys
        450                 455             460

Asp Glu Asp Gly Tyr Ser Asn Val Glu Lys Ile Met Ser Val Phe Thr
465                     470             475                 480

Phe Arg Ile Pro Tyr Tyr Val Gly Pro Leu Arg Asn Asp Asp Lys Ser
                    485             490                 495

Pro Tyr Ala Trp Ile Arg Arg Lys Ala Asp Gly Lys Ile Tyr Pro Trp
                500             505             510

Asp Phe Glu Glu Lys Val Asp Leu Asp Ala Ser Glu Asn Ala Phe Ile
            515                 520             525

Asp Arg Met Thr Asn Ser Cys Thr Tyr Ile Pro Gly Ala Asp Val Leu
        530                 535             540

Pro Lys Trp Ser Leu Leu Tyr Thr Lys Tyr Met Val Leu Asn Glu Ile
545                 550             555                 560

Asn Asn Ile Lys Val Asn Asn Ile Gly Ile Ser Val Glu Ala Lys Gln
                565             570             575

Gly Ile Tyr Asn Glu Leu Phe Cys Lys Lys Ala Lys Val Ser Leu Lys
            580             585             590

Ala Ile Arg Glu Tyr Leu Ile Ser Asn Gly Phe Met Gln Lys Asp Asp
        595             600             605

Glu Met Ser Gly Ile Asp Ile Thr Val Lys Ser Ser Leu Lys Ser Arg
610                 615             620

Tyr Asp Phe Arg His Leu Leu Glu Lys Asn Glu Leu Thr Thr Asp Asp
625                 630             635                 640

Val Glu Ala Ile Ile Ser Arg Ser Thr Tyr Ala Glu Asp Lys Ala Arg
                645             650             655

Phe Lys Lys Trp Leu Lys Lys Glu Phe Pro Gln Leu Ser Asp Glu Asp
            660             665             670

Tyr Lys Tyr Val Ser Lys Leu Lys Tyr Lys Asp Phe Gly Arg Leu Ser
        675             680             685

Arg Ser Leu Leu Asn Gly Leu Glu Gly Ala Ser Lys Glu Thr Gly Glu
    690                 695             700

Ile Gly Thr Ile Met His Phe Leu Trp Glu Thr Asn Asp Asn Leu Met
705                 710             715                 720

Gln Leu Leu Ser Asp Arg Tyr Thr Phe Met Glu Glu Ile Asn Lys Lys
                725             730             735

Arg Gln Asp Tyr Tyr Ile Glu His Lys Leu Thr Leu Asn Glu Gln Met
            740             745             750

Glu Glu Leu Gly Ile Ser Asn Ala Val Lys Arg Pro Val Thr Arg Thr
        755             760             765
```

-continued

```
Leu Ala Val Val Lys Asp Val Ser Ala Ile Gly Tyr Ala Pro Gln
    770                 775                 780

Lys Ile Phe Val Glu Met Ala Arg Gln Glu Asp Lys Lys Lys Arg
785                 790                 795                 800

Ser Val Thr Arg Lys Glu Gln Ile Leu Glu Leu Tyr Lys Asn Val Glu
                805                 810                 815

Glu Asp Thr Lys Glu Leu Glu Arg Gln Leu Lys Lys Met Gly Asp Thr
                820                 825                 830

Ala Asn Asn Glu Leu Gln Ser Asp Ala Leu Phe Leu Tyr Tyr Leu Gln
            835                 840                 845

Leu Gly Lys Cys Met Tyr Ser Gly Lys Pro Ile Asp Leu Thr Gln Ile
    850                 855                 860

Lys Thr Thr Lys Lys Tyr Asp Ile Asp His Ile Trp Pro Gln Ser Met
865                 870                 875                 880

Val Lys Asp Asp Ser Leu Leu Asn Asn Arg Val Leu Val Leu Ser Glu
                885                 890                 895

Ile Asn Gly Asp Lys Lys Asp Val Tyr Pro Ile Asp Glu Ser Ile Arg
                900                 905                 910

Ser Lys Met His Ser Tyr Trp Lys Met Leu Leu Asp Lys Asn Leu Ile
            915                 920                 925

Thr Lys Glu Lys Tyr Ser Arg Leu Thr Arg Pro Thr Pro Phe Thr Glu
    930                 935                 940

Ser Glu Lys Leu Gly Phe Ile Asn Arg Gln Leu Val Glu Thr Arg Gln
945                 950                 955                 960

Ser Met Lys Ala Val Thr Gln Leu Leu Asn Asn Met Tyr Pro Asp Ser
                965                 970                 975

Glu Ile Val Tyr Val Lys Ala Lys Leu Ala Ala Asp Phe Lys Gln Asp
            980                 985                 990

Phe Lys Leu Ala Pro Lys Ser Arg Ile Ile Asn Asp Leu His His Ala
    995                 1000                1005

Lys Asp Thr Tyr Leu Asn Val Val Ala Gly Asn Val Tyr Asn Glu
    1010                1015                1020

Arg Phe Thr Lys Lys Trp Phe Asn Val Asn Glu Lys Tyr Ser Met
    1025                1030                1035

Lys Thr Lys Val Leu Phe Gly His Asp Val Lys Ile Gly Asp Arg
    1040                1045                1050

Leu Ile Trp Asp Ser Lys Lys Asp Leu Gln Thr Val Lys Asn Thr
    1055                1060                1065

Tyr Glu Lys Asn Asn Ile His Leu Thr Arg Tyr Ala Tyr Cys Gln
    1070                1075                1080

Lys Gly Gly Leu Phe Asp Gln Met Pro Val Lys Lys Gly Gln Gly
    1085                1090                1095

Gln Ile Gln Leu Lys Lys Gly Met Asp Ile Asp Arg Tyr Gly Gly
    1100                1105                1110

Tyr Asn Lys Ala Thr Ala Ser Phe Phe Ile Ile Ala Arg Tyr Leu
    1115                1120                1125

Arg Gly Gly Lys Lys Glu Val Ser Phe Val Pro Val Glu Leu Met
    1130                1135                1140

Val Ser Glu Lys Phe Leu Asn Asp Asp Asn Phe Ala Ile Glu Tyr
    1145                1150                1155

Ile Thr Asn Val Leu Thr Gly Met Asn Thr Lys Lys Ile Glu Asn
    1160                1165                1170
```

-continued

| | | | | | | | | | | | | | | |
|---|---|---|---|---|---|---|---|---|---|---|---|---|---|---|
| Val | Glu | Leu | Pro | Leu | Gly | Lys | Arg | Val | Ile | Lys | Ile | Lys | Thr | Val |
| | 1175 | | | | 1180 | | | | | 1185 | | | | |
| Leu | Leu | Leu | Asp | Gly | Tyr | Lys | Val | Trp | Val | Asn | Gly | Lys | Ala | Ser |
| | 1190 | | | | 1195 | | | | | 1200 | | | | |
| Gly | Gly | Thr | Arg | Val | Met | Leu | Thr | Ser | Ala | Glu | Ser | Leu | Arg | Met |
| | 1205 | | | | 1210 | | | | | 1215 | | | | |
| Pro | Lys | Glu | Tyr | Val | Glu | Tyr | Leu | Lys | Lys | Met | Glu | Asn | Tyr | Ser |
| | 1220 | | | | 1225 | | | | | 1230 | | | | |
| Glu | Lys | Lys | Lys | Ser | Asn | Arg | Asn | Phe | Met | His | Asp | Ser | Glu | Asn |
| | 1235 | | | | 1240 | | | | | 1245 | | | | |
| Asp | Gly | Leu | Ser | Glu | Glu | Lys | Asn | Ile | Leu | Leu | Tyr | Asp | Lys | Leu |
| | 1250 | | | | 1255 | | | | | 1260 | | | | |
| Leu | Glu | Lys | Leu | Asp | Glu | Asn | His | Phe | Lys | Lys | Met | Pro | Gly | Asn |
| | 1265 | | | | 1270 | | | | | 1275 | | | | |
| Gln | Cys | Glu | Thr | Met | Lys | Ser | Gly | Arg | Val | Lys | Phe | Ile | Glu | Leu |
| | 1280 | | | | 1285 | | | | | 1290 | | | | |
| Asp | Phe | Asp | Val | Gln | Ile | Ser | Thr | Leu | Leu | Asn | Cys | Ile | Asp | Leu |
| | 1295 | | | | 1300 | | | | | 1305 | | | | |
| Leu | Lys | Ser | Gly | Arg | Thr | Gly | Gly | Cys | Asp | Leu | Lys | Asn | Ile | Gly |
| | 1310 | | | | 1315 | | | | | 1320 | | | | |
| Gly | Lys | Ser | Ala | Ser | Gly | Val | Val | Tyr | Ile | Ser | Ala | Asn | Leu | Ser |
| | 1325 | | | | 1330 | | | | | 1335 | | | | |
| Ala | Cys | Lys | Tyr | Asn | Asp | Val | His | Ile | Ile | Asp | Ile | Ser | Pro | Ala |
| | 1340 | | | | 1345 | | | | | 1350 | | | | |
| Gly | Leu | His | Glu | Asn | Ile | Ser | Cys | Asn | Leu | Met | Glu | Leu | Phe | Glu |
| | 1355 | | | | 1360 | | | | | 1365 | | | | |

<210> SEQ ID NO 26
<211> LENGTH: 36
<212> TYPE: DNA
<213> ORGANISM: Artificial Sequence
<220> FEATURE:
<223> OTHER INFORMATION: CR RNA

<400> SEQUENCE: 26
gtttgagagt agtgtaaatc cagagggctc caaaac                                36

<210> SEQ ID NO 27
<211> LENGTH: 99
<212> TYPE: DNA
<213> ORGANISM: Artificial Sequence
<220> FEATURE:
<223> OTHER INFORMATION: TRACR RNA

<400> SEQUENCE: 27
gagccctctg gatttacact acgagttcaa ataaaaatta tttcaaatcg ccgctatgtc      60
ggccgcacag tgtgtgcatt aagaaaagtc cgaaagggc                             99

<210> SEQ ID NO 28
<211> LENGTH: 1384
<212> TYPE: PRT
<213> ORGANISM: Artificial Sequence
<220> FEATURE:
<223> OTHER INFORMATION: Ruminococcaceae

<400> SEQUENCE: 28

| | | | | | | | | | | | | | | |
|---|---|---|---|---|---|---|---|---|---|---|---|---|---|---|
| Met | Ser | Phe | Lys | Glu | Asn | Ser | Lys | Phe | Tyr | Phe | Gly | Leu | Asp | Ile | Gly |
| 1 | | | | 5 | | | | | 10 | | | | | 15 | |

| | | | | | | | | | | | | | | |
|---|---|---|---|---|---|---|---|---|---|---|---|---|---|---|
| Thr | Asp | Ser | Val | Gly | Trp | Ala | Val | Thr | Asp | Asn | Leu | Tyr | Lys | Leu | Tyr |

```
            20              25              30
Lys Tyr Lys Asn Asn Leu Met Trp Gly Val Ser Leu Phe Glu Ala Ala
        35              40              45

Ser Pro Ala Glu Asp Arg Arg Asn His Arg Thr Ala Arg Arg Leu
50              55              60

Asp Arg Arg Gln Gln Arg Val Ala Leu Leu Arg Glu Leu Phe Ala Lys
65              70              75              80

Glu Ile Leu Lys Thr Asp Pro Asp Phe Phe Leu Arg Leu Lys Glu Ser
                85              90              95

Ser Leu Tyr Pro Glu Asp Arg Thr Asn Lys Asn Val Asn Thr Tyr Phe
            100             105             110

Asp Asp Ala Asp Phe Lys Asp Ser Asp Tyr Phe Lys Met Tyr Pro Thr
            115             120             125

Val His His Leu Ile Lys Glu Leu Ser Glu Ser Asp Lys Pro His Asp
            130             135             140

Val Arg Leu Val Tyr Leu Ala Cys Ala Phe Ile Val Ala His Arg Gly
145             150             155             160

His Phe Leu Asn Gly Ala Asp Glu Asn Asn Val Gln Glu Val Leu Asp
                165             170             175

Phe Asn Ser Ser Tyr Cys Glu Phe Thr Asp Trp Phe Lys Ser Asn Asp
            180             185             190

Ile Glu Asp Asn Pro Phe Ser Glu Ser Thr Glu Asn Glu Phe Ser Val
            195             200             205

Ile Leu Arg Lys Lys Ile Gly Ile Thr Ala Lys Glu Lys Glu Ile Lys
210             215             220

Asn Leu Leu Phe Gly Thr Thr Lys Thr Pro Asp Cys Tyr Lys Asp Glu
225             230             235             240

Glu Tyr Pro Ile Asp Ile Asp Val Leu Ile Lys Phe Ile Ser Gly Gly
            245             250             255

Lys Thr Asn Leu Ala Lys Leu Phe Arg Asn Pro Ala Tyr Asp Glu Leu
            260             265             270

Asp Ile Gln Thr Val Glu Val Gly Lys Ala Asp Phe Ala Asp Thr Ile
            275             280             285

Asp Leu Leu Ala Ser Ser Met Glu Asp Thr Asp Val Pro Leu Leu Ser
        290             295             300

Ala Val Lys Ala Met Tyr Asp Trp Ser Leu Leu Ile Asp Val Leu Lys
305             310             315             320

Gly Gln Lys Thr Ile Ser Asp Ala Lys Val Cys Glu Tyr Glu Gln His
                325             330             335

Lys Ser Asp Leu Lys Ala Leu Lys His Ile Val Arg Lys Tyr Leu Asp
            340             345             350

Lys Ala Gln Tyr Asp Glu Ile Phe Arg Thr Ala Gly Glu Lys Pro Asn
            355             360             365

Tyr Val Ser Tyr Ser Tyr Asn Val Thr Asp Val Lys Leu Lys Gln Leu
            370             375             380

Pro Ser Asn Phe Lys Lys Lys Tyr Ser Glu Glu Phe Cys Lys Tyr Ile
385             390             395             400

Asn Ser Lys Leu Glu Lys Ile Lys Pro Glu Pro Asp Asp Glu Ala Val
            405             410             415

Tyr Asn Glu Leu Ile Glu Lys Cys Asn Ser Lys Thr Leu Cys Pro Lys
            420             425             430

Gln Val Thr Asp Glu Asn Arg Val Ile Pro Tyr Gln Leu Tyr Tyr His
            435             440             445
```

```
Glu Leu Ser Met Ile Leu Asp Lys Ala Ser Ala Tyr Leu Asp Phe Leu
    450                 455                 460
Asn Glu Thr Glu Asp Gly Ile Ser Val Lys Gln Lys Ile Leu Thr Leu
465                 470                 475                 480
Met Lys Phe Arg Ile Pro Tyr Phe Val Gly Pro Ser Val Lys Arg Asn
                485                 490                 495
Glu Thr Asp Asn Val Trp Ile Val Arg Lys Ala Glu Gly Arg Ile Tyr
                500                 505                 510
Pro Trp Asn Phe Glu Asn Met Val Asp Tyr Asp Lys Ser Glu Asp Gly
            515                 520                 525
Phe Ile Arg Arg Met Thr Cys Lys Cys Thr Tyr Leu Ala Gly Glu Asp
    530                 535                 540
Val Leu Pro Lys Tyr Ser Leu Leu Tyr Ser Arg Tyr Thr Val Leu Asn
545                 550                 555                 560
Glu Ile Asn Asn Ile Lys Val Lys Asp Val Lys Ile Ser Pro Glu Leu
                565                 570                 575
Lys Gln Asp Ile Phe Asn Glu Leu Phe Met Lys Thr Ser Arg Val Thr
                580                 585                 590
Val Lys Lys Ile Thr Glu Leu Leu Lys Arg Lys Gly Ala Phe Ser Glu
            595                 600                 605
Glu Asn Gly Asp Ser Leu Ser Gly Val Asp Ile Asn Ile Lys Ser Ser
    610                 615                 620
Leu Lys Ser Tyr Leu Asp Phe Arg Arg Leu Leu Glu Asn Gly Ser Leu
625                 630                 635                 640
Ser Glu Ser Asp Val Glu Arg Ile Ile Glu Arg Ile Thr Val Thr Thr
                645                 650                 655
Asp Lys Pro Arg Leu Ile Ser Trp Leu Lys Thr Glu Tyr Pro Ala Leu
                660                 665                 670
Pro Ala Glu Asp Ile Arg Tyr Ile Ser Arg Leu Ser Tyr Lys Asp Tyr
            675                 680                 685
Gly Arg Leu Ser Ala Lys Met Leu Thr Gly Cys Tyr Glu Leu Asp Met
    690                 695                 700
Asp Thr Gly Glu Ile Gly Gly Arg Ser Ile Ile Asp Leu Met Trp Ala
705                 710                 715                 720
Glu Asn Ile Asn Leu Met Gln Ile Met Ser Asp Ser Tyr Gly Tyr Lys
                725                 730                 735
Ser Phe Ile Glu Glu Asn Lys Lys Tyr Tyr Ala Ile Asn Pro Thr
                740                 745                 750
Gly Ser Ile Ala Gln Thr Leu Arg Glu Met Tyr Val Ser Pro Ser Ala
            755                 760                 765
Ser Arg Ala Ile Ile Arg Thr Met Asp Ile Val Lys Glu Leu Arg Lys
    770                 775                 780
Ile Ile Lys Arg Asp Pro Asp Lys Ile Phe Val Glu Met Ala Arg Gly
785                 790                 795                 800
Ser Lys Pro Glu Asp Lys Gly Lys Arg Thr Ser Ser Arg Arg Glu Gln
                805                 810                 815
Ile Glu Lys Leu Phe Ala Ser Ala Lys Glu Phe Val Ser Asp Glu Glu
                820                 825                 830
Ile Ser His Leu Arg Ser Gln Leu Gly Ser Leu Ser Asp Glu Gln Leu
            835                 840                 845
Arg Ser Glu Lys Tyr Tyr Leu Tyr Phe Thr Gln Phe Gly Lys Cys Val
    850                 855                 860
```

```
Tyr Ser Gly Glu Ala Ile Asp Phe Ser Arg Leu Gly Asp Asn His Cys
865                 870                 875                 880

Tyr Asp Ile Asp His Ile Tyr Pro Gln Ser Lys Val Lys Asp Asp Ser
            885                 890                 895

Leu His Asn Lys Val Leu Val Lys Ser Gln Leu Asn Gly Glu Lys Ser
        900                 905                 910

Asp Asp Tyr Pro Ile Lys Glu Gln Ile Arg Asn Lys Met His Pro Ile
    915                 920                 925

Trp Lys Asn Leu Phe Tyr Arg Asp Pro Lys Asn Pro Thr Asp Lys Ile
930                 935                 940

Lys Tyr Glu Arg Leu Thr Arg Ser Thr Pro Phe Thr Glu Asp Glu Leu
945                 950                 955                 960

Ala Gly Phe Ile Glu Arg Gln Leu Val Glu Thr Arg Gln Ser Thr Lys
            965                 970                 975

Ala Val Ala Thr Leu Leu Lys Glu Met Phe Pro Asp Ser Lys Ile Val
        980                 985                 990

Tyr Val Lys Ala Gly Gln Val Ser Lys Phe Arg His Asp Phe Asp Met
    995                 1000                1005

Leu Lys Cys Arg Glu Ile Asn Asp Leu His His Ala Lys Asp Ala
    1010                1015                1020

Tyr Leu Asn Val Val Val Gly Asn Val His Asp Val Lys Phe Thr
    1025                1030                1035

Ser Asn Pro Leu Asn Phe Val Lys Asn Ala Asp Lys His Tyr Thr
    1040                1045                1050

Ile Lys Ile Lys Glu Thr Leu Lys His Lys Val Ala Arg Asn Gly
    1055                1060                1065

Glu Thr Ala Trp Asn Pro Thr Asp Phe Asp Thr Val Lys Arg
    1070                1075                1080

Met Met Ser Lys Asn Ser Val Arg Tyr Val Arg Tyr Cys Tyr Lys
    1085                1090                1095

Arg Lys Gly Glu Leu Phe Lys Gln Gln Pro Lys Lys Ala Gly Asn
    1100                1105                1110

Pro Asp Leu Ala Trp Leu Lys Lys Asn Leu Asp Pro Val Lys Tyr
    1115                1120                1125

Gly Gly Tyr Asn Ser Lys Ser Ile Ser Cys Phe Ser Leu Ile Lys
    1130                1135                1140

Cys Thr Gly Val Gly Val Val Ile Ile Pro Val Glu Leu Leu Cys
    1145                1150                1155

Glu Lys Arg Tyr Phe Ser Asp Ser Phe Ala Ser Glu Tyr Ala
    1160                1165                1170

Tyr Ser Val Leu Lys Asn Ala Leu Pro Ala Lys Asn Ile Ala Lys
    1175                1180                1185

Ile Ser Ile Asp Asp Ile Ser Phe Pro Leu Lys Arg Arg Pro Ile
    1190                1195                1200

Lys Ile Asn Thr Leu Phe Glu Phe Asp Gly Tyr Arg Val Asn Ile
    1205                1210                1215

Arg Ser Lys Asp Ser Tyr Val Phe Arg Ile Ser Ser Ala Met
    1220                1225                1230

Ala Ala Ile Tyr Ser Lys Asp Thr Ser Asp Tyr Ile Lys Ala Ile
    1235                1240                1245

Ser Ser Tyr Ile Asp Lys Ser Asp Lys Gly Ser Lys Phe Lys Pro
    1250                1255                1260

Gly Glu Ala Phe Asp Val Leu Ser Asn Leu Lys Ala Tyr Asp Glu
```

-continued

```
                1265                1270                1275
Ile Ala Lys Lys Cys Ile Ser Glu Pro Phe Cys Lys Ile Ser Lys
            1280                1285                1290

Leu Ala Glu Ala Gly Lys Lys Met Glu Gly Arg Asn Lys Phe
        1295                1300                1305

Ala Glu Leu Ser Ile Ile Glu Gln Met Lys Thr Leu Leu Leu Leu
    1310                1315                1320

Val Asp Val Leu Lys Thr Gly Arg Val Asp Lys Cys Asn Leu Lys
1325                1330                1335

Pro Val Gly Gly Val Asp Asn Phe His Thr Glu Arg Met Ser Ala
    1340                1345                1350

Ile Leu Lys Asn Thr Lys Tyr Ser Asp Ile Arg Ile Ile Asp Gln
        1355                1360                1365

Ser Pro Thr Gly Leu Tyr Glu Asn Lys Ser Asp Asn Leu Leu Glu
            1370                1375                1380

Leu
```

<210> SEQ ID NO 29
<211> LENGTH: 36
<212> TYPE: DNA
<213> ORGANISM: Artificial Sequence
<220> FEATURE:
<223> OTHER INFORMATION: CR RNA

<400> SEQUENCE: 29
gtttgagagt agtgtaaatt tatagggtag taaaac                         36

<210> SEQ ID NO 30
<211> LENGTH: 108
<212> TYPE: DNA
<213> ORGANISM: Artificial Sequence
<220> FEATURE:
<223> OTHER INFORMATION: TRACR RNA

<400> SEQUENCE: 30
ttttactacc ctataaattt acactacgag ttcaaataaa aattatttca aatcgtactt    60
tttagtacct tcacaagtgt tgtgaatatt aactcacctt cgggtgag             108

<210> SEQ ID NO 31
<211> LENGTH: 1370
<212> TYPE: PRT
<213> ORGANISM: Artificial Sequence
<220> FEATURE:
<223> OTHER INFORMATION: Firmicutes bacterium

<400> SEQUENCE: 31

```
Met Glu Gln Lys Asp Tyr Tyr Ile Gly Leu Asp Ile Gly Thr Asn Ser
1               5                   10                  15

Val Gly Trp Ala Val Val Asp Glu Gly Tyr Gln Leu Cys Arg Phe Lys
            20                  25                  30

Lys Tyr Asp Met Trp Gly Val Arg Leu Phe Asp Ser Ala Glu Thr Ala
        35                  40                  45

Ala Glu Arg Arg Met Asn Arg Val Asn Arg Arg Asn Arg Lys
    50                  55                  60

Lys Gln Arg Ile Asp Leu Leu Gln Gly Leu Phe Ala Glu Glu Ile Ala
65                  70                  75                  80

Lys Ile Asp Arg Thr Phe Phe Val Arg Leu Asn Glu Ser Arg Leu His
                85                  90                  95
```

```
Pro Glu Asp Lys Ser Thr Ala Phe Arg His Pro Leu Phe Asn Asp Pro
            100                 105                 110

Asn Tyr Thr Asp Val Asp Tyr Tyr Lys Glu Tyr Pro Thr Ile Tyr His
            115                 120                 125

Leu Arg Lys Glu Leu Met Asp Ser Ala Glu Pro His Asp Ile Arg Leu
        130                 135                 140

Val Tyr Leu Ala Leu His His Ile Leu Lys Asn Arg Gly His Phe Leu
145                 150                 155                 160

Ile Glu Gly Gly Phe Glu Asp Ser Lys Lys Phe Glu Pro Thr Phe Arg
                165                 170                 175

Gln Leu Leu Glu Val Leu Thr Glu Glu Leu Gly Leu Lys Met Asp Gly
            180                 185                 190

Ala Asp Ala Ala Leu Ala Glu Ser Val Leu Lys Asp Arg Gly Met Lys
        195                 200                 205

Lys Thr Glu Lys Val Lys Arg Leu Lys Asn Val Phe Thr Leu Asn Thr
        210                 215                 220

Thr Asp Met Asp Gln Glu Ser Gln Lys Lys Gln Lys Ala Gln Ile Asp
225                 230                 235                 240

Ala Val Cys Lys Phe Leu Ala Gly Ser Lys Gly Asp Phe Lys Lys Leu
                245                 250                 255

Val Ala Asp Glu Ala Leu Asn Glu Leu Lys Leu Asp Thr Phe Ala Leu
            260                 265                 270

Gly Thr Ser Lys Ala Glu Asp Ile Gly Leu Glu Ile Glu Lys Ser Ala
        275                 280                 285

Pro Gln Tyr Cys Val Val Phe Glu Ser Val Lys Ser Val Phe Asp Trp
        290                 295                 300

Lys Ile Met Thr Gln Ile Leu Gly Asp Glu Ser Thr Phe Ser Ser Ala
305                 310                 315                 320

Lys Val Lys Glu Tyr Glu Lys His His Glu Asn Leu Ile Ile Leu Arg
                325                 330                 335

Glu Leu Ile Arg Lys Tyr Cys Asp Lys Glu Thr Tyr Arg His Phe Phe
            340                 345                 350

Asn Asn Val Asn Gly Gly Tyr Ser Arg Tyr Ile Gly Ser Leu Lys Lys
        355                 360                 365

Asn Gly Lys Lys Tyr Tyr Val Ala Gly Cys Thr Gln Glu Glu Phe Tyr
        370                 375                 380

Lys Glu Leu Lys Gly Leu Leu Lys Ser Ile Asp Gln Arg Val Asp Pro
385                 390                 395                 400

Glu Asp Arg Pro Val Tyr Gln Arg Val Leu Ala Glu Thr Glu Asp Glu
                405                 410                 415

Thr Phe Leu Pro Leu Leu Arg Ser Lys Ala Asn Ser Ala Ile Pro Arg
            420                 425                 430

Gln Ile His Gln Lys Glu Leu Asp Asp Ile Leu Gln Asn Ala Ser Val
        435                 440                 445

Tyr Leu Pro Phe Leu Asn Asp Val Asp Glu Asp Gly Leu Ser Ala Ala
        450                 455                 460

Glu Lys Ile Arg Ser Ile Phe Thr Phe Arg Ile Pro Tyr Tyr Val Gly
465                 470                 475                 480

Pro Leu Ser Leu Arg His Lys Asp Lys Gly Ala His Val Trp Ile Lys
                485                 490                 495

Arg Lys Glu Glu Gly Tyr Ile Tyr Pro Trp Asn Tyr Glu Lys Lys Ile
            500                 505                 510

Asp Arg Glu Lys Ser Asn Glu Glu Phe Ile Arg Arg Leu Ile Asn Gln
```

```
            515                 520                 525
Cys Thr Tyr Leu Lys Asp Glu Lys Val Leu Pro Lys Lys Ser Leu Leu
    530                 535                 540

Tyr Ser Glu Phe Met Val Leu Asn Glu Leu Asn Asn Leu Arg Ile Arg
545                 550                 555                 560

Gly Lys Arg Leu Ser Glu Glu Gln Val Glu Leu Lys Gln Arg Ile Tyr
                565                 570                 575

Arg Asp Leu Phe Met Thr Lys Thr Arg Val Thr Lys Lys Thr Leu Leu
            580                 585                 590

Asn Tyr Leu Arg Lys Glu Asp Ser Asp Leu Thr Glu Glu Asp Leu Ser
        595                 600                 605

Gly Phe Asp Asn Asp Phe Lys Ala Ser Leu Ser Ser Cys Leu Glu Leu
    610                 615                 620

Lys Asn Lys Val Phe Gly Asp Arg Ile Glu Asp Arg Val Arg Lys
625                 630                 635                 640

Ile Ala Glu Asp Leu Ile Arg Trp Leu Thr Ile Tyr Asp Asp Lys
                645                 650                 655

Lys Met Ile Lys Glu Val Ile Arg Ala Glu Tyr Pro Asn Glu Phe Thr
            660                 665                 670

Asn Glu Gln Leu Asp Val Ile Cys Arg Leu Lys Phe Ser Gly Trp Gly
        675                 680                 685

Asn Leu Ser Glu Ala Phe Leu Cys Gly Val Glu Gly Ala Asp Lys Asp
    690                 695                 700

Thr Gly Glu Val Phe Thr Ile Glu Ala Leu Arg Asn Thr Asn His
705                 710                 715                 720

Asn Leu Met Glu Leu Leu Ser Gly Asn Tyr Thr Phe Thr Glu Lys Ile
                725                 730                 735

Arg Glu His Asn Ala Ala Leu Ser Glu Ile Lys Ala Lys Asp Tyr
            740                 745                 750

Glu Ser Leu Val Arg Asp Leu Tyr Val Ser Pro Ala Cys Lys Arg Gly
        755                 760                 765

Ile Trp Gln Thr Ile Arg Ile Thr Glu Glu Ile Lys Lys Ile Met Gly
    770                 775                 780

His Glu Pro Lys Lys Ile Phe Val Glu Met Thr Arg Glu His Arg Asp
785                 790                 795                 800

Ser Gly Arg Thr Thr Ser Arg Lys Asp Gln Leu Leu Ala Leu Tyr Gln
                805                 810                 815

Lys Cys Glu Glu Asp Ala Arg Asp Trp Val Lys Glu Ile Glu Asp Arg
            820                 825                 830

Glu Glu Arg Asp Phe Ser Ser Ile Lys Leu Phe Leu Tyr Tyr Leu Gln
        835                 840                 845

Gln Gly Lys Cys Met Tyr Ser Gly Glu Ala Ile Asp Leu Asp Glu Leu
    850                 855                 860

Met Ser Lys Asn Ser Arg Trp Asp Arg Asp His Ile Tyr Pro Gln Ser
865                 870                 875                 880

Lys Ile Lys Asp Asp Ser Leu Asp Asn Leu Val Leu Lys Lys Glu
                885                 890                 895

Leu Asn Ala Val Lys Asp Asn Gly Glu Ile Ala Pro Asp Ile Gln Lys
            900                 905                 910

Arg Met Lys Gly Phe Trp Leu Ser Leu Leu Arg Gln Gly Phe Leu Ser
        915                 920                 925

Lys Lys Lys Phe Asp Arg Leu Thr Arg Thr Gly Pro Phe Thr Ser Glu
    930                 935                 940
```

```
Glu Leu Ala Gly Phe Ile Ser Arg Gln Leu Val Glu Thr Ser Gln Met
945                 950                 955                 960

Ser Lys Ala Val Ala Glu Leu Leu Asn Gln Leu Tyr Glu Asp Ser Arg
            965                 970                 975

Val Val Tyr Val Lys Ala Gly Leu Val Ser Gln Phe Arg Gln Lys Asp
                980                 985                 990

Leu Gly Val Leu Lys Ser Arg Ser Val Asn Asp Tyr His His Ala Lys
            995                 1000                1005

Asp Ala Tyr Leu Asn Val Val Gly Asp Met Phe Asp Arg Lys
    1010                1015                1020

Phe Thr Ser Asp Pro Ala Arg Trp Phe Lys Lys Asn Lys Lys Val
    1025                1030                1035

Asn Tyr Ser Ile Asn Gln Val Phe Arg Arg Asp Tyr Glu Glu Asn
    1040                1045                1050

Gly Lys Leu Ile Trp Lys Gly Ile Asp Arg Gly Glu Asp Gly Lys
    1055                1060                1065

Pro Leu Phe Arg Asp Gly Leu Ile His Gly Gly Thr Ile Asp Leu
    1070                1075                1080

Val Arg Ala Ile Ala Lys Arg Asn Thr Asn Ile Arg Tyr Thr Glu
    1085                1090                1095

Tyr Thr Tyr Cys Glu Thr Gly Gln Leu Tyr Asn Leu Thr Leu Leu
    1100                1105                1110

Pro Lys Thr Asp Thr Ala Ile Thr Ile Pro Leu Lys Lys Glu Leu
    1115                1120                1125

Pro Ala Ala Lys Tyr Gly Gly Phe Lys Gly Ala Gly Thr Ser Tyr
    1130                1135                1140

Phe Ser Leu Ile Glu Phe Asp Asp Lys Lys Gly His His His Lys
    1145                1150                1155

Gln Ile Val Gly Val Pro Ile Tyr Val Ala Asn Met Leu Glu His
    1160                1165                1170

Asn Glu Asn Ala Phe Ile Glu Tyr Leu Glu Thr Val Cys Ser Phe
    1175                1180                1185

Arg Asn Ile Thr Val Leu Cys Glu Lys Ile Lys Lys Asn Ala Leu
    1190                1195                1200

Ile Ser Val Asn Gly Tyr Pro Met Arg Ile Arg Gly Glu Asn Glu
    1205                1210                1215

Ile Leu Asn Met Leu Lys Asn Asn Leu Gln Leu Val Leu Ser Gln
    1220                1225                1230

Glu Gly Glu Glu Thr Leu Arg His Ile Glu Lys Tyr Phe Asn Lys
    1235                1240                1245

Lys Pro Gly Phe Glu Pro Asp Lys Glu His Asp Gly Ile Asp Arg
    1250                1255                1260

Asp Ala Met Ala Ala Leu Tyr Asp Glu Met Thr Glu Lys Leu Cys
    1265                1270                1275

Thr Val Tyr Lys Lys Arg Pro Thr Asn Gln Gly Glu Leu Leu Lys
    1280                1285                1290

Asn Asn Arg Gly Leu Phe Leu Asn Leu Glu Lys Arg Ser Glu Met
    1295                1300                1305

Ala Lys Val Leu Ser Glu Thr Ala Lys Met Phe Gly Thr Thr Ala
    1310                1315                1320

Gln Thr Thr Ala Asp Leu Ser Leu Ile Lys Gly Ser Lys Tyr Ala
    1325                1330                1335
```

```
Gly Lys Ile Val Ile Asn Lys Asn Thr Leu Gly Ala Ala Lys Leu
            1340                1345                1350

Ile Leu Ile His Gln Ser Val Thr Gly Leu Phe Glu Thr Arg Val
    1355                1360                1365

Glu Leu
    1370

<210> SEQ ID NO 32
<211> LENGTH: 36
<212> TYPE: DNA
<213> ORGANISM: Artificial Sequence
<220> FEATURE:
<223> OTHER INFORMATION: CR RNA

<400> SEQUENCE: 32
gtttgagagt agtgtaattt catatggtag tcaaac                              36

<210> SEQ ID NO 33
<211> LENGTH: 102
<212> TYPE: DNA
<213> ORGANISM: Artificial Sequence
<220> FEATURE:
<223> OTHER INFORMATION: TRACR RNA

<400> SEQUENCE: 33
gactaccata tgagattaca ctacacggtt caaataaaga atgttcgaaa ccgcccttg     60 gggcccgctt gttgcggatt tacagacttg atatcaagtc tg                     102

<210> SEQ ID NO 34
<211> LENGTH: 1370
<212> TYPE: PRT
<213> ORGANISM: Artificial Sequence
<220> FEATURE:
<223> OTHER INFORMATION: uncultured Succiniclasticum sp.

<400> SEQUENCE: 34

Met Ser Lys Lys Phe Ala Gly Glu Tyr Tyr Leu Gly Leu Asp Ile Gly
1               5                   10                  15

Thr Asp Ser Val Gly Trp Ala Val Thr Asp Asn Gln Tyr Asn Val Leu
            20                  25                  30

Lys Phe Asn Gly Lys Ser Met Trp Gly Ile Arg Leu Phe Asp Ala Ala
        35                  40                  45

Gln Thr Ala Ala Glu Arg Arg Met Phe Arg Thr Ala Arg Arg Arg Val
    50                  55                  60

Glu Arg Arg Arg Trp Arg Leu Glu Leu Leu Gln Glu Leu Phe Gln Asn
65                  70                  75                  80

Glu Ile Glu Lys Lys Asp Pro Asp Phe Phe Gln Arg Met Lys Asp Ser
                85                  90                  95

Ala Leu Tyr Pro Glu Asp Ser Lys Thr Gly Lys Pro Phe Ala Leu Phe
            100                 105                 110

Cys Asp Lys Asp Leu Asn Asp Lys Leu Tyr Tyr Lys Gln Tyr Pro Thr
        115                 120                 125

Ile Tyr His Leu Arg Lys Ala Leu Leu Thr Glu Asn Ser Lys Phe Asp
    130                 135                 140

Ile Arg Leu Val Tyr Leu Ala Ile His His Ile Leu Lys His Arg Gly
145                 150                 155                 160

His Phe Leu Phe Asn Gly Asp Phe Ser Asn Val Thr Arg Phe Ser Phe
                165                 170                 175

Ala Phe Glu Gln Leu Gln Thr Cys Leu Cys Asn Glu Leu Asp Met Asp
```

```
                180                 185                 190
Phe Glu Cys Asn Asn Val Gln Lys Leu Ser Glu Ile Leu Lys Asp Thr
            195                 200                 205
His Met Ser Lys Asn Asp Lys Val Lys Ala Ser Val Ala Leu Phe Glu
            210                 215                 220
Asn Ser Gly Asp Lys Lys Gln Leu Gln Ala Val Ile Gly Leu Phe Cys
225                 230                 235                 240
Gly Ala Lys Lys Lys Leu Ala Asp Val Phe Leu Asp Glu Thr Leu Asn
                245                 250                 255
Asp Thr Glu Met Pro Ser Ile Ser Ile Ala Asp Lys Pro Tyr Glu Glu
            260                 265                 270
Leu Arg Pro Glu Leu Glu Ser Ile Leu Ala Glu Lys Cys Cys Val Ile
            275                 280                 285
Asp Tyr Ile Lys Ala Val Tyr Asp Trp Ala Ile Leu Ala Asp Met Leu
            290                 295                 300
Asp Gly Gly Glu Tyr Gly Asn Arg Thr Tyr Ile Ser Val Ala Arg Val
305                 310                 315                 320
Arg Gln Tyr Glu Lys His His Asp Asp Leu Lys Lys Leu Lys Lys Leu
                325                 330                 335
Val Arg Arg Tyr Cys Lys Ser Glu Tyr Lys Ser Phe Phe Ser Val Ala
                340                 345                 350
Gly Thr Asp Asn Tyr Cys Ala Tyr Ile Gly Asp Asp Ile Glu Thr Asp
            355                 360                 365
Asp Arg Lys Ser Val Lys Lys Cys Lys Gln Glu Asp Phe Tyr Lys Arg
            370                 375                 380
Ile Lys Gly Leu Leu Lys Lys Ala Ile Glu Asn Gly Cys Pro Lys Asp
385                 390                 395                 400
Glu Val Val Glu Ile Ile Lys Asp Ile Asp Ala Gln Val Phe Leu Pro
                405                 410                 415
Leu Gln Val Thr Lys Asp Asn Gly Val Ile Pro His Gln Val His Glu
            420                 425                 430
Met Glu Leu Lys Gln Ile Leu Lys Asn Ala Glu Lys Tyr Tyr Pro Phe
            435                 440                 445
Leu Cys Lys Lys Asp Glu Glu Gly Ile Val Thr Ser Asn Lys Ile Leu
            450                 455                 460
Gln Leu Phe Lys Phe Arg Ile Pro Tyr Tyr Val Gly Pro Leu Asn Ser
465                 470                 475                 480
Arg Ile Gly Lys Asn Ser Trp Ile Val Arg Arg Ala Glu Gly Lys Ile
                485                 490                 495
Tyr Pro Trp Asn Phe Glu Glu Lys Val Asp Phe Asp Lys Ser Glu Glu
            500                 505                 510
Gly Phe Ile Arg Arg Met Thr Asn Pro Cys Thr Tyr Met Ala Gly Ala
            515                 520                 525
Asp Val Leu Pro Lys Tyr Ser Leu Leu Tyr Ser Glu Phe Met Val Leu
530                 535                 540
Asn Glu Leu Asn Asn Val Arg Ile Cys Gly Asp Lys Leu Ser Val Glu
545                 550                 555                 560
Ile Lys Gln Thr Ile Ile Lys Asp Leu Phe Gln Arg Thr Arg Arg Val
                565                 570                 575
Thr Val Arg Lys Leu Cys Asp Lys Leu Lys Ala Glu Gly Val Ile Ser
            580                 585                 590
Arg Asn Ser Asn Gln Lys Asp Ile Asp Ile Lys Gly Ile Asp Gln Asp
            595                 600                 605
```

-continued

Leu Lys Ser Ser Met Val Ser Tyr Val Asp Phe Lys Asn Ile Phe Gly
610                 615                 620

Lys Glu Ile Glu Lys Tyr Ser Val Gln Gln Met Cys Glu Arg Ile Ile
625                 630                 635                 640

Phe Leu Leu Thr Ile His His Asp Asp Lys Arg Arg Leu Gln Lys Arg
                645                 650                 655

Ile Arg Ala Glu Phe Thr Glu Ala Gln Ile Thr Asp Asp Gln Leu Gln
                660                 665                 670

Lys Val Leu Arg Leu Asn Tyr Gln Gly Trp Gly Arg Phe Ser Ala Glu
                675                 680                 685

Phe Leu Lys Glu Leu Lys Gly Val Asp Thr Glu Thr Gly Glu Val Phe
690                 695                 700

Ser Ile Ile Asn Ala Leu Arg Glu Thr Asp Asp Asn Leu Met Gln Leu
705                 710                 715                 720

Leu Ser Asn Arg Tyr Thr Phe Ala Glu Glu Leu Glu Lys Tyr Asn Ser
                725                 730                 735

Asn Lys Arg Lys Lys Ile Glu Ala Leu Thr Tyr Asp Asn Ile Met Glu
                740                 745                 750

Gly Ile Val Ala Ser Pro Ala Ile Lys Arg Ser Ala Trp Gln Ala Ile
                755                 760                 765

Ser Ile Val Met Glu Leu Ser Lys Ile Met Gly Arg Glu Pro Lys Arg
770                 775                 780

Ile Phe Val Glu Met Ala Arg Gly Pro Glu Glu Lys Lys His Thr Ile
785                 790                 795                 800

Ser Arg Lys Asn Gln Leu Leu Glu Leu Tyr Lys Ser Val Lys Asp Glu
                805                 810                 815

Ser Arg Asp Trp Lys Thr Glu Leu Glu Thr Lys Thr Glu Ser Asp Phe
                820                 825                 830

Arg Ser Ile Lys Leu Phe Leu Tyr Tyr Thr Gln Met Gly Arg Cys Met
                835                 840                 845

Tyr Thr Gly Glu Pro Ile Asp Leu Asp Gln Leu Ala Asn Thr Thr Ile
850                 855                 860

Tyr Asp Arg Asp His Ile Tyr Pro Gln Ser Leu Thr Lys Asp Asp Ser
865                 870                 875                 880

Leu Asn Asn Leu Val Leu Val Lys Lys Val Glu Asn Ala Asn Lys Gly
                885                 890                 895

Asn Gly Leu Ile Ser Ala Asp Ile Gln Lys Lys Met Arg Gly Phe Trp
                900                 905                 910

Ala Glu Leu Lys Lys Lys Gly Leu Ile Ser Asp Glu Lys Phe Ser Arg
                915                 920                 925

Leu Thr Arg Thr Thr Pro Leu Ser Asp Asp Glu Leu Ala Gly Phe Ile
930                 935                 940

Asn Arg Gln Leu Val Glu Thr Arg Gln Ser Ser Lys Ile Val Ala Asp
945                 950                 955                 960

Leu Phe His Gln Leu Tyr Pro Thr Thr Gln Val Val Tyr Val Lys Ala
                965                 970                 975

Lys Ile Val Ser Asp Phe Arg His Glu Thr Leu Asp Met Val Lys Val
                980                 985                 990

Arg Ser Leu Asn Asp Leu His His Ala Lys Asp Ala Tyr Leu Asn Ile
                995                 1000                1005

Val Thr Gly Asn Val Tyr Tyr Glu Lys Phe Ser Gly Asn Pro Leu
     1010                1015                1020

```
Thr Trp Leu Arg Lys Asn Pro Asp Arg Asn Tyr Ser Leu Asn Gln
1025                1030                1035

Met Phe Asn Tyr Asp Ile Val Lys Lys Thr Lys Glu Gly Thr Ser
1040                1045                1050

Tyr Val Trp Lys Lys Gly Lys Asp Gly Ser Ile Ala Val Val Arg
1055                1060                1065

Arg Thr Met Glu Arg Asn Asp Ile Leu Tyr Thr Arg Gln Ala Thr
1070                1075                1080

Glu Asn Lys Asn Gly Gly Leu Phe Asp Gln Asn Ile Val Ser Ser
1085                1090                1095

Lys Asn Lys Pro Phe Ile Pro Val Lys Lys Gly Leu Asp Val Asn
1100                1105                1110

Lys Tyr Gly Gly Tyr Lys Gly Ile Thr Pro Ala Tyr Phe Ala Leu
1115                1120                1125

Ile Glu Phe Thr Asp Lys Lys Gly Ser Arg Gln Arg Leu Leu Glu
1130                1135                1140

Ala Val Pro Leu Tyr Leu Arg Ala Asp Ile Asp Asn Asp Ser Asn
1145                1150                1155

Val Leu Arg Asp Phe Tyr Lys Asn Val Leu Gly Leu Glu Asn Pro
1160                1165                1170

Val Val Ile Leu Asn Arg Ile Lys Lys Asn Ser Leu Leu Lys Ile
1175                1180                1185

Asn Gly Phe Leu Ile His Leu Arg Gly Thr Thr Gly Phe Ser Ala
1190                1195                1200

Ser Gln Leu Lys Val Gln Asn Ala Val Glu Phe Ser Leu Pro His
1205                1210                1215

His Met Glu Asp Tyr Val Lys Lys Leu Glu Asn Tyr Glu Lys His
1220                1225                1230

Ile Ile Ala Glu Arg Gly Ser Thr Lys Asn Ser Gln Ile Lys Ile
1235                1240                1245

Thr Glu Trp Asp Gly Ile Ser Lys Glu Lys Asn Leu Gln Leu Tyr
1250                1255                1260

Asp Met Phe Ile Asn Lys Met Glu Asn Thr Ile Tyr Lys Phe Arg
1265                1270                1275

Pro Ala Asn Gln Val Ser Asn Leu Lys Glu Asn Arg Glu Val Phe
1280                1285                1290

Asn Ser Leu Ala Val Glu Asp Gln Cys Ser Val Leu Asn Gln Val
1295                1300                1305

Leu Met Leu Phe Val Cys Lys Pro Val Thr Ala Asn Leu Ser Leu
1310                1315                1320

Ile Lys Gly Ser Lys Asn Ala Gly Asn Met Ala Leu Ser Lys Ile
1325                1330                1335

Ile Ser Asn Met Arg Ser Ala Tyr Leu Ile His Gln Ser Val Thr
1340                1345                1350

Gly Leu Phe Glu Gln Lys Ile Asp Leu Leu Lys Val Ser Ser Gln
1355                1360                1365

Lys Asp
1370

<210> SEQ ID NO 35
<211> LENGTH: 36
<212> TYPE: DNA
<213> ORGANISM: Artificial Sequence
<220> FEATURE:
<223> OTHER INFORMATION: CR RNA
```

<400> SEQUENCE: 35
gtttgagagt aatgtaaatt cataggatgg taaaac                                    36

<210> SEQ ID NO 36
<211> LENGTH: 103
<212> TYPE: DNA
<213> ORGANISM: Artificial Sequence
<220> FEATURE:
<223> OTHER INFORMATION: TRACR RNA

<400> SEQUENCE: 36
tttaccatcc agtgagttta cattacaagt tcaaataaaa atttattcaa cccgttcttc          60
ggaacctcca ccgtgtggaa cattaaggtc tgctttgcag gcc                          103

<210> SEQ ID NO 37
<211> LENGTH: 1369
<212> TYPE: PRT
<213> ORGANISM: Artificial Sequence
<220> FEATURE:
<223> OTHER INFORMATION: Bacillales bacterium

<400> SEQUENCE: 37

Met Ala Asn Lys Leu Phe Ile Gly Leu Asp Val Gly Ser Asp Ser Val
1               5                   10                  15

Gly Trp Ala Ala Thr Asp Glu Asn Phe His Leu Tyr Arg Leu Lys Gly
            20                  25                  30

Lys Thr Ala Trp Gly Ala Arg Ile Phe Ser Glu Ala Ser Asp Ala Lys
        35                  40                  45

Gly Arg Arg Gly Phe Arg Val Ala Gly Arg Arg Leu Ala Arg Arg Lys
    50                  55                  60

Glu Arg Ile Arg Leu Leu Asn Thr Leu Phe Asp Pro Leu Leu Lys Glu
65                  70                  75                  80

Lys Asp Pro Thr Phe Leu Leu Arg Leu Glu Asn Ser Ala Ile Gln Asn
                85                  90                  95

Asp Asp Pro Asn Lys Pro Ala Gln Ala Val Thr Asp Cys Leu Leu Phe
            100                 105                 110

Ala Asn Lys Gln Glu Glu Lys Gly Phe Tyr Lys Arg Tyr Pro Thr Ile
        115                 120                 125

Trp His Leu Arg Lys Ala Leu Met Asp Asn Gly Asp Cys Ala Phe Ser
    130                 135                 140

Asp Ile Arg Phe Leu Tyr Leu Ala Ile His His Ile Ile Lys Tyr Arg
145                 150                 155                 160

Gly Asn Phe Leu Arg Asp Gly Glu Ile Lys Ile Gly Gln Phe Asp Tyr
                165                 170                 175

Ser Val Phe Asp Lys Leu Asn Glu Thr Leu Ser Val Leu Phe Asp Leu
            180                 185                 190

Gln Ser Glu Asp Glu Asp Ser Gln Glu Gly His Phe Val Gly Leu Pro
        195                 200                 205

Lys Ser Gln Tyr Glu Ala Phe Ile Thr Thr Ala Asn Asp Arg Asn Leu
    210                 215                 220

Pro Lys Gln Thr Lys Thr Lys Leu Leu Ser Met Phe Glu Lys Asp
225                 230                 235                 240

Glu Glu Ser Lys Ser Phe Leu Glu Met Phe Cys Thr Leu Cys Ala Gly
                245                 250                 255

Gly Glu Phe Ser Thr Lys Lys Leu Asn Lys Lys Gly Glu Glu Thr Phe
            260                 265                 270

```
Asp Asp Thr Lys Ile Ser Phe Asn Ala Ser Tyr Asp Gln Asn Glu Pro
        275                 280                 285

Asn Tyr Gln Glu Ile Leu Gly Asp Ala Phe Asp Leu Val Asp Ile Ala
    290                 295                 300

Lys Ala Val Phe Asp Tyr Cys Asp Leu Ser Asp Ile Leu Asn Gly Asn
305                 310                 315                 320

Asp Asn Leu Ser Asn Ala Phe Val Glu Leu Tyr Asp Ser His Lys Ser
                325                 330                 335

Gln Leu Ser Ala Leu Lys Ala Ile Cys Lys Gln Ile Asp Asn Gln Ser
            340                 345                 350

Asn Leu Lys Gly Asp Ala Ser Val Tyr Val Lys Leu Phe Asn Asp Pro
        355                 360                 365

Asn Asp Lys Ser Asn Tyr Pro Ala Phe Thr His Asn Lys Thr Leu Val
    370                 375                 380

Asp Lys Arg Cys Asp Ile His Thr Phe Asp Lys Tyr Val Ile Asp Thr
385                 390                 395                 400

Val Leu Pro Tyr Glu Pro Leu Leu Met Gly Gln Asp Ala Thr Asn Trp
                405                 410                 415

Gln Met Leu Lys Ser Leu Ala Glu Gln Asp Arg Leu Leu Gln Thr Ile
            420                 425                 430

Ala Leu Arg Ser Thr Ser Val Ile Pro Met Gln Leu His Gln Lys Glu
        435                 440                 445

Leu Lys Ile Ile Leu Lys Asn Ala Ile Ser Arg Asn Val Lys Gly Ile
    450                 455                 460

Ala Glu Ile Glu Glu Lys Ile Leu Lys Leu Phe Gln Tyr Lys Ile Pro
465                 470                 475                 480

Tyr Tyr Cys Gly Pro Leu Thr Thr Lys Ser Ala Tyr Ser Asn Val Val
                485                 490                 495

Phe Lys Asn Asn Glu Tyr Arg Pro Leu Lys Pro Trp Asp Tyr Glu Glu
            500                 505                 510

Ala Ile Asp Trp Asp Glu Thr Lys Lys Phe Met Glu Gly Leu Thr
        515                 520                 525

Asn Lys Cys Thr Tyr Leu Lys Asp Lys Asn Val Leu Pro Lys Gln Ser
            530                 535                 540

Ile Leu Tyr Gln Asp Phe Asp Ala Trp Asn Lys Leu Asn Asn Leu Lys
545                 550                 555                 560

Val Asn Gly Ser Lys Pro Ser Leu Lys Glu Leu Lys Asp Leu Phe Ser
                565                 570                 575

Phe Val Ser Gln Arg Pro Lys Thr Thr Met Lys Asp Ile Gln Arg His
            580                 585                 590

Phe Lys Ser Asp Thr Asn Ser Lys Asp Lys Asp Val Val Val Ser Gly
        595                 600                 605

Trp Asn Pro Glu Asp Tyr Ile Cys Cys Ser Ser Arg Ala Ser Phe Gly
    610                 615                 620

Lys Asn Gly Val Phe Asp Leu Asn Asn Pro Asp Ser Ser Asp Pro Lys
625                 630                 635                 640

Asp Leu Ser Lys Cys Glu Arg Met Ile Phe Leu Lys Thr Ile Tyr Ala
                645                 650                 655

Asp Ser Pro Lys Asp Ala Asp Val Ala Ile Leu Lys Glu Phe Pro Asp
            660                 665                 670

Leu Thr Asn Asp Gln Lys Ser Leu Leu Lys Thr Ile Lys Cys Lys Glu
        675                 680                 685
```

```
Trp Ser Pro Leu Ser Lys Glu Phe Leu Glu Leu Arg Tyr Ala Asp Lys
690             695                 700

Tyr Gly Glu Ile Arg Glu Ser Ile Ile Asn Leu Leu Arg Ser Gly Glu
705                 710                 715                 720

Gly Asn Leu Met Gln Ile Leu Ala Lys Tyr Asp Tyr Gln Glu Arg Ile
            725                 730                 735

Asp Ala Tyr Asn Ala Asp Ser Phe Gln Thr Lys Ser Lys Ser Gln Ile
                740                 745                 750

Val Ser Asp Leu Ile Glu Glu Met Pro Pro Lys Met Arg Arg Pro Val
        755                 760                 765

Ile Gln Ala Val Arg Ile Val His Glu Val Val Lys Val Ala Lys Lys
770                 775                 780

Glu Pro Asp Gln Ile Ser Ile Glu Val Thr Arg Glu Asn Asn Asn Lys
785                 790                 795                 800

Glu Lys Lys Gln Gln Leu Thr Lys Lys Ala Lys Ser Arg Ser Ala Gln
                805                 810                 815

Ile Gln Thr Phe Leu Lys Asn Leu Val Lys Ile Asp Thr Phe Glu Glu
                820                 825                 830

Lys Arg Val Asp Glu Val Leu Glu Glu Leu Lys Lys Tyr Ser Asp Arg
835                 840                 845

Ser Ile Asn Gly Lys His Leu Tyr Leu Tyr Phe Leu Gln Asn Gly Lys
850                 855                 860

Asp Ala Tyr Thr Gly Lys Pro Ile Asn Ile Asp Asp Val Leu Ser Gly
865                 870                 875                 880

Asn Lys Tyr Asp Thr Asp His Val Ile Pro Gln Ser Lys Met Lys Asp
                885                 890                 895

Asp Ser Ile Asp Asn Leu Val Leu Val Glu Arg Ser Ile Asn Gln His
                900                 905                 910

Arg Ser Asn Glu Tyr Pro Leu Pro Glu Ser Ile Arg Lys Asn Pro Ala
        915                 920                 925

Asn Val Ala Phe Trp Ser Lys Leu Lys Lys Ala Gly Met Met Ser Glu
            930                 935                 940

Lys Lys Phe Asn Asn Leu Thr Arg Ala Asn Pro Leu Thr Glu Glu Glu
945                 950                 955                 960

Leu Ser Ala Phe Val Ala Ala Gln Ile Asn Val Val Asn Arg Ser Asn
                965                 970                 975

Ile Val Ile Arg Asp Val Leu Lys Val Leu Tyr Pro Asn Ala Lys Leu
                980                 985                 990

Ile Phe Ser Lys Ala Gln Tyr Pro Ser Gln Ile Arg Lys Glu Leu Asn
            995                 1000                1005

Ile Pro Lys Leu Arg Asp Leu Asn Asp Thr His His Ala Val Asp
1010                1015                1020

Ala Tyr Leu Asn Ile Val Ser Gly Val Ser Leu Thr Glu Arg Tyr
1025                1030                1035

Gly Asn Leu Ser Phe Ile Lys Ala Ala Gln Lys Asn Glu Asn Gln
1040                1045                1050

Thr Asp Tyr Ser Leu Asn Met Glu Arg Tyr Ile Ser Ser Leu Ile
1055                1060                1065

Gln Thr Lys Glu Gly Glu Lys Thr Ser Leu Gly Lys Leu Ile Asp
1070                1075                1080

Gln Thr Ser Arg Arg His Asp Phe Leu Leu Thr Tyr Arg Phe Ser
1085                1090                1095

Tyr Gln Asp Ser Ala Phe Tyr Asn Gln Thr Ile Tyr Lys Lys Asn
```

| | | | | | | | | | | |
|---|---|---|---|---|---|---|---|---|---|---|
| | | | | 1100 | | 1105 | | | 1110 | |
| Ala | Gly 1115 | Leu | Ile | Pro | Val 1120 | His | Glu | Lys | Leu 1125 | Pro | Pro | Glu | Arg | Tyr |

Ala Gly Leu Ile Pro Val His Glu Lys Leu Pro Pro Glu Arg Tyr
    1115              1120              1125

Gly Gly Tyr Asn Ser Met Ser Thr Glu Val Asn Cys Val Val Thr
    1130              1135              1140

Ile Lys Gly Lys Lys Glu Arg Arg Tyr Leu Val Gly Val Pro His
    1145              1150              1155

Leu Leu Leu Glu Lys Gly Asn Lys Val Ala Asp Ile Asn Lys Glu
    1160              1165              1170

Ile Ala Asn Ser Val Pro His Lys Glu Asn Glu Thr Ile Ala Val
    1175              1180              1185

Ser Leu Lys Asp Ile Ile Gln Leu Asp Ser Met Val Lys Lys Asp
    1190              1195              1200

Gly Leu Val Tyr Leu Cys Thr Thr Gln Asn Lys Asp Leu Val Lys
    1205              1210              1215

Leu Lys Pro Phe Gly Pro Ile Phe Leu Ser Arg Glu Ser Glu Val
    1220              1225              1230

Tyr Leu Ser Asn Leu Asn Lys Phe Val Glu Lys Tyr Pro Asn Ile
    1235              1240              1245

Ala Asp Gly Asn Glu Asn Tyr Ser Leu Lys Thr Asn Arg Tyr Gly
    1250              1255              1260

Glu Lys Ser Ile Asp Phe Leu Gln Glu Lys Thr Gly Asn Val Leu
    1265              1270              1275

Lys Glu Leu Val Asp Leu Ser Asn Gln Lys Arg Phe Asp Tyr Cys
    1280              1285              1290

Pro Met Ile Cys Lys Leu Arg Thr Ile Asp Tyr Arg Lys Gly Val
    1295              1300              1305

Glu Gly Lys Thr Leu Thr Glu Gln Leu Ile Leu Ile Arg Ser Phe
    1310              1315              1320

Val Gly Val Phe Thr Arg Lys Ser Glu Ala Leu Ser Asn Gly Ser
    1325              1330              1335

Asn Phe Arg Lys Ala Arg Gly Leu Val Leu Gln Asp Gly Leu Val
    1340              1345              1350

Leu Cys Ser Asp Ser Ile Thr Gly Leu Tyr His Thr Glu Arg Lys
    1355              1360              1365

Leu

<210> SEQ ID NO 38
<211> LENGTH: 36
<212> TYPE: DNA
<213> ORGANISM: Artificial Sequence
<220> FEATURE:
<223> OTHER INFORMATION: CR RNA

<400> SEQUENCE: 38
gtttgagagc agtgttgtct tatatagctc gaaaac         36

<210> SEQ ID NO 39
<211> LENGTH: 103
<212> TYPE: DNA
<213> ORGANISM: Artificial Sequence
<220> FEATURE:
<223> OTHER INFORMATION: TRACR RNA

<400> SEQUENCE: 39
gcattgtaag acaacactgc tacgttcaaa taagcatatt gctacaaggt tctccctcgg     60
agaatgacca ttaggtcact tagatagccg gttcttctgg cta 103

<210> SEQ ID NO 40
<211> LENGTH: 1360
<212> TYPE: PRT
<213> ORGANISM: Artificial Sequence
<220> FEATURE:
<223> OTHER INFORMATION: Bacillales bacterium

<400> SEQUENCE: 40

```
Met Ala Asp Lys Leu Phe Ile Gly Leu Asp Val Gly Ser Glu Ser Val
1               5                   10                  15

Gly Trp Ala Ala Thr Asp Glu Asn Phe His Leu Tyr Arg Leu Lys Gly
            20                  25                  30

Lys Thr Ala Trp Gly Ala Arg Ile Phe Ser Glu Ala Asn Asp Ala Lys
        35                  40                  45

Thr Arg Arg Gly Phe Arg Val Ala Gly Arg Arg Leu Ala Arg Arg Lys
    50                  55                  60

Glu Arg Ile Arg Leu Leu Asn Thr Leu Phe Asp Pro Leu Leu Lys Lys
65                  70                  75                  80

Asp Pro Ala Phe Leu Leu Arg Leu Glu Asn Ser Ala Ile Gln Asn Asp
                85                  90                  95

Asp Pro Asn Lys Pro Ile Gln Ala Ile Ala Asp Cys Pro Leu Leu Val
            100                 105                 110

Asn Lys Gln Glu Glu Lys Asp Tyr Tyr Lys Arg Tyr Pro Thr Ile Trp
        115                 120                 125

His Leu Arg Lys Ala Leu Met Glu Asn Asp Asp His Ala Phe Ser Asp
    130                 135                 140

Ile Arg Phe Leu Tyr Leu Ala Ile His His Ile Ile Lys Tyr Arg Gly
145                 150                 155                 160

Asn Phe Leu Arg Glu Gly Asp Ile Lys Ile Gly Gln Phe Asp Tyr Ser
                165                 170                 175

Ile Phe Asp Lys Leu Asn Glu Thr Leu Ala Val Leu Phe Asp Leu Gln
            180                 185                 190

Asn Glu Asp Gly Glu Asn Glu Glu Gly Arg Phe Ile Gly Leu Pro Lys
        195                 200                 205

Ser Gln Tyr Glu Ala Phe Ile Thr Cys Ala Asn Asp Arg Asn Leu Pro
    210                 215                 220

Lys Gln Pro Lys Lys Ala Lys Leu Leu Ser Met Phe Glu Lys Thr Glu
225                 230                 235                 240

Glu Ser Lys Ala Phe Leu Glu Met Phe Cys Thr Leu Cys Ser Gly Gly
                245                 250                 255

Glu Phe Ser Thr Lys Lys Leu Asn Ala Lys Gly Glu Glu Thr Tyr Gln
            260                 265                 270

Asp Ala Lys Ile Ser Phe Asn Ser Ser Tyr Asp Glu Asn Glu Gly Ala
        275                 280                 285

Tyr Gln Glu Ile Leu Gly Asp Phe Phe Asp Leu Val Asp Ile Ala Lys
    290                 295                 300

Ala Val Phe Asp Tyr Cys Asp Leu Ser Asp Ile Leu Asn Gly Asn Asp
305                 310                 315                 320

Asn Leu Ser Ser Ala Phe Val Glu Leu Tyr Asp Ser His Lys Ser Gln
                325                 330                 335

Leu Ser Ala Leu Lys Ser Ile Cys Lys Arg Ile Asp Asn Gln Asn Gly
            340                 345                 350

Phe Ile Gly Glu Lys Ser Ile Tyr Val Lys Leu Phe Asn Asp Pro Asn
```

-continued

```
                355                 360                 365
Asp Lys Ser Asn Tyr Pro Ala Phe Thr Asn Asn Lys Thr Leu Val Asp
    370                 375                 380

Lys Arg Cys Asp Ile His Thr Phe Asp Lys Tyr Val Lys Glu Thr Ile
385                 390                 395                 400

Leu Pro Tyr Glu Ser Ser Leu Thr Gly Arg Asp Ala Val Asn Trp Gln
                    405                 410                 415

Met Leu Lys Ser Leu Ala Glu Gln Asp Arg Leu Leu Gln Thr Ile Ala
                420                 425                 430

Leu Arg Ser Thr Ser Val Ile Pro Met Gln Leu His Gln Lys Glu Leu
                435                 440                 445

Lys Ile Ile Leu Lys Asn Ala Val Ser Arg Asn Ile Lys Gly Val Ala
            450                 455                 460

Glu Ile Glu Glu Lys Ile Leu Lys Leu Phe Gln Tyr Lys Ile Pro Tyr
465                 470                 475                 480

Tyr Cys Gly Pro Leu Thr Thr Lys Ser Asp Tyr Ser Asn Val Val Phe
                    485                 490                 495

Lys Asn Asn Glu Tyr Arg Pro Leu Lys Pro Trp Asp Tyr Glu Glu Ala
                500                 505                 510

Ile Asp Trp Asp Gly Thr Lys Gln Lys Phe Met Glu Gly Leu Thr Asn
            515                 520                 525

Lys Cys Thr Tyr Leu Lys Asp Lys Asn Val Leu Pro Lys Gln Ser Val
530                 535                 540

Leu Tyr Gln Asp Phe Asp Thr Trp Asn Lys Leu Asn Asn Leu Lys Val
545                 550                 555                 560

Asn Gly Asn Lys Pro Ser Leu Glu Asp Leu Asn Asp Leu Phe Ser Phe
                565                 570                 575

Val Ser Gln Arg Ser Lys Thr Thr Met Arg Asp Ile Gln Arg Tyr Leu
                580                 585                 590

Lys Ser Lys Thr Asn Ser Lys Glu Asn Asp Val Val Ser Gly Trp
                595                 600                 605

Asn Ser Glu Asp Tyr Ile Cys Cys Ser Ser Arg Ala Ser Phe Asn Lys
                610                 615                 620

Asn Gly Ile Phe Asn Leu Asn Asn Ser Glu Val Leu Lys Glu Cys Glu
625                 630                 635                 640

Arg Ile Ile Phe Leu Lys Thr Ile Tyr Thr Asp Ser Pro Lys Asp Ala
                645                 650                 655

Asp Ala Ala Val Leu Lys Glu Phe Pro Asp Leu Thr Asn Asn Gln Lys
                660                 665                 670

Thr Leu Leu Lys Thr Ile Lys Cys Lys Glu Trp Ser Pro Leu Ser Lys
                675                 680                 685

Glu Phe Leu Glu Leu Arg Tyr Ser Asp Lys Tyr Gly Glu Ile Arg Gln
                690                 695                 700

Ser Ile Ile Asp Leu Leu Arg Asn Gly Glu Gly Asn Leu Met Gln Ile
705                 710                 715                 720

Leu Ala Lys Tyr Asp Tyr Gln Glu Val Ile Asp Ala Cys Asn Ala Ala
                725                 730                 735

Ser Phe Gln Thr Lys Ser Lys Ser Gln Ile Val Ser Asp Leu Ile Glu
                740                 745                 750

Glu Met Pro Pro Lys Met Arg Arg Pro Val Ile Gln Ala Val Arg Ile
                755                 760                 765

Val Gln Glu Val Ala Lys Val Ala Lys Lys Glu Pro Asp Glu Ile Ser
770                 775                 780
```

-continued

```
Ile Glu Val Thr Arg Glu Asn Asn Asp Lys Glu Lys Gln Gln Leu
785                 790                 795                 800

Thr Lys Lys Ala Lys Ser Arg Ser Thr Gln Ile Gln Asn Phe Leu Lys
                805                 810                 815

Asn Leu Val Lys Ile Asp Ala Ser Glu Lys Lys Gln Ala Asn Glu Val
                820                 825                 830

Leu Glu Glu Leu Lys Lys Tyr Ser Asp Gln Ser Ile Asn Gly Lys His
                835                 840                 845

Leu Tyr Leu Tyr Phe Leu Gln Asn Gly Lys Asp Ala Tyr Thr Gly Lys
                850                 855                 860

Pro Ile Asn Ile Asp Asp Val Leu Ser Gly Asn Lys Tyr Asp Thr Asp
865                 870                 875                 880

His Ile Ile Pro Gln Ser Lys Met Lys Asp Asp Ser Ile Asp Asn Leu
                885                 890                 895

Val Leu Val Glu Arg Glu Ile Asn Gln His Arg Ser Asn Glu Tyr Pro
                900                 905                 910

Leu Pro Glu Ser Ile Arg Lys Asn Pro Ala Asn Val Ala Phe Trp Arg
                915                 920                 925

Lys Leu Lys Lys Ala Gly Met Met Ser Glu Lys Lys Phe Asn Asn Leu
930                 935                 940

Thr Arg Ser Asn Pro Leu Thr Glu Glu Leu Gly Ala Phe Val Ala
945                 950                 955                 960

Ala Gln Ile Asn Val Val Asn Arg Ser Asn Val Val Ile Arg Asp Val
                965                 970                 975

Leu Lys Ile Leu Tyr Pro Asn Ala Lys Leu Ile Phe Ser Lys Ala Gln
                980                 985                 990

Tyr Pro Ser Gln Ile Arg Lys Glu Leu Asn Ile Pro Lys Leu Arg Asp
                995                 1000                1005

Leu Asn Asp Thr His His Ala Val Asp Ala Tyr Leu Asn Ile Val
                1010                1015                1020

Ser Gly Val Thr Leu Thr Asp Arg Tyr Gly Asn Met Arg Phe Ile
                1025                1030                1035

Lys Ala Ser Gln Asp Glu Glu Lys His Ser Leu Asn Met Glu Arg
                1040                1045                1050

Tyr Ile Ser Ser Leu Ile Gln Thr Lys Glu Gly Gln Arg Thr Glu
                1055                1060                1065

Leu Gly Glu Leu Ile Asp Gln Thr Ser Arg Arg His Asp Phe Leu
                1070                1075                1080

Leu Thr Tyr Arg Phe Ser Tyr Gln Asp Ser Ala Phe Tyr Lys Gln
                1085                1090                1095

Thr Ile Tyr Lys Lys Asn Ala Gly Leu Ile Pro Ala His Asp Asn
                1100                1105                1110

Leu Pro Pro Glu Arg Tyr Gly Gly Tyr Asp Ser Met Ser Thr Glu
                1115                1120                1125

Val Asn Cys Val Ala Thr Ile Ile Gly Lys Lys Thr Thr Arg Tyr
                1130                1135                1140

Leu Val Gly Val Pro His Leu Leu Ile Lys Lys Ala Lys Asp Gly
                1145                1150                1155

Ile Asp Val Asn Asp Glu Leu Ile Lys Leu Val Pro His Lys Glu
                1160                1165                1170

Asn Glu Val Val Lys Val Asp Leu Asn Thr Thr Leu Gln Leu Asp
                1175                1180                1185
```

| | | | | | | | | | | | |
|---|---|---|---|---|---|---|---|---|---|---|---|
|Cys|Thr|Val|Lys|Lys|Asp|Gly|Phe|Met|Tyr|Leu|Cys|Thr|Ser|Asn|
| |1190| | | |1195| | | |1200| | | | | |

Cys Thr Val Lys Lys Asp Gly Phe Met Tyr Leu Cys Thr Ser Asn
      1190              1195              1200

Asn Ile Ala Leu Val Lys Leu Lys Pro Phe Ser Pro Ile Phe Leu
    1205              1210              1215

Ser Arg Glu Ser Glu Ile Tyr Leu Ser Asn Leu Met Lys Tyr Val
    1220              1225              1230

Glu Lys Tyr Pro Asn Ile Ser Asp Glu Asn Ser Glu Tyr Glu Phe
    1235              1240              1245

Lys Ile Asn Arg Glu Asn Val Asp Pro Ile Lys Phe Thr Glu Lys
    1250              1255              1260

Gln Ser Ile Glu Val Val Gln Asp Leu Ile Ile Lys Ala Lys Gln
    1265              1270              1275

Asp Arg Phe Ser Tyr Cys Ser Met Ile Ser Lys Leu Arg Asp Ile
    1280              1285              1290

Asn Ala Glu Glu Met Ile His Ser Lys Ser Leu Thr Glu Gln Leu
    1295              1300              1305

Lys Ile Ile Lys Ser Leu Ile Gly Val Phe Thr Arg Lys Ser Glu
    1310              1315              1320

Ile Leu Ser Asp Lys Asn Asn Phe Arg Lys Ser Arg Gly Ala Ile
    1325              1330              1335

Leu Gln Glu Asp Leu Phe Leu Cys Ser Asp Ser Ile Thr Gly Leu
    1340              1345              1350

Tyr His Thr Glu Arg Lys Leu
    1355              1360

<210> SEQ ID NO 41
<211> LENGTH: 36
<212> TYPE: DNA
<213> ORGANISM: Artificial Sequence
<220> FEATURE:
<223> OTHER INFORMATION: CR RNA

<400> SEQUENCE: 41
gtttgagagc agtgttgtct tatatagctc gaaaac                                36

<210> SEQ ID NO 42
<211> LENGTH: 103
<212> TYPE: DNA
<213> ORGANISM: Artificial Sequence
<220> FEATURE:
<223> OTHER INFORMATION: TRACR RNA

<400> SEQUENCE: 42
gcattgtaag acaacactgc tacgttcaaa taagcatatt gctacaaggt tctccattgg      60
agaatgacca ttaggtcgct tagatagcca gttcttctgg cta                       103

<210> SEQ ID NO 43
<211> LENGTH: 1369
<212> TYPE: PRT
<213> ORGANISM: Artificial Sequence
<220> FEATURE:
<223> OTHER INFORMATION: Bacillales bacterium

<400> SEQUENCE: 43

Met Glu Gln Asn Thr Lys Lys Leu Phe Ile Gly Leu Asp Val Gly Thr
 1               5                  10                  15

Asp Ser Val Gly Trp Ala Ala Thr Asp Glu Tyr Phe Asn Leu Tyr Arg
            20                  25                  30

Leu Lys Gly Lys Thr Ala Trp Gly Ala Arg Leu Phe Leu Asp Ala Ala

```
                35                  40                  45
Asn Ala Lys Asp Arg Arg Gln His Arg Val Ser Gly Arg Arg Leu Ala
 50                  55                  60
Arg Arg Lys Glu Arg Ile Arg Leu Leu Asn Ala Leu Phe Asp Pro Leu
 65                  70                  75                  80
Leu Lys Lys Val Asp Pro Thr Phe Leu Leu Arg Leu Glu Ser Ser Thr
                 85                  90                  95
Leu Gln Asn Asp Asp Pro Asn Lys Asp Gln Arg Ala Val Ser Asp Ala
                100                 105                 110
Leu Leu Phe Gly Asn Lys Lys His Glu Lys Ala Tyr Tyr Ala Ala Phe
                115                 120                 125
Pro Thr Ile Trp His Leu Arg Lys Ala Leu Ile Glu Asn Asp Asp Lys
                130                 135                 140
Ala Phe Ser Asp Ile Arg Tyr Leu Tyr Leu Ala Ile His His Ile Ile
145                 150                 155                 160
Lys Tyr Arg Gly Asn Phe Leu Arg Gln Gly Glu Ile Lys Ile Gly Glu
                165                 170                 175
Phe Asp Phe Ser Cys Phe Asp Lys Leu Asn Gln Phe Phe Asp Ile Tyr
                180                 185                 190
Phe Ser Lys Glu Asp Glu Glu Val Glu Phe Ile Gly Leu Pro Asn
                195                 200                 205
Glu Asn Tyr Gln Arg Phe Ile Asp Cys Ala Ala Asp Lys Asn Leu Gly
                210                 215                 220
Lys Gly Lys Lys Lys Gly Asp Leu Leu Lys Leu Met Ser Phe Ser Glu
225                 230                 235                 240
Asp Glu Lys Pro Phe Cys Glu Met Phe Cys Ser Leu Cys Ala Gly Leu
                245                 250                 255
Ala Phe Ser Thr Lys Lys Leu Asn Lys Lys Asp Glu Thr Val Phe Glu
                260                 265                 270
Asp Ile Lys Val Glu Phe Asn Gly Lys Phe Asp Lys Gln Glu Glu
                275                 280                 285
Ile Lys Ser Val Leu Gly Asp Ala Tyr Asp Leu Val Glu Leu Ala Lys
                290                 295                 300
Phe Ile Phe Asp Tyr Cys Asp Leu Lys Asp Ile Leu Gly Ala Ser Thr
305                 310                 315                 320
Asn Arg Leu Ser Glu Ala Phe Ala Gly Ile Tyr Asp Ser His Lys Glu
                325                 330                 335
Glu Leu Lys Ala Leu Lys Gly Ile Cys Arg Glu Ile Asp Arg Ser Leu
                340                 345                 350
Gly Asn Glu Ser Lys Asn Ser Leu Tyr Arg Glu Val Phe Asn Asp Lys
                355                 360                 365
Gly Ile Pro Asn Asn Tyr Ala Ala Phe Ile His Glu Thr Asn Ser
                370                 375                 380
Ser Arg Cys Gly Ile Ala Asp Phe Asn Asn Tyr Val Leu Gln Lys Ile
385                 390                 395                 400
Glu Pro Leu Glu Asn Leu Leu Ser Lys Gln Asn Tyr Lys Asn Trp Ile
                405                 410                 415
Gln Leu Lys Gln Leu Ala Ser Gln Gly Arg Leu Leu Gln Thr Ile Ala
                420                 425                 430
Ile Arg Ser Thr Ser Ile Ile Pro Met Gln Leu His Leu Lys Asp Leu
                435                 440                 445
Lys Leu Ile Leu Ala Asn Ala Glu Lys Arg Asp Ile Pro Gly Ile Lys
                450                 455                 460
```

```
Asp Ile Lys Glu Lys Ile Leu Leu Leu Phe Gln Phe Lys Val Pro Tyr
465                 470                 475                 480

Tyr Cys Gly Pro Leu Thr Asp Arg Ser Gln Tyr Ser Asn Val Val Leu
                485                 490                 495

Lys Ala Gly Thr Arg Glu Lys Ile Thr Pro Trp Asn Phe Ala Asp Gln
            500                 505                 510

Val Asp Leu Glu Glu Thr Lys Lys Lys Phe Met Glu Gly Leu Thr Asn
            515                 520                 525

Lys Cys Thr Tyr Leu Lys Asp Cys Asn Val Leu Pro Arg Gln Ser Leu
530                 535                 540

Met Phe Gln Glu Tyr Asp Ala Trp Asn Lys Leu Asn Asn Leu Ser Ile
545                 550                 555                 560

Asn Gly Asn Lys Pro Ser Pro Glu Glu Met Asn Ala Leu Phe Asp Phe
                565                 570                 575

Ala Ser Lys Arg Arg Lys Thr Thr Met Ser Asp Ile Lys Lys Phe Glu
            580                 585                 590

Lys Arg Ala Thr Met Ser Lys Glu Asn Asp Val Thr Val Ser Gly Trp
            595                 600                 605

Asn Glu Asn Asp Phe Ile Asp Leu Ser Ser Phe Val Ser Leu Ser Gly
610                 615                 620

Phe Phe Asp Leu Gly Glu Ile His Ser Ala Asp Tyr Met Ala Cys Glu
625                 630                 635                 640

Glu Ala Ile Leu Leu Lys Thr Ile Phe Thr Asp Ala Pro Gln Asp Ala
                645                 650                 655

Asp Pro Ile Ile Ala Glu Lys Phe Pro Asn Leu Lys Pro Asn Gln Leu
            660                 665                 670

Ala Ala Leu Lys Lys Met Ser Cys Lys Gly Trp Ala Thr Leu Ser Arg
            675                 680                 685

Glu Phe Leu Thr Leu Lys Ala Val Asp Ala Asp Gly Glu Val Met Asn
690                 695                 700

Glu Thr Leu Leu Gly Leu Met Lys Glu Gly Lys Gly Asn Leu Met Gln
705                 710                 715                 720

Leu Leu His Ser Ser Leu Tyr Asn Phe Gln Asp Val Ile Asp Ser His
                725                 730                 735

Asn Arg Ala Val Phe Gly Asp Lys Ser Pro Lys Gln Ile Ala Asn Asp
            740                 745                 750

Leu Ile Glu Glu Met Pro Pro Gln Met Arg Arg Pro Val Ile Gln Ala
            755                 760                 765

Leu Arg Ile Val Arg Glu Val Ser Lys Val Ala Lys Lys Gln Pro Asp
            770                 775                 780

Val Ile Ser Ile Glu Val Thr Arg Glu Ser Asn Asp Lys Lys Lys Lys
785                 790                 795                 800

Glu Glu Trp Ser Lys Lys Ala Thr Asp Arg Lys Lys Gln Ile Asp Leu
                805                 810                 815

Phe Leu Lys Asn Leu Lys Lys Thr Glu Asp Val Lys Gln Thr Glu Ser
            820                 825                 830

Glu Leu Asp Gly Gln Ala Ile Asn Asp Ile Asp Ser Ile Arg Gly Lys
            835                 840                 845

His Leu Tyr Leu Tyr Phe Leu Gln Asn Gly Lys Asp Ala Tyr Thr Gly
            850                 855                 860

Leu Pro Ile Asp Ile Asn Asp Val Leu Asn Gly Thr Lys Tyr Asp Thr
865                 870                 875                 880
```

-continued

Asp His Ile Ile Pro Gln Ser Leu Met Lys Asp Asp Ser Ile Asp Asn
            885                 890                 895

Leu Val Leu Val Asn Arg Glu Lys Asn Gln His Lys Ser Asn Glu Phe
            900                 905                 910

Pro Leu Pro Arg Asp Ile Gln Thr Lys Ala Asn Ile Glu Arg Trp Arg
            915                 920                 925

Ala Leu Lys Lys Ala Gly Gly Met Ser Glu Lys Phe Asn Asn Leu
            930                 935             940

Thr Arg Thr Thr Pro Leu Thr Glu Glu Glu Leu Ser Ala Phe Val Ala
945                 950                 955                 960

Ala Gln Ile Asn Val Val Asn Arg Ser Asn Val Val Ile Arg Asp Val
            965                 970                 975

Leu Lys Ile Leu Tyr Pro Asn Ala Lys Leu Ile Phe Ser Lys Ala Gln
            980                 985                 990

Tyr Pro Ser Gln Ile Arg Arg Asp Leu Glu Ile Pro Lys Leu Arg Asp
            995                 1000                1005

Leu Asn Asp Thr His His Ala Val Asp Ala Phe Leu Asn Ile Val
            1010                1015                1020

Ser Gly Val Glu Leu Thr Lys Gln Phe Gly Arg Met Asp Val Ile
            1025                1030                1035

Lys Ala Ala Ala Lys Gly Asp Lys Asp His Ser Leu Asn Met Thr
            1040                1045                1050

Arg Tyr Leu Glu Arg Leu Leu Lys Lys Val Asp Glu Asn Lys Asn
            1055                1060                1065

Glu Thr Met Thr Glu Leu Gly Asn His Val Phe Val Thr Ser Gln
            1070                1075                1080

Arg His Asp Phe Leu Leu Thr Tyr Arg Phe Asp Tyr Gln Asp Ser
            1085                1090                1095

Ala Phe Tyr Asn Ala Thr Ile Tyr Ser Pro Asp Lys Asn Leu Ile
            1100                1105                1110

Pro Met His Asp Gly Met Asp Pro Glu Arg Tyr Gly Gly Tyr Ser
            1115                1120                1125

Ser Leu Asn Ile Glu Tyr Asn Cys Ile Ala Thr Ile Lys Gly Lys
            1130                1135                1140

Lys Lys Thr Thr Arg Tyr Leu Leu Gly Val Pro His Leu Leu Ala
            1145                1150                1155

Leu Lys Phe Lys Asn Asp Gly Ile Asp Ile Thr Ser Asp Leu Ile
            1160                1165                1170

Lys Leu Val Pro His Lys Gly Asp Glu Glu Val Ser Ile Asp Trp
            1175                1180                1185

Lys Asn Pro Ile Pro Leu Arg Ile Thr Val Lys Lys Asp Gly Val
            1190                1195                1200

Glu Tyr Leu Leu Ala Pro Phe Asn Ala Gln Val Met Glu Leu Lys
            1205                1210                1215

Pro Val Ser Pro Val Phe Leu Pro Arg Glu Ala Ala Glu Tyr Leu
            1220                1225                1230

Ala Arg Leu Lys Lys Ala Val Asp Gln Lys Lys Gln Phe Ile Tyr
            1235                1240                1245

Gln Asn Ser Ala Glu Ile Phe Gln Ser Lys Asp Lys Asn Asn Ala
            1250                1255                1260

Leu Gln Phe Gly Pro Glu Gln Ser Lys Asn Val Ala Leu Lys Ile
            1265                1270                1275

Tyr Ala Leu Ala Asp Ala Lys Lys Tyr Asp Tyr Cys Ala Met Ile

```
                 1280              1285              1290

Ser Lys Leu Arg Asp Ala Ala Leu Arg Ala Glu Met Leu Asp Ser
        1295              1300              1305

Leu Ser Ser Glu Ala Leu Phe Lys Gln Tyr Asn Asp Leu Ile Ser
        1310              1315              1320

Leu Leu Ser Gln Leu Thr Arg Arg Ser Lys Lys Ile Ser Ser Lys
        1325              1330              1335

Tyr Phe Ser Lys Ser Arg Gly Ala Leu Leu Gln Asp Gly Leu Lys
        1340              1345              1350

Ile Val Ser Lys Ser Ile Thr Gly Leu Tyr Glu Thr Glu Arg Asn
        1355              1360              1365

Leu

<210> SEQ ID NO 44
<211> LENGTH: 36
<212> TYPE: DNA
<213> ORGANISM: Artificial Sequence
<220> FEATURE:
<223> OTHER INFORMATION: CR RNA

<400> SEQUENCE: 44
gtttgagagc agtgttgtct taaatagctc gaaaac                              36

<210> SEQ ID NO 45
<211> LENGTH: 104
<212> TYPE: DNA
<213> ORGANISM: Artificial Sequence
<220> FEATURE:
<223> OTHER INFORMATION: TRACR RNA

<400> SEQUENCE: 45
gcattgtaag acaacactgc acgttcaaat aagcagattg ctacaaggtt cccgtaaggg    60
aatgaccatc tggtcacatg aatagccccc ggcaacggtg gctg                    104

<210> SEQ ID NO 46
<211> LENGTH: 1121
<212> TYPE: PRT
<213> ORGANISM: Artificial Sequence
<220> FEATURE:
<223> OTHER INFORMATION: Selenomonadaceae

<400> SEQUENCE: 46

Met Asn Tyr Ile Leu Gly Leu Asp Ile Gly Ile Ala Ser Val Gly Trp
1               5                   10                  15

Ala Ala Val Ala Leu Asp Ala Asn Asp Glu Pro Cys Lys Ile Leu Asp
            20                  25                  30

Leu Asn Ala Arg Ile Phe Glu Ala Ala Glu Gln Pro Lys Thr Gly Ala
        35                  40                  45

Ser Leu Ala Ala Pro Arg Arg Glu Ala Arg Gly Ser Arg Arg Arg Thr
    50                  55                  60

Arg Arg Arg Arg His Arg Met Glu Arg Leu His Leu Phe Ala Arg
65                  70                  75                  80

Glu Glu Leu Ile Ser Ala Glu Asn Ile Ala Ala Leu Phe Glu Ala Pro
                85                  90                  95

Ala Asp Val Tyr Arg Leu Arg Ala Glu Gly Leu Ser Arg Arg Leu Asp
            100                 105                 110

Glu Gly Glu Trp Ala Arg Val Leu Tyr His Ile Ala Lys Arg Arg Gly
        115                 120                 125
```

```
Phe Lys Ser Asn Arg Lys Gly Ala Ala Ser Asp Ala Asp Glu Gly Lys
    130                 135                 140

Val Leu Glu Ala Val Lys Glu Asn Glu Ala Leu Leu Lys Asn Tyr Lys
145                 150                 155                 160

Thr Val Gly Glu Met Met Phe Arg Asp Glu Lys Phe Gln Thr Ala Lys
                    165                 170                 175

Arg Asn Lys Gly Gly Ser Tyr Thr Phe Cys Val Ser Arg Gly Met Leu
                180                 185                 190

Ala Glu Glu Ile Gly Glu Leu Phe Ala Ala Gln Arg Glu Gln Gly Asn
                195                 200                 205

Pro His Ala Ser Glu Thr Phe Glu Thr Ala Tyr Ser Lys Ile Phe Ala
    210                 215                 220

Asp Gln Arg Ser Phe Asp Asp Gly Pro Asp Ala Asn Ser Arg Ser Pro
225                 230                 235                 240

Tyr Ala Gly Asn Gln Ile Glu Lys Met Ile Gly Thr Cys Ser Leu Glu
                245                 250                 255

Thr Asp Pro Pro Glu Lys Arg Ala Ala Lys Ala Ser Tyr Ser Phe Met
                260                 265                 270

Arg Phe Ser Leu Leu Gln Lys Ile Asn His Leu Arg Leu Lys Asp Ala
        275                 280                 285

Lys Gly Glu Glu Arg Pro Leu Thr Asp Glu Arg Ala Ala Val Glu
    290                 295                 300

Ala Leu Ala Trp Lys Ser Pro Ser Leu Thr Tyr Gly Ala Ile Arg Lys
305                 310                 315                 320

Ala Leu Pro Leu Pro Asp Glu Leu Arg Phe Thr Asp Leu Tyr Tyr Arg
                325                 330                 335

Trp Asp Lys Lys Pro Glu Glu Ile Glu Lys Lys Lys Leu Pro Phe Ala
                340                 345                 350

Ala Pro Tyr His Glu Ile Arg Lys Ala Leu Asp Lys Arg Glu Lys Gly
                355                 360                 365

Arg Ile Gln Ser Leu Thr Pro Asp Ala Leu Asp Ala Val Gly Tyr Ala
    370                 375                 380

Phe Thr Val Phe Lys Asn Asp Ala Lys Ile Glu Ala Ala Leu Ser Ala
385                 390                 395                 400

Ala Gly Ile Asp Gly Glu Asp Ala Val Ala Leu Met Ala Ala Gly Leu
                405                 410                 415

Thr Phe Arg Gly Phe Gly His Ile Ser Val Lys Ala Cys Arg Lys Leu
                420                 425                 430

Ile Pro His Leu Glu Lys Gly Met Thr Tyr Asp Lys Ala Cys Lys Glu
        435                 440                 445

Ala Gly Tyr Asp Leu Gln Lys Thr Gly Gly Glu Lys Thr Lys Leu Leu
    450                 455                 460

Ser Gly Asn Leu Asp Glu Ile Arg Glu Ile Pro Asn Pro Val Val Arg
465                 470                 475                 480

Arg Ala Ile Ala Gln Thr Val Lys Val Asn Ala Val Ile Arg Arg
                485                 490                 495

Tyr Gly Ser Pro Val Ala Val Asn Val Glu Leu Ala Arg Glu Met Gly
                500                 505                 510

Arg Thr Phe Gln Glu Arg Arg Asp Met Met Lys Ser Met Glu Asp Asn
                515                 520                 525

Asn Ala Glu Asn Glu Lys Arg Lys Glu Leu Lys Gly Tyr Gly Val
    530                 535                 540

Val His Pro Ser Gly Leu Asp Ile Val Lys Leu Lys Leu Tyr Lys Glu
```

-continued

```
              545                 550                 555                 560
          Gln Gly Gly Val Cys Ala Tyr Ser Leu Ala Ala Met Pro Ile Glu Lys
                          565                 570                 575
          Val Leu Lys Asp His Asp Tyr Ala Glu Val Asp His Ile Leu Pro Tyr
                          580                 585                 590
          Ser Arg Ser Phe Asp Asp Ser Tyr Ala Asn Lys Val Leu Val Leu Ser
                          595                 600                 605
          Lys Glu Asn Arg Asp Lys Gly Asn Arg Thr Pro Met Glu Tyr Met Ala
                          610                 615                 620
          Asn Met Pro Gly Arg Arg His Asp Phe Ile Thr Trp Val Lys Ser Ala
          625                 630                 635                 640
          Val Arg Asn Pro Arg Lys Arg Asp Asn Leu Leu Glu Lys Phe Gly
                          645                 650                 655
          Glu Asp Lys Glu Ala Ala Trp Lys Glu Arg His Leu Thr Asp Thr Lys
                          660                 665                 670
          Tyr Ile Gly Ser Phe Ile Ala Asn Leu Leu Arg Asp His Leu Glu Phe
                          675                 680                 685
          Ala Pro Trp Leu Asn Gly Lys Lys Gln His Val Leu Ala Val Asn
                          690                 695                 700
          Gly Ala Val Thr Asp Tyr Thr Arg Lys Arg Leu Gly Ile Arg Lys Ile
          705                 710                 715                 720
          Arg Glu Asp Gly Asp Leu His His Ala Val Asp Ala Ala Val Ile Ala
                          725                 730                 735
          Thr Val Thr Gln Gly Asn Ile Gln Lys Leu Thr Asp Tyr Ser Lys Gln
                          740                 745                 750
          Ile Glu Arg Ala Phe Val Lys Asn Arg Asp Gly Arg Tyr Val Asn Pro
                          755                 760                 765
          Asp Thr Gly Glu Val Leu Lys Lys Asp Glu Trp Ile Val Gln Arg Ser
                          770                 775                 780
          Arg His Phe Pro Glu Pro Trp Pro Gly Phe Arg His Glu Leu Glu Ala
          785                 790                 795                 800
          Arg Val Ser Asp His Pro Lys Glu Met Ile Glu Ser Leu Arg Leu Pro
                          805                 810                 815
          Thr Tyr Thr Pro Glu Glu Ile Asp Gly Leu Lys Pro Pro Phe Val Ser
                          820                 825                 830
          Arg Met Pro Thr Arg Lys Val Arg Gly Ala Ala His Leu Glu Thr Val
                          835                 840                 845
          Val Ser Pro Arg Leu Lys Asp Glu Gly Met Ile Val Lys Lys Val Ser
          850                 855                 860
          Leu Asp Ala Leu Lys Leu Thr Lys Asp Lys Asp Ala Ile Glu Asn Tyr
          865                 870                 875                 880
          Tyr Ala Pro Glu Ser Asp His Leu Leu Tyr Glu Ala Leu Leu His Arg
                          885                 890                 895
          Leu Gln Ala Phe Gly Gly Asp Gly Glu Lys Ala Phe Ala Glu Ser Phe
                          900                 905                 910
          His Lys Pro Lys Ala Asp Gly Thr Pro Gly Pro Val Val Lys Lys Val
                          915                 920                 925
          Lys Ile Ala Glu Lys Ser Thr Leu Ser Val Pro Val His His Gly Arg
                          930                 935                 940
          Gly Leu Ala Ala Asn Gly Gly Met Val Arg Val Asp Val Phe Phe Ile
          945                 950                 955                 960
          Pro Glu Gly Lys Asp Arg Gly Tyr Tyr Leu Val Pro Val Tyr Thr Ser
                          965                 970                 975
```

Asp Val Val Arg Gly Glu Leu Pro Met Arg Ala Val Val Gln Gly Lys
             980                 985                 990

Ser Tyr Ala Glu Trp Lys Leu Met Arg Glu Glu Asp Phe Ile Phe Ser
        995                1000                1005

Leu Tyr Pro Asn Asp Leu Val Tyr Ile Glu His Glu Lys Gly Val
   1010                1015                1020

Lys Val Lys Ile Gln Lys Lys Leu Arg Glu Ile Ser Thr Leu Pro
   1025                1030                1035

Arg Glu Lys Thr Met Thr Ser Gly Leu Phe Tyr Tyr Arg Thr Met
   1040                1045                1050

Gly Ile Ala Val Ala Ser Ile His Ile Tyr Ala Pro Asp Gly Val
   1055                1060                1065

Tyr Val Gln Glu Ser Leu Gly Val Lys Thr Leu Lys Glu Phe Lys
   1070                1075                1080

Lys Trp Thr Ile Asp Ile Leu Gly Gly Glu Pro His Pro Val Gln
   1085                1090                1095

Lys Glu Lys Arg Gln Asp Phe Ala Ser Val Lys Arg Asp Pro His
   1100                1105                1110

Ala Ala Lys Ser Thr Ser Ser Gly
   1115                1120

<210> SEQ ID NO 47
<211> LENGTH: 36
<212> TYPE: DNA
<213> ORGANISM: Artificial Sequence
<220> FEATURE:
<223> OTHER INFORMATION: CR RNA

<400> SEQUENCE: 47
attgtaccat agcgagttaa attagggaat tacaac                                    36

<210> SEQ ID NO 48
<211> LENGTH: 101
<212> TYPE: DNA
<213> ORGANISM: Artificial Sequence
<220> FEATURE:
<223> OTHER INFORMATION: TRACR RNA

<400> SEQUENCE: 48
ttgtaataac ctattttacc tcgctatggc acaatttgtt attacatgga cattatacta         60
aacatttcct aaaaaagcaa cgaaaaacgt gctggcagca a                            101

<210> SEQ ID NO 49
<211> LENGTH: 1087
<212> TYPE: PRT
<213> ORGANISM: Ruminococcus albus

<400> SEQUENCE: 49

Met Lys Tyr Ile Ile Gly Leu Asp Met Gly Ile Thr Ser Val Gly Phe
1               5                  10                  15

Ala Thr Met Met Leu Asp Asp Lys Asp Glu Pro Cys Arg Ile Ile Arg
            20                  25                  30

Met Gly Ser Arg Ile Phe Glu Ala Ala Glu His Pro Lys Asp Gly Ser
        35                  40                  45

Ser Leu Ala Ala Pro Arg Arg Ile Asn Arg Gly Met Arg Arg Arg Leu
    50                  55                  60

Arg Arg Lys Ser His Arg Lys Glu Arg Ile Lys Asp Leu Ile Ile Lys
65                  70                  75                  80

-continued

```
Asn Glu Leu Met Thr Ala Asp Glu Ile Ser Ala Ile Tyr Ser Thr Gly
                85                  90                  95
Lys Gln Leu Ser Asp Ile Tyr Gln Ile Arg Ala Glu Ala Leu Asp Arg
            100                 105                 110
Lys Leu Asn Thr Glu Glu Phe Val Arg Leu Leu Ile His Leu Ser Gln
        115                 120                 125
Arg Arg Gly Phe Lys Ser Asn Arg Lys Val Asp Ala Lys Glu Lys Gly
    130                 135                 140
Ser Asp Ala Gly Lys Leu Leu Ser Ala Val Asn Ser Asn Lys Glu Leu
145                 150                 155                 160
Met Ile Glu Lys Asn Tyr Arg Thr Ile Gly Glu Met Leu Tyr Lys Asp
                165                 170                 175
Glu Lys Phe Ser Glu Tyr Lys Arg Asn Lys Ala Asp Asp Tyr Ser Asn
            180                 185                 190
Thr Phe Ala Arg Ser Glu Tyr Glu Asp Glu Ile Arg Gln Ile Phe Ser
        195                 200                 205
Ala Gln Gln Glu His Gly Asn Pro Tyr Ala Thr Asp Glu Leu Lys Glu
    210                 215                 220
Ser Tyr Leu Asp Ile Tyr Leu Ser Gln Arg Ser Phe Asp Glu Gly Pro
225                 230                 235                 240
Gly Gly Ser Ser Pro Tyr Gly Gly Asn Gln Ile Glu Lys Met Ile Gly
                245                 250                 255
Asn Cys Thr Leu Glu Pro Glu Glu Lys Arg Ala Ala Lys Ala Thr Phe
            260                 265                 270
Ser Phe Glu Tyr Phe Asn Leu Leu Ser Lys Val Asn Ser Ile Lys Ile
        275                 280                 285
Val Ser Ser Gly Lys Arg Ala Leu Asn Asn Asp Glu Arg Gln Ser
    290                 295                 300
Val Ile Arg Leu Ala Phe Ala Lys Asn Ala Ile Ser Tyr Thr Ser Leu
305                 310                 315                 320
Arg Lys Glu Leu Asn Met Glu Tyr Ser Glu Arg Phe Asn Ile Ser Tyr
                325                 330                 335
Ser Gln Ser Asp Lys Ser Ile Glu Glu Ile Lys Lys Thr Lys Phe
            340                 345                 350
Thr Tyr Leu Thr Ala Tyr His Thr Phe Lys Lys Ala Tyr Gly Ser Val
        355                 360                 365
Phe Val Glu Trp Ser Ala Asp Lys Lys Asn Ser Leu Ala Tyr Ala Leu
    370                 375                 380
Thr Ala Tyr Lys Asn Asp Thr Lys Ile Ile Glu Tyr Leu Thr Gln Lys
385                 390                 395                 400
Gly Phe Asp Ala Ala Glu Thr Asp Ile Ala Leu Thr Leu Pro Ser Phe
                405                 410                 415
Ser Lys Trp Gly Asn Leu Ser Glu Lys Ala Leu Asn Asn Ile Ile Pro
            420                 425                 430
Tyr Leu Glu Gln Gly Met Leu Tyr His Asp Ala Cys Thr Ala Ala Gly
        435                 440                 445
Tyr Asn Phe Lys Ala Asp Asp Thr Asp Lys Arg Met Tyr Leu Pro Ala
    450                 455                 460
His Glu Lys Glu Ala Pro Glu Leu Asp Asp Ile Thr Asn Pro Val Val
465                 470                 475                 480
Arg Arg Ala Ile Ser Gln Thr Ile Lys Val Ile Asn Ala Leu Ile Arg
                485                 490                 495
```

-continued

Glu Met Gly Glu Ser Pro Cys Phe Val Asn Ile Glu Leu Ala Arg Glu
                500                 505                 510

Leu Ser Lys Asn Lys Ala Glu Arg Ser Lys Ile Glu Lys Gly Gln Lys
            515                 520                 525

Glu Asn Gln Val Arg Asn Asp Arg Ile Met Glu Arg Leu Arg Asn Glu
        530                 535                 540

Phe Gly Leu Leu Ser Pro Thr Gly Gln Asp Leu Ile Lys Leu Lys Leu
545                 550                 555                 560

Trp Glu Glu Gln Asp Gly Ile Cys Pro Tyr Ser Leu Lys Pro Ile Lys
                565                 570                 575

Ile Glu Lys Leu Phe Asp Val Gly Tyr Thr Asp Ile Asp His Ile Ile
            580                 585                 590

Pro Tyr Ser Leu Ser Phe Asp Asp Thr Tyr Asn Asn Lys Val Leu Val
        595                 600                 605

Met Ser Ser Glu Asn Arg Gln Lys Gly Asn Arg Ile Pro Met Gln Tyr
        610                 615                 620

Leu Glu Gly Lys Arg Gln Asp Asp Phe Trp Leu Trp Val Asp Asn Ser
625                 630                 635                 640

Asn Leu Ser Arg Arg Lys Lys Gln Asn Leu Thr Lys Glu Thr Leu Ser
                645                 650                 655

Glu Asp Asp Leu Ser Gly Phe Lys Lys Arg Asn Leu Gln Asp Thr Gln
            660                 665                 670

Tyr Leu Ser Arg Phe Met Met Asn Tyr Leu Lys Lys Tyr Leu Ala Leu
        675                 680                 685

Ala Pro Asn Thr Thr Gly Arg Lys Asn Thr Ile Gln Ala Val Asn Gly
690                 695                 700

Ala Val Thr Ser Tyr Leu Arg Lys Arg Trp Gly Ile Gln Lys Val Arg
705                 710                 715                 720

Glu Asn Gly Asp Thr His His Ala Val Asp Ala Val Val Ile Ser Cys
                725                 730                 735

Val Thr Ala Gly Met Thr Lys Arg Val Ser Glu Tyr Ala Lys Tyr Lys
            740                 745                 750

Glu Thr Glu Phe Gln Asn Pro Gln Thr Gly Glu Phe Phe Asp Val Asp
        755                 760                 765

Ile Arg Thr Gly Glu Val Ile Asn Arg Phe Pro Leu Pro Tyr Ala Arg
        770                 775                 780

Phe Arg Asn Glu Leu Leu Met Arg Cys Ser Glu Asn Pro Ser Arg Ile
785                 790                 795                 800

Leu His Glu Met Pro Leu Pro Thr Tyr Ala Ala Asp Glu Lys Val Ala
                805                 810                 815

Pro Ile Phe Val Ser Arg Met Pro Lys His Lys Val Lys Gly Ser Ala
            820                 825                 830

His Lys Glu Thr Ile Arg Arg Ala Phe Glu Glu Asp Gly Lys Lys Tyr
        835                 840                 845

Thr Val Ser Lys Val Pro Leu Thr Asp Leu Lys Leu Lys Asn Gly Glu
        850                 855                 860

Ile Glu Asn Tyr Tyr Asn Pro Glu Ser Asp Gly Leu Leu Tyr Asn Ala
865                 870                 875                 880

Leu Lys Glu Gln Leu Ile Ala Phe Gly Gly Asp Ala Ala Lys Ala Phe
                885                 890                 895

Glu Gln Pro Phe Tyr Lys Pro Lys Ser Asp Gly Ser Glu Gly Pro Leu
            900                 905                 910

Val Lys Lys Val Lys Leu Ile Asn Lys Ala Thr Leu Thr Val Pro Val

```
                    915                 920                 925
Leu Asn Asn Thr Ala Val Ala Asp Asn Gly Ser Met Val Arg Val Asp
        930                 935                 940

Val Phe Phe Val Glu Gly Gly Tyr Tyr Leu Val Pro Ile Tyr Val
945                 950                 955                 960

Ala Asp Thr Val Lys Glu Leu Pro Asn Lys Ala Ile Ile Ala Asn
                965                 970                 975

Lys Pro Tyr Glu Glu Trp Lys Glu Met Arg Glu Glu Asn Phe Val Phe
            980                 985                 990

Ser Leu Tyr Pro Asn Asp Leu Ile Lys Ile Ser Ser Arg Lys Asp Met
                995                 1000                1005

Lys Phe Asn Leu Val Asn Lys Glu Ser Thr Leu Ala Pro Asn Cys
    1010                1015                1020

Gln Ser Lys Glu Ala Leu Val Tyr Tyr Lys Gly Ser Asp Ile Ser
    1025                1030                1035

Thr Ala Ala Val Thr Ala Ile Asn His Asp Asn Thr Tyr Lys Leu
    1040                1045                1050

Arg Gly Leu Gly Val Lys Thr Leu Leu Lys Ile Glu Lys Tyr Gln
    1055                1060                1065

Val Asp Val Leu Gly Asn Val Phe Lys Val Gly Lys Glu Lys Arg
    1070                1075                1080

Val Arg Phe Lys
    1085

<210> SEQ ID NO 50
<211> LENGTH: 36
<212> TYPE: DNA
<213> ORGANISM: Artificial Sequence
<220> FEATURE:
<223> OTHER INFORMATION: CR RNA

<400> SEQUENCE: 50
gttgtagttc cctaattatt cttggtatgg tataat                              36

<210> SEQ ID NO 51
<211> LENGTH: 89
<212> TYPE: PRT
<213> ORGANISM: Artificial Sequence
<220> FEATURE:
<223> OTHER INFORMATION: TRACR RNA

<400> SEQUENCE: 51

Ala Thr Thr Gly Thr Ala Thr Cys Ala Thr Ala Cys Cys Ala Ala Gly
1               5                   10                  15

Ala Ala Cys Ala Ala Thr Thr Ala Gly Gly Thr Thr Ala Cys Thr Ala
                20                  25                  30

Thr Gly Ala Thr Ala Ala Gly Gly Thr Ala Gly Thr Ala Thr Ala Cys
        35                  40                  45

Cys Gly Cys Ala Ala Ala Gly Cys Thr Cys Ala Ala Cys Ala Cys
    50                  55                  60

Cys Thr Cys Ala Thr Cys Thr Cys Gly Gly Ala Thr Gly Ala Gly
65                  70                  75                  80

Gly Thr Gly Thr Thr Ala Thr Cys Thr
                85

<210> SEQ ID NO 52
<211> LENGTH: 1084
<212> TYPE: PRT
```

-continued

<213> ORGANISM: Artificial Sequence
<220> FEATURE:
<223> OTHER INFORMATION: Faecalibacterium

<400> SEQUENCE: 52

| Met | Lys | Asn | Thr | Leu | Tyr | Gly | Ile | Gly | Leu | Asp | Ile | Gly | Val | Ala | Ser |
| 1 | | | | 5 | | | | | 10 | | | | | 15 | |

| Val | Gly | Trp | Ala | Val | Val | Gly | Leu | Asn | Gly | Thr | Gly | Glu | Pro | Val | Gly |
| | | | 20 | | | | | 25 | | | | | 30 | | |

| Leu | His | Arg | Leu | Gly | Val | Arg | Ile | Phe | Asp | Lys | Ala | Glu | Gln | Pro | Lys |
| | | 35 | | | | | 40 | | | | | 45 | | | |

| Thr | Gly | Glu | Ser | Leu | Ala | Ala | Pro | Arg | Arg | Met | Ala | Arg | Gly | Met | Arg |
| | 50 | | | | | 55 | | | | | 60 | | | | |

| Arg | Arg | Leu | Arg | Arg | Lys | Ala | Leu | Arg | Arg | Ala | Asp | Val | Tyr | Ala | Leu |
| 65 | | | | | 70 | | | | | 75 | | | | | 80 |

| Leu | Glu | Arg | Ser | Gly | Leu | Ser | Thr | Arg | Glu | Ala | Leu | Ala | Gln | Met | Phe |
| | | | | 85 | | | | | 90 | | | | | 95 | |

| Glu | Ala | Gly | Gly | Leu | Glu | Asp | Ile | Tyr | Ala | Leu | Arg | Thr | Arg | Ala | Leu |
| | | | 100 | | | | | 105 | | | | | 110 | | |

| Asp | Glu | Pro | Val | Gly | Lys | Ala | Glu | Phe | Ser | Arg | Ile | Leu | Leu | His | Leu |
| | | 115 | | | | | 120 | | | | | 125 | | | |

| Ala | Gln | Arg | Arg | Gly | Phe | Lys | Ser | Asn | Arg | Arg | Thr | Ala | Ser | Asp | Gly |
| | 130 | | | | | 135 | | | | | 140 | | | | |

| Glu | Asp | Gly | Arg | Leu | Leu | Ala | Ala | Val | Asn | Glu | Asn | Arg | Arg | Arg | Met |
| 145 | | | | | 150 | | | | | 155 | | | | | 160 |

| Ala | Gln | Gly | Gly | Trp | Arg | Thr | Val | Gly | Glu | Met | Leu | Tyr | Arg | His | Glu |
| | | | | 165 | | | | | 170 | | | | | 175 | |

| Ala | Phe | Ala | Leu | Arg | Lys | Arg | Asn | Lys | Ala | Asp | Glu | Tyr | Leu | Ser | Thr |
| | | | 180 | | | | | 185 | | | | | 190 | | |

| Val | Gly | Arg | Asp | Met | Val | Ala | Glu | Glu | Ala | Ser | Leu | Leu | Phe | Gln | Arg |
| | | 195 | | | | | 200 | | | | | 205 | | | |

| Gln | Arg | Glu | Leu | Gly | Cys | Ala | Trp | Ala | Thr | Pro | Glu | Leu | Gln | Ala | Glu |
| | 210 | | | | | 215 | | | | | 220 | | | | |

| Tyr | Leu | Ser | Ile | Leu | Leu | Arg | Gln | Arg | Ser | Phe | Asp | Glu | Gly | Pro | Gly |
| 225 | | | | | 230 | | | | | 235 | | | | | 240 |

| Gly | Asn | Ser | Pro | Tyr | Gly | Gly | Asn | Gln | Val | Glu | Lys | Met | Val | Gly | Arg |
| | | | | 245 | | | | | 250 | | | | | 255 | |

| Cys | Thr | Phe | Glu | Pro | Asp | Glu | Pro | Arg | Ala | Ala | Lys | Ala | Ala | Tyr | Ser |
| | | | 260 | | | | | 265 | | | | | 270 | | |

| Phe | Glu | Tyr | Phe | Ser | Leu | Leu | Gln | Lys | Leu | Asn | His | Ile | Arg | Leu | Ala |
| | | 275 | | | | | 280 | | | | | 285 | | | |

| Glu | Asn | Gly | Glu | Thr | Arg | Pro | Leu | Thr | Gln | Pro | Gln | Arg | Gln | Gln | Leu |
| | 290 | | | | | 295 | | | | | 300 | | | | |

| Leu | Ser | Leu | Ala | His | Lys | Thr | Pro | Asp | Val | Ser | Leu | Ala | Arg | Ile | Arg |
| 305 | | | | | 310 | | | | | 315 | | | | | 320 |

| Lys | Glu | Leu | Ala | Leu | Pro | Glu | Thr | Val | Gln | Phe | Asn | Gly | Val | Arg | Cys |
| | | | | 325 | | | | | 330 | | | | | 335 | |

| Arg | Ala | Asn | Glu | Thr | Leu | Glu | Glu | Ser | Glu | Lys | Lys | Glu | Lys | Phe | Ala |
| | | | 340 | | | | | 345 | | | | | 350 | | |

| Cys | Leu | Pro | Ala | Tyr | His | Lys | Met | Arg | Lys | Ala | Leu | Asp | Gly | Val | Val |
| | | 355 | | | | | 360 | | | | | 365 | | | |

| Lys | Gly | Arg | Ile | Ser | Ser | Leu | Ser | Ile | Ser | Gln | Arg | Asp | Ala | Ala | Ala |
| | 370 | | | | | 375 | | | | | 380 | | | | |

| Thr | Ala | Leu | Ser | Leu | Tyr | Lys | Asn | Glu | Asp | Thr | Leu | Arg | Ala | Lys | Leu |

```
            385                 390                 395                 400
        Thr Glu Ala Gly Phe Gln Ala Pro Glu Ile Asp Ala Leu Ala Gly Leu
                        405                 410                 415

Thr Gly Phe Ser Lys Phe Gly His Leu Ser Leu Lys Ala Cys Arg Lys
                        420                 425                 430

Leu Ile Pro His Leu Glu Gln Gly Leu Thr Tyr Asp Gln Ala Cys Ser
                        435                 440                 445

Ala Ala Gly Tyr Asp Phe Lys Gly His Gly Ala Gly Glu Arg Ala Phe
                    450                 455                 460

Thr Leu Pro Ala Ala Pro Glu Met Glu Gln Ile Thr Ser Pro Val
        465                 470                 475                 480

Val Arg Arg Ala Val Ala Gln Thr Ile Lys Val Val Asn Gly Ile Ile
                        485                 490                 495

Arg Glu Met Asp Ala Ser Pro Ala Trp Val Arg Ile Glu Leu Ala Arg
                        500                 505                 510

Glu Leu Ser Lys Thr Phe Gly Glu Arg Gln Glu Met Asp Arg Ser Met
                        515                 520                 525

Arg Glu Asn Ala Ala Gln Asn Glu Arg Leu Met Gln Glu Leu Arg Asp
                        530                 535                 540

Thr Phe His Leu Leu Ser Pro Thr Gly Gln Asp Leu Val Lys Tyr Arg
        545                 550                 555                 560

Leu Trp Lys Glu Gln Asp Gly Val Cys Ala Tyr Ser Leu Arg Arg Leu
                        565                 570                 575

Asp Val Glu Arg Leu Phe Glu Pro Gly Tyr Val Asp Val Asp His Ile
                        580                 585                 590

Val Pro Tyr Ser Leu Ser Phe Asp Asp Arg Arg Ser Asn Lys Val Leu
                        595                 600                 605

Val Leu Ser Ser Glu Asn Arg Gln Lys Gly Asn Arg Leu Pro Leu Gln
                    610                 615                 620

Tyr Leu Gln Gly Lys Arg Arg Glu Asp Phe Ile Val Trp Thr Asn Ser
        625                 630                 635                 640

Ser Val Arg Asp Tyr Arg Lys Arg Gln Asn Leu Leu Arg Glu Lys Phe
                        645                 650                 655

Ser Gly Asp Glu Ala Glu Gly Phe Arg Gln Arg Asn Leu Gln Asp Thr
                        660                 665                 670

Gln His Met Ala Arg Phe Leu Tyr Asn Tyr Ile Ser Asp His Leu Ala
                        675                 680                 685

Phe Ala Gln Ser Glu Ala Leu Gly Lys Lys Arg Val Phe Ala Val Ser
                    690                 695                 700

Gly Ala Val Thr Ser His Leu Arg Lys Arg Trp Gly Leu Ser Lys Val
        705                 710                 715                 720

Arg Ala Asp Gly Asp Leu His His Ala Leu Asp Ala Ala Val Ile Ala
                        725                 730                 735

Cys Thr Thr Asp Gly Met Ile Arg Arg Ile Ser Gly Tyr Tyr Gly His
                        740                 745                 750

Ile Glu Gly Glu Tyr Leu Gln Asp Ala Asp Gly Ala Gly Ser Gln His
                        755                 760                 765

Ala Arg Thr Lys Glu Arg Phe Pro Ala Pro Trp Pro Arg Phe Arg Asp
                        770                 775                 780

Glu Leu Ile Val Arg Leu Ser Glu Gln Pro Gly Glu His Leu Leu Asp
        785                 790                 795                 800

Ile Asn Pro Ala Phe Tyr Cys Glu Tyr Gly Thr Glu His Ile Cys Pro
                        805                 810                 815
```

Val Phe Val Ser Arg Met Pro Arg Arg Lys Val Thr Gly Pro Gly His
            820                 825                 830

Lys Glu Thr Ile Lys Gly Ala Ala Ala Asp Glu Gly Leu Leu Thr
        835                 840                 845

Val Arg Lys Ala Leu Thr Glu Leu Lys Leu Asp Lys Asp Gly Glu Ile
850                 855                 860

Lys Asp Tyr Tyr Met Pro Ser Ser Asp Thr Leu Leu Tyr Glu Ala Leu
865                 870                 875                 880

Lys Ala Gln Leu Arg Arg Phe Gly Gly Asp Gly Lys Lys Ala Phe Ala
                885                 890                 895

Glu Pro Phe Tyr Lys Pro Lys Ala Asp Gly Thr Pro Gly Pro Leu Val
            900                 905                 910

Arg Lys Val Lys Thr Ile Glu Lys Ala Thr Leu Thr Val Pro Val His
            915                 920                 925

Gly Gly Ala Ala Ser Asn Asp Thr Met Val Arg Val Asp Val Phe Leu
        930                 935                 940

Val Pro Gly Asp Gly Tyr Tyr Trp Val Pro Val Tyr Val Ala Asp Thr
945                 950                 955                 960

Leu Lys Pro Glu Leu Pro Asn Arg Ala Val Val Ala Phe Lys Pro Tyr
                965                 970                 975

Ser Glu Trp Lys Glu Met Arg Glu Glu Asp Phe Ile Phe Ser Leu Tyr
            980                 985                 990

Pro Asn Asp Leu Val Tyr Val Glu  His Lys Ser Gly Leu  Lys Phe Thr
            995                 1000                 1005

Leu Gln  Asn Ala Asp Ser Thr  Leu Glu Lys Thr  Trp  Val Pro Lys
    1010                1015                 1020

Ala Ser  Phe Ala Tyr Phe Val  Gly Gly Asp Ile Ser  Thr Ala Ala
    1025                1030                  1035

Ile Ser  Leu Arg Thr His Asp  Asn Ala Tyr Gly Leu  Arg Gly Leu
    1040                1045                 1050

Gly Ile  Lys Thr Leu Lys Val  Leu Lys Lys Tyr Gln  Val Asp Val
    1055                1060                 1065

Leu Gly  Asn Ile Ser Pro Val  His Arg Glu Thr Arg  Gln Arg Phe
    1070                1075                 1080

Arg

<210> SEQ ID NO 53
<211> LENGTH: 36
<212> TYPE: DNA
<213> ORGANISM: Artificial Sequence
<220> FEATURE:
<223> OTHER INFORMATION: CR RNA

<400> SEQUENCE: 53
gttgtagttc cctaacagtt cttggtatgg tataat                                    36

<210> SEQ ID NO 54
<211> LENGTH: 117
<212> TYPE: DNA
<213> ORGANISM: Artificial Sequence
<220> FEATURE:
<223> OTHER INFORMATION: TRACR RNA

<400> SEQUENCE: 54
ttataccata ccaagaactg ttatggttgc tatgataagg tcttagcacc gtaaagctct          60
gacgcctcgc tttcagcggg gcgtcatctt ttttgcccaa aagacacgga tattttt            117

<210> SEQ ID NO 55
<211> LENGTH: 1084
<212> TYPE: PRT
<213> ORGANISM: Artificial Sequence
<220> FEATURE:
<223> OTHER INFORMATION: Clostridia

<400> SEQUENCE: 55

```
Met Ala Tyr Gly Ile Gly Leu Asp Ile Gly Ile Ala Ser Val Gly Phe
1               5                   10                  15

Ala Thr Val Ala Leu Asn Glu Gln Asp Glu Pro Cys Gly Ile Leu Arg
            20                  25                  30

Met Gly Ser Arg Ile Phe Asp Ala Ala Glu His Pro Lys Asn Gly Ala
        35                  40                  45

Ser Leu Ala Ala Pro Arg Arg Glu Ala Arg Ser Ala Arg Arg Arg Leu
    50                  55                  60

Arg Arg His Arg His Arg Leu Glu Arg Ile Arg Asn Leu Leu Val Glu
65                  70                  75                  80

Ser Cys Leu Ile Ser Gln Asp Gly Leu Gly Ser Leu Phe Glu Gly Arg
                85                  90                  95

Leu Glu Asp Ile Tyr Ala Leu Arg Thr Arg Ala Leu Asp Glu Arg Leu
            100                 105                 110

Thr Asp Ala Glu Leu Cys Arg Val Leu Ile His Leu Ala Gln Arg Arg
        115                 120                 125

Gly Phe Arg Ser Asn Arg Lys Ala Asp Ala Ala Asp Lys Glu Ala Gly
    130                 135                 140

Lys Leu Leu Lys Ala Val Ser Glu Asn Asp Arg Arg Met Glu Glu Asn
145                 150                 155                 160

Gly Tyr Arg Thr Val Gly Glu Met Leu Tyr Lys Asp Pro Leu Phe Ala
                165                 170                 175

Glu His Arg Arg Asn Lys Gly Glu Ala Tyr Leu Ser Thr Val Thr Arg
            180                 185                 190

Thr Ala Val Glu Gln Glu Ala Arg Leu Val Leu Ser Thr Gln Arg Glu
        195                 200                 205

Lys Gly Asn Ala Ala Ile Thr Glu Asp Phe Val Glu Lys Tyr Leu Asp
    210                 215                 220

Ile Leu Leu Ser Gln Arg Pro Phe Asp Val Gly Pro Gly Gly Asn Ser
225                 230                 235                 240

Pro Tyr Gly Gly Asn Met Ile Glu Lys Met Ile Gly Arg Cys Thr Phe
                245                 250                 255

Glu Pro Asp Glu Leu Arg Ala Pro Lys Ala Ser Tyr Ser Phe Glu Tyr
            260                 265                 270

Phe Gln Leu Leu Gln Lys Val Asn His Ile Arg Leu Leu Arg Asp Gly
        275                 280                 285

Arg Ser Glu Pro Leu Ser Glu Glu Gln Arg Arg Ala Ile Ile Asp Leu
    290                 295                 300

Ala Leu Ala Ser Ala Asp Val Thr Phe Ala Lys Ile Arg Lys Ala Leu
305                 310                 315                 320

Ser Leu Pro Asp Ser Val Arg Phe Asn Asp Val Tyr Tyr Arg Glu Ser
                325                 330                 335

Ala Glu Glu Ala Glu Lys Lys Lys Leu Gly Cys Met Asp Ala Tyr
            340                 345                 350

His Glu Met Arg Lys Ala Leu Asp Lys Val Ala Lys Gly Arg Ile Cys
        355                 360                 365
```

```
Ala Ile Pro Val Glu Gln Arg Asn Ala Ile Ala Tyr Val Leu Thr Val
    370                 375                 380

His Lys Thr Asp Glu Arg Ile Leu Thr Glu Leu Gln Asn Ile Asn Leu
385                 390                 395                 400

Glu Arg Ser Asp Ile Asp Gln Leu Met Gln Met Lys Gly Phe Ser Lys
                405                 410                 415

Phe Gly His Leu Ser Ile Lys Ala Cys Asp Arg Ile Ile Pro Tyr Leu
            420                 425                 430

Glu Gln Gly Met Thr Tyr Ser Asp Ala Cys Thr Ala Ala Gly Tyr Ala
            435                 440                 445

Phe Arg Gly His Glu Gly Gly Glu His Ser Leu Tyr Leu Pro Ala Gln
    450                 455                 460

Thr Pro Glu Met Asp Glu Ile Thr Ser Pro Val Val Arg Arg Ala Val
465                 470                 475                 480

Ser Gln Thr Ile Lys Val Val Asn Ala Leu Ile Arg Glu Gln Gly Glu
                485                 490                 495

Ser Pro Thr Phe Val Asn Ile Glu Leu Ala Arg Glu Met Ser Lys Asp
            500                 505                 510

Phe Ala Glu Arg Asn Asp Ile Arg Arg Glu Asn Glu Lys Asn Ala Lys
    515                 520                 525

Ala Asn Glu Ala Val Met Asn Glu Leu Arg Arg Thr Phe Gly Leu Val
    530                 535                 540

Asn Pro Ser Gly Gln Asp Leu Val Lys Tyr Lys Leu Phe Leu Glu Gln
545                 550                 555                 560

Gly Gly Val Cys Pro Tyr Thr Gln Arg Pro Met Glu Pro Gly Arg Leu
            565                 570                 575

Phe Glu Ala Gly Tyr Ala Asp Val Asp His Ile Val Pro Tyr Ser Ile
            580                 585                 590

Ser Phe Asp Asp Arg Tyr Cys Asn Lys Val Leu Thr Phe Ala Ser Val
    595                 600                 605

Asn Arg Lys Glu Lys Gly Asn Arg Leu Pro Leu Gln Phe Leu Lys Gly
610                 615                 620

Glu Arg Arg Glu Ser Phe Ile Val Tyr Val Lys Ala Asn Val Arg Asp
625                 630                 635                 640

Tyr Arg Lys Gln Arg Leu Leu Leu Lys Glu Thr Val Thr Glu Glu Asp
                645                 650                 655

Arg Lys Gly Phe Arg Asp Arg Asn Leu Gln Asp Thr Lys His Met Ala
            660                 665                 670

Ala Phe Leu His Ser Tyr Ile Asn Asp His Leu Gln Phe Ala Pro Phe
    675                 680                 685

Gln Thr Asp Arg Lys Arg His Val Thr Ala Val Asn Gly Ala Val Thr
690                 695                 700

Ala Tyr Leu Arg Lys Arg Trp Gly Ile Arg Lys Val Arg Ala Glu Gly
705                 710                 715                 720

Asp Leu His His Ala Ser Asp Ala Leu Val Ile Ala Cys Thr Thr Pro
                725                 730                 735

Gly Met Ile Gln Arg Leu Ser Arg Tyr Ala Glu Leu Arg Glu Ala Glu
            740                 745                 750

Tyr Met Gln Thr Glu Asp Gly Ala Val Arg Phe Asp Pro Ala Thr Gly
            755                 760                 765

Glu Val Leu Glu Lys Phe Pro Tyr Pro Trp Pro Cys Phe Arg Gln Glu
    770                 775                 780
```

Trp Thr Ala Arg Val Ser Asp Asp Pro Gln Ala Met Leu Gln Asp Met
785                 790                 795                 800

Lys Leu Thr Asp Tyr Arg Gly Leu Pro Leu Glu Gln Val Lys Pro Val
            805                 810                 815

Phe Val Ser Arg Met Pro Lys His Lys Val Thr Gly Ala Ala His Lys
        820                 825                 830

Asp Thr Val Lys Ser Ala Lys Ala Leu Asp Arg Gly Val Val Leu Val
            835                 840                 845

Lys Arg Ala Leu Thr Asp Leu Lys Leu Lys Asp Gly Glu Ile Glu Asn
        850                 855                 860

Tyr Tyr Asp Pro Ala Ser Asp Arg Leu Leu Tyr Glu Ala Leu Lys Glu
865                 870                 875                 880

Arg Leu Ile Ala Phe Gly Gly Asp Ala Gln Lys Ala Phe Ala Glu Pro
            885                 890                 895

Phe His Lys Pro Lys Arg Asp Gly Thr Pro Gly Pro Leu Val Lys Lys
        900                 905                 910

Val Lys Leu Met Glu Lys Ser Ser Leu Thr Val Pro Val His Asp Gly
            915                 920                 925

Lys Gly Val Ala Asp Asn Asp Ser Met Val Arg Ile Asp Val Phe Phe
        930                 935                 940

Val Ala Gly Glu Gly Tyr Tyr Phe Val Pro Ile Tyr Val Ala Asp Thr
945                 950                 955                 960

Val Lys Pro Glu Leu Pro Asn Arg Ala Val Val Ala Asn Lys Pro Tyr
            965                 970                 975

Ala Glu Trp Lys Glu Met Lys Asp Glu Asp Phe Leu Phe Ser Leu Tyr
        980                 985                 990

Pro Ser Asp Leu Met Arg Val Thr Gln Lys Lys Gly Ile Lys Leu Ser
            995                 1000                1005

Leu Ile Asn Lys Glu Ser Thr Leu Lys Lys Glu Glu Met Ala Gln
        1010                1015                1020

Ser Ile Leu Leu Tyr Tyr Val Lys Gly Ser Ile Ser Thr Gly Ser
        1025                1030                1035

Ile Thr Ala Glu Asn His Asp Arg Thr Tyr Ala Ile Asn Ser Leu
        1040                1045                1050

Gly Ile Lys Thr Leu Glu Lys Leu Glu Lys Tyr Gln Val Asp Val
        1055                1060                1065

Leu Gly Asn Val Ser Pro Val Gly Lys Glu Lys Arg Leu Thr Phe
        1070                1075                1080

Cys

<210> SEQ ID NO 56
<211> LENGTH: 36
<212> TYPE: DNA
<213> ORGANISM: Artificial Sequence
<220> FEATURE:
<223> OTHER INFORMATION: CR RNA

<400> SEQUENCE: 56
gttgtagttc cctaacggtt cttggtatgg tataat         36

<210> SEQ ID NO 57
<211> LENGTH: 102
<212> TYPE: DNA
<213> ORGANISM: Artificial Sequence
<220> FEATURE:
<223> OTHER INFORMATION: TRACR RNA

<400> SEQUENCE: 57

```
ttataccata ccaagaactg ttgggttact acaataaggt agtaaaccga aaagctctga      60
cgtcttgttt gcgcaggacg tcatctttat atcagacgga tg                       102
```

<210> SEQ ID NO 58
<211> LENGTH: 1058
<212> TYPE: PRT
<213> ORGANISM: Artificial Sequence
<220> FEATURE:
<223> OTHER INFORMATION: Chloroflexi

<400> SEQUENCE: 58

```
Met Leu Pro Tyr Ala Ile Gly Leu Asp Ile Gly Ile Ala Ser Val Gly
1               5                   10                  15

Trp Ala Val Val Gly Leu Asp Thr Asn Glu Arg Pro Phe Cys Ile Leu
            20                  25                  30

Gly Met Gly Ser Arg Ile Phe Asp Lys Ala Glu Gln Pro Lys Thr Gly
        35                  40                  45

Ala Ser Leu Ala Leu Pro Arg Arg Glu Ala Arg Ser Leu Arg Arg Arg
    50                  55                  60

Leu Arg Arg His Arg His Arg Asn Glu Arg Ile Arg Asn Leu Leu Leu
65                  70                  75                  80

Arg Glu Lys Ile Ile Ser Glu Ser Glu Leu Gln Asp Leu Phe Ser Gly
                85                  90                  95

Thr Leu Ser Asp Ile Tyr Gln Leu Arg Val Glu Ala Leu Asp Arg Lys
            100                 105                 110

Leu Asp Asp Lys Glu Phe Ser Arg Val Leu Ile His Ile Ala Gln Arg
        115                 120                 125

Arg Gly Phe Lys Ser Asn Arg Lys Asn Ala Ala Ala Ser Gln Glu Asp
    130                 135                 140

Gly Lys Leu Leu Ser Ala Val Thr Glu Asn Gln Gln Arg Met Asn Asp
145                 150                 155                 160

Lys Gly Tyr Arg Thr Val Ser Glu Met Leu Leu Arg Asp Asp Lys Phe
                165                 170                 175

Lys Asp His Lys Arg Asn Lys Gly Gly Glu Tyr Leu Thr Thr Val Thr
            180                 185                 190

Arg Thr Met Val Glu Asp Glu Val His Lys Ile Phe Ser Ala Gln Arg
        195                 200                 205

Thr His Gly Asn Leu Lys Ala Asp Asn Gln Leu Glu Ser Glu Tyr Leu
    210                 215                 220

Glu Ile Leu Leu Ser Gln Arg Ser Phe Asp Glu Gly Pro Gly Gly Asp
225                 230                 235                 240

Ser Pro Tyr Gly Gly Ser Gln Ile Glu Lys Met Ile Gly Lys Cys Thr
                245                 250                 255

Phe Phe Pro Glu Glu Lys Arg Ala Ala Lys Ala Thr Tyr Thr Phe Glu
            260                 265                 270

Tyr Phe Asn Leu Leu Glu Lys Ile Asn His Ile Arg Leu Val Ser Lys
        275                 280                 285

Asp Asn Leu Pro Glu Pro Leu Ser Asp Phe Gln Arg Arg Ser Leu Ile
    290                 295                 300

Glu Leu Ala Tyr Lys Val Glu Asn Leu Thr Tyr Asp Arg Ile Arg Lys
305                 310                 315                 320

Glu Leu His Ile Ser Pro Glu Leu Lys Phe Asn Thr Ile Arg Tyr Glu
                325                 330                 335
```

```
Ser Asp Asp Leu Pro Glu Asn Glu Lys Lys Gln Lys Leu Asn Cys Leu
            340                 345                 350

Lys Ala Tyr His Glu Ile Arg Lys Ala Leu Asp Lys Leu Gly Lys Gly
        355                 360                 365

Thr Ile Asn Thr Leu Ser Lys Glu Gln Leu Asn Thr Ile Gly Thr Val
    370                 375                 380

Leu Ser Met Tyr Lys Thr Ser Glu Ile Ile Lys Asn Lys Met Glu Gln
385                 390                 395                 400

Ile Pro Ala Glu Ile Val Asp Lys Leu Asp Glu Glu Gly Ile Asn Phe
                405                 410                 415

Ser Lys Phe Gly His Leu Ser Ile Lys Ala Cys Glu Leu Ile Ile Pro
            420                 425                 430

Gly Leu Glu Lys Gly Leu Asn Tyr Asn Asp Ala Cys Glu Glu Ala Gly
        435                 440                 445

Leu Asn Phe Lys Ala His Asn Asn Glu Glu Lys Ser Phe Leu Leu His
    450                 455                 460

Pro Thr Glu Asp Asp Tyr Ala Asp Ile Thr Ser Pro Val Val Lys Arg
465                 470                 475                 480

Ala Ala Ser Gln Thr Ile Lys Val Ile Asn Ala Ile Arg Lys Gln
                485                 490                 495

Gly Cys Ser Pro Thr Tyr Ile Asn Ile Glu Val Ala Arg Glu Leu Ser
            500                 505                 510

Lys Asp Phe Tyr Glu Arg Asp Lys Ile Asn Lys Arg Asn Glu Ala Asn
        515                 520                 525

Arg Ala Glu Asn Glu Arg Ser Leu Glu Gln Ile Arg Lys Glu Tyr Gly
    530                 535                 540

Lys Ser Asn Ala Ser Gly Leu Asp Leu Val Lys Phe Lys Leu Tyr Gln
545                 550                 555                 560

Lys Gln Asp Gly Val Cys Ala Tyr Ser Gln Lys Gln Ile Ser Phe Glu
                565                 570                 575

Arg Leu Phe Glu Pro Asn Tyr Val Glu Val Asp His Ile Ile Pro Tyr
            580                 585                 590

Ser Lys Cys Phe Asp Asp Arg Glu Ser Asn Lys Val Leu Val Phe Ala
        595                 600                 605

Lys Glu Asn Arg Glu Lys Gly Asn Arg Leu Pro Leu Glu Tyr Leu Asp
    610                 615                 620

Gly Lys Lys Arg Glu Ser Phe Ile Val Trp Val Asn Ser Lys Val Lys
625                 630                 635                 640

Asp Tyr Arg Lys Lys Gln Asn Leu Leu Lys Glu Ser Leu Ser Glu Glu
                645                 650                 655

Glu Glu Lys Gln Phe Lys Glu Arg Asn Leu Gln Asp Thr Lys Thr Val
            660                 665                 670

Ser Lys Phe Leu Met Asn Tyr Ile Asn Asp Asn Leu Ile Phe Ser Ser
        675                 680                 685

Ser Asn Lys Arg Lys Lys His Val Thr Ala Val Ser Gly Gly Val Thr
    690                 695                 700

Ser Tyr Met Arg Lys Arg Trp Gly Ile Ser Lys Val Arg Glu Asp Gly
705                 710                 715                 720

Asp Gln His His Ala Val Asp Ala Leu Val Ile Val Cys Thr Thr Asp
                725                 730                 735

Gly Met Ile Gln Gln Val Ser Lys Tyr Val Glu Tyr Lys Glu Cys Gln
            740                 745                 750

Tyr Ile Gln Thr Asp Ala Gly Ser Leu Ala Val Asp Pro Tyr Thr Gly
```

```
                755               760               765
Glu Val Leu Arg Ser Phe Pro Tyr Pro Trp Ala Arg Phe His Glu Asp
770               775               780
Ala Val Thr Trp Thr Glu Lys Ile Phe Val Ser Arg Met Pro Met Arg
785               790               795               800
Lys Val Thr Gly Pro Ala His Lys Glu Thr Ile Lys Ser Pro Lys Ala
            805               810               815
Leu Gly Glu Gly Leu Leu Ile Val Arg Lys Pro Leu Thr Glu Leu Lys
            820               825               830
Leu Lys Asn Gly Glu Ile Glu Asn Tyr Tyr Lys Pro Glu Ala Asp Leu
            835               840               845
Leu Leu Tyr Asn Gly Leu Lys Glu Arg Leu Met Glu Phe Gly Gly Asp
        850               855               860
Ala Lys Lys Ala Phe Ala Glu Pro Phe Pro Lys Pro Gly Asn Pro Gln
865               870               875               880
Lys Ile Val Lys Lys Val Arg Leu Thr Glu Lys Ser Thr Leu Asn Val
            885               890               895
Pro Val Leu Lys Gly Glu Gly Arg Ala Asp Asn Asp Ser Met Val Arg
            900               905               910
Val Asp Val Phe Leu Lys Asp Gly Lys Tyr Tyr Leu Val Pro Ile Tyr
            915               920               925
Val Ala Asp Thr Leu Lys Pro Glu Leu Pro Asn Lys Ala Cys Ile Ala
            930               935               940
His Lys Pro Tyr Asp Glu Trp Ala Thr Met Asp Asp Gly Asp Phe Leu
945               950               955               960
Phe Ser Leu Tyr Pro Asn Asp Leu Ile Tyr Ile Lys His Lys Lys Gly
            965               970               975
Ile Lys Leu Thr Lys Ile Asn Lys Asn Ser Thr Leu Ala Asp Ser Ile
            980               985               990
Glu Gly Lys Glu Phe Phe Leu Phe  Tyr Lys Thr Met Gly  Ile Ser Ser
            995               1000              1005
Ala Val  Leu Thr Cys Thr Asn  His Asp Asn Thr Tyr  Tyr Ile Glu
            1010              1015              1020
Ser Leu  Gly Val Lys Thr Leu  Glu Ser Leu Glu Lys  Cys Val Val
            1025              1030              1035
Gly Val  Leu Gly Glu Ile His  Lys Val Arg Lys Glu  Lys Arg Thr
            1040              1045              1050
Gly Phe  Ser Gly Asn
            1055

<210> SEQ ID NO 59
<211> LENGTH: 36
<212> TYPE: DNA
<213> ORGANISM: Artificial Sequence
<220> FEATURE:
<223> OTHER INFORMATION: CR RNA

<400> SEQUENCE: 59
gttgtagtcc cctgatggtt tctggaatgg tataat                                    36

<210> SEQ ID NO 60
<211> LENGTH: 120
<212> TYPE: DNA
<213> ORGANISM: Artificial Sequence
<220> FEATURE:
<223> OTHER INFORMATION: TRACR RNA
```

-continued

<400> SEQUENCE: 60

```
ttataccatt ccagaaacta ttatggtcac tacaataagg tattagaccg tagagcacta      60
acaccccatt tggggtgtta tctctttaaa ctgtccaaaa tttagtattg caattattga     120
```

<210> SEQ ID NO 61
<211> LENGTH: 1087
<212> TYPE: PRT
<213> ORGANISM: Artificial Sequence
<220> FEATURE:
<223> OTHER INFORMATION: Ruminococcaceae bacterium

<400> SEQUENCE: 61

```
Met Leu Pro Tyr Ala Ile Gly Leu Asp Ile Gly Ile Ser Ser Val Gly
 1               5                  10                  15

Trp Ala Ser Val Ala Leu Asp Glu Glu Asp Lys Pro Cys Gly Ile Ile
            20                  25                  30

Gly Met Gly Ser Arg Ile Phe Asp Ala Ala Glu Gln Pro Lys Thr Gly
        35                  40                  45

Asp Ser Leu Ala Ala Pro Arg Arg Ala Arg Ser Ala Arg Arg Arg
    50                  55                  60

Leu Arg Arg Arg His Arg Asn Glu Arg Ile Arg Ala Leu Met Leu
 65                  70                  75                  80

Arg Glu Gly Leu Leu Ser Glu Ala Glu Leu Ala Ala Leu Phe Asp Gly
                85                  90                  95

Arg Leu Glu Asp Ile Cys Ala Leu Arg Val Arg Ala Leu Asp Glu Ala
            100                 105                 110

Val Thr Asn Asp Glu Leu Ala Arg Ile Leu Leu His Leu Ser Gln Arg
        115                 120                 125

Arg Gly Phe Arg Ser Asn Arg Lys Thr Ala Ala Thr Gln Glu Asp Gly
    130                 135                 140

Glu Leu Leu Ala Ala Val Ser Ala Asn Arg Ala Leu Met Gln Glu Arg
145                 150                 155                 160

Gly Tyr Arg Thr Val Ala Glu Met Leu Leu Arg Asp Glu Arg Tyr Arg
                165                 170                 175

Asp His Arg Arg Asn Lys Gly Gly Ala Tyr Ile Ala Thr Val Gly Arg
            180                 185                 190

Asp Met Val Glu Asp Glu Val Arg Gln Ile Phe Ala Ala Gln Arg Ala
        195                 200                 205

Leu Gly Ser Thr Ala Ala Ser Glu Thr Leu Glu Thr Ala Tyr Leu Glu
    210                 215                 220

Ile Leu Leu Ser Gln Arg Ser Phe Asp Ala Gly Pro Gly Glu Pro Ser
225                 230                 235                 240

Pro Tyr Ala Gly Gly Gln Ile Glu Arg Met Ile Gly Arg Cys Thr Phe
                245                 250                 255

Glu Pro Asp Glu Pro Arg Ala Ala Arg Ala Thr Tyr Ser Phe Glu Tyr
            260                 265                 270

Phe Ser Leu Leu Glu Ala Val Asn His Ile Arg Leu Thr Glu Ala Gly
        275                 280                 285

Glu Ser Val Pro Leu Thr Lys Glu Gln Arg Glu Lys Leu Ile Ala Leu
    290                 295                 300

Ala His Arg Thr Ala Asp Leu Ser Tyr Ala Lys Ile Arg Lys Glu Leu
305                 310                 315                 320

Gly Val Pro Glu Ser Gln Arg Phe Asn Met Val Thr Tyr Gly Lys Thr
                325                 330                 335
```

```
Asp Ser Ala Asp Glu Ala Glu Lys Lys Thr Lys Leu Lys Gln Leu Arg
            340                 345                 350
Ala Tyr His Gln Met Arg Ala Ala Phe Glu Lys Ala Ala Lys Gly Ser
        355                 360                 365
Phe Val Leu Leu Thr Lys Glu Gln Arg Asn Ala Val Gly Gln Thr Leu
    370                 375                 380
Ser Ile Tyr Lys Thr Ser Asp Asn Ile Arg Pro Arg Leu Arg Glu Ala
385                 390                 395                 400
Gly Leu Thr Glu Ala Glu Ile Asp Val Ala Glu Gly Leu Ser Phe Ser
                405                 410                 415
Lys Phe Gly His Leu Ser Val Lys Ala Cys Asp Lys Ile Ile Pro Phe
            420                 425                 430
Leu Glu Gln Gly Met Lys Tyr Ser Glu Ala Cys Val Ala Ala Gly Tyr
        435                 440                 445
Ala Phe Arg Gly His Glu Gly Gln Asp Lys Gln Arg Leu Leu Pro Pro
    450                 455                 460
Leu Asp Asn Asp Ala Lys Asp Thr Ile Thr Ser Pro Val Val Leu Arg
465                 470                 475                 480
Ala Val Ser Gln Thr Ile Lys Val Val Asn Ala Ile Ile Arg Glu Arg
                485                 490                 495
Gly Gly Ser Pro Thr Phe Ile Asn Ile Glu Leu Ala Arg Glu Met Ala
            500                 505                 510
Lys Asp Phe Ser Glu Arg Ser Gln Ile Lys Arg Glu Gln Asp Ser Asn
        515                 520                 525
Arg Ala Arg Asn Glu Arg Met Met Glu Arg Ile Lys Thr Glu Tyr Gly
    530                 535                 540
Lys Ser Ser Pro Thr Gly Leu Asp Leu Val Lys Leu Lys Leu Tyr Glu
545                 550                 555                 560
Glu Gln Ala Gly Val Cys Ala Tyr Ser Leu Lys Gln Met Ser Leu Glu
                565                 570                 575
His Leu Phe Asp Pro Asn Tyr Ala Glu Ile Asp His Ile Ile Pro Tyr
            580                 585                 590
Ser Ile Ser Phe Asp Asp Gly Tyr Lys Asn Lys Val Leu Val Leu Ala
        595                 600                 605
Lys Glu Asn Arg Asp Lys Gly Asn Arg Leu Pro Leu Glu Tyr Leu Asn
    610                 615                 620
Gly Lys Arg Arg Glu Asp Phe Ile Val Trp Val Asn Ser Ser Val Arg
625                 630                 635                 640
Asp Trp Arg Lys Lys Gln Asn Leu Leu Lys Glu His Val Thr Pro Glu
                645                 650                 655
Asp Glu Ala Lys Phe Lys Glu Arg Asn Leu Gln Asp Thr Lys Thr Ala
            660                 665                 670
Ser Arg Phe Leu Leu Asn Tyr Ile Ala Asp Asn Leu Ala Phe Ala Pro
        675                 680                 685
Phe Gln Thr Glu Arg Lys Lys Arg Val Thr Ala Val Asn Gly Ser Val
    690                 695                 700
Thr Ala Tyr Leu Arg Lys Arg Trp Gly Ile Ala Lys Val Arg Ala Asn
705                 710                 715                 720
Gly Asp Leu His His Ala Val Asp Ala Leu Val Ile Ala Cys Thr Thr
                725                 730                 735
Asp Gly Leu Ile Gln Lys Val Ser Arg Tyr Ala Cys Tyr Gln Glu Asn
            740                 745                 750
Arg Tyr Ser Glu Ala Gly Gly Val Ile Val Asp Ser Ala Thr Gly Glu
```

```
              755                 760                 765
Val Val Ala Gln Phe Pro Glu Pro Trp Pro Arg Phe Arg His Glu Leu
    770                 775                 780

Glu Ala Arg Leu Ser Asp Asp Pro Ala Arg Ala Val Leu Gly Leu Gly
785                 790                 795                 800

Leu Ala His Tyr Met Thr Gly Glu Ile Arg Pro Arg Pro Leu Phe Val
                805                 810                 815

Ser Arg Met Pro Arg Arg Lys Val Thr Gly Ala Ala His Lys Glu Thr
            820                 825                 830

Val Lys Ser Pro Arg Ala Leu Asp Glu Gly Gln Leu Val Thr Lys Thr
        835                 840                 845

Pro Leu Ser Ala Leu Lys Leu Gly Lys Asp Gly Glu Ile Pro Gly Tyr
    850                 855                 860

Tyr Lys Pro Glu Ser Asp Arg Leu Leu Tyr Glu Ala Leu Lys Ala Arg
865                 870                 875                 880

Leu Arg Gln Phe Gly Gly Asp Gly Lys Lys Ala Phe Ala Glu Pro Phe
                885                 890                 895

His Lys Pro Lys His Asp Gly Thr Pro Gly Pro Val Val Thr Lys Val
            900                 905                 910

Lys Leu Cys Glu Pro Ala Thr Leu Ser Val Pro Val His Gly Gly Leu
        915                 920                 925

Gly Ala Ala Asn Asn Asp Ser Met Val Arg Ile Asp Val Phe His Val
    930                 935                 940

Glu Gly Asp Gly Tyr Tyr Phe Val Pro Ile Tyr Ile Ala Asp Thr Leu
945                 950                 955                 960

Lys Leu Glu Leu Pro Asn Lys Ala Cys Val Lys Ile Lys Lys Ile Ser
                965                 970                 975

Glu Trp Lys His Met Lys Pro Gln Asp Phe Met Phe Ser Leu Tyr Pro
            980                 985                 990

Asn Asp Leu Phe Arg Ile Val Ser Lys Lys Gly Ile Thr Leu Asn Leu
        995                 1000                1005

Val Ser Lys Glu Ser Thr Leu Pro Thr Ser Val Asn Val Ser Asp
    1010                1015                1020

Thr Leu Leu Tyr Phe Val Ser Ala Gly Ile Ala Ser Ala Cys Leu
    1025                1030                1035

Thr Cys Arg Asn His Asp Asn Thr Tyr Gln Ile Glu Ser Leu Gly
    1040                1045                1050

Ile Lys Thr Leu Glu Lys Leu Glu Lys Tyr Thr Val Asp Val Leu
    1055                1060                1065

Gly Asn Val His Arg Val Glu Lys Glu Pro Arg Met Ser Phe Ser
    1070                1075                1080

Gln Lys Gly Asp
    1085

<210> SEQ ID NO 62
<211> LENGTH: 36
<212> TYPE: DNA
<213> ORGANISM: Artificial Sequence
<220> FEATURE:
<223> OTHER INFORMATION: CR RNA

<400> SEQUENCE: 62
gttatagttc cctgttcgtt cttggtatgg tataat                              36

<210> SEQ ID NO 63
```

-continued

```
<211> LENGTH: 89
<212> TYPE: DNA
<213> ORGANISM: Artificial Sequence
<220> FEATURE:
<223> OTHER INFORMATION: TRACR RNA

<400> SEQUENCE: 63
ttataccata ccaagaacga agcaggttac tatgataagg tagtataccg cagagctcca    60
acgcctcgct tttgcggggc gttgtctct                                      89

<210> SEQ ID NO 64
<211> LENGTH: 1097
<212> TYPE: PRT
<213> ORGANISM: Clostridium absonum

<400> SEQUENCE: 64
```

Met Leu Pro Tyr Gly Ile Gly Leu Asp Ile Gly Ile Thr Ser Val Gly
1               5                   10                  15

Trp Ala Thr Val Ala Leu Asp Glu Asn Asp Arg Pro Tyr Gly Ile Ile
            20                  25                  30

Gly Met Gly Ser Arg Ile Phe Asp Ala Ala Glu Gln Pro Lys Thr Gly
        35                  40                  45

Glu Ser Leu Ala Ala Pro Arg Arg Ala Ala Arg Ser Ala Arg Arg Arg
    50                  55                  60

Leu Arg Arg His Arg His Arg Asn Glu Arg Ile Arg Ala Leu Ile Leu
65                  70                  75                  80

Arg Glu Asn Leu Leu Ser Glu Gly Gln Leu Leu His Leu Tyr Asp Gly
                85                  90                  95

Gln Leu Ser Asp Val Tyr Ser Leu Arg Val Lys Ala Leu Asp Glu Arg
            100                 105                 110

Val Ser Asn Glu Glu Phe Ala Arg Ile Leu Ile His Ile Ser Gln Arg
        115                 120                 125

Arg Gly Phe Lys Ser Asn Arg Lys Gly Ala Ser Ser Lys Glu Asp Ser
    130                 135                 140

Glu Leu Leu Ala Ala Ile Ser Ala Asn Gln Val Arg Met Gln Gln Gln
145                 150                 155                 160

Gly Tyr Arg Thr Val Ala Glu Met Tyr Leu Lys Asp Pro Ile Tyr Gln
                165                 170                 175

Glu His Arg Arg Asn Lys Gly Gly Asn Tyr Ile Ala Thr Val Ser Arg
            180                 185                 190

Ala Met Val Glu Asp Glu Val His Gln Ile Phe Thr Gly Gln Arg Ala
        195                 200                 205

Cys Gly Asn Pro Ala Ala Thr Lys Glu Leu Glu Glu Ala Tyr Val Glu
    210                 215                 220

Ile Leu Leu Ser Gln Arg Ser Phe Asp Asp Gly Pro Gly Asp Gly Ser
225                 230                 235                 240

Pro Tyr Ala Gly Ser Gln Ile Glu Arg Met Ile Gly Lys Cys Gln Leu
                245                 250                 255

Glu Lys Glu Ala Gly Glu Pro Arg Ala Ala Lys Ala Thr Tyr Ser Phe
            260                 265                 270

Glu Tyr Phe Ser Leu Leu Ala Ala Ile Asn Asn Ile Ser Ile Ile Ser
        275                 280                 285

Asn Gly Gln Leu Ser Pro Leu Thr Lys Glu Gly Arg Glu Met Leu Ile
    290                 295                 300

Ala Leu Ala His Lys Thr Ser Glu Leu Asn Tyr Ala Arg Ile Arg Lys
305                 310                 315                 320

```
Glu Leu Gly Leu Ser Glu Ala Gln Arg Phe Asn Thr Val Ser Tyr Gly
            325                 330                 335
Lys Met Glu Ile Ala Glu Ala Glu Lys Lys Thr Lys Phe Glu His Leu
            340                 345                 350
Lys Ala Tyr His Lys Met Arg Arg Glu Phe Glu Arg Ile Ala Lys Gly
            355                 360                 365
His Phe Ala Ser Ile Thr Ile Glu Gln Arg Asn Ala Ile Gly Asp Val
            370                 375                 380
Leu Ser Lys Tyr Lys Thr Asp Ala Lys Ile Arg Pro Ala Leu Arg Glu
385                 390                 395                 400
Ala Gly Leu Thr Glu Leu Asp Ile Asp Ala Ala Glu Ala Leu Asn Phe
            405                 410                 415
Ser Lys Phe Gly His Ile Ser Ile Lys Ala Cys Lys Lys Ile Ile Pro
            420                 425                 430
Trp Leu Glu Gln Gly Met Lys Tyr Ser Glu Ala Cys Asn Ala Ala Gly
            435                 440                 445
Tyr Asn Phe Lys Gly His Asp Gly Gln Glu Lys Ser His Leu Leu Pro
            450                 455                 460
Pro Leu Asp Glu Glu Ser Arg Asn Val Ile Thr Ser Pro Val Ala Leu
465                 470                 475                 480
Arg Ala Ile Ser Gln Thr Ile Lys Val Val Asn Ala Ile Ile Arg Glu
            485                 490                 495
Arg Gly Cys Ser Pro Thr Phe Ile Asn Ile Glu Leu Ala Arg Glu Met
            500                 505                 510
Ser Lys Asp Phe Tyr Glu Arg Ile Glu Lys Lys Glu Gln Asp Gly
            515                 520                 525
Asn Arg Ala Lys Asn Glu Arg Met Met Glu Arg Ile Arg Thr Glu Tyr
            530                 535                 540
Gly Lys Ala Ser Pro Thr Gly Gln Asp Leu Val Lys Phe Lys Leu Tyr
545                 550                 555                 560
Glu Glu Gln Gly Gly Val Cys Ala Tyr Ser Leu Lys Gln Met Ser Leu
            565                 570                 575
Ala His Leu Phe Glu Pro Asp Tyr Ala Glu Val Asp His Ile Val Pro
            580                 585                 590
Tyr Ser Ile Ser Phe Asp Asp Gly Tyr Lys Asn Lys Val Leu Val Leu
            595                 600                 605
Ala Lys Glu Asn Arg Asp Lys Gly Asn Arg Leu Pro Leu Gln Tyr Leu
            610                 615                 620
Gln Gly Lys Arg Arg Glu Asp Phe Ile Ala Trp Val Asn Ser Cys Val
625                 630                 635                 640
Arg Asp Tyr Lys Lys Arg Gln Arg Leu Leu Lys Glu Ser Ile Ser Glu
            645                 650                 655
Asp Asp Leu Arg Ala Phe Lys Glu Arg Asn Leu Gln Asp Thr Lys Thr
            660                 665                 670
Ala Ser Arg Phe Leu Leu Asn Tyr Ile Ser Asp His Leu Glu Phe Thr
            675                 680                 685
Gln Phe Ala Thr Glu Arg Lys Lys His Val Thr Ala Val Asn Gly Ser
            690                 695                 700
Val Thr Ala Tyr Leu Arg Lys Arg Trp Gly Ile Thr Lys Ile Arg Glu
705                 710                 715                 720
Asn Gly Asp Leu His His Ala Val Asp Ala Leu Val Ile Ala Cys Thr
            725                 730                 735
```

-continued

Thr Asp Gly Met Ile Gln Gln Val Ser Arg Phe Ala Gln His Arg Glu
          740                 745                 750

Asn Gln Tyr Ser Leu Ala Glu Asp Ser Arg Phe Ile Ile Asp Pro Glu
      755                 760                 765

Thr Gly Glu Val Ile Lys Glu Phe Pro Tyr Pro Trp Pro Arg Phe Arg
  770                 775                 780

Gln Glu Leu Glu Ala Arg Leu Ser Ser Asn Pro Gly Leu Ala Val Arg
785                 790                 795                 800

Asp Arg Gly Phe Leu Leu Tyr Met Ala Glu Ser Ile Pro Val His Pro
              805                 810                 815

Leu Phe Val Ser Arg Met Pro Arg Arg Lys Val Thr Gly Ala Ala His
          820                 825                 830

Lys Glu Thr Ile Lys Ser Gly Lys Ala Gln Lys Asp Gly Leu Leu Ile
      835                 840                 845

Val Lys Lys Pro Leu Thr Asp Leu Lys Leu Asp Lys Glu Gly Glu Ile
  850                 855                 860

Ala Asn Tyr Tyr Asn Pro Met Ser Asp Arg Leu Leu Tyr Glu Ala Leu
865                 870                 875                 880

Lys Lys Arg Leu Thr Ala Phe Asn Gly Asp Gly Lys Lys Ala Phe Ala
              885                 890                 895

Asp Pro Phe Tyr Lys Pro Lys Ser Asp Gly Thr Gln Gly Pro Leu Val
          900                 905                 910

Asn Lys Val Lys Leu Cys Glu Pro Ser Thr Leu Asn Val Ser Val Ile
      915                 920                 925

Gly Gly Lys Gly Val Ala Glu Asn Asp Ser Met Val Arg Ile Asp Val
  930                 935                 940

Phe Arg Val Glu Gly Asp Gly Tyr Tyr Phe Val Pro Val Tyr Val Ala
945                 950                 955                 960

Asp Thr Val Lys Pro Glu Leu Pro Asn Lys Ala Cys Val Ala Asn Lys
              965                 970                 975

Pro Tyr Thr Asp Trp Lys Glu Met Arg Glu Ser Asp Phe Leu Phe Ser
          980                 985                 990

Leu Tyr Pro Asn Asp Leu Leu Lys Val Thr His Lys Lys Ala Leu Ile
      995                 1000                1005

Leu Thr Lys Ala Gln Lys Asp Ser Asp Leu Pro Asp Cys Lys Glu
      1010                1015                1020

Thr Lys Ser Glu Met Leu Tyr Phe Val Ser Ala Ser Ile Ser Thr
      1025                1030                1035

Ala Ser Leu Ala Cys Arg Thr His Asp Asn Ser Tyr Arg Ile Asn
      1040                1045                1050

Ser Leu Gly Ile Lys Thr Leu Glu Ala Leu Glu Lys Tyr Thr Val
      1055                1060                1065

Asp Val Leu Gly Glu Tyr His Pro Val Arg Arg Glu Thr Arg Gln
      1070                1075                1080

Thr Phe Thr Gly Arg Glu Ser Ser Gly His Ser Gly Ile Ser
      1085                1090                1095

<210> SEQ ID NO 65
<211> LENGTH: 36
<212> TYPE: DNA
<213> ORGANISM: Artificial Sequence
<220> FEATURE:
<223> OTHER INFORMATION: CR RNA

<400> SEQUENCE: 65

```
gttatagttc cctgatagtt cttggtatgg tataat                              36
```

<210> SEQ ID NO 66
<211> LENGTH: 88
<212> TYPE: DNA
<213> ORGANISM: Artificial Sequence
<220> FEATURE:
<223> OTHER INFORMATION: TRACR RNA

<400> SEQUENCE: 66

```
ttataccata ccaagaacta tgaggttgct ataataaggt agtaaaccgc agagctctaa   60
cgcctcacat ttgtggggcg ttatctct                                      88
```

<210> SEQ ID NO 67
<211> LENGTH: 1088
<212> TYPE: PRT
<213> ORGANISM: Ruminococcus albus

<400> SEQUENCE: 67

```
Met Arg Pro Tyr Gly Ile Gly Leu Asp Ile Gly Ile Ser Ser Val Gly
1               5                   10                  15

Trp Ala Ala Ile Ala Leu Asp His Gln Asp Ser Pro Cys Gly Ile Leu
            20                  25                  30

Asp Met Gly Ala Arg Ile Phe Asp Ala Ala Glu Asn Pro Lys Asp Gly
        35                  40                  45

Ala Ser Leu Ala Ala Pro Arg Arg Glu Lys Arg Ser Gln Arg Arg Arg
    50                  55                  60

Leu Arg Arg His Arg His Arg Asn Glu Arg Ile Arg Arg Met Leu Leu
65                  70                  75                  80

Lys Glu Gly Leu Leu Thr Glu Ala Glu Leu Thr Gly Leu Phe Asp Gly
                85                  90                  95

Ala Leu Glu Asp Ile Tyr Ala Leu Arg Thr Arg Ala Leu Asp Glu Ala
            100                 105                 110

Leu Thr Lys Gln Glu Phe Ala Arg Val Leu Leu His Leu Ser Gln Arg
        115                 120                 125

Arg Gly Phe Arg Ser Asn Arg Arg Ala Thr Ala Ala Gln Glu Asp Gly
    130                 135                 140

Lys Leu Leu Asp Ala Val Ser Glu Asn Ala Lys Arg Met Ala Asp Cys
145                 150                 155                 160

Gly Tyr Arg Thr Val Gly Glu Met Leu Cys Arg Asp Ala Thr Phe Ala
                165                 170                 175

Lys His Lys Arg Asn Lys Gly Gly Glu Tyr Leu Thr Thr Val Ser Arg
            180                 185                 190

Ala Met Ile Glu Asp Glu Val Lys Leu Val Phe Ala Ser Gln Arg Arg
        195                 200                 205

Leu Gly Ser Ala Phe Ala Ser Glu Ala Leu Glu Gln Gly Tyr Leu Asp
    210                 215                 220

Ile Leu Leu Ser Gln Arg Ser Phe Asp Glu Gly Pro Gly Gly Asn Ser
225                 230                 235                 240

Pro Tyr Gly Gly Ala Gln Ile Glu Arg Met Ile Gly Lys Cys Thr Phe
                245                 250                 255

Tyr Pro Glu Glu Pro Arg Ala Ala Arg Ala Cys Tyr Ser Phe Glu Tyr
            260                 265                 270

Phe Ser Leu Leu Gln Lys Val Asn His Ile Arg Leu Gln Lys Asp Gly
        275                 280                 285

Glu Ser Thr Pro Leu Thr Ser Glu Gln Arg Leu Gln Leu Ile Glu Leu
```

```
            290                 295                 300
Ala His Lys Thr Glu Asn Leu Asp Tyr Ala Arg Ile Arg Arg Ala Leu
305                 310                 315                 320

Gln Ile Pro Asp Ala Tyr Arg Phe Asn Thr Val Ser Tyr Arg Ile Glu
                325                 330                 335

Ser Asp Pro Ala Ala Glu Lys Lys Glu Lys Phe Gln Tyr Leu Arg
                340                 345                 350

Ala Tyr His Thr Met Arg Lys Ala Ile Asp Gly Ala Ser Lys Gly Arg
                355                 360                 365

Phe Ala Leu Leu Ser Gln Glu Gln Arg Asp Gln Ile Gly Thr Val Leu
                370                 375                 380

Thr Leu Tyr Lys Ser Gln Glu Arg Ile Ser Glu Lys Leu Thr Glu Ala
385                 390                 395                 400

Gly Ile Glu Pro Cys Asp Ile Ala Ala Leu Glu Ser Val Ser Gly Phe
                405                 410                 415

Ser Lys Thr Gly His Ile Ser Leu Arg Ala Cys Lys Glu Leu Ile Pro
                420                 425                 430

Tyr Leu Glu Gln Gly Met Asn Tyr Asn Glu Ala Cys Ala Ala Gly
                435                 440                 445

Ile Glu Phe His Gly His Ser Gly Thr Glu Arg Thr Val Val Leu His
450                 455                 460

Pro Thr Pro Asp Asp Leu Ala Asp Ile Thr Ser Pro Val Val Arg Arg
465                 470                 475                 480

Ala Val Ala Gln Thr Val Lys Val Ile Asn Ala Val Ile Arg Arg Tyr
                485                 490                 495

Gly Ser Pro Val Phe Val Asn Ile Glu Leu Ala Arg Glu Leu Ala Lys
                500                 505                 510

Asp Phe Thr Glu Arg Lys Lys Leu Glu Lys Asp Asn Lys Thr Asn Arg
                515                 520                 525

Ala Glu Asn Glu Arg Leu Met Arg Arg Ile Arg Glu Glu Tyr Gly Lys
                530                 535                 540

Met Asn Pro Thr Gly Leu Asp Leu Val Lys Leu Arg Leu Tyr Glu Glu
545                 550                 555                 560

Gln Ala Gly Val Cys Pro Tyr Ser Gln Lys Gln Met Ser Leu Gln Arg
                565                 570                 575

Leu Phe Glu Pro Asn Tyr Ala Glu Val Asp His Ile Ile Pro Tyr Ser
                580                 585                 590

Ile Ser Phe Asp Asp Ser Arg Arg Asn Lys Val Leu Val Leu Ala Glu
                595                 600                 605

Glu Asn Arg Asn Lys Gly Asn Arg Leu Pro Leu Gln Tyr Leu Thr Gly
                610                 615                 620

Glu Arg Arg Asp Asn Phe Ile Val Trp Val Asn Ser Ser Val Arg Asp
625                 630                 635                 640

Tyr Arg Lys Lys Gln Lys Leu Leu Lys Pro Thr Val Thr Asp Glu Asp
                645                 650                 655

Lys Gln Gln Phe Lys Glu Arg Asn Leu Gln Asp Thr Lys Thr Met Ser
                660                 665                 670

Arg Phe Leu Met Asn Tyr Ile Asn Asp His Leu Gln Phe Gly Val Ser
                675                 680                 685

Ala Lys Glu Arg Lys Lys Arg Val Thr Ala Val Asn Gly Ile Val Thr
                690                 695                 700

Ser Tyr Leu Arg Lys Arg Trp Gly Ile Thr Lys Ile Arg Gly Asp Gly
705                 710                 715                 720
```

Asp Leu His His Ala Val Asp Ala Leu Val Ile Ala Cys Ala Thr Asp
            725                 730                 735

Gly Met Ile Arg Gln Ile Thr Arg Tyr Ala Gln Tyr Arg Glu Cys Arg
        740                 745                 750

Tyr Met Gln Thr Asp Thr Gly Ser Ala Ala Ile Asp Glu Ala Thr Gly
        755                 760                 765

Glu Val Leu Arg Ile Phe Pro Tyr Pro Trp Glu His Phe Arg Lys Glu
    770                 775                 780

Leu Glu Ala Arg Leu Ser Ser Asp Pro Ala Arg Ala Val Asn Ala Leu
785                 790                 795                 800

Arg Leu Pro Phe Tyr Leu Asp Ser Gly Glu Pro Leu Pro Lys Pro Leu
            805                 810                 815

Phe Val Ser Arg Met Pro Arg Arg Lys Val Ser Gly Ala Ala His Lys
        820                 825                 830

Asp Thr Val Lys Ser Pro Lys Ala Met Ala Glu Gly Lys Val Ile Val
        835                 840                 845

Arg Arg Ala Leu Thr Asp Leu Lys Leu Lys Asn Gly Glu Ile Glu Asn
850                 855                 860

Tyr Phe Asp Pro Gly Ser Asp Arg Leu Leu Tyr Asp Ala Leu Lys Ala
865                 870                 875                 880

Arg Leu Ala Ala Phe Gly Gly Asp Gly Ala Lys Ala Phe Arg Glu Pro
            885                 890                 895

Phe Tyr Lys Pro Arg His Asp Gly Thr Pro Gly Pro Leu Val Lys Lys
        900                 905                 910

Val Lys Leu Cys Glu Pro Thr Thr Leu Asn Val Ala Val His Gly Gly
        915                 920                 925

Lys Gly Val Ala Asp Asn Asp Ser Met Val Arg Ile Asp Val Phe Arg
930                 935                 940

Val Glu Gly Asp Gly Tyr Tyr Phe Val Pro Ile Tyr Ile Ala Asp Thr
945                 950                 955                 960

Leu Lys Pro Val Leu Pro Asn Lys Ala Cys Val Ala Phe Lys Pro Tyr
            965                 970                 975

Ser Glu Trp Arg Thr Met Asp Asp Arg Asp Phe Ile Phe Ser Leu Tyr
        980                 985                 990

Pro Asn Asp Leu Ile Arg Val Thr His Lys Ser Ala Leu Lys Leu Ser
        995                 1000                1005

Arg Val Ser Lys Glu Ser Thr Leu Pro Glu Ser Ile Glu Ser Lys
    1010                1015                1020

Thr Ala Leu Leu Tyr Tyr Val Ser Ala Gly Ile Ser Gly Ala Ala
    1025                1030                1035

Val Ser Cys Arg Asn His Asp Asn Ser Tyr Glu Ile Lys Ser Met
    1040                1045                1050

Gly Ile Lys Thr Leu Glu Lys Leu Glu Lys Tyr Thr Val Asp Val
    1055                1060                1065

Leu Gly Glu Tyr His Lys Val Glu Lys Glu Arg Arg Met Pro Phe
    1070                1075                1080

Thr Gly Lys Arg Ser
    1085

<210> SEQ ID NO 68
<211> LENGTH: 36
<212> TYPE: DNA
<213> ORGANISM: Artificial Sequence
<220> FEATURE:

<223> OTHER INFORMATION: CR RNA

<400> SEQUENCE: 68
gttgtagttc cctgatcgtt cttggtatgg tataat                                    36

<210> SEQ ID NO 69
<211> LENGTH: 90
<212> TYPE: DNA
<213> ORGANISM: Artificial Sequence
<220> FEATURE:
<223> OTHER INFORMATION: TRACR RNA

<400> SEQUENCE: 69
ttataccata ccaagaacga tcaggttgct acaataaggt agtaaaccga agagctctaa          60
cgccccgttt ctttacgggg cgttatctct                                          90

<210> SEQ ID NO 70
<211> LENGTH: 1095
<212> TYPE: PRT
<213> ORGANISM: Ruminococcus albus

<400> SEQUENCE: 70

Met Arg Pro Tyr Ala Ile Gly Leu Asp Ile Gly Ile Thr Ser Val Gly
1               5                   10                  15

Trp Ala Thr Val Ala Leu Asp Ala Asp Glu Ser Pro Cys Gly Ile Ile
            20                  25                  30

Gly Leu Gly Ser Arg Ile Phe Asp Ala Ala Glu Gln Pro Lys Thr Gly
        35                  40                  45

Glu Ser Leu Ala Ala Pro Arg Arg Ala Arg Gly Ser Arg Arg Arg
    50                  55                  60

Leu Arg Arg His Arg His Arg Asn Glu Arg Ile Arg Ser Leu Met Leu
65                  70                  75                  80

Glu Glu Arg Leu Ile Ser Gln Asp Glu Leu Glu Thr Leu Phe Asp Gly
                85                  90                  95

Arg Leu Glu Asp Ile Tyr Ala Leu Arg Val Lys Ala Leu Asp Glu Ile
            100                 105                 110

Val Ser Arg Thr Asp Phe Ala Arg Ile Leu Leu His Ile Ser Gln Arg
        115                 120                 125

Arg Gly Phe Lys Ser Asn Arg Lys Asn Pro Thr Thr Lys Glu Asp Gly
    130                 135                 140

Val Leu Leu Ala Ala Val Asn Glu Asn Lys Gln Arg Met Ser Glu His
145                 150                 155                 160

Gly Tyr Arg Thr Val Gly Glu Met Phe Leu Leu Asp Glu Thr Phe Lys
                165                 170                 175

Asp His Lys Arg Asn Lys Gly Gly Asn Tyr Ile Thr Thr Val Ala Arg
            180                 185                 190

Asp Met Val Ala Asp Glu Val Arg Ala Ile Phe Ser Ala Gln Arg Glu
        195                 200                 205

Leu Gly Ala Ser Phe Ala Ser Glu Glu Phe Glu Glu Arg Tyr Leu Glu
    210                 215                 220

Ile Leu Leu Ser Gln Arg Ser Phe Asp Glu Gly Pro Gly Gly Asn Ser
225                 230                 235                 240

Pro Tyr Gly Gly Ser Gln Ile Glu Arg Met Val Gly Arg Cys Thr Phe
                245                 250                 255

Phe Pro Asp Glu Pro Arg Ala Ala Lys Ala Thr Tyr Ser Phe Glu Tyr
            260                 265                 270

```
Phe Thr Leu Leu Gln Lys Val Asn His Ile Arg Ile Glu Asn Gly
            275                 280                 285

Val Ala Ser Lys Leu Thr Asp Glu Gln Arg Arg Ile Ile Ile Glu Leu
    290                 295                 300

Ala His Thr Thr Lys Asp Val Ser Tyr Ala Lys Ile Arg Lys Val Leu
305                 310                 315                 320

Lys Leu Ser Asp Lys Gln Leu Phe Asn Ile Arg Tyr Ser Asp Asn Ser
                325                 330                 335

Pro Ala Glu Asp Ser Glu Lys Lys Glu Lys Leu Gly Ile Met Lys Ala
                340                 345                 350

Tyr His Gln Met Arg Ser Ala Ile Asp Arg Val Ser Lys Gly Arg Phe
            355                 360                 365

Ala Met Met Pro Arg Ala Gln Arg Asn Ala Ile Gly Thr Ala Leu Ser
370                 375                 380

Leu Tyr Lys Thr Ser Asp Lys Ile Arg Lys Tyr Leu Thr Asp Ala Gly
385                 390                 395                 400

Leu Asp Glu Ile Asp Ile Asn Ser Ala Asp Ser Ile Gly Ser Phe Ser
                405                 410                 415

Lys Phe Gly His Ile Ser Val Lys Ala Cys Asp Met Leu Ile Pro Phe
                420                 425                 430

Leu Glu Gln Gly Met Asn Tyr Asn Glu Ala Cys Ala Ala Ala Gly Leu
            435                 440                 445

Asn Phe Lys Gly His Asp Ala Gly Glu Lys Ser Lys Leu Leu His Pro
        450                 455                 460

Lys Glu Glu Asp Tyr Glu Asp Ile Thr Ser Pro Val Val Arg Arg Ala
465                 470                 475                 480

Ile Ala Gln Thr Ile Lys Val Ile Asn Ala Ile Ile Arg Arg Glu Gly
                485                 490                 495

Cys Ser Pro Thr Phe Ile Asn Ile Glu Leu Ala Arg Glu Met Ala Lys
            500                 505                 510

Asp Phe Arg Glu Arg Asn Arg Ile Lys Lys Glu Asn Asp Asp Asn Arg
        515                 520                 525

Ala Lys Asn Glu Arg Leu Leu Glu Arg Ile Arg Thr Glu Tyr Gly Lys
    530                 535                 540

Asn Asn Pro Thr Gly Leu Asp Leu Val Lys Leu Arg Leu Tyr Glu Glu
545                 550                 555                 560

Gln Ser Gly Val Cys Met Tyr Ser Leu Lys Gln Met Ser Leu Glu Lys
                565                 570                 575

Leu Phe Glu Pro Asn Tyr Ala Glu Val Asp His Ile Val Pro Tyr Ser
            580                 585                 590

Ile Ser Phe Asp Asp Ser Arg Lys Asn Lys Val Leu Val Leu Thr Glu
        595                 600                 605

Glu Asn Arg Asn Lys Gly Asn Arg Leu Pro Leu Gln Tyr Leu Lys Gly
        610                 615                 620

Arg Arg Arg Glu Asp Phe Ile Val Trp Val Asn Asn Val Lys Asp
625                 630                 635                 640

Tyr Arg Lys Arg Arg Leu Leu Leu Lys Glu Glu Leu Thr Ala Glu Asp
                645                 650                 655

Glu Ser Gly Phe Lys Glu Arg Asn Leu Gln Asp Thr Lys Thr Met Ser
            660                 665                 670

Arg Phe Leu Leu Asn Tyr Ile Ala Asp Asn Leu Glu Phe Ala Glu Ser
        675                 680                 685

Thr Arg Gly Arg Lys Lys Lys Val Thr Ala Val Asn Gly Ala Val Thr
```

-continued

```
            690                 695                 700
Ala Tyr Met Arg Lys Arg Trp Gly Ile Thr Lys Ile Arg Glu Asp Gly
705                 710                 715                 720

Asp Cys His His Ala Val Asp Ala Val Val Ile Ala Cys Thr Thr Asp
                725                 730                 735

Ala Met Ile Arg Gln Val Ser Arg Tyr Ala Gln Phe Arg Glu Cys Glu
                740                 745                 750

Tyr Met Gln Thr Glu Ser Gly Ser Val Ala Val Asp Thr Gly Thr Gly
            755                 760                 765

Glu Val Leu Arg Thr Phe Pro Tyr Pro Trp Pro Asp Phe Arg Lys Glu
770                 775                 780

Leu Glu Ala Arg Leu Ala Asn Asp Pro Ala Lys Val Ile Asn Asp Leu
785                 790                 795                 800

His Leu Pro Phe Tyr Met Ser Ala Gly Arg Pro Leu Pro Glu Pro Val
                805                 810                 815

Phe Val Ser Arg Met Pro Arg Arg Lys Val Thr Gly Ala Ala His Lys
                820                 825                 830

Asp Thr Ile Lys Ser Ala Arg Glu Leu Asp Asn Gly Tyr Leu Ile Val
            835                 840                 845

Lys Arg Pro Leu Thr Asp Leu Lys Leu Lys Asn Gly Glu Ile Glu Asn
850                 855                 860

Tyr Tyr Asn Pro Gln Ser Asp Lys Cys Leu Tyr Asp Ala Leu Lys Asn
865                 870                 875                 880

Ala Leu Ile Glu His Gly Gly Asp Ala Lys Lys Ala Phe Ala Gly Glu
                885                 890                 895

Phe Arg Lys Pro Lys Arg Asp Gly Thr Pro Gly Pro Ile Val Lys Lys
                900                 905                 910

Val Lys Leu Leu Glu Pro Thr Thr Met Cys Val Pro Val His Gly Gly
            915                 920                 925

Lys Gly Ala Ala Asp Asn Asp Ser Met Arg Val Asp Val Phe Leu
930                 935                 940

Ser Gly Gly Lys Tyr Tyr Leu Val Pro Ile Tyr Val Ala Asp Thr Leu
945                 950                 955                 960

Lys Pro Glu Leu Pro Asn Lys Ala Val Thr Arg Gly Lys Lys Tyr Ser
                965                 970                 975

Glu Trp Leu Glu Met Ala Asp Gly Asp Phe Ile Phe Ser Leu Tyr Pro
            980                 985                 990

Asn Asp Leu Ile Cys Ala Thr Ser Lys Asn Gly Ile Thr Leu Ser Val
                995                 1000                1005

Cys Arg Lys Asp Ser Thr Leu Pro Pro Thr Val Glu Ser Lys Ser
    1010                1015                1020

Phe Met Leu Tyr Tyr Arg Gly Thr Asp Ile Ser Thr Gly Ser Ile
    1025                1030                1035

Ser Cys Ile Thr His Asp Asn Ala Tyr Lys Leu Arg Gly Leu Gly
    1040                1045                1050

Val Lys Thr Leu Glu Lys Leu Glu Lys Tyr Thr Val Asp Val Leu
    1055                1060                1065

Gly Glu Tyr His Lys Val Gly Lys Glu Val Arg Gln Pro Phe Asn
    1070                1075                1080

Ile Lys Arg Arg Lys Ala Cys Pro Ser Glu Met Leu
    1085                1090                1095
```

<210> SEQ ID NO 71

```
<211> LENGTH: 36
<212> TYPE: DNA
<213> ORGANISM: Artificial Sequence
<220> FEATURE:
<223> OTHER INFORMATION: CR RNA

<400> SEQUENCE: 71
gttatagttc cctgatagtt cttggtatgg tataat                                36

<210> SEQ ID NO 72
<211> LENGTH: 131
<212> TYPE: DNA
<213> ORGANISM: Artificial Sequence
<220> FEATURE:
<223> OTHER INFORMATION: TRACR RNA

<400> SEQUENCE: 72
ttataccata ccaagaacta tttaggttac tatgataagg tttagtacac cttagagctc      60
tgacgcctcg cttttgcgag gcgttatctc tttatattgc caaaaatgca aatatatcgt     120
acaatggtgg c                                                          131

<210> SEQ ID NO 73
<211> LENGTH: 1086
<212> TYPE: PRT
<213> ORGANISM: Clostridium absonum

<400> SEQUENCE: 73
```

Met His Arg Tyr Ala Ile Gly Leu Asp Ile Gly Ile Thr Ser Val Gly
1               5                   10                  15

Trp Ala Ala Ile Ala Leu Asp Ala Glu Glu Asn Pro Cys Gly Met Leu
            20                  25                  30

Asp Phe Gly Ser Arg Ile Phe Thr Gly Ala Glu His Pro Lys Thr Gly
        35                  40                  45

Ala Ser Leu Ala Ala Pro Arg Arg Glu Ala Arg Gly Ala Arg Arg Arg
    50                  55                  60

Leu Arg Arg His Arg His Arg Asn Glu Arg Ile Arg Arg Leu Met Val
65                  70                  75                  80

Ser Gly Gly Leu Ile Ser Gln Glu Gln Leu Glu Ser Leu Phe Ala Gly
                85                  90                  95

Gln Leu Glu Asp Ile Tyr Ala Leu Arg Thr Arg Ala Leu Asp Glu Gln
            100                 105                 110

Val Ala Arg Glu Glu Leu Ala Arg Ile Met Leu His Leu Ser Gln Arg
        115                 120                 125

Arg Gly Phe Arg Ser Asn Arg Lys Gly Gly Ala Ala Glu Asp Gly
        130                 135                 140

Lys Leu Leu Glu Ala Val Gly Asp Asn Lys Arg Met Asp Glu Lys
145                 150                 155                 160

Gly Tyr Arg Thr Ala Gly Glu Met Phe Phe Lys Asp Glu Ala Phe Ala
                165                 170                 175

Ala His Lys Arg Asn Lys Gly Gly Asn Tyr Ile Ala Thr Val Thr Arg
            180                 185                 190

Ala Met Thr Glu Asp Glu Val His Arg Ile Phe Ala Ala Gln Arg Gly
        195                 200                 205

Phe Gly Ala Glu Tyr Ala Asn Glu Lys Leu Glu Ala Ala Tyr Leu Asp
    210                 215                 220

Ile Leu Leu Ser Gln Arg Ser Phe Asp Glu Gly Pro Gly Gly Asp Ser
225                 230                 235                 240

-continued

```
Pro Tyr Gly Gly Ser Gln Ile Glu Arg Met Ile Gly Thr Cys Ala Phe
            245                 250                 255

Glu Pro Asp Gln Pro Arg Ala Ala Lys Ala Ala Tyr Ser Phe Glu Tyr
        260                 265                 270

Phe Ser Leu Leu Glu Lys Leu Asn His Ile Arg Leu Val Ser Gly Gly
    275                 280                 285

Lys Ser Glu Pro Leu Thr Asp Ala Gln Arg Lys Lys Leu Ile Glu Leu
290                 295                 300

Ala His Lys Gln Asp Thr Leu Ser Tyr Ala Lys Ile Arg Lys Glu Leu
305                 310                 315                 320

Glu Leu Asn Glu Ala Val Arg Phe Asn Ser Val Arg Tyr Thr Asp Asp
                325                 330                 335

Ala Thr Phe Glu Glu Gln Glu Lys Lys Glu Lys Ile Val Cys Met Lys
            340                 345                 350

Ala Tyr His Ala Met Arg Lys Ala Val Asp Lys Asn Ala Lys Gly Arg
        355                 360                 365

Phe Ala Tyr Leu Thr Ile Pro Gln Arg Asn Glu Ile Gly Arg Val Leu
    370                 375                 380

Ser Thr Tyr Lys Thr Ser Ala Lys Ile Glu Pro Ala Leu Ala Ala Ala
385                 390                 395                 400

Gly Ile Glu Pro Cys Asp Ile Ala Ala Leu Glu Gly Leu Ser Phe Ser
                405                 410                 415

Lys Phe Gly His Leu Ser Ile Lys Ala Cys Asp Lys Leu Ile Pro Phe
            420                 425                 430

Leu Glu Lys Ala Met Asn Tyr Asn Asp Ala Cys Ala Ala Ala Gly Tyr
        435                 440                 445

Asp Phe Arg Gly His Ser Arg Asp Gly Arg Gln Met Tyr Leu Pro Pro
    450                 455                 460

Leu Gly Gly Asp Cys Thr Glu Ile Thr Ser Pro Val Val Arg Arg Ala
465                 470                 475                 480

Val Ser Gln Thr Ile Lys Val Ile Asn Ala Ile Ile Arg Arg Tyr Gly
                485                 490                 495

Thr Ser Pro Val Tyr Val Asn Ile Glu Leu Ala Arg Glu Met Ser Lys
            500                 505                 510

Asp Phe Ala Glu Arg Asn Lys Ile Lys Lys Gln Asn Asp Asp Asn Arg
        515                 520                 525

Ser Lys Asn Glu Lys Ile Lys Glu Gln Val Ala Glu Tyr Lys His Gly
    530                 535                 540

Ala Ala Thr Gly Leu Asp Ile Val Lys Met Lys Leu Phe Asn Glu Gln
545                 550                 555                 560

Gly Gly Ile Cys Ala Tyr Ser Gln Arg Gln Met Ser Leu Glu Arg Leu
                565                 570                 575

Phe Asp Pro Asn Tyr Ala Glu Val Asp His Ile Val Pro Tyr Ser Ile
            580                 585                 590

Ser Phe Asp Asp Arg Tyr Lys Asn Lys Val Leu Val Leu Thr Glu Glu
        595                 600                 605

Asn Arg Asn Lys Gly Asn Arg Leu Pro Leu Gln Tyr Leu Thr Gly Glu
    610                 615                 620

Arg Arg Asp Arg Phe Ile Val Trp Val Asn Asn Ser Val Arg Asp Phe
625                 630                 635                 640

Gln Lys Arg Lys Leu Leu Leu Lys Glu Ala Leu Thr Pro Glu Glu Glu
                645                 650                 655

Asn Asp Trp Lys Glu Arg Asn Leu Gln Asp Thr Lys Phe Val Ser Ser
```

```
                    660                 665                 670
Phe Leu Leu Asn Tyr Ile Asn Asp Asn Leu Leu Phe Ala Pro Ser Val
            675                 680                 685
Arg Arg Lys Lys Arg Val Thr Ala Val Asn Gly Ala Val Thr Asp Tyr
            690                 695                 700
Met Arg Lys Arg Trp Gly Ile Ser Lys Val Arg Glu Asp Gly Asp Arg
705                 710                 715                 720
His His Ala Val Asp Ala Val Val Ile Ala Cys Thr Asn Asp Ala Leu
                    725                 730                 735
Ile Gln Lys Val Ser Arg Tyr Glu Ser Trp His Glu Arg His Tyr Met
            740                 745                 750
Pro Thr Glu Asn Gly Ser Ile Leu Val Asp Pro Ala Thr Gly Glu Ile
            755                 760                 765
Lys Gln Thr Phe Pro Tyr Pro Trp Ala Met Phe Arg Lys Glu Leu Glu
            770                 775                 780
Ala Arg Leu Ser Asn Asp Pro Ser Arg Ala Val Ala Asp Leu Lys Leu
785                 790                 795                 800
Pro Phe Tyr Met Asp Ala Asp Ala Pro Pro Val Lys Pro Leu Phe Val
                    805                 810                 815
Ser Arg Met Pro Thr Arg Lys Val Thr Gly Ala Ala His Lys Asp Thr
                    820                 825                 830
Val Lys Ser Ala Arg Ala Leu Ala Asp Gly Leu Ala Ile Val Arg Arg
            835                 840                 845
Pro Leu Thr Ala Leu Lys Leu Asp Lys Asp Gly Glu Ile Ala Gly Tyr
            850                 855                 860
Tyr Asn Lys Asp Ser Asp Arg Leu Leu Tyr Asp Ala Leu Lys Ala Arg
865                 870                 875                 880
Leu Thr Glu Tyr Gly Gly Asn Ala Ala Lys Ala Phe Ala Glu Pro Phe
                    885                 890                 895
Tyr Lys Pro Lys Ser Asp Gly Thr Pro Gly Pro Val Val Asn Lys Val
                    900                 905                 910
Lys Leu Thr Glu Pro Thr Thr Leu Ser Val Pro Val Gln Asp Gly Thr
            915                 920                 925
Gly Ile Ala Asp Asn Asp Ser Met Val Arg Ile Asp Val Phe Arg Val
            930                 935                 940
Val Gly Asp Gly Tyr Tyr Phe Val Pro Val Tyr Val Ala Asp Thr Leu
945                 950                 955                 960
Lys Gln Glu Leu Pro Asp Arg Ala Val Val Ala Phe Lys Ala His Ser
                    965                 970                 975
Glu Trp Lys Val Met Ser Asp Gly Asp Phe Val Phe Ser Leu Tyr Pro
                    980                 985                 990
Asn Asp Leu Val Lys Val Thr Arg  Lys Lys Asp Val Ile  Leu Lys Arg
            995                 1000                1005
Ser Phe Asp Asn Ser Thr Leu  Pro Glu Thr Ile Ala  Ser Asn Glu
            1010                1015                1020
Cys Leu Leu Tyr Tyr Ala Gly  Ala Asp Ile Ser Thr  Gly Ala Ile
            1025                1030                1035
Ser Cys Val Thr Asn Asp Asn  Ala Tyr Ser Ile Arg  Gly Leu Gly
            1040                1045                1050
Ile Lys Thr Leu Val Ser Met  Glu Lys Tyr Thr Val  Asp Ile Leu
            1055                1060                1065
Gly Glu Tyr His Pro Val Arg  Lys Glu Glu Arg Gln  Arg Phe Asn
            1070                1075                1080
```

Thr Lys Arg
    1085

<210> SEQ ID NO 74
<211> LENGTH: 36
<212> TYPE: DNA
<213> ORGANISM: Artificial Sequence
<220> FEATURE:
<223> OTHER INFORMATION: CR RNA

<400> SEQUENCE: 74
gttgtagttc cctgatggtt cttggtatgg tataat                                36

<210> SEQ ID NO 75
<211> LENGTH: 107
<212> TYPE: DNA
<213> ORGANISM: Artificial Sequence
<220> FEATURE:
<223> OTHER INFORMATION: TRACR RNA

<400> SEQUENCE: 75
ttataccata ccaagaactg ctcaggttac tatgataagg tagtaaaccg aagagctcta      60
atgccccgtc tcgcacgggg cattatctct aacagcgaaa aggcaaa                  107

<210> SEQ ID NO 76
<211> LENGTH: 120
<212> TYPE: DNA
<213> ORGANISM: Artificial Sequence
<220> FEATURE:
<223> OTHER INFORMATION: GRNA

<400> SEQUENCE: 76
gttttagagc tatgctgttt tgaatgcttc caaaacgaaa tgttggtagc attcaaaaca     60
acatagcaag ttaaaataag ctttgtccg ttctcaactt ttagtgacgc tgtttcggcg     120

<210> SEQ ID NO 77
<211> LENGTH: 105
<212> TYPE: DNA
<213> ORGANISM: Artificial Sequence
<220> FEATURE:
<223> OTHER INFORMATION: GRNA

<400> SEQUENCE: 77
gttttagagc tatgctgttt tgaatgcttc gtagcattca aaacaacata gcaagttaaa     60
ataaggcttt gtccgttctc aactttagt gacgctgttt cggcg                     105

<210> SEQ ID NO 78
<211> LENGTH: 83
<212> TYPE: DNA
<213> ORGANISM: Artificial Sequence
<220> FEATURE:
<223> OTHER INFORMATION: GRNA

<400> SEQUENCE: 78
gttttagagc tatgctgtta acaacatagc aagttaaaat aaggctttgt ccgttctcaa     60
cttttagtga cgctgtttcg gcg                                             83

<210> SEQ ID NO 79
<211> LENGTH: 77
<212> TYPE: DNA
<213> ORGANISM: Artificial Sequence
<220> FEATURE:
<223> OTHER INFORMATION: GRNA

```
<400> SEQUENCE: 79
gttttagagc tatgcaaaca tagcaagtta aaataaggct tgtccgttc tcaacttta      60 gtgacgctgt ttcggcg                                                    77

<210> SEQ ID NO 80
<211> LENGTH: 121
<212> TYPE: DNA
<213> ORGANISM: Artificial Sequence
<220> FEATURE:
<223> OTHER INFORMATION: GRNA

<400> SEQUENCE: 80
gttttagagt catgttgttt agaatggtac caaaacatct tttgggacta ttctaaacaa    60
catagcaagt taaaataagg ttttaaccgt aatcaactgt aaagtggcgc tgtttcggcg   120
c                                                                    121

<210> SEQ ID NO 81
<211> LENGTH: 87
<212> TYPE: DNA
<213> ORGANISM: Artificial Sequence
<220> FEATURE:
<223> OTHER INFORMATION: GRNA

<400> SEQUENCE: 81
gttttagagt catgttgtaa aaacaacata gcaagttaaa ataaggtttt aaccgtaatc    60
aactgtaaag tggcgctgtt tcggcgc                                        87

<210> SEQ ID NO 82
<211> LENGTH: 79
<212> TYPE: DNA
<213> ORGANISM: Artificial Sequence
<220> FEATURE:
<223> OTHER INFORMATION: GRNA

<400> SEQUENCE: 82
gttttagagt catgttgtaa aaacaacata gcaagttaaa ataagcgtaa tcaactgtaa    60
agtggcgctg tttcggcgc                                                 79

<210> SEQ ID NO 83
<211> LENGTH: 127
<212> TYPE: DNA
<213> ORGANISM: Artificial Sequence
<220> FEATURE:
<223> OTHER INFORMATION: GRNA

<400> SEQUENCE: 83
gttttagagc tgtgctgttt cgaatggttc caaaacgaaa tgttggaact attcgaaaca    60
acacagcgag ttaaaataag gctttgtccg tacacaactt gtaaaagggg cacccgattc   120
gggtgca                                                              127

<210> SEQ ID NO 84
<211> LENGTH: 101
<212> TYPE: DNA
<213> ORGANISM: Artificial Sequence
<220> FEATURE:
<223> OTHER INFORMATION: GRNA

<400> SEQUENCE: 84
gttttagagc tgtgctgttt cgaaaaatcg aaacaacaca gcgagttaaa ataaggcttt    60
```

```
gtccgtacac aacttgtaaa aggggcaccc gattcgggtg c                         101
```

<210> SEQ ID NO 85
<211> LENGTH: 91
<212> TYPE: DNA
<213> ORGANISM: Artificial Sequence
<220> FEATURE:
<223> OTHER INFORMATION: GRNA

<400> SEQUENCE: 85

```
gttttagagc tgtgctgtaa aaacaacaca gcgagttaaa ataaggcttt gtccgtacac     60
aacttgtaaa aggggcaccc gattcgggtg c                                   91
```

<210> SEQ ID NO 86
<211> LENGTH: 83
<212> TYPE: DNA
<213> ORGANISM: Artificial Sequence
<220> FEATURE:
<223> OTHER INFORMATION: GRNA

<400> SEQUENCE: 86

```
gttttagagc tgtgcaaaca cagcgagtta aaataaggct ttgtccgtac acaacttgta     60 aaagggcac ccgattcggg tgc                                             83
```

<210> SEQ ID NO 87
<211> LENGTH: 123
<212> TYPE: DNA
<213> ORGANISM: Artificial Sequence
<220> FEATURE:
<223> OTHER INFORMATION: GRNA

<400> SEQUENCE: 87

```
gttttagagc tgtgttgttt cgaatggttc caaaacggtt tgaaaccatt cgaaacaata     60
cagcaaagtt aaaataaggc tagtccgtat acaacgtgaa aacacgtggc accgattcgg    120
tgc                                                                 123
```

<210> SEQ ID NO 88
<211> LENGTH: 91
<212> TYPE: DNA
<213> ORGANISM: Artificial Sequence
<220> FEATURE:
<223> OTHER INFORMATION: GRNA

<400> SEQUENCE: 88

```
gttttagagc tgtgttgtaa aaacaataca gcaaagttaa aataaggcta gtccgtatac     60
aacgtgaaaa cacgtggcac cgattcggtg c                                   91
```

<210> SEQ ID NO 89
<211> LENGTH: 90
<212> TYPE: DNA
<213> ORGANISM: Artificial Sequence
<220> FEATURE:
<223> OTHER INFORMATION: GRNA

<400> SEQUENCE: 89

```
gttttagagc tgtgttgtaa aaacaataca gcaagttaaa ataaggctag tccgtataca     60
acgtgaaaac acgtggcacc gattcggtgc                                     90
```

<210> SEQ ID NO 90
<211> LENGTH: 118
<212> TYPE: DNA
<213> ORGANISM: Artificial Sequence

<220> FEATURE:
<223> OTHER INFORMATION: GRNA

<400> SEQUENCE: 90
gtttgctagt tatgttattt atagtattaa gcaaactgta ataacataa cgagtgcaaa    60 taagcgtttc gcgaaaattt acagtggccc tgctgtgggg ccttttttat ttatcaaa    118

<210> SEQ ID NO 91
<211> LENGTH: 99
<212> TYPE: DNA
<213> ORGANISM: Artificial Sequence
<220> FEATURE:
<223> OTHER INFORMATION: GRNA

<400> SEQUENCE: 91
gtttgctagt tatgttataa aataacata acgagtgcaa ataagcgttt cgcgaaaatt    60
tacagtggcc ctgctgtggg gccttttta tttatcaaa                            99

<210> SEQ ID NO 92
<211> LENGTH: 83
<212> TYPE: DNA
<213> ORGANISM: Artificial Sequence
<220> FEATURE:
<223> OTHER INFORMATION: GRNA

<400> SEQUENCE: 92
gtttgctagt tatgttataa aataacata acgagtgcaa ataagcgttt cgcgaaaatt    60
tacagtggcc ctgctgtggg gcc                                            83

<210> SEQ ID NO 93
<211> LENGTH: 137
<212> TYPE: DNA
<213> ORGANISM: Artificial Sequence
<220> FEATURE:
<223> OTHER INFORMATION: GRNA

<400> SEQUENCE: 93
gtttgagagc cttgtaaaac cgtatatctc tcaagcgaaa gataatgttt tacaaggcga    60
gttcaaataa ggatttatcc gaaatcgctt gcgtgcattg gcaccatcta tcttttaaga    120
ctttctttga aagtctt                                                    137

<210> SEQ ID NO 94
<211> LENGTH: 136
<212> TYPE: DNA
<213> ORGANISM: Artificial Sequence
<220> FEATURE:
<223> OTHER INFORMATION: GRNA

<400> SEQUENCE: 94
gtttgagagt cttgttaatt cttaaaggtg taaaacgaga attaacaaga cgagtgcaaa    60
taaggtttat ccggaatcgt caatatgacc tgcattgtgc agaatcttta aaatcatatg    120
atttcatatg gtttta                                                    136

<210> SEQ ID NO 95
<211> LENGTH: 111
<212> TYPE: DNA
<213> ORGANISM: Artificial Sequence
<220> FEATURE:
<223> OTHER INFORMATION: GRNA

<400> SEQUENCE: 95

```
gtttgagagt cttgtaaaaa caagacgagt gcaaataagg tttatccgga atcgtcaata        60
tgacctgcat tgtgcagaat ctttaaaatc atatgatttc atatggtttt a                111

<210> SEQ ID NO 96
<211> LENGTH: 77
<212> TYPE: DNA
<213> ORGANISM: Artificial Sequence
<220> FEATURE:
<223> OTHER INFORMATION: GRNA

<400> SEQUENCE: 96
gtttgagagt cttgtaaaaa caagacgagt gcaaataagg tttatccgga atcgtcaata        60
tgacctgcat tgtgcag                                                       77

<210> SEQ ID NO 97
<211> LENGTH: 123
<212> TYPE: DNA
<213> ORGANISM: Artificial Sequence
<220> FEATURE:
<223> OTHER INFORMATION: GRNA

<400> SEQUENCE: 97
gtttgagagt cttgttaatt caaaagaatt aacaagacga gtgcaaataa ggtttatccg        60
gaatcgtcaa tatgacctgc attgtgcaga atctttaaaa tcatatgatt tcatatggtt       120
tta                                                                    123

<210> SEQ ID NO 98
<211> LENGTH: 142
<212> TYPE: DNA
<213> ORGANISM: Artificial Sequence
<220> FEATURE:
<223> OTHER INFORMATION: GRNA

<400> SEQUENCE: 98
gtttgagagt agtgtaaatc catagggtc tcaaacgaaa agaccccctat ggatttacat        60 tgcgagttca ataaaagtt tactcaaatc gttggcttga ccaaccgcac agcgtgtgct       120
taaagatctc ttcagtgagg tc                                               142

<210> SEQ ID NO 99
<211> LENGTH: 135
<212> TYPE: DNA
<213> ORGANISM: Artificial Sequence
<220> FEATURE:
<223> OTHER INFORMATION: GRNA

<400> SEQUENCE: 99
gtttgagagt agtgtaaatc cagagggctc caaaacgagc cctctggatt tacactacga        60
gttcaaataa aaattatttc aaatcgccgc tatgtcggcc gcacagtgtg tgcattaaga      120
aaagtccgaa agggc                                                       135

<210> SEQ ID NO 100
<211> LENGTH: 147
<212> TYPE: DNA
<213> ORGANISM: Artificial Sequence
<220> FEATURE:
<223> OTHER INFORMATION: GRNA

<400> SEQUENCE: 100
gtttgagagt agtgtaaatt tatagggtag taaaacaaat tttactaccc tataaattta        60
cactacgagt tcaaataaaa attatttcaa atcgtacttt ttagtacctt cacaagtgtt      120
```

```
gtgaatatta actcaccttc gggtgag                                         147

<210> SEQ ID NO 101
<211> LENGTH: 109
<212> TYPE: DNA
<213> ORGANISM: Artificial Sequence
<220> FEATURE:
<223> OTHER INFORMATION: GRNA

<400> SEQUENCE: 101
gtttgagagt agtgtaaaaa tacactacga gttcaaataa aaattatttc aaatcgtact     60
ttttagtacc ttcacaagtg ttgtgaatat taactcacct tcgggtgag               109

<210> SEQ ID NO 102
<211> LENGTH: 87
<212> TYPE: DNA
<213> ORGANISM: Artificial Sequence
<220> FEATURE:
<223> OTHER INFORMATION: GRNA

<400> SEQUENCE: 102
gtttgagagt agtgtaaaaa tacactacga gttcaaataa aaattatttc aaatcgtact     60
ttttagtacc ttcacaagtg ttgtgaa                                         87

<210> SEQ ID NO 103
<211> LENGTH: 129
<212> TYPE: DNA
<213> ORGANISM: Artificial Sequence
<220> FEATURE:
<223> OTHER INFORMATION: GRNA

<400> SEQUENCE: 103
gtttgagagt agtgtaaatt tataggaaaa cctataaatt tacactacga gttcaaataa     60
aaattatttc aaatcgtact ttttagtacc ttcacaagtg ttgtgaatat taactcacct    120
tcgggtgag                                                            129

<210> SEQ ID NO 104
<211> LENGTH: 138
<212> TYPE: DNA
<213> ORGANISM: Artificial Sequence
<220> FEATURE:
<223> OTHER INFORMATION: GRNA

<400> SEQUENCE: 104
gtttgagagt agtgtaattt catatggtag tcaaacgact accatatgag attacactac     60
acggttcaaa taagaatgt tcgaaaccgc cctttggggc ccgcttgttg cggatttaca    120
gacttgatat caagtctg                                                  138

<210> SEQ ID NO 105
<211> LENGTH: 121
<212> TYPE: DNA
<213> ORGANISM: Artificial Sequence
<220> FEATURE:
<223> OTHER INFORMATION: GRNA

<400> SEQUENCE: 105
gtttgagagt aatgtaaatt cataggatgg taaaacgaaa tttaccatcc agtgagttta     60
cattacaagt tcaaataaaa atttattcaa cccgttcttc ggaacctcca ccgtgtggaa    120
c                                                                    121
```

<210> SEQ ID NO 106
<211> LENGTH: 105
<212> TYPE: DNA
<213> ORGANISM: Artificial Sequence
<220> FEATURE:
<223> OTHER INFORMATION: GRNA

<400> SEQUENCE: 106
gtttgagagt aatgtaaaaa tacattacaa gttcaaataa aaatttattc aacccgttct    60
tcggaacctc caccgtgtgg aacattaagg tctgctttgc aggcc                   105

<210> SEQ ID NO 107
<211> LENGTH: 81
<212> TYPE: DNA
<213> ORGANISM: Artificial Sequence
<220> FEATURE:
<223> OTHER INFORMATION: GRNA

<400> SEQUENCE: 107
gtttgagagt aatgtaaaaa tacattacaa gttcaaataa aaatttattc aacccgttct    60
tcggaacctc caccgtgtgg a                                              81

<210> SEQ ID NO 108
<211> LENGTH: 103
<212> TYPE: DNA
<213> ORGANISM: Artificial Sequence
<220> FEATURE:
<223> OTHER INFORMATION: GRNA

<400> SEQUENCE: 108
gtttgagagt aatgtaaatt cataaaagtg agtttacatt acaagttcaa ataaaaattt    60
attcaacccg ttcttcggaa cctccaccgt gtggaacatt aag                     103

<210> SEQ ID NO 109
<211> LENGTH: 139
<212> TYPE: DNA
<213> ORGANISM: Artificial Sequence
<220> FEATURE:
<223> OTHER INFORMATION: GRNA

<400> SEQUENCE: 109
gtttgagagc agtgttgtct tatatagctc gaaaacgcat tgtaagacaa cactgctacg    60
ttcaaataag catattgcta caaggttctc cctcggagaa tgaccattag gtcacttaga   120
tagccggttc ttctggcta                                                139

<210> SEQ ID NO 110
<211> LENGTH: 139
<212> TYPE: DNA
<213> ORGANISM: Artificial Sequence
<220> FEATURE:
<223> OTHER INFORMATION: GRNA

<400> SEQUENCE: 110
gtttgagagc agtgttgtct tatatagctc gaaaacgcat tgtaagacaa cactgctacg    60
ttcaaataag catattgcta caaggttctc cattggagaa tgaccattag gtcgcttaga   120
tagccagttc ttctggcta                                                139

<210> SEQ ID NO 111
<211> LENGTH: 109
<212> TYPE: DNA
<213> ORGANISM: Artificial Sequence

```
<220> FEATURE:
<223> OTHER INFORMATION: GRNA

<400> SEQUENCE: 111
gtttgagagc agtgtaaaaa cactgctacg ttcaaataag catattgcta caaggttctc      60
cattggagaa tgaccattag gtcgcttaga tagccagttc ttctggcta               109

<210> SEQ ID NO 112
<211> LENGTH: 83
<212> TYPE: DNA
<213> ORGANISM: Artificial Sequence
<220> FEATURE:
<223> OTHER INFORMATION: GRNA

<400> SEQUENCE: 112
gtttgagagc agtgtaaaaa cactgctacg ttcaaataag catattgcta caaggttctc      60
cattggagaa tgaccattag gtc                                            83

<210> SEQ ID NO 113
<211> LENGTH: 117
<212> TYPE: DNA
<213> ORGANISM: Artificial Sequence
<220> FEATURE:
<223> OTHER INFORMATION: GRNA

<400> SEQUENCE: 113
gtttgagagc agtgttgtca aagacaaca ctgctacgtt caaataagca tattgctaca       60
aggttctcca ttggagaatg accattaggt cgcttagata gccagttctt ctggcta      117

<210> SEQ ID NO 114
<211> LENGTH: 140
<212> TYPE: DNA
<213> ORGANISM: Artificial Sequence
<220> FEATURE:
<223> OTHER INFORMATION: GRNA

<400> SEQUENCE: 114
gtttgagagc agtgttgtct aaatagctc gaaaacgcat tgtaagacaa cactgcacgt       60
tcaaataagc agattgctac aaggttcccg taagggaatg accatctggt cacatgaata   120
gcccccggca acggtggctg                                              140

<210> SEQ ID NO 115
<211> LENGTH: 133
<212> TYPE: DNA
<213> ORGANISM: Artificial Sequence
<220> FEATURE:
<223> OTHER INFORMATION: GRNA

<400> SEQUENCE: 115
attgtaccat agcgagttaa attagggaat tacaacgaaa ttgtaataac ctattttacc      60
tcgctatggc acaatttgtt attacatgga cattatacta aacatttcct aaaaaagcaa   120
cgaaaaacgt gct                                                     133

<210> SEQ ID NO 116
<211> LENGTH: 129
<212> TYPE: DNA
<213> ORGANISM: Artificial Sequence
<220> FEATURE:
<223> OTHER INFORMATION: GRNA

<400> SEQUENCE: 116
```

```
gttgtagttc cctaattatt cttggtatgg tataatgaaa attgtatcat accaagaaca        60
attaggttac tatgataagg tagtataccg caaagctcta acacctcatc ttcggatgag       120
gtgttatct                                                              129

<210> SEQ ID NO 117
<211> LENGTH: 106
<212> TYPE: DNA
<213> ORGANISM: Artificial Sequence
<220> FEATURE:
<223> OTHER INFORMATION: GRNA

<400> SEQUENCE: 117
gttgtagttc cctaattatt cttggtaaaa accaagaaca attaggttac tatgataagg        60
tagtataccg caaagctcta acacctcatc ttcggatgag gtgtta                      106

<210> SEQ ID NO 118
<211> LENGTH: 100
<212> TYPE: DNA
<213> ORGANISM: Artificial Sequence
<220> FEATURE:
<223> OTHER INFORMATION: GRNA

<400> SEQUENCE: 118
gttgtagttc cctaattatt cttggtaaaa accaagaaca attaggttac tatgataagg        60
tagtataccg caaagctcta acacctcatc ttcggatgag                             100

<210> SEQ ID NO 119
<211> LENGTH: 121
<212> TYPE: DNA
<213> ORGANISM: Artificial Sequence
<220> FEATURE:
<223> OTHER INFORMATION: GRNA

<400> SEQUENCE: 119
gttgtagttc cctaattatt cttggtatgg taaaaatatc ataccaagaa caattaggtt        60
actatgataa ggtagtatac cgcaaagctc taacacctca tcttcggatg aggtgttatc       120
t                                                                      121

<210> SEQ ID NO 120
<211> LENGTH: 158
<212> TYPE: DNA
<213> ORGANISM: Artificial Sequence
<220> FEATURE:
<223> OTHER INFORMATION: GRNA

<400> SEQUENCE: 120
gttgtagttc cctaacagtt cttggtatgg tataataaaa attataccat accaagaact        60
gttatggttg ctatgataag gtcttagcac cgtaaagctc tgacgcctcg ctttcagcgg       120
ggcgtcatct tttttgccca aaagacacgg atattttt                               158

<210> SEQ ID NO 121
<211> LENGTH: 99
<212> TYPE: DNA
<213> ORGANISM: Artificial Sequence
<220> FEATURE:
<223> OTHER INFORMATION: GRNA

<400> SEQUENCE: 121
gttgtagttc cctaacagtt ctaaaaagaa ctgttatggt tgctatgata aggtcttagc        60
accgtaaagc tctgacgcct cgctttcagc ggggcgtca                              99
```

<210> SEQ ID NO 122
<211> LENGTH: 94
<212> TYPE: DNA
<213> ORGANISM: Artificial Sequence
<220> FEATURE:
<223> OTHER INFORMATION: GRNA

<400> SEQUENCE: 122
gttgtagttc cctaacagtt ctaaaaagaa ctgttatggt tgctatgata aggtcttagc    60
accgtaaagc tctgacgcct cgctttcagc gggg                               94

<210> SEQ ID NO 123
<211> LENGTH: 93
<212> TYPE: DNA
<213> ORGANISM: Artificial Sequence
<220> FEATURE:
<223> OTHER INFORMATION: GRNA

<400> SEQUENCE: 123
gttgtagttc cctaacagta aaaactgtta tggttgctat gataaggtct tagcaccgta    60
aagctctgac gcctcgcttt cagcggggcg tca                                93

<210> SEQ ID NO 124
<211> LENGTH: 126
<212> TYPE: DNA
<213> ORGANISM: Artificial Sequence
<220> FEATURE:
<223> OTHER INFORMATION: GRNA

<400> SEQUENCE: 124
cggttcttgg tatggtataa tgaattatac cataccaaga actgttgggt tactacaata    60
aggtagtaaa ccgaaaagct ctgacgtctt gtttgcgcag acgtcatct ttatatcaga   120 cggatg                                                             126

<210> SEQ ID NO 125
<211> LENGTH: 90
<212> TYPE: DNA
<213> ORGANISM: Artificial Sequence
<220> FEATURE:
<223> OTHER INFORMATION: GRNA

<400> SEQUENCE: 125
cggtactgtt gggttactac aataaggtag taaaccgaaa agctctgacg tcttgtttgc    60
gcaggacgtc atctttatat cagacggatg                                    90

<210> SEQ ID NO 126
<211> LENGTH: 91
<212> TYPE: DNA
<213> ORGANISM: Artificial Sequence
<220> FEATURE:
<223> OTHER INFORMATION: GRNA

<400> SEQUENCE: 126
gttgtagttc cctaacggta ctgttgggtt actacaataa ggtagtaaac cgaaaagctc    60
tgacgtcttg tttgcgcagg acgtcatctt t                                  91

<210> SEQ ID NO 127
<211> LENGTH: 108
<212> TYPE: DNA
<213> ORGANISM: Artificial Sequence
<220> FEATURE:

```
<223> OTHER INFORMATION: GRNA

<400> SEQUENCE: 127
ctaacggttc ttgaaaacaa gaactgttgg gttactacaa taaggtagta aaccgaaaag      60
ctctgacgtc ttgtttgcgc aggacgtcat ctttatatca gacggatg                  108

<210> SEQ ID NO 128
<211> LENGTH: 160
<212> TYPE: DNA
<213> ORGANISM: Artificial Sequence
<220> FEATURE:
<223> OTHER INFORMATION: GRNA

<400> SEQUENCE: 128
gttgtagtcc cctgatggtt tctggaatgg tataatgaaa ttataccatt ccagaaacta      60
ttatggtcac tacaataagg tattagaccg tagagcacta acaccccatt tggggtgtta    120
tctctttaaa ctgtccaaaa tttagtattg caattattga                          160

<210> SEQ ID NO 129
<211> LENGTH: 128
<212> TYPE: DNA
<213> ORGANISM: Artificial Sequence
<220> FEATURE:
<223> OTHER INFORMATION: GRNA

<400> SEQUENCE: 129
gttatagttc cctgatagtt cttggtatgg tataatgaaa ttataccata ccaagaacta      60
tgaggttgct ataataaggt agtaaaccgc agagctctaa cgcctcacat tgtggggcg     120 ttatctct                                                             128

<210> SEQ ID NO 130
<211> LENGTH: 115
<212> TYPE: DNA
<213> ORGANISM: Artificial Sequence
<220> FEATURE:
<223> OTHER INFORMATION: GRNA

<400> SEQUENCE: 130
tcgttcttgg tatggtataa tgaaattata ccataccaag aacgatcagg ttgctacaat      60
aaggtagtaa accgaagagc tctaacgccc cgtttcttta cggggcgtta tctct         115

<210> SEQ ID NO 131
<211> LENGTH: 170
<212> TYPE: DNA
<213> ORGANISM: Artificial Sequence
<220> FEATURE:
<223> OTHER INFORMATION: GRNA

<400> SEQUENCE: 131
gttatagttc cctgatagtt cttggtatgg tataatgaat tataccatac caagaactat      60
ttaggttact atgataaggt ttagtacacc ttagagctct gacgcctcgc ttttgcgagg    120
cgttatctct ttatattgcc aaaaatgcaa atatatcgta caatggtggc                170

<210> SEQ ID NO 132
<211> LENGTH: 130
<212> TYPE: DNA
<213> ORGANISM: Artificial Sequence
<220> FEATURE:
<223> OTHER INFORMATION: GRNA

<400> SEQUENCE: 132
```

```
gttatagttc cctgatagtt cttggtatgg tataatgaat tataccatac caagaactat    60
ttaggttact atgataaggt ttagtacacc ttagagctct gacgcctcgc ttttgcgagg   120
cgttatctct                                                         130

<210> SEQ ID NO 133
<211> LENGTH: 106
<212> TYPE: DNA
<213> ORGANISM: Artificial Sequence
<220> FEATURE:
<223> OTHER INFORMATION: GRNA

<400> SEQUENCE: 133
gttatagttc cctgatagtt cttaaccaag aactatttag gttactatga taaggtttag    60
tacaccttag agctctgacg cctcgctttt gcgaggcgtt atctct                  106

<210> SEQ ID NO 134
<211> LENGTH: 104
<212> TYPE: DNA
<213> ORGANISM: Artificial Sequence
<220> FEATURE:
<223> OTHER INFORMATION: GRNA

<400> SEQUENCE: 134
gttatagttc cctgatagtt cttgcaagaa ctatttaggt tactatgata aggtttagta    60
caccttagag ctctgacgcc tcgcttttgc gaggcgttat ctct                    104

<210> SEQ ID NO 135
<211> LENGTH: 96
<212> TYPE: DNA
<213> ORGANISM: Artificial Sequence
<220> FEATURE:
<223> OTHER INFORMATION: GRNA

<400> SEQUENCE: 135
gttatagttc cctgatagtt cttgcaagaa ctatttaggt tactatgata aggtttagta    60
caccttagag ctctgacgcc aaaaggcgtt atctct                              96

<210> SEQ ID NO 136
<211> LENGTH: 129
<212> TYPE: DNA
<213> ORGANISM: Artificial Sequence
<220> FEATURE:
<223> OTHER INFORMATION: GRNA

<400> SEQUENCE: 136
gttgtagttc cctgatggtt cttggtatgg tataataaat tataccatac caagaactgc    60
tcaggttact atgataaggt agtaaaccga agagctctaa tgccccgtct cgcacgggc    120 attatctct                                                          129

<210> SEQ ID NO 137
<211> LENGTH: 105
<212> TYPE: DNA
<213> ORGANISM: Artificial Sequence
<220> FEATURE:
<223> OTHER INFORMATION: GRNA

<400> SEQUENCE: 137
gttgtagttc cctgatggtt cttgaaaaag aactgctcag gttactatga taaggtagta    60
aaccgaagag ctctaatgcc ccgtctcgca cggggcatta tctct                   105
```

```
<210> SEQ ID NO 138
<211> LENGTH: 96
<212> TYPE: DNA
<213> ORGANISM: Artificial Sequence
<220> FEATURE:
<223> OTHER INFORMATION: GRNA

<400> SEQUENCE: 138
gttgtagttc cctgatggtt cttgaaaaag aactgctcag gttactatga taaggtagta    60
aaccgaagag ctctaatgcc aaagggcatt atctct                              96

<210> SEQ ID NO 139
<211> LENGTH: 195
<212> TYPE: DNA
<213> ORGANISM: Artificial Sequence
<220> FEATURE:
<223> OTHER INFORMATION: GRNA

<400> SEQUENCE: 139
aaacccctcc gtttagagag gggttatgct agttagcgcc gaaacagcgc cactttacag    60
ttgattacgg ttaaaacctt attttaactt gctatgttgt ttagaatagt cccaaaagat   120 gtttggtac cattctaaac aacatgactc taaaacccag taacattact gactggccta   180
tagtgagtcg tatta                                                   195

<210> SEQ ID NO 140
<211> LENGTH: 161
<212> TYPE: DNA
<213> ORGANISM: Artificial Sequence
<220> FEATURE:
<223> OTHER INFORMATION: GRNA

<400> SEQUENCE: 140
aaacccctcc gtttagagag gggttatgct agttagcgcc gaaacagcgc cactttacag    60
ttgattacgg ttaaaacctt attttaactt gctatgttgt ttttacaaca tgactctaaa   120
acccagtaac attactgact ggcctatagt gagtcgtatt a                       161

<210> SEQ ID NO 141
<211> LENGTH: 153
<212> TYPE: DNA
<213> ORGANISM: Artificial Sequence
<220> FEATURE:
<223> OTHER INFORMATION: GRNA

<400> SEQUENCE: 141
aaacccctcc gtttagagag gggttatgct agttagcgcc gaaacagcgc cactttacag    60
ttgattacgc ttattttaac ttgctatgtt gttttttacaa catgactcta aacccagta   120 acattactga ctggcctata gtgagtcgta tta                                153

<210> SEQ ID NO 142
<211> LENGTH: 197
<212> TYPE: DNA
<213> ORGANISM: Artificial Sequence
<220> FEATURE:
<223> OTHER INFORMATION: GRNA

<400> SEQUENCE: 142
aaacccctcc gtttagagag gggttatgct agttagcacc gaatcggtgc cacgtgtttt    60
cacgttgtat acggactagc cttatttttaa ctttgctgta ttgtttcgaa tggtttcaaa   120
ccgttttgga accattcgaa acaacacagc tctaaaaccc agtaacatta ctgactggcc   180
```

```
tatagtgagt cgtatta                                                    197
```

```
<210> SEQ ID NO 143
<211> LENGTH: 165
<212> TYPE: DNA
<213> ORGANISM: Artificial Sequence
<220> FEATURE:
<223> OTHER INFORMATION: GRNA

<400> SEQUENCE: 143
aaacccctcc gtttagagag gggttatgct agttagcacc gaatcggtgc cacgtgtttt     60
cacgttgtat acggactagc cttatttaa ctttgctgta ttgttttac aacacagctc      120 taaaacccag taacattact gactggccta tagtgagtcg tatta                    165

<210> SEQ ID NO 144
<211> LENGTH: 164
<212> TYPE: DNA
<213> ORGANISM: Artificial Sequence
<220> FEATURE:
<223> OTHER INFORMATION: GRNA

<400> SEQUENCE: 144
aaacccctcc gtttagagag gggttatgct agttagcacc gaatcggtgc cacgtgtttt     60
cacgttgtat acggactagc cttatttaa cttgctgtat tgttttaca acacagctct      120 aaaacccagt aacattactg actggcctat agtgagtcgt atta                     164

<210> SEQ ID NO 145
<211> LENGTH: 192
<212> TYPE: DNA
<213> ORGANISM: Artificial Sequence
<220> FEATURE:
<223> OTHER INFORMATION: GRNA

<400> SEQUENCE: 145
aaacccctcc gtttagagag gggttatgct agttatttga taaataaaaa aggccccaca     60
gcagggccac tgtaaatttt cgcgaaacgc ttatttgcac tcgttatgtt atttacagtt    120
tgcttaatac tataaataac ataactagca aacccagtaa cattactgac tggcctatag    180
tgagtcgtat ta                                                        192

<210> SEQ ID NO 146
<211> LENGTH: 173
<212> TYPE: DNA
<213> ORGANISM: Artificial Sequence
<220> FEATURE:
<223> OTHER INFORMATION: GRNA

<400> SEQUENCE: 146
aaacccctcc gtttagagag gggttatgct agttatttga taaataaaaa aggccccaca     60
gcagggccac tgtaaatttt cgcgaaacgc ttatttgcac tcgttatgtt attttttataa   120 cataactagc aaacccagta acattactga ctggcctata gtgagtcgta tta           173

<210> SEQ ID NO 147
<211> LENGTH: 157
<212> TYPE: DNA
<213> ORGANISM: Artificial Sequence
<220> FEATURE:
<223> OTHER INFORMATION: GRNA

<400> SEQUENCE: 147
```

```
aaaccectcc gtttagagag gggttatgct agttaggccc cacagcaggg ccactgtaaa    60
ttttcgcgaa acgcttattt gcactcgtta tgttattttt ataacataac tagcaaaccc   120
agtaacatta ctgactggcc tatagtgagt cgtatta                            157
```

```
<210> SEQ ID NO 148
<211> LENGTH: 197
<212> TYPE: DNA
<213> ORGANISM: Artificial Sequence
<220> FEATURE:
<223> OTHER INFORMATION: GRNA

<400> SEQUENCE: 148
```

```
aaaccectcc gtttagagag gggttatgct agttatatana ccatatgaaa tcatatgatt    60
ttaaagattc tgcacaatgc aggtcatatt gacgattccg gataaacctt atttgcactc   120
gtcttgttaa ttcttttgaa ttaacaagac tctcaaaccc agtaacatta ctgactggcc   180
tatagtgagt cgtatta                                                  197
```

```
<210> SEQ ID NO 149
<211> LENGTH: 185
<212> TYPE: DNA
<213> ORGANISM: Artificial Sequence
<220> FEATURE:
<223> OTHER INFORMATION: GRNA

<400> SEQUENCE: 149
```

```
aaaccectcc gtttagagag gggttatgct agttatatana ccatatgaaa tcatatgatt    60
ttaaagattc tgcacaatgc aggtcatatt gacgattccg gataaacctt atttgcactc   120
gtcttgtttt tacaagactc tcaaacccag taacattact gactggccta tagtgagtcg   180
tatta                                                               185
```

```
<210> SEQ ID NO 150
<211> LENGTH: 151
<212> TYPE: DNA
<213> ORGANISM: Artificial Sequence
<220> FEATURE:
<223> OTHER INFORMATION: GRNA

<400> SEQUENCE: 150
```

```
aaaccectcc gtttagagag gggttatgct agttactgca caatgcaggt catattgacg    60
attccggata aaccttattt gcactcgtct tgtttttaca agactctcaa acccagtaac   120
attactgact ggcctatagt gagtcgtatt a                                  151
```

```
<210> SEQ ID NO 151
<211> LENGTH: 200
<212> TYPE: DNA
<213> ORGANISM: Artificial Sequence
<220> FEATURE:
<223> OTHER INFORMATION: GRNA

<400> SEQUENCE: 151
```

```
aaaccectcc gtttagagag gggttatgct agctcacccg aaggtgagtt aatattcaca    60
acacttgtga aggtactaaa aagtacgatt tgaaataatt tttatttgaa ctcgtagtgt   120
aaatttatag gttttcctat aaatttacac tactctcaaa cccagtaaca ttactgactg   180
gcctatagtg agtcgtatta                                               200
```

```
<210> SEQ ID NO 152
<211> LENGTH: 183
```

```
<212> TYPE: DNA
<213> ORGANISM: Artificial Sequence
<220> FEATURE:
<223> OTHER INFORMATION: GRNA

<400> SEQUENCE: 152
aaacccctcc gtttagagag gggttatgct agttactcac ccgaaggtga gttaatattc    60
acaacacttg tgaaggtact aaaaagtacg atttgaaata attttattt gaactcgtag    120 tgtatttta cactactctc aaacccagta acattactga ctggcctata gtgagtcgta    180
tta                                                                  183

<210> SEQ ID NO 153
<211> LENGTH: 161
<212> TYPE: DNA
<213> ORGANISM: Artificial Sequence
<220> FEATURE:
<223> OTHER INFORMATION: GRNA

<400> SEQUENCE: 153
aaacccctcc gtttagagag gggttatgct agttattcac aacacttgtg aaggtactaa    60
aaagtacgat tgaaataat ttttatttga actcgtagtg tatttttaca ctactctcaa    120
acccagtaac attactgact ggcctatagt gagtcgtatt a                        161

<210> SEQ ID NO 154
<211> LENGTH: 193
<212> TYPE: DNA
<213> ORGANISM: Artificial Sequence
<220> FEATURE:
<223> OTHER INFORMATION: GRNA

<400> SEQUENCE: 154
aaacccctcc gtttagagag gggttatgct agttaggcct gcaaagcaga ccttaatgtt    60
ccacacggtg gaggttccga agaacgggtt gaataaattt ttatttgaac ttgtaatgta    120
aactcacttt tatgaattta cattactctc aaacccagta acattactga ctggcctata    180
gtgagtcgta tta                                                       193

<210> SEQ ID NO 155
<211> LENGTH: 179
<212> TYPE: DNA
<213> ORGANISM: Artificial Sequence
<220> FEATURE:
<223> OTHER INFORMATION: GRNA

<400> SEQUENCE: 155
aaacccctcc gtttagagag gggttatgct agttaggcct gcaaagcaga ccttaatgtt    60
ccacacggtg gaggttccga agaacgggtt gaataaattt ttatttgaac ttgtaatgta    120
tttttacatt actctcaaac ccagtaacat tactgactgg cctatagtga gtcgtatta    179

<210> SEQ ID NO 156
<211> LENGTH: 155
<212> TYPE: DNA
<213> ORGANISM: Artificial Sequence
<220> FEATURE:
<223> OTHER INFORMATION: GRNA

<400> SEQUENCE: 156
aaacccctcc gtttagagag gggttatgct agttatccac acggtggagg ttccgaagaa    60
cgggttgaat aaatttttat ttgaacttgt aatgtatttt tacattactc tcaaacccag    120
```
taacattact gactggccta tagtgagtcg tatta    155

```
<210> SEQ ID NO 157
<211> LENGTH: 191
<212> TYPE: DNA
<213> ORGANISM: Artificial Sequence
<220> FEATURE:
<223> OTHER INFORMATION: GRNA

<400> SEQUENCE: 157
```
aaacccctcc gtttagagag gggttatgct agttatagcc agaagaactg gctatctaag    60
cgacctaatg gtcattctcc aatggagaac cttgtagcaa tatgcttatt tgaacgtagc    120
agtgttgtct tttgacaaca ctgctctcaa acccagtaac attactgact ggcctatagt    180
gagtcgtatt a    191

```
<210> SEQ ID NO 158
<211> LENGTH: 183
<212> TYPE: DNA
<213> ORGANISM: Artificial Sequence
<220> FEATURE:
<223> OTHER INFORMATION: GRNA

<400> SEQUENCE: 158
```
aaacccctcc gtttagagag gggttatgct agttatagcc agaagaactg gctatctaag    60
cgacctaatg gtcattctcc aatggagaac cttgtagcaa tatgcttatt tgaacgtagc    120 agtgtttta cactgctctc aaacccagta acattactga ctggcctata gtgagtcgta    180
tta    183

```
<210> SEQ ID NO 159
<211> LENGTH: 157
<212> TYPE: DNA
<213> ORGANISM: Artificial Sequence
<220> FEATURE:
<223> OTHER INFORMATION: GRNA

<400> SEQUENCE: 159
```
aaacccctcc gtttagagag gggttatgct agttagacct aatggtcatt ctccaatgga    60
gaaccttgta gcaatatgct tatttgaacg tagcagtgtt tttacactgc tctcaaaccc    120
agtaacatta ctgactggcc tatagtgagt cgtatta    157

```
<210> SEQ ID NO 160
<211> LENGTH: 195
<212> TYPE: DNA
<213> ORGANISM: Artificial Sequence
<220> FEATURE:
<223> OTHER INFORMATION: GRNA

<400> SEQUENCE: 160
```
aaacccctcc gtttagagag gggttatgct agttaagata cacctcatc cgaagatgag    60 gtgttagagc tttgcggtat actaccttat catagtaacc taattgttct tggtatgata    120
tttttaccat accaagaata attagggaac tacaacccag taacattact gactggccta    180
tagtgagtcg tatta    195

```
<210> SEQ ID NO 161
<211> LENGTH: 180
<212> TYPE: DNA
<213> ORGANISM: Artificial Sequence
<220> FEATURE:
<223> OTHER INFORMATION: GRNA
```

<400> SEQUENCE: 161

```
aaacccctcc gtttagagag gggttatgct agttataaca cctcatccga agatgaggtg      60
ttagagcttt gcggtatact accttatcat agtaacctaa ttgttcttgg ttttttaccaa    120 gaataattag ggaactacaa cccagtaaca ttactgactg gcctatagtg agtcgtatta    180
```

<210> SEQ ID NO 162
<211> LENGTH: 174
<212> TYPE: DNA
<213> ORGANISM: Artificial Sequence
<220> FEATURE:
<223> OTHER INFORMATION: GRNA

<400> SEQUENCE: 162

```
aaacccctcc gtttagagag gggttatgct agttactcat ccgaagatga ggtgttagag      60
ctttgcggta tactacctta tcatagtaac ctaattgttc ttggtttttta ccaagaataa    120 ttagggaact acaacccagt aacattactg actggcctat agtgagtcgt atta           174
```

<210> SEQ ID NO 163
<211> LENGTH: 167
<212> TYPE: DNA
<213> ORGANISM: Artificial Sequence
<220> FEATURE:
<223> OTHER INFORMATION: GRNA

<400> SEQUENCE: 163

```
aaacccctcc gtttagagag gggttatgct agttatgacg ccccgctgaa agcgaggcgt      60
cagagcttta cggtgctaag accttatcat agcaaccata acagttttta ctgttaggga    120
actacaaccc agtaacatta ctgactggcc tatagtgagt cgtatta                   167
```

<210> SEQ ID NO 164
<211> LENGTH: 173
<212> TYPE: DNA
<213> ORGANISM: Artificial Sequence
<220> FEATURE:
<223> OTHER INFORMATION: GRNA

<400> SEQUENCE: 164

```
aaacccctcc gtttagagag gggttatgct agttatgacg ccccgctgaa agcgaggcgt      60
cagagcttta cggtgctaag accttatcat agcaaccata acagttcttt ttagaactgt    120
tagggaacta caacccagta acattactga ctggcctata gtgagtcgta tta            173
```

<210> SEQ ID NO 165
<211> LENGTH: 168
<212> TYPE: DNA
<213> ORGANISM: Artificial Sequence
<220> FEATURE:
<223> OTHER INFORMATION: GRNA

<400> SEQUENCE: 165

```
aaacccctcc gtttagagag gggttatgct agttaccccg ctgaaagcga ggcgtcagag      60
ctttacggtg ctaagacctt atcatagcaa ccataacagt tcttttttaga actgttaggg   120 aactacaacc cagtaacatt actgactggc tatagtgagt cgtatta                   168
```

<210> SEQ ID NO 166
<211> LENGTH: 193
<212> TYPE: DNA
<213> ORGANISM: Artificial Sequence
<220> FEATURE:

<223> OTHER INFORMATION: GRNA

<400> SEQUENCE: 166

| aaacccctcc gtttagagag gggttatgct agttacatcc gtctgatata aagatgacgt | 60 |
| cctgcgcaaa caagacgtca gagcttttcg gtttactacc ttattgtagt aacccaacag | 120 |
| ttcttgtttt caagaaccgt tagggaacta caacccagta acattactga ctggcctata | 180 |
| gtgagtcgta tta | 193 |

<210> SEQ ID NO 167
<211> LENGTH: 179
<212> TYPE: DNA
<213> ORGANISM: Artificial Sequence
<220> FEATURE:
<223> OTHER INFORMATION: GRNA

<400> SEQUENCE: 167

| aaacccctcc gtttagagag gggttatgct agttacatcc gtctgatata aagatgacgt | 60 |
| cctgcgcaaa caagacgtca gagcttttcg gtttactacc ttattgtagt aacccaacag | 120 |
| taccgttagg gaactacaac ccagtaacat tactgactgg cctatagtga gtcgtatta | 179 |

<210> SEQ ID NO 168
<211> LENGTH: 165
<212> TYPE: DNA
<213> ORGANISM: Artificial Sequence
<220> FEATURE:
<223> OTHER INFORMATION: GRNA

<400> SEQUENCE: 168

| aaacccctcc gtttagagag gggttatgct agttaaaaga tgacgtcctg cgcaaacaag | 60 |
| acgtcagagc ttttcggttt actacttat tgtagtaacc caacagtacc gttagggaac | 120 |
| tacaacccag taacattact gactggccta tagtgagtcg tatta | 165 |

<210> SEQ ID NO 169
<211> LENGTH: 178
<212> TYPE: DNA
<213> ORGANISM: Artificial Sequence
<220> FEATURE:
<223> OTHER INFORMATION: GRNA

<400> SEQUENCE: 169

| aaacccctcc gtttagagag gggttatgct agttaagaga taacgcctcg caaaagcgag | 60 |
| gcgtcagagc tctaaggtgt actaaaacctt atcatagtaa cctaaatagt tcttgcaaga | 120 |
| actatcaggg aactataacc cagtaacatt actgactggc ctatagtgag tcgtatta | 178 |

<210> SEQ ID NO 170
<211> LENGTH: 170
<212> TYPE: DNA
<213> ORGANISM: Artificial Sequence
<220> FEATURE:
<223> OTHER INFORMATION: GRNA

<400> SEQUENCE: 170

| aaacccctcc gtttagagag gggttatgct agttaagaga taacgccttt tggcgtcaga | 60 |
| gctctaaggt gtactaaacc ttatcatagt aacctaaata gttcttgcaa gaactatcag | 120 |
| ggaactataa cccagtaaca ttactgactg gcctatagtg agtcgtatta | 170 |

<210> SEQ ID NO 171
<211> LENGTH: 180

```
<212> TYPE: DNA
<213> ORGANISM: Artificial Sequence
<220> FEATURE:
<223> OTHER INFORMATION: GRNA

<400> SEQUENCE: 171
aaacccctcc gtttagagag gggttatgct agttaagaga taacgcctcg caaaagcgag     60
gcgtcagagc tctaaggtgt actaaacctt atcatagtaa cctaaatagt tcttggttaa   120
gaactatcag ggaactataa cccagtaaca ttactgactg gcctatagtg agtcgtatta   180

<210> SEQ ID NO 172
<211> LENGTH: 20
<212> TYPE: DNA
<213> ORGANISM: Artificial Sequence
<220> FEATURE:
<223> OTHER INFORMATION: PRIMER

<400> SEQUENCE: 172
ttgggtaacg ccagggtttt                                                 20

<210> SEQ ID NO 173
<211> LENGTH: 20
<212> TYPE: DNA
<213> ORGANISM: Artificial Sequence
<220> FEATURE:
<223> OTHER INFORMATION: PRIMER

<400> SEQUENCE: 173
tgtgtggaat tgtgagcgga                                                 20

<210> SEQ ID NO 174
<211> LENGTH: 20
<212> TYPE: DNA
<213> ORGANISM: Artificial Sequence
<220> FEATURE:
<223> OTHER INFORMATION: PRIMER

<400> SEQUENCE: 174
aaacccctcc gtttagagag                                                 20

<210> SEQ ID NO 175
<211> LENGTH: 29
<212> TYPE: DNA
<213> ORGANISM: Artificial Sequence
<220> FEATURE:
<223> OTHER INFORMATION: PRIMER

<400> SEQUENCE: 175
aagctaatac gactcactat aggccagtc                                       29

<210> SEQ ID NO 176
<211> LENGTH: 20
<212> TYPE: DNA
<213> ORGANISM: Artificial Sequence
<220> FEATURE:
<223> OTHER INFORMATION: PRIMER

<400> SEQUENCE: 176
ccagtcagta atgttactgg                                                 20

<210> SEQ ID NO 177
<211> LENGTH: 1337
<212> TYPE: PRT
<213> ORGANISM: Artificial Sequence
<220> FEATURE:
```

<223> OTHER INFORMATION: ENGINEERED NICKASE

<400> SEQUENCE: 177

```
Met Lys Lys Asp Tyr Val Ile Gly Leu Asp Ile Gly Thr Asn Ser Val
1               5                   10                  15

Gly Trp Ala Val Met Thr Glu Asp Tyr Gln Leu Val Lys Lys Lys Met
            20                  25                  30

Pro Ile Tyr Gly Asn Thr Glu Lys Lys Ile Lys Lys Asn Phe Trp
        35                  40                  45

Gly Val Arg Leu Phe Glu Gly His Thr Ala Glu Asp Arg Arg Leu
    50                  55                  60

Lys Arg Thr Ala Arg Arg Ile Ile Ser Arg Arg Asn Arg Leu Arg
65              70                  75                  80

Tyr Leu Gln Ala Phe Phe Glu Glu Ala Met Thr Asp Leu Asp Glu Asn
                85                  90                  95

Phe Phe Ala Arg Leu Gln Glu Ser Phe Leu Val Pro Glu Asp Lys Lys
            100                 105                 110

Trp His Arg His Pro Ile Phe Ala Lys Leu Glu Asp Glu Val Ala Tyr
            115                 120                 125

His Glu Thr Tyr Pro Thr Ile Tyr His Leu Arg Lys Lys Leu Ala Asp
130                 135                 140

Ser Ser Glu Gln Ala Asp Leu Arg Leu Ile Tyr Leu Ala Leu Ala His
145                 150                 155                 160

Ile Val Lys Tyr Arg Gly His Phe Leu Ile Glu Gly Lys Leu Ser Thr
                165                 170                 175

Glu Asn Ile Ser Val Lys Glu Gln Phe Gln Gln Phe Met Ile Ile Tyr
            180                 185                 190

Asn Gln Thr Phe Val Asn Gly Glu Ser Arg Leu Val Ser Ala Pro Leu
            195                 200                 205

Pro Glu Ser Val Leu Ile Glu Glu Leu Thr Glu Lys Ala Ser Arg
210                 215                 220

Thr Lys Lys Ser Glu Lys Val Leu Gln Gln Phe Pro Gln Glu Lys Ala
225                 230                 235                 240

Asn Gly Leu Phe Gly Gln Phe Leu Lys Leu Met Val Gly Asn Lys Ala
                245                 250                 255

Asp Phe Lys Lys Val Phe Gly Leu Glu Glu Ala Lys Ile Thr Tyr
            260                 265                 270

Ala Ser Glu Ser Tyr Glu Glu Asp Leu Glu Gly Ile Leu Ala Lys Val
            275                 280                 285

Gly Asp Glu Tyr Ser Asp Val Phe Leu Ala Ala Lys Asn Val Tyr Asp
            290                 295                 300

Ala Val Glu Leu Ser Thr Ile Leu Ala Asp Ser Asp Lys Lys Ser His
305                 310                 315                 320

Ala Lys Leu Ser Ser Ser Met Ile Val Arg Phe Thr Glu His Gln Glu
                325                 330                 335

Asp Leu Lys Lys Phe Lys Arg Phe Ile Arg Glu Asn Cys Pro Asp Glu
            340                 345                 350

Tyr Asp Asn Leu Phe Lys Asn Glu Gln Lys Asp Gly Tyr Ala Gly Tyr
            355                 360                 365

Ile Ala His Ala Gly Lys Val Ser Gln Leu Lys Phe Tyr Gln Tyr Val
        370                 375                 380

Lys Lys Ile Ile Gln Asp Ile Ala Gly Ala Glu Tyr Phe Leu Glu Lys
385                 390                 395                 400
```

```
Ile Ala Gln Glu Asn Phe Leu Arg Lys Gln Arg Thr Phe Asp Asn Gly
                405                 410                 415

Val Ile Pro His Gln Ile His Leu Ala Glu Leu Gln Ala Ile Ile His
            420                 425                 430

Arg Gln Ala Ala Tyr Tyr Pro Phe Leu Lys Glu Asn Gln Glu Lys Ile
        435                 440                 445

Glu Gln Leu Val Thr Phe Arg Ile Pro Tyr Tyr Val Gly Pro Leu Ser
    450                 455                 460

Lys Gly Asp Ala Ser Thr Phe Ala Trp Leu Lys Arg Gln Ser Glu Glu
465                 470                 475                 480

Pro Ile Arg Pro Trp Asn Leu Gln Glu Thr Val Asp Leu Asp Gln Ser
                485                 490                 495

Ala Thr Ala Phe Ile Glu Arg Met Thr Asn Phe Asp Thr Tyr Leu Pro
            500                 505                 510

Ser Glu Lys Val Leu Pro Lys His Ser Leu Leu Tyr Glu Lys Phe Met
        515                 520                 525

Val Phe Asn Glu Leu Thr Lys Ile Ser Tyr Thr Asp Asp Arg Gly Ile
    530                 535                 540

Lys Ala Asn Phe Ser Gly Lys Glu Lys Glu Lys Ile Phe Asp Tyr Leu
545                 550                 555                 560

Phe Lys Thr Arg Arg Lys Val Lys Lys Lys Asp Ile Ile Gln Phe Tyr
                565                 570                 575

Arg Asn Glu Tyr Asn Thr Glu Ile Val Thr Leu Ser Gly Leu Glu Glu
            580                 585                 590

Asp Gln Phe Asn Ala Ser Phe Ser Thr Tyr Gln Asp Leu Leu Lys Cys
        595                 600                 605

Gly Leu Thr Arg Ala Glu Leu Asp His Pro Asp Asn Ala Glu Lys Leu
    610                 615                 620

Glu Asp Ile Ile Lys Ile Leu Thr Ile Phe Glu Asp Arg Gln Arg Ile
625                 630                 635                 640

Arg Thr Gln Leu Ser Thr Phe Lys Gly Gln Phe Ser Ala Glu Val Leu
                645                 650                 655

Lys Lys Leu Glu Arg Lys His Tyr Thr Gly Trp Gly Arg Leu Ser Lys
            660                 665                 670

Lys Leu Ile Asn Gly Ile Tyr Asp Lys Glu Ser Gly Lys Thr Ile Leu
        675                 680                 685

Gly Tyr Leu Ile Lys Asp Asp Gly Val Ser Lys His Tyr Asn Arg Asn
    690                 695                 700

Phe Met Gln Leu Ile Asn Asp Ser Gln Leu Ser Phe Lys Asn Ala Ile
705                 710                 715                 720

Gln Lys Ala Gln Ser Ser Glu His Glu Glu Thr Leu Ser Glu Thr Val
                725                 730                 735

Asn Glu Leu Ala Gly Ser Pro Ala Ile Lys Lys Gly Ile Tyr Gln Ser
            740                 745                 750

Leu Lys Ile Val Asp Glu Leu Val Ala Ile Met Gly Tyr Ala Pro Lys
        755                 760                 765

Arg Ile Val Val Glu Met Ala Arg Glu Asn Gln Thr Thr Ser Thr Gly
    770                 775                 780

Lys Arg Arg Ser Ile Gln Arg Leu Lys Ile Val Glu Lys Ala Met Ala
785                 790                 795                 800

Glu Ile Gly Ser Asn Leu Leu Lys Glu Gln Pro Thr Thr Asn Glu Gln
                805                 810                 815

Leu Arg Asp Thr Arg Leu Phe Leu Tyr Tyr Met Gln Asn Gly Lys Asp
```

```
                820             825             830
Met Tyr Thr Gly Asp Glu Leu Ser Leu His Arg Leu Ser His Tyr Asp
            835             840             845

Ile Asp Ala Ile Ile Pro Gln Ser Phe Met Lys Asp Ser Leu Asp
850             855             860

Asn Leu Val Leu Val Gly Ser Thr Glu Asn Arg Gly Lys Ser Asp Asp
865             870             875             880

Val Pro Ser Lys Glu Val Val Lys Asp Met Lys Ala Tyr Trp Glu Lys
            885             890             895

Leu Tyr Ala Ala Gly Leu Ile Ser Gln Arg Lys Phe Gln Arg Leu Thr
            900             905             910

Lys Gly Glu Gln Gly Gly Leu Thr Leu Glu Asp Lys Ala His Phe Ile
            915             920             925

Gln Arg Gln Leu Val Glu Thr Arg Gln Ile Thr Lys Asn Val Ala Gly
            930             935             940

Ile Leu Asp Gln Arg Tyr Asn Ala Asn Ser Lys Glu Lys Lys Val Gln
945             950             955             960

Ile Ile Thr Leu Lys Ala Ser Leu Thr Ser Gln Phe Arg Ser Ile Phe
            965             970             975

Gly Leu Tyr Lys Val Arg Glu Val Asn Asp Tyr His His Gly Gln Asp
            980             985             990

Ala Tyr Leu Asn Cys Val Val Ala Thr Thr Leu Leu Lys Val Tyr Pro
            995             1000            1005

Asn Leu Ala Pro Glu Phe Val Tyr Gly Glu Tyr Pro Lys Phe Gln
        1010            1015            1020

Thr Phe Lys Glu Asn Lys Ala Thr Ala Lys Ala Ile Ile Tyr Thr
        1025            1030            1035

Asn Leu Leu Arg Phe Phe Thr Glu Asp Glu Pro Arg Phe Thr Lys
        1040            1045            1050

Asp Gly Glu Ile Leu Trp Ser Asn Ser Tyr Leu Lys Thr Ile Lys
        1055            1060            1065

Lys Glu Leu Asn Tyr His Gln Met Asn Ile Val Lys Lys Val Glu
        1070            1075            1080

Val Gln Lys Gly Gly Phe Ser Lys Glu Ser Ile Lys Pro Lys Gly
        1085            1090            1095

Pro Ser Asn Lys Leu Ile Pro Val Lys Asn Gly Leu Asp Pro Gln
        1100            1105            1110

Lys Tyr Gly Gly Phe Asp Ser Pro Ile Val Ala Tyr Thr Val Leu
        1115            1120            1125

Phe Thr His Glu Lys Gly Lys Lys Pro Leu Ile Lys Gln Glu Ile
        1130            1135            1140

Leu Gly Ile Thr Ile Met Glu Lys Thr Arg Phe Glu Gln Asn Pro
        1145            1150            1155

Ile Leu Phe Leu Glu Glu Lys Gly Phe Leu Arg Pro Arg Val Leu
        1160            1165            1170

Met Lys Leu Pro Lys Tyr Thr Leu Tyr Glu Phe Pro Glu Gly Arg
        1175            1180            1185

Arg Arg Leu Leu Ala Ser Ala Lys Glu Ala Gln Lys Gly Asn Gln
        1190            1195            1200

Met Val Leu Pro Glu His Leu Leu Thr Leu Leu Tyr His Ala Lys
        1205            1210            1215

Gln Cys Leu Leu Pro Asn Gln Ser Glu Ser Leu Thr Tyr Val Glu
        1220            1225            1230
```

Gln His Gln Pro Glu Phe Gln Glu Ile Leu Glu Arg Val Val Asp
    1235                1240                1245

Phe Ala Glu Val His Thr Leu Ala Lys Ser Lys Val Gln Gln Ile
    1250                1255                1260

Val Lys Leu Phe Glu Ala Asn Gln Thr Ala Asp Val Lys Glu Ile
    1265                1270                1275

Ala Ala Ser Phe Ile Gln Leu Met Gln Phe Asn Ala Met Gly Ala
    1280                1285                1290

Pro Ser Thr Phe Lys Phe Gln Lys Asp Ile Glu Arg Ala Arg
    1295                1300                1305

Tyr Thr Ser Ile Lys Glu Ile Phe Asp Ala Thr Ile Ile Tyr Gln
    1310                1315                1320

Ser Thr Thr Gly Leu Tyr Glu Thr Arg Arg Lys Val Val Asp
    1325                1330                1335

<210> SEQ ID NO 178
<211> LENGTH: 1337
<212> TYPE: PRT
<213> ORGANISM: Artificial Sequence
<220> FEATURE:
<223> OTHER INFORMATION: ENGINEERED NICKASE

<400> SEQUENCE: 178

Met Lys Lys Asp Tyr Val Ile Gly Leu Asp Ile Gly Thr Asn Ser Val
1               5                   10                  15

Gly Trp Ala Val Met Thr Glu Asp Tyr Gln Leu Val Lys Lys Lys Met
            20                  25                  30

Pro Ile Tyr Gly Asn Thr Glu Lys Lys Ile Lys Lys Asn Phe Trp
        35                  40                  45

Gly Val Arg Leu Phe Glu Glu Gly His Thr Ala Glu Asp Arg Arg Leu
    50                  55                  60

Lys Arg Thr Ala Arg Arg Ile Ile Ser Arg Arg Asn Arg Leu Arg
65                  70                  75                  80

Tyr Leu Gln Ala Phe Phe Glu Glu Ala Met Thr Asp Leu Asp Glu Asn
                85                  90                  95

Phe Phe Ala Arg Leu Gln Glu Ser Phe Leu Val Pro Glu Asp Lys Lys
                100                 105                 110

Trp His Arg His Pro Ile Phe Ala Lys Leu Glu Asp Glu Val Ala Tyr
            115                 120                 125

His Glu Thr Tyr Pro Thr Ile Tyr His Leu Arg Lys Lys Leu Ala Asp
        130                 135                 140

Ser Ser Glu Gln Ala Asp Leu Arg Leu Ile Tyr Leu Ala Leu Ala His
145                 150                 155                 160

Ile Val Lys Tyr Arg Gly His Phe Leu Ile Glu Gly Lys Leu Ser Thr
                165                 170                 175

Glu Asn Ile Ser Val Lys Glu Gln Phe Gln Gln Phe Met Ile Ile Tyr
                180                 185                 190

Asn Gln Thr Phe Val Asn Gly Glu Ser Arg Leu Val Ser Ala Pro Leu
            195                 200                 205

Pro Glu Ser Val Leu Ile Glu Glu Leu Thr Glu Lys Ala Ser Arg
        210                 215                 220

Thr Lys Lys Ser Glu Lys Val Leu Gln Gln Phe Pro Gln Glu Lys Ala
225                 230                 235                 240

Asn Gly Leu Phe Gly Gln Phe Leu Lys Leu Met Val Gly Asn Lys Ala
                245                 250                 255

-continued

```
Asp Phe Lys Lys Val Phe Gly Leu Glu Glu Ala Lys Ile Thr Tyr
        260                 265                 270

Ala Ser Glu Ser Tyr Glu Asp Leu Glu Gly Ile Leu Ala Lys Val
        275                 280                 285

Gly Asp Glu Tyr Ser Asp Val Phe Leu Ala Ala Lys Asn Val Tyr Asp
290                 295                 300

Ala Val Glu Leu Ser Thr Ile Leu Ala Asp Ser Asp Lys Lys Ser His
305                 310                 315                 320

Ala Lys Leu Ser Ser Ser Met Ile Val Arg Phe Thr Glu His Gln Glu
                325                 330                 335

Asp Leu Lys Lys Phe Lys Arg Phe Ile Arg Glu Asn Cys Pro Asp Glu
        340                 345                 350

Tyr Asp Asn Leu Phe Lys Asn Glu Gln Lys Asp Gly Tyr Ala Gly Tyr
        355                 360                 365

Ile Ala His Ala Gly Lys Val Ser Gln Leu Lys Phe Tyr Gln Tyr Val
    370                 375                 380

Lys Lys Ile Ile Gln Asp Ile Ala Gly Ala Glu Tyr Phe Leu Glu Lys
385                 390                 395                 400

Ile Ala Gln Glu Asn Phe Leu Arg Lys Gln Arg Thr Phe Asp Asn Gly
                405                 410                 415

Val Ile Pro His Gln Ile His Leu Ala Glu Leu Gln Ala Ile Ile His
        420                 425                 430

Arg Gln Ala Ala Tyr Tyr Pro Phe Leu Lys Glu Asn Gln Glu Lys Ile
        435                 440                 445

Glu Gln Leu Val Thr Phe Arg Ile Pro Tyr Tyr Val Gly Pro Leu Ser
        450                 455                 460

Lys Gly Asp Ala Ser Thr Phe Ala Trp Leu Lys Arg Gln Ser Glu Glu
465                 470                 475                 480

Pro Ile Arg Pro Trp Asn Leu Gln Glu Thr Val Asp Leu Asp Gln Ser
                485                 490                 495

Ala Thr Ala Phe Ile Glu Arg Met Thr Asn Phe Asp Thr Tyr Leu Pro
        500                 505                 510

Ser Glu Lys Val Leu Pro Lys His Ser Leu Leu Tyr Glu Lys Phe Met
        515                 520                 525

Val Phe Asn Glu Leu Thr Lys Ile Ser Tyr Thr Asp Asp Arg Gly Ile
        530                 535                 540

Lys Ala Asn Phe Ser Gly Lys Glu Lys Glu Lys Ile Phe Asp Tyr Leu
545                 550                 555                 560

Phe Lys Thr Arg Arg Lys Val Lys Lys Lys Asp Ile Ile Gln Phe Tyr
                565                 570                 575

Arg Asn Glu Tyr Asn Thr Glu Ile Val Thr Leu Ser Gly Leu Glu Glu
        580                 585                 590

Asp Gln Phe Asn Ala Ser Phe Ser Thr Tyr Gln Asp Leu Leu Lys Cys
        595                 600                 605

Gly Leu Thr Arg Ala Glu Leu Asp His Pro Asp Asn Ala Glu Lys Leu
        610                 615                 620

Glu Asp Ile Ile Lys Ile Leu Thr Ile Phe Glu Asp Arg Gln Arg Ile
625                 630                 635                 640

Arg Thr Gln Leu Ser Thr Phe Lys Gly Gln Phe Ser Ala Glu Val Leu
                645                 650                 655

Lys Lys Leu Glu Arg Lys His Tyr Thr Gly Trp Gly Arg Leu Ser Lys
        660                 665                 670
```

Lys Leu Ile Asn Gly Ile Tyr Asp Lys Glu Ser Gly Lys Thr Ile Leu
            675                 680                 685

Gly Tyr Leu Ile Lys Asp Asp Gly Val Ser Lys His Tyr Asn Arg Asn
        690                 695                 700

Phe Met Gln Leu Ile Asn Asp Ser Gln Leu Ser Phe Lys Asn Ala Ile
705                 710                 715                 720

Gln Lys Ala Gln Ser Ser Glu His Glu Glu Thr Leu Ser Glu Thr Val
                725                 730                 735

Asn Glu Leu Ala Gly Ser Pro Ala Ile Lys Lys Gly Ile Tyr Gln Ser
            740                 745                 750

Leu Lys Ile Val Asp Glu Leu Val Ala Ile Met Gly Tyr Ala Pro Lys
        755                 760                 765

Arg Ile Val Val Glu Met Ala Arg Glu Asn Gln Thr Thr Ser Thr Gly
        770                 775                 780

Lys Arg Arg Ser Ile Gln Arg Leu Lys Ile Val Glu Lys Ala Met Ala
785                 790                 795                 800

Glu Ile Gly Ser Asn Leu Leu Lys Glu Gln Pro Thr Thr Asn Glu Gln
            805                 810                 815

Leu Arg Asp Thr Arg Leu Phe Leu Tyr Tyr Met Gln Asn Gly Lys Asp
        820                 825                 830

Met Tyr Thr Gly Asp Glu Leu Ser Leu His Arg Leu Ser His Tyr Asp
        835                 840                 845

Ile Asp His Ile Ile Pro Gln Ser Phe Met Lys Asp Asp Ser Leu Asp
850                 855                 860

Asn Leu Val Leu Val Gly Ser Thr Glu Ala Arg Gly Lys Ser Asp Asp
865                 870                 875                 880

Val Pro Ser Lys Glu Val Val Lys Asp Met Lys Ala Tyr Trp Glu Lys
            885                 890                 895

Leu Tyr Ala Ala Gly Leu Ile Ser Gln Arg Lys Phe Gln Arg Leu Thr
        900                 905                 910

Lys Gly Glu Gln Gly Gly Leu Thr Leu Glu Asp Lys Ala His Phe Ile
        915                 920                 925

Gln Arg Gln Leu Val Glu Thr Arg Gln Ile Thr Lys Asn Val Ala Gly
930                 935                 940

Ile Leu Asp Gln Arg Tyr Asn Ala Asn Ser Lys Glu Lys Lys Val Gln
945                 950                 955                 960

Ile Ile Thr Leu Lys Ala Ser Leu Thr Ser Gln Phe Arg Ser Ile Phe
            965                 970                 975

Gly Leu Tyr Lys Val Arg Glu Val Asn Asp Tyr His His Gly Gln Asp
        980                 985                 990

Ala Tyr Leu Asn Cys Val Val Ala  Thr Thr Leu Leu Lys  Val Tyr Pro
        995                 1000                1005

Asn Leu  Ala Pro Glu Phe Val  Tyr Gly Glu Tyr Pro  Lys Phe Gln
   1010                1015                1020

Thr Phe  Lys Glu Asn Lys Ala  Thr Ala Lys Ala Ile  Ile Tyr Thr
   1025                1030                1035

Asn Leu  Leu Arg Phe Phe Thr  Glu Asp Glu Pro Arg  Phe Thr Lys
   1040                1045                1050

Asp Gly  Glu Ile Leu Trp Ser  Asn Ser Tyr Leu Lys  Thr Ile Lys
   1055                1060                1065

Lys Glu  Leu Asn Tyr His Gln  Met Asn Ile Val Lys  Lys Val Glu
   1070                1075                1080

Val Gln  Lys Gly Gly Phe Ser  Lys Glu Ser Ile Lys  Pro Lys Gly

```
            1085                1090                1095

Pro Ser Asn Lys Leu Ile Pro Val Lys Asn Gly Leu Asp Pro Gln
        1100                1105                1110

Lys Tyr Gly Gly Phe Asp Ser Pro Ile Val Ala Tyr Thr Val Leu
    1115                1120                1125

Phe Thr His Glu Lys Gly Lys Lys Pro Leu Ile Lys Gln Glu Ile
    1130                1135                1140

Leu Gly Ile Thr Ile Met Glu Lys Thr Arg Phe Glu Gln Asn Pro
    1145                1150                1155

Ile Leu Phe Leu Glu Glu Lys Gly Phe Leu Arg Pro Arg Val Leu
    1160                1165                1170

Met Lys Leu Pro Lys Tyr Thr Leu Tyr Glu Phe Pro Glu Gly Arg
    1175                1180                1185

Arg Arg Leu Leu Ala Ser Ala Lys Glu Ala Gln Lys Gly Asn Gln
    1190                1195                1200

Met Val Leu Pro Glu His Leu Leu Thr Leu Leu Tyr His Ala Lys
    1205                1210                1215

Gln Cys Leu Leu Pro Asn Gln Ser Glu Ser Leu Thr Tyr Val Glu
    1220                1225                1230

Gln His Gln Pro Glu Phe Gln Glu Ile Leu Glu Arg Val Val Asp
    1235                1240                1245

Phe Ala Glu Val His Thr Leu Ala Lys Ser Lys Val Gln Gln Ile
    1250                1255                1260

Val Lys Leu Phe Glu Ala Asn Gln Thr Ala Asp Val Lys Glu Ile
    1265                1270                1275

Ala Ala Ser Phe Ile Gln Leu Met Gln Phe Asn Ala Met Gly Ala
    1280                1285                1290

Pro Ser Thr Phe Lys Phe Phe Gln Lys Asp Ile Glu Arg Ala Arg
    1295                1300                1305

Tyr Thr Ser Ile Lys Glu Ile Phe Asp Ala Thr Ile Ile Tyr Gln
    1310                1315                1320

Ser Thr Thr Gly Leu Tyr Glu Thr Arg Arg Lys Val Val Asp
    1325                1330                1335

<210> SEQ ID NO 179
<211> LENGTH: 1087
<212> TYPE: PRT
<213> ORGANISM: Artificial Sequence
<220> FEATURE:
<223> OTHER INFORMATION: ENGINEERED NICKASE

<400> SEQUENCE: 179

Met Lys Tyr Ile Ile Gly Leu Asp Met Gly Ile Thr Ser Val Gly Phe
1               5                   10                  15

Ala Thr Met Met Leu Asp Asp Lys Asp Glu Pro Cys Arg Ile Ile Arg
            20                  25                  30

Met Gly Ser Arg Ile Phe Glu Ala Ala Glu His Pro Lys Asp Gly Ser
        35                  40                  45

Ser Leu Ala Ala Pro Arg Arg Ile Asn Arg Gly Met Arg Arg Arg Leu
    50                  55                  60

Arg Arg Lys Ser His Arg Lys Glu Arg Ile Lys Asp Leu Ile Ile Lys
65                  70                  75                  80

Asn Glu Leu Met Thr Ala Asp Glu Ile Ser Ala Ile Tyr Ser Thr Gly
                85                  90                  95

Lys Gln Leu Ser Asp Ile Tyr Gln Ile Arg Ala Glu Ala Leu Asp Arg
```

```
                100             105              110
Lys Leu Asn Thr Glu Glu Phe Val Arg Leu Ile His Leu Ser Gln
            115                 120             125
Arg Arg Gly Phe Lys Ser Asn Arg Lys Val Asp Ala Lys Glu Lys Gly
        130                 135             140
Ser Asp Ala Gly Lys Leu Leu Ser Ala Val Asn Ser Asn Lys Glu Leu
145                 150                 155                 160
Met Ile Glu Lys Asn Tyr Arg Thr Ile Gly Glu Met Leu Tyr Lys Asp
                165                 170                 175
Glu Lys Phe Ser Glu Tyr Lys Arg Asn Lys Ala Asp Asp Tyr Ser Asn
            180                 185                 190
Thr Phe Ala Arg Ser Glu Tyr Glu Asp Glu Ile Arg Gln Ile Phe Ser
        195                 200                 205
Ala Gln Gln Glu His Gly Asn Pro Tyr Ala Thr Asp Glu Leu Lys Glu
    210                 215                 220
Ser Tyr Leu Asp Ile Tyr Leu Ser Gln Arg Ser Phe Asp Glu Gly Pro
225                 230                 235                 240
Gly Gly Ser Ser Pro Tyr Gly Gly Asn Gln Ile Glu Lys Met Ile Gly
                245                 250                 255
Asn Cys Thr Leu Glu Pro Glu Glu Lys Arg Ala Ala Lys Ala Thr Phe
                260                 265                 270
Ser Phe Glu Tyr Phe Asn Leu Leu Ser Lys Val Asn Ser Ile Lys Ile
            275                 280                 285
Val Ser Ser Ser Gly Lys Arg Ala Leu Asn Asn Asp Glu Arg Gln Ser
        290                 295                 300
Val Ile Arg Leu Ala Phe Ala Lys Asn Ala Ile Ser Tyr Thr Ser Leu
305                 310                 315                 320
Arg Lys Glu Leu Asn Met Glu Tyr Ser Glu Arg Phe Asn Ile Ser Tyr
                325                 330                 335
Ser Gln Ser Asp Lys Ser Ile Glu Glu Ile Glu Lys Lys Thr Lys Phe
            340                 345                 350
Thr Tyr Leu Thr Ala Tyr His Thr Phe Lys Lys Ala Tyr Gly Ser Val
        355                 360                 365
Phe Val Glu Trp Ser Ala Asp Lys Lys Asn Ser Leu Ala Tyr Ala Leu
    370                 375                 380
Thr Ala Tyr Lys Asn Asp Thr Lys Ile Ile Glu Tyr Leu Thr Gln Lys
385                 390                 395                 400
Gly Phe Asp Ala Ala Glu Thr Asp Ile Ala Leu Thr Leu Pro Ser Phe
                405                 410                 415
Ser Lys Trp Gly Asn Leu Ser Glu Lys Ala Leu Asn Asn Ile Ile Pro
            420                 425                 430
Tyr Leu Glu Gln Gly Met Leu Tyr His Asp Ala Cys Thr Ala Ala Gly
        435                 440                 445
Tyr Asn Phe Lys Ala Asp Asp Thr Asp Lys Arg Met Tyr Leu Pro Ala
    450                 455                 460
His Glu Lys Glu Ala Pro Glu Leu Asp Asp Ile Thr Asn Pro Val Val
465                 470                 475                 480
Arg Arg Ala Ile Ser Gln Thr Ile Lys Val Ile Asn Ala Leu Ile Arg
                485                 490                 495
Glu Met Gly Glu Ser Pro Cys Phe Val Asn Ile Glu Leu Ala Arg Glu
            500                 505                 510
Leu Ser Lys Asn Lys Ala Glu Arg Ser Lys Ile Glu Lys Gly Gln Lys
        515                 520                 525
```

```
Glu Asn Gln Val Arg Asn Asp Arg Ile Met Glu Arg Leu Arg Asn Glu
530                 535                 540

Phe Gly Leu Leu Ser Pro Thr Gly Gln Asp Leu Ile Lys Leu Lys Leu
545                 550                 555                 560

Trp Glu Glu Gln Asp Gly Ile Cys Pro Tyr Ser Leu Lys Pro Ile Lys
                565                 570                 575

Ile Glu Lys Leu Phe Asp Val Gly Tyr Thr Asp Ile Asp Ala Ile Ile
                580                 585                 590

Pro Tyr Ser Leu Ser Phe Asp Asp Thr Tyr Asn Asn Lys Val Leu Val
                595                 600                 605

Met Ser Ser Glu Asn Arg Gln Lys Gly Asn Arg Ile Pro Met Gln Tyr
610                 615                 620

Leu Glu Gly Lys Arg Gln Asp Asp Phe Trp Leu Trp Val Asp Asn Ser
625                 630                 635                 640

Asn Leu Ser Arg Arg Lys Lys Gln Asn Leu Thr Lys Glu Thr Leu Ser
                645                 650                 655

Glu Asp Asp Leu Ser Gly Phe Lys Lys Arg Asn Leu Gln Asp Thr Gln
                660                 665                 670

Tyr Leu Ser Arg Phe Met Met Asn Tyr Leu Lys Lys Tyr Leu Ala Leu
                675                 680                 685

Ala Pro Asn Thr Thr Gly Arg Lys Asn Thr Ile Gln Ala Val Asn Gly
690                 695                 700

Ala Val Thr Ser Tyr Leu Arg Lys Arg Trp Gly Ile Gln Lys Val Arg
705                 710                 715                 720

Glu Asn Gly Asp Thr His His Ala Val Asp Ala Val Val Ile Ser Cys
                725                 730                 735

Val Thr Ala Gly Met Thr Lys Arg Val Ser Glu Tyr Ala Lys Tyr Lys
                740                 745                 750

Glu Thr Glu Phe Gln Asn Pro Gln Thr Gly Glu Phe Phe Asp Val Asp
                755                 760                 765

Ile Arg Thr Gly Glu Val Ile Asn Arg Phe Pro Leu Pro Tyr Ala Arg
                770                 775                 780

Phe Arg Asn Glu Leu Leu Met Arg Cys Ser Glu Asn Pro Ser Arg Ile
785                 790                 795                 800

Leu His Glu Met Pro Leu Pro Thr Tyr Ala Ala Asp Glu Lys Val Ala
                805                 810                 815

Pro Ile Phe Val Ser Arg Met Pro Lys His Lys Val Lys Gly Ser Ala
                820                 825                 830

His Lys Glu Thr Ile Arg Arg Ala Phe Glu Glu Asp Gly Lys Lys Tyr
                835                 840                 845

Thr Val Ser Lys Val Pro Leu Thr Asp Leu Lys Leu Lys Asn Gly Glu
850                 855                 860

Ile Glu Asn Tyr Tyr Asn Pro Glu Ser Asp Gly Leu Leu Tyr Asn Ala
865                 870                 875                 880

Leu Lys Glu Gln Leu Ile Ala Phe Gly Gly Asp Ala Ala Lys Ala Phe
                885                 890                 895

Glu Gln Pro Phe Tyr Lys Pro Lys Ser Asp Gly Ser Glu Gly Pro Leu
                900                 905                 910

Val Lys Lys Val Lys Leu Ile Asn Lys Ala Thr Leu Thr Val Pro Val
                915                 920                 925

Leu Asn Asn Thr Ala Val Ala Asp Asn Gly Ser Met Val Arg Val Asp
930                 935                 940
```

```
Val Phe Phe Val Glu Gly Glu Gly Tyr Tyr Leu Val Pro Ile Tyr Val
945                 950                 955                 960

Ala Asp Thr Val Lys Lys Glu Leu Pro Asn Lys Ala Ile Ile Ala Asn
                965                 970                 975

Lys Pro Tyr Glu Glu Trp Lys Glu Met Arg Glu Glu Asn Phe Val Phe
            980                 985                 990

Ser Leu Tyr Pro Asn Asp Leu Ile Lys Ile Ser Ser Arg Lys Asp Met
        995                1000               1005

Lys Phe Asn Leu Val Asn Lys Glu Ser Thr Leu Ala Pro Asn Cys
   1010               1015               1020

Gln Ser Lys Glu Ala Leu Val Tyr Tyr Lys Gly Ser Asp Ile Ser
   1025               1030               1035

Thr Ala Ala Val Thr Ala Ile Asn His Asp Asn Thr Tyr Lys Leu
   1040               1045               1050

Arg Gly Leu Gly Val Lys Thr Leu Leu Lys Ile Glu Lys Tyr Gln
   1055               1060               1065

Val Asp Val Leu Gly Asn Val Phe Lys Val Gly Lys Glu Lys Arg
   1070               1075               1080

Val Arg Phe Lys
   1085

<210> SEQ ID NO 180
<211> LENGTH: 1095
<212> TYPE: PRT
<213> ORGANISM: Artificial Sequence
<220> FEATURE:
<223> OTHER INFORMATION: ENGINEERED NICKASE

<400> SEQUENCE: 180

Met Arg Pro Tyr Ala Ile Gly Leu Asp Ile Gly Ile Thr Ser Val Gly
1               5                   10                  15

Trp Ala Thr Val Ala Leu Asp Ala Asp Glu Ser Pro Cys Gly Ile Ile
            20                  25                  30

Gly Leu Gly Ser Arg Ile Phe Asp Ala Ala Glu Gln Pro Lys Thr Gly
        35                  40                  45

Glu Ser Leu Ala Ala Pro Arg Arg Ala Arg Gly Ser Arg Arg Arg
 50                  55                  60

Leu Arg Arg His Arg His Arg Asn Glu Arg Ile Arg Ser Leu Met Leu
65                  70                  75                  80

Glu Glu Arg Leu Ile Ser Gln Asp Gly Leu Glu Thr Leu Phe Asp Gly
                85                  90                  95

Arg Leu Glu Asp Ile Tyr Ala Leu Arg Val Lys Ala Leu Asp Glu Ile
            100                 105                 110

Val Ser Arg Thr Asp Phe Ala Arg Ile Leu Leu His Ile Ser Gln Arg
        115                 120                 125

Arg Gly Phe Lys Ser Asn Arg Lys Asn Pro Thr Thr Lys Glu Asp Gly
    130                 135                 140

Val Leu Leu Ala Ala Val Asn Glu Asn Lys Gln Arg Met Ser Glu His
145                 150                 155                 160

Gly Tyr Arg Thr Val Gly Glu Met Phe Leu Leu Asp Glu Thr Phe Lys
                165                 170                 175

Asp His Lys Arg Asn Lys Gly Gly Asn Tyr Ile Thr Thr Val Ala Arg
            180                 185                 190

Asp Met Val Ala Asp Glu Val Arg Ala Ile Phe Ser Ala Gln Arg Glu
        195                 200                 205
```

```
Leu Gly Ala Ser Phe Ala Ser Glu Glu Phe Glu Arg Tyr Leu Glu
    210                 215                 220

Ile Leu Leu Ser Gln Arg Ser Phe Asp Glu Gly Pro Gly Gly Asn Ser
225                 230                 235                 240

Pro Tyr Gly Gly Ser Gln Ile Glu Arg Met Val Gly Arg Cys Thr Phe
                245                 250                 255

Phe Pro Asp Glu Pro Arg Ala Ala Lys Ala Thr Tyr Ser Phe Glu Tyr
            260                 265                 270

Phe Thr Leu Leu Gln Lys Val Asn His Ile Arg Ile Val Glu Asn Gly
        275                 280                 285

Val Ala Ser Lys Leu Thr Asp Glu Gln Arg Arg Ile Ile Ile Glu Leu
    290                 295                 300

Ala His Thr Thr Lys Asp Val Ser Tyr Ala Lys Ile Arg Lys Val Leu
305                 310                 315                 320

Lys Leu Ser Asp Lys Gln Leu Phe Asn Ile Arg Tyr Ser Asp Asn Ser
                325                 330                 335

Pro Ala Glu Asp Ser Glu Lys Lys Glu Lys Leu Gly Ile Met Lys Ala
            340                 345                 350

Tyr His Gln Met Arg Ser Ala Ile Asp Arg Val Ser Lys Gly Arg Phe
        355                 360                 365

Ala Met Met Pro Arg Ala Gln Arg Asn Ala Ile Gly Thr Ala Leu Ser
    370                 375                 380

Leu Tyr Lys Thr Ser Asp Lys Ile Arg Lys Tyr Leu Thr Asp Ala Gly
385                 390                 395                 400

Leu Asp Glu Ile Asp Ile Asn Ser Ala Asp Ser Ile Gly Ser Phe Ser
                405                 410                 415

Lys Phe Gly His Ile Ser Val Lys Ala Cys Asp Met Leu Ile Pro Phe
            420                 425                 430

Leu Glu Gln Gly Met Asn Tyr Asn Glu Ala Cys Ala Ala Ala Gly Leu
        435                 440                 445

Asn Phe Lys Gly His Asp Ala Gly Glu Lys Ser Lys Leu Leu His Pro
    450                 455                 460

Lys Glu Glu Asp Tyr Glu Asp Ile Thr Ser Pro Val Val Arg Arg Ala
465                 470                 475                 480

Ile Ala Gln Thr Ile Lys Val Ile Asn Ala Ile Ile Arg Arg Glu Gly
                485                 490                 495

Cys Ser Pro Thr Phe Ile Asn Ile Glu Leu Ala Arg Glu Met Ala Lys
            500                 505                 510

Asp Phe Arg Glu Arg Asn Arg Ile Lys Lys Glu Asn Asp Asp Asn Arg
        515                 520                 525

Ala Lys Asn Glu Arg Leu Leu Glu Arg Ile Arg Thr Glu Tyr Gly Lys
    530                 535                 540

Asn Asn Pro Thr Gly Leu Asp Leu Val Lys Leu Arg Leu Tyr Glu Glu
545                 550                 555                 560

Gln Ser Gly Val Cys Met Tyr Ser Leu Lys Gln Met Ser Leu Glu Lys
                565                 570                 575

Leu Phe Glu Pro Asn Tyr Ala Glu Val Asp Ala Ile Val Pro Tyr Ser
            580                 585                 590

Ile Ser Phe Asp Asp Ser Arg Lys Asn Lys Val Leu Val Leu Thr Glu
        595                 600                 605

Glu Asn Arg Asn Lys Gly Asn Arg Leu Pro Leu Gln Tyr Leu Lys Gly
    610                 615                 620

Arg Arg Arg Glu Asp Phe Ile Val Trp Val Asn Asn Asn Val Lys Asp
```

-continued

```
            625                 630                 635                 640
Tyr Arg Lys Arg Arg Leu Leu Lys Glu Glu Leu Thr Ala Glu Asp
                    645                 650                 655

Glu Ser Gly Phe Lys Glu Arg Asn Leu Gln Asp Thr Lys Thr Met Ser
                    660                 665                 670

Arg Phe Leu Leu Asn Tyr Ile Ala Asp Asn Leu Glu Phe Ala Glu Ser
                    675                 680                 685

Thr Arg Gly Arg Lys Lys Val Thr Ala Val Asn Gly Ala Val Thr
            690                 695                 700

Ala Tyr Met Arg Lys Arg Trp Gly Ile Thr Lys Ile Arg Glu Asp Gly
705                 710                 715                 720

Asp Cys His His Ala Val Asp Ala Val Val Ile Ala Cys Thr Thr Asp
                    725                 730                 735

Ala Met Ile Arg Gln Val Ser Arg Tyr Ala Gln Phe Arg Glu Cys Glu
                    740                 745                 750

Tyr Met Gln Thr Glu Ser Gly Ser Val Ala Val Asp Thr Gly Thr Gly
                    755                 760                 765

Glu Val Leu Arg Thr Phe Pro Tyr Pro Trp Pro Asp Phe Arg Lys Glu
                    770                 775                 780

Leu Glu Ala Arg Leu Ala Asn Asp Pro Ala Lys Val Ile Asn Asp Leu
785                 790                 795                 800

His Leu Pro Phe Tyr Met Ser Ala Gly Arg Pro Leu Pro Glu Pro Val
                    805                 810                 815

Phe Val Ser Arg Met Pro Arg Arg Lys Val Thr Gly Ala Ala His Lys
                    820                 825                 830

Asp Thr Ile Lys Ser Ala Arg Glu Leu Asp Asn Gly Tyr Leu Ile Val
                    835                 840                 845

Lys Arg Pro Leu Thr Asp Leu Lys Leu Lys Asn Gly Glu Ile Glu Asn
                    850                 855                 860

Tyr Tyr Asn Pro Gln Ser Asp Lys Cys Leu Tyr Asp Ala Leu Lys Asn
865                 870                 875                 880

Ala Leu Ile Glu His Gly Gly Asp Ala Lys Lys Ala Phe Ala Gly Glu
                    885                 890                 895

Phe Arg Lys Pro Lys Arg Asp Gly Thr Pro Gly Pro Ile Val Lys Lys
                    900                 905                 910

Val Lys Leu Leu Glu Pro Thr Thr Met Cys Val Pro Val His Gly Gly
                    915                 920                 925

Lys Gly Ala Ala Asp Asn Asp Ser Met Val Arg Val Asp Val Phe Leu
            930                 935                 940

Ser Gly Gly Lys Tyr Tyr Leu Val Pro Ile Tyr Val Ala Asp Thr Leu
945                 950                 955                 960

Lys Pro Glu Leu Pro Asn Lys Ala Val Thr Arg Gly Lys Lys Tyr Ser
                    965                 970                 975

Glu Trp Leu Glu Met Ala Asp Glu Asp Phe Ile Phe Ser Leu Tyr Pro
                    980                 985                 990

Asn Asp Leu Ile Cys Ala Thr Ser Lys Asn Gly Ile Thr Leu Ser Val
            995                 1000                1005

Cys Arg Lys Asp Ser Thr Leu Pro Pro Thr Val Glu Ser Lys Ser
    1010                1015                1020

Phe Met Leu Tyr Tyr Arg Gly Thr Asp Ile Ser Thr Gly Ser Ile
    1025                1030                1035

Ser Cys Ile Thr His Asp Asn Ala Tyr Lys Leu Arg Gly Leu Gly
    1040                1045                1050
```

```
Val Lys  Thr Leu Glu Lys Leu  Glu Lys Tyr Thr Val  Asp Val Leu
    1055             1060              1065

Gly Glu  Tyr His Lys Val Gly  Lys Glu Val Arg Gln  Pro Phe Asn
    1070             1075              1080

Ile Lys  Arg Arg Lys Ala Cys  Pro Ser Glu Met Leu
    1085             1090              1095

<210> SEQ ID NO 181
<211> LENGTH: 1095
<212> TYPE: PRT
<213> ORGANISM: Artificial Sequence
<220> FEATURE:
<223> OTHER INFORMATION: ENGINEERED NICKASE

<400> SEQUENCE: 181

Met Arg Pro Tyr Ala Ile Gly Leu Asp Ile Gly Ile Thr Ser Val Gly
1               5                   10                  15

Trp Ala Thr Val Ala Leu Asp Ala Asp Glu Ser Pro Cys Gly Ile Ile
                20                  25                  30

Gly Leu Gly Ser Arg Ile Phe Asp Ala Ala Glu Gln Pro Lys Thr Gly
            35                  40                  45

Glu Ser Leu Ala Ala Pro Arg Ala Ala Arg Gly Ser Arg Arg Arg
    50                  55                  60

Leu Arg Arg His Arg His Arg Asn Glu Arg Ile Arg Ser Leu Met Leu
65                  70                  75                  80

Glu Glu Arg Leu Ile Ser Gln Asp Glu Leu Glu Thr Leu Phe Asp Gly
                85                  90                  95

Arg Leu Glu Asp Ile Tyr Ala Leu Arg Val Lys Ala Leu Asp Glu Ile
                100                 105                 110

Val Ser Arg Thr Asp Phe Ala Arg Ile Leu Leu His Ile Ser Gln Arg
                115                 120                 125

Arg Gly Phe Lys Ser Asn Arg Lys Asn Pro Thr Thr Lys Glu Asp Gly
            130                 135                 140

Val Leu Leu Ala Ala Val Asn Glu Asn Lys Gln Arg Met Ser Glu His
145                 150                 155                 160

Gly Tyr Arg Thr Val Gly Glu Met Phe Leu Leu Asp Glu Thr Phe Lys
                165                 170                 175

Asp His Lys Arg Asn Lys Gly Gly Asn Tyr Ile Thr Thr Val Ala Arg
                180                 185                 190

Asp Met Val Ala Asp Glu Val Arg Ala Ile Phe Ser Ala Gln Arg Glu
                195                 200                 205

Leu Gly Ala Ser Phe Ala Ser Glu Glu Phe Glu Glu Arg Tyr Leu Glu
        210                 215                 220

Ile Leu Leu Ser Gln Arg Ser Phe Asp Glu Gly Pro Gly Gly Asn Ser
225                 230                 235                 240

Pro Tyr Gly Gly Ser Gln Ile Glu Arg Met Val Gly Arg Cys Thr Phe
                245                 250                 255

Phe Pro Asp Glu Pro Arg Ala Ala Lys Ala Thr Tyr Ser Phe Glu Tyr
                260                 265                 270

Phe Thr Leu Leu Gln Lys Val Asn His Ile Arg Ile Val Glu Asn Gly
            275                 280                 285

Val Ala Ser Lys Leu Thr Asp Glu Gln Arg Ile Ile Ile Glu Leu
    290                 295                 300

Ala His Thr Thr Lys Asp Val Ser Tyr Ala Lys Ile Arg Lys Val Leu
305                 310                 315                 320
```

```
Lys Leu Ser Asp Lys Gln Leu Phe Asn Ile Arg Tyr Ser Asp Asn Ser
            325                 330                 335

Pro Ala Glu Asp Ser Glu Lys Lys Glu Lys Leu Gly Ile Met Lys Ala
            340                 345                 350

Tyr His Gln Met Arg Ser Ala Ile Asp Arg Val Ser Lys Gly Arg Phe
            355                 360                 365

Ala Met Met Pro Arg Ala Gln Arg Asn Ala Ile Gly Thr Ala Leu Ser
            370                 375                 380

Leu Tyr Lys Thr Ser Asp Lys Ile Arg Lys Tyr Leu Thr Asp Ala Gly
385                 390                 395                 400

Leu Asp Glu Ile Asp Ile Asn Ser Ala Asp Ser Ile Gly Ser Phe Ser
            405                 410                 415

Lys Phe Gly His Ile Ser Val Lys Ala Cys Asp Met Leu Ile Pro Phe
            420                 425                 430

Leu Glu Gln Gly Met Asn Tyr Asn Glu Ala Cys Ala Ala Ala Gly Leu
            435                 440                 445

Asn Phe Lys Gly His Asp Ala Gly Glu Lys Ser Lys Leu Leu His Pro
            450                 455                 460

Lys Glu Glu Asp Tyr Glu Asp Ile Thr Ser Pro Val Val Arg Arg Ala
465                 470                 475                 480

Ile Ala Gln Thr Ile Lys Val Ile Asn Ala Ile Ile Arg Arg Glu Gly
            485                 490                 495

Cys Ser Pro Thr Phe Ile Asn Ile Glu Leu Ala Arg Glu Met Ala Lys
            500                 505                 510

Asp Phe Arg Glu Arg Asn Arg Ile Lys Lys Glu Asn Asp Asn Arg
            515                 520                 525

Ala Lys Asn Glu Arg Leu Leu Glu Arg Ile Arg Thr Glu Tyr Gly Lys
            530                 535                 540

Asn Asn Pro Thr Gly Leu Asp Leu Val Lys Leu Arg Leu Tyr Glu Glu
545                 550                 555                 560

Gln Ser Gly Val Cys Met Tyr Ser Leu Lys Gln Met Ser Leu Glu Lys
            565                 570                 575

Leu Phe Glu Pro Asn Tyr Ala Glu Val Asp His Ile Val Pro Tyr Ser
            580                 585                 590

Ile Ser Phe Asp Asp Ser Arg Lys Asn Lys Val Leu Val Leu Thr Glu
            595                 600                 605

Glu Asn Arg Asn Lys Gly Asn Arg Leu Pro Leu Gln Tyr Leu Lys Gly
            610                 615                 620

Arg Arg Arg Glu Asp Phe Ile Val Trp Val Asn Asn Val Lys Asp
625                 630                 635                 640

Tyr Arg Lys Arg Arg Leu Leu Leu Lys Glu Glu Leu Thr Ala Glu Asp
            645                 650                 655

Glu Ser Gly Phe Lys Glu Arg Asn Leu Gln Asp Thr Lys Thr Met Ser
            660                 665                 670

Arg Phe Leu Leu Asn Tyr Ile Ala Asp Asn Leu Glu Phe Ala Glu Ser
            675                 680                 685

Thr Arg Gly Arg Lys Lys Val Thr Ala Val Asn Gly Ala Val Thr
            690                 695                 700

Ala Tyr Met Arg Lys Arg Trp Gly Ile Thr Lys Ile Arg Glu Asp Gly
705                 710                 715                 720

Asp Cys His His Ala Val Asp Ala Val Val Ile Ala Cys Thr Thr Asp
            725                 730                 735
```

```
Ala Met Ile Arg Gln Val Ser Arg Tyr Ala Gln Phe Arg Glu Cys Glu
                740                 745                 750

Tyr Met Gln Thr Glu Ser Gly Ser Val Ala Val Asp Thr Gly Thr Gly
            755                 760                 765

Glu Val Leu Arg Thr Phe Pro Tyr Pro Trp Pro Asp Phe Arg Lys Glu
        770                 775                 780

Leu Glu Ala Arg Leu Ala Asn Asp Pro Ala Lys Val Ile Asn Asp Leu
785                 790                 795                 800

His Leu Pro Phe Tyr Met Ser Ala Gly Arg Pro Leu Pro Glu Pro Val
                805                 810                 815

Phe Val Ser Arg Met Pro Arg Arg Lys Val Thr Gly Ala Ala His Lys
            820                 825                 830

Asp Thr Ile Lys Ser Ala Arg Glu Leu Asp Asn Gly Tyr Leu Ile Val
        835                 840                 845

Lys Arg Pro Leu Thr Asp Leu Lys Leu Lys Asn Gly Glu Ile Glu Asn
850                 855                 860

Tyr Tyr Asn Pro Gln Ser Asp Lys Cys Leu Tyr Asp Ala Leu Lys Asn
865                 870                 875                 880

Ala Leu Ile Glu His Gly Gly Asp Ala Lys Lys Ala Phe Ala Gly Glu
                885                 890                 895

Phe Arg Lys Pro Lys Arg Asp Gly Thr Pro Gly Pro Ile Val Lys Lys
            900                 905                 910

Val Lys Leu Leu Glu Pro Thr Thr Met Cys Val Pro His Gly Gly
        915                 920                 925

Lys Gly Ala Ala Asp Asn Asp Ser Met Val Arg Val Asp Val Phe Leu
930                 935                 940

Ser Gly Gly Lys Tyr Tyr Leu Val Pro Ile Tyr Val Ala Asp Thr Leu
945                 950                 955                 960

Lys Pro Glu Leu Pro Ala Lys Ala Val Thr Arg Gly Lys Lys Tyr Ser
                965                 970                 975

Glu Trp Leu Glu Met Ala Asp Glu Asp Phe Ile Phe Ser Leu Tyr Pro
            980                 985                 990

Asn Asp Leu Ile Cys Ala Thr Ser  Lys Asn Gly Ile Thr Leu Ser Val
        995                 1000                1005

Cys Arg  Lys Asp Ser Thr Leu  Pro Pro Thr Val Glu  Ser Lys Ser
    1010                1015                1020

Phe Met  Leu Tyr Tyr Arg Gly  Thr Asp Ile Ser Thr  Gly Ser Ile
    1025                1030                1035

Ser Cys  Ile Thr His Asp Asn  Ala Tyr Lys Leu Arg  Gly Leu Gly
    1040                1045                1050

Val Lys  Thr Leu Glu Lys Leu  Glu Lys Tyr Thr Val  Asp Val Leu
    1055                1060                1065

Gly Glu  Tyr His Lys Val Gly  Lys Glu Val Arg Gln  Pro Phe Asn
    1070                1075                1080

Ile Lys  Arg Arg Lys Ala Cys  Pro Ser Glu Met Leu
    1085                1090                1095

<210> SEQ ID NO 182
<211> LENGTH: 129
<212> TYPE: DNA
<213> ORGANISM: Artificial Sequence
<220> FEATURE:
<223> OTHER INFORMATION: GRNA

<400> SEQUENCE: 182
```

```
gttatagttc cctgttcgtt cttggtatgg tataatgaaa ttataccata ccaagaacga        60
agcaggttac tatgataagg tagtataccg cagagctcca acgcctcgct tttgcggggc       120
gttgtctct                                                               129
```

MAD NUCLEASES

RELATED CASES

This application claims priority to U.S. Ser. No. 63/133,502, filed 4 Jan. 2021, entitled "MAD NUCLEASES", which is incorporated herein in its entirety.

FIELD OF THE INVENTION

The present disclosure provides new RNA-guided nuclease systems and engineered nickases for making rational, direct edits to nucleic acids in live cells.

INCORPORATION BY REFERENCE

Submitted with the present application is an electronically filed sequence listing via EFS-Web as an ASCII formatted sequence listing, entitled "INSC083US_seqlist_20210812", created Aug. 12, 2021, and 359,000 bytes in size. The sequence listing is part of the specification filed herewith and is incorporated by reference in its entirety.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the methods referenced herein do not constitute prior art under the applicable statutory provisions.

The ability to make precise, targeted changes to the genome of living cells has been a long-standing goal in biomedical research and development. Recently, various nucleases have been identified that allow manipulation of gene sequence; hence, gene function. These nucleases include nucleic acid-guided nucleases. The range of target sequences that nucleic acid-guided nucleases can recognize, however, is constrained by the need for a specific PAM to be located near the desired target sequence. PAMs are short nucleotide sequences recognized by a gRNA/nuclease complex where this complex directs editing of the target sequence. The precise PAM sequence and PAM length requirements for different nucleic acid-guided nucleases vary; however, PAMs typically are 2-7 base-pair sequences adjacent or in proximity to the target sequence and, depending on the nuclease, can be 5' or 3' to the target sequence. Engineering nucleic acid-guided nucleases or mining for new nucleic acid-guided nucleases may provide nucleases with altered PAM preferences and/or altered activity or fidelity; all changes that may increase the versatility of a nucleic acid-guided nuclease for certain editing tasks.

There is thus a need in the art of nucleic acid-guided nuclease gene editing for novel nucleases with varied PAM preferences, varied activity in cells from different organisms such as mammals and/or altered enzyme fidelity. The novel MAD nucleases described herein satisfy this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides Type II MAD nucleases (e.g., RNA-guided nucleases or RGNs) with varied PAM preferences, and/or varied activity in mammalian cells.

Thus, in one embodiment there are provided MAD nuclease systems that perform nucleic acid-guided nuclease editing including a MAD2015 system comprising SEQ ID Nos. 1 (MAD2015 nuclease), 2 (CRISPR RNA) and 3 (trans-activating crispr RNA); a MAD2016 system comprising SEQ ID Nos. 4 (MAD2016 nuclease), 5 (CRISPR RNA) and 6 (trans-activating crispr RNA); a MAD2017 system comprising SEQ ID Nos. 7 (MAD2017 nuclease), 8 (CRISPR RNA) and 9 (trans-activating crispr RNA); a MAD2019 system comprising SEQ ID Nos. 10 (MAD2019 nuclease), 11 (CRISPR RNA) and 12 (trans-activating crispr RNA); a MAD2020 system comprising SEQ ID Nos. 13 (MAD2020 nuclease), 14 (CRISPR RNA) and 15 (trans-activating crispr RNA); a MAD2021 system comprising SEQ ID Nos. 16 (MAD2021 nuclease), 17 (CRISPR RNA) and 18 (trans-activating crispr RNA); a MAD2022 system comprising SEQ ID Nos. 19 (MAD2022 nuclease), 20 (CRISPR RNA) and 21 (trans-activating crispr RNA); a MAD2023 system comprising SEQ ID Nos. 22 (MAD2023 nuclease), 23 (CRISPR RNA) and 24 (trans-activating crispr RNA); a MAD2024 system comprising SEQ ID Nos. 25 (MAD2024 nuclease), 26 (CRISPR RNA) and 27 (trans-activating crispr RNA); a MAD2025 system comprising SEQ ID Nos. 28 (MAD2025 nuclease), 29 (CRISPR RNA) and 30 (trans-activating crispr RNA); a MAD2026 system comprising SEQ ID Nos. 31 (MAD2026 nuclease), 32 (CRISPR RNA) and 33 (trans-activating crispr RNA); a MAD2027 system comprising SEQ ID Nos. 34 (MAD2034 nuclease), 35 (CRISPR RNA) and 36 (trans-activating crispr RNA); a MAD2028 system comprising SEQ ID Nos. 37 (MAD2028 nuclease), 38 (CRISPR RNA) and 39 (trans-activating crispr RNA); a MAD2029 system comprising SEQ ID Nos. 40 (MAD2029 nuclease), 41 (CRISPR RNA) and 42 (trans-activating crispr RNA); a MAD2030 system comprising SEQ ID Nos. 43 (MAD2030 nuclease), 44 (CRISPR RNA) and 45 (trans-activating crispr RNA); a MAD2031 system comprising SEQ ID Nos. 46 (MAD2031 nuclease), 47 (CRISPR RNA) and 48 (trans-activating crispr RNA); a MAD2032 system comprising SEQ ID Nos. 49 (MAD2032 nuclease), 50 (CRISPR RNA) and 51 (trans-activating crispr RNA); a MAD2033 system comprising SEQ ID Nos. 52 (MAD2033 nuclease), 53 (CRISPR RNA) and 54 (trans-activating crispr RNA); a MAD2034 system comprising SEQ ID Nos. 55 (MAD2034 nuclease), 56 (CRISPR RNA) and 57 (trans-activating crispr RNA); a MAD2035 system comprising SEQ ID Nos. 58 (MAD2035 nuclease), 59 (CRISPR RNA) and 60 (trans-activating crispr RNA); a MAD2036 system comprising SEQ ID Nos. 61 (MAD2036 nuclease), 62 (CRISPR RNA) and 63 (trans-activating crispr RNA); a MAD2037 system comprising SEQ ID Nos. 64 (MAD2031 nuclease), 65 (CRISPR RNA) and 66 (trans-activating crispr RNA); a MAD2038 system comprising SEQ ID Nos. 67 (MAD2038 nuclease), 68 (CRISPR RNA) and 69 (trans-activating crispr RNA); a MAD2039 system comprising SEQ ID Nos. 70 (MAD2039 nuclease), 71 (CRISPR RNA) and 72 (trans-activating crispr RNA); and a MAD2040 system comprising SEQ ID Nos. 73 (MAD2040 nuclease), 74 (CRISPR RNA) and 75 (trans-activating crispr RNA). In some aspects, the MAD system components are delivered as sequences to be transcribed (in the case of the gRNA components) and transcribed and translated (in the case of the MAD nuclease), and in some aspects, the coding sequence for the MAD nuclease and the gRNA component sequences are on the same vector. In other aspects, the coding sequence for the MAD nuclease and the gRNA component sequences are on a different vector and in some aspects, the gRNA component sequences are located in an editing cassette which also comprises a donor DNA (e.g., homology arm). In other aspects, the MAD nuclease is delivered to the cells as a peptide or the MAD nuclease and gRNA components are delivered to the cells as a ribonuclease complex.

Additionally there is provided engineered nickases derived from the nucleases from the above-referenced systems, including MAD2016-H851A (SEQ ID NO: 177); MAD2016-N874A (SEQ ID NO: 178); MAD2032-H590A (SEQ ID NO: 179); MAD2039-H587A (SEQ ID NO: 180); MAD2039-N610A (SEQ ID NO: 181).

These aspects and other features and advantages of the invention are described below in more detail.

BRIEF DESCRIPTION OF THE FIGURES

FIG. 3 is a list of novel Type II MADzymes that have been identified.

Figure 1:
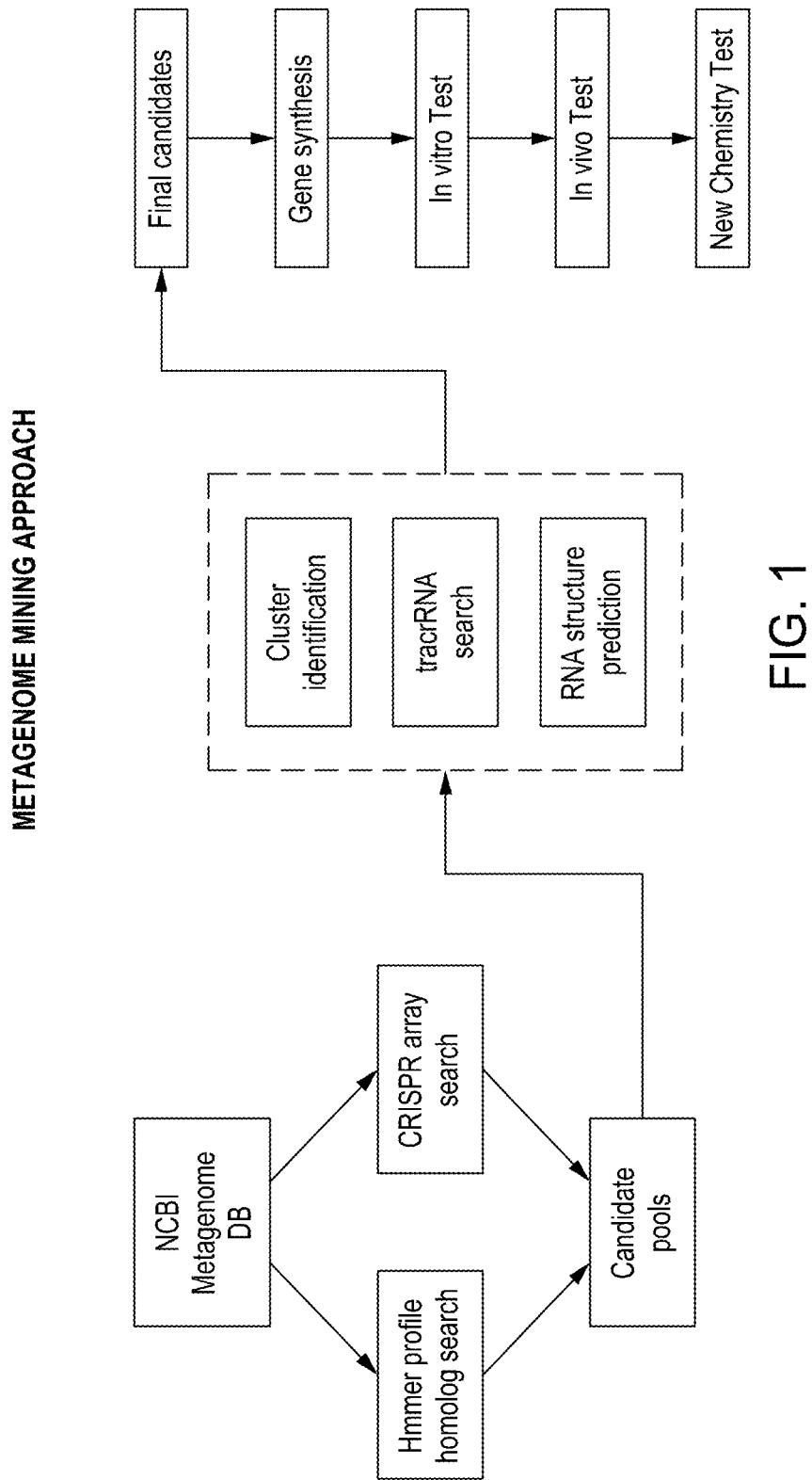
FIG. 1 is an exemplary workflow for creating and screening mined MAD nucleases or RGNs.

It should be understood that the drawings are not necessarily to scale.

DETAILED DESCRIPTION

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities. Moreover, all of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry, biological emulsion generation, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. *Freeman*, New York N.Y.; Gait, "*Oligonucleotide Synthesis: A Practical Approach*" 1984, IRL Press, London; Nelson and Cox (2000), *Lehninger, Principles of Biochemistry* $3^{rd}$ Ed., W. H. Freeman Pub., New York, N.Y.; Berg et al. (2002) *Biochemistry, $5^{th}$* Ed., W.H. Freeman Pub., New York, N.Y.; *Cell and Tissue Culture: Laboratory Procedures in Biotechnology* (Doyle & Griffiths, eds., John Wiley & Sons 1998), all of which are herein incorporated in their entirety by reference for all purposes. Nuclease-specific techniques can be found in, e.g., *Genome Editing and Engineering From TALENs and CRISPRs to Molecular Surgery*, Appasani and Church, 2018; and *CRISPR: Methods and Protocols*, Lindgren and Charpentier, 2015; both of which are herein incorporated in their entirety by reference for all purposes. Basic methods for enzyme engineering may be found in, *Enzyme Engineering Methods and Protocols*, Samuelson, ed., 2013; *Protein Engineering*, Kaumaya, ed., (2012); and Kaur and Sharma, "*Directed Evolution: An Approach to Engineer Enzymes*", Crit. Rev. Biotechnology, 26:165-69 (2006).

Note that as used herein and in the appended claims, the singular forms "a," "an," and "the" include plural referents unless the context clearly dictates otherwise. Thus, for example, reference to "an oligonucleotide" refers to one or more oligonucleotides. Terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of ordinary skill in the art that the present invention may be practiced without one or more of these specific details. In other instances, well-known features and procedures well known to those skilled in the art have not been described in order to avoid obscuring the invention.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the term "donor DNA" or "donor nucleic acid" refers to nucleic acid that is designed to introduce a DNA sequence modification (insertion, deletion, substitution) into a locus by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region— the nucleic acid modification that one desires to be introduced into a genome target locus in a cell—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible and, in some embodiments—particularly many embodiments in which selection is employed—the transcription of at least one component of the nucleic acid-guided nuclease editing system is under the control of an inducible promoter.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, erythromycin, tetracycline, gentamicin, bleomycin, streptomycin, rhamnose, puromycin, hygromycin, blasticidin, and G418 may be employed. In other embodiments, selectable markers include, but are not limited to human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34+cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2α; detectable by Mab-FITC); Methylguanine-DNA methyltransferase (MGMT; selectable by carmustine); and Cytidine deaminase (CD; selectable by Ara-C). "Selective medium" as used herein refers to cell growth medium to which has been added a chemical compound or biological moiety that selects for or against selectable markers.

The terms "target genomic DNA sequence", "target sequence", or "genomic target locus" refer to any locus in vitro or in vivo, or in a nucleic acid (e.g., genome) of a cell or population of cells, in which a change of at least one nucleotide is desired using a nucleic acid-guided nuclease editing system. The target sequence can be a genomic locus or extrachromosomal locus.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like. As used herein, the phrase "engine vector" comprises a coding sequence for a nuclease to be used in the nucleic acid-guided nuclease systems and methods of the present disclosure. The engine vector may also comprise, in a bacterial system, the λ Red recombineering system or an equivalent thereto. Engine vectors also typically comprise a selectable marker. As used herein the phrase "editing vector" comprises a donor nucleic acid, optionally including an alteration to the target sequence that prevents nuclease binding at a PAM or spacer in the target sequence after editing has taken place, and a coding sequence for a gRNA. The editing vector may also comprise a selectable marker and/or a barcode. In some embodiments, the engine vector and editing vector may be combined; that is, the contents of the engine vector may be found on the editing vector. Further, the engine and editing vectors comprise control sequences operably linked to, e.g., the nuclease coding sequence, recombineering system coding sequences (if present), donor nucleic acid, guide nucleic acid, and selectable marker(s).

Editing in Nucleic Acid-Guided Nuclease Genome Systems

RNA-guided nucleases (RGNs) have rapidly become the foundational tools for genome engineering of prokaryotes and eukaryotes. Clustered Rapidly Interspaced Short Palindromic Repeats (CRISPR) systems are an adaptive immunity system which protect prokaryotes against mobile genetic elements (MGEs). RGNs are a major part of this defense system because they identify and destroy MGEs. RGNs can be repurposed for genome editing in various organisms by reprogramming the CRISPR RNA (crRNA) that guides the RGN to a specific target DNA. A number of different RGNs have been identified to date for various applications; however, there are various properties that make some RGNs more desirable than others for specific applications. RGNs can be used for creating specific double strand breaks (DSBs), specific nicks of one strand of DNA, or guide another moiety to a specific DNA sequence.

The ability of an RGN to specifically target any genomic sequence is perhaps the most desirable feature of RGNs; however, RGNs can only access their desired target if the target DNA also contains a short motif called PAM (protospacer adjacent motif) that is specific for every RGN. Type V RGNs such as MAD7, AsCas12a and LbCas12a tend to access DNA targets that contain YTTN/TTTN on the 5' end whereas type II RGNs—such as the MADzymes disclosed herein—target DNA sequences containing a specific short motif on the 3' end. An example well known in the art for a type II RGN is SpCas9 which requires an NGG on the 3' end of the target DNA. Type II RGNs, unlike type V RGNS, require a transactivating RNA (tracrRNA) in addition to a crRNA for optimal function. Compared to type V RGNs, the type II RGNs create a double-strand break closer to the PAM sequence, which is highly desirable for precise genome editing applications.

A number of type II RGNs have been discovered so far; however, their use in widespread applications is limited by restrictive PAMs. For example, the PAM of SpCas9 occurs less frequently in AT-rich regions of the genome. New type II RGNs with new and less restrictive PAMs are beneficial for the field. Further, not all type II nucleases are active in multiple organisms. For example, a number of RGNs have been discussed in the scientific literature but only a few have been demonstrated to be active in vitro and fewer still are active in cells, particularly in mammalian cells. The present disclosure identifies multiple type II RGNs that have novel PAMs and are active in mammalian cells.

In performing nucleic acid-guided nuclease editing, the type II RGNs or MADzymes may be delivered to cells to be edited as a polypeptide; alternatively, a polynucleotide sequence encoding the MADzyme are transformed or transfected into the cells to be edited. The polynucleotide sequence encoding the MADzyme may be codon optimized for expression in particular cells, such as archaeal, prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammals including non-human primates. The choice of the MADzyme to be employed depends on many factors, such as what type of edit is to be made in the target sequence and whether an appropriate PAM is located close to the desired target sequence. The MADzyme may be encoded by a DNA sequence on a vector (e.g., the engine vector) and be under the control of a constitutive or inducible promoter. In some embodiments, the sequence encoding the nuclease is under the control of an inducible promoter, and the inducible promoter may be separate from but the same as an inducible promoter controlling transcription of the guide nucleic acid; that is, a separate inducible promoter may drive the transcription of the nuclease and guide nucleic acid sequences but the two inducible promoters may be the same type of inducible promoter (e.g., both are pL promoters). Alternatively, the inducible promoter controlling expression of the nuclease may be different from the inducible promoter controlling transcription of the guide nucleic acid; that is, e.g., the nuclease may be under the control of the pBAD inducible promoter, and the guide nucleic acid may be under the control of the pL inducible promoter.

In general, a guide nucleic acid (e.g., gRNA) complexes with a compatible nucleic acid-guided nuclease and can then hybridize with a target sequence, thereby directing the nuclease to the target sequence. With the type II MADzymes described herein, the nucleic acid-guided nuclease editing system uses two separate guide nucleic acid components that combine and function as a guide nucleic acid; that is, a CRISPR RNA (crRNA) and a transactivating CRISPR RNA (tracrRNA). The gRNA may be encoded by a DNA sequence on a polynucleotide molecule such as a plasmid, linear construct, or the coding sequence may reside within an editing cassette and is under the control of a constitutive promoter, or, in some embodiments, an inducible promoter as described below.

A guide nucleic acid comprises a guide polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In the present methods and compositions, the components of the guide nucleic acid is provided as a sequence to be expressed from a plasmid or vector and comprises both the guide sequence and the scaffold sequence as a single transcript under the control of a promoter, and in some embodiments, an inducible promoter. In general, to generate an edit in a target sequence, the gRNA/nuclease complex binds to a target sequence as determined by the guide RNA, and the nuclease recognizes a protospacer adjacent motif PAM) sequence adjacent to the target sequence. The target sequence can be any polynucleotide endogenous or exogenous to a prokaryotic or eukaryotic cell, or in vitro. For example, the target sequence can be a polynucleotide residing in the nucleus of a eukaryotic cell. A target sequence can be a sequence encoding a gene product (e.g., a protein) or a non-coding sequence (e.g., a regulatory polynucleotide, an intron, a PAM, or "junk" DNA).

The guide nucleic acid may be part of an editing cassette that encodes the donor nucleic acid. Alternatively, the guide nucleic acid may not be part of the editing cassette and instead may be encoded on the engine or editing vector backbone. For example, a sequence coding for a guide nucleic acid can be assembled or inserted into a vector backbone first, followed by insertion of the donor nucleic acid in, e.g., the editing cassette. In other cases, the donor nucleic acid in, e.g., an editing cassette can be inserted or assembled into a vector backbone first, followed by insertion of the sequence coding for the guide nucleic acid. In yet other cases, the sequence encoding the guide nucleic acid and the donor nucleic acid (inserted, for example, in an editing cassette) are simultaneously but separately inserted or assembled into a vector. In yet other embodiments, the sequence encoding the guide nucleic acid and the sequence encoding the donor nucleic acid are both included in the editing cassette.

The target sequence is associated with a PAM, which is a short nucleotide sequence recognized by the gRNA/nuclease complex. The precise PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve fidelity, or decrease fidelity. In certain embodiments, the genome editing of a target sequence both introduces a desired DNA change to a target sequence, e.g., the genomic DNA of a cell, and removes, mutates, or renders inactive a proto-spacer mutation (PAM) region in the target sequence. Rendering the PAM at the target sequence inactive precludes additional editing of the cell genome at that target sequence, e.g., upon subsequent exposure to a nucleic acid-guided nuclease complexed with a synthetic guide nucleic acid in later rounds of editing. Thus, cells having the desired target sequence edit and an altered PAM can be selected using a nucleic acid-guided nuclease complexed with a synthetic guide nucleic acid complementary to the target sequence. Cells that did not undergo the first editing event will be cut rendering a double-stranded DNA break, and thus will not continue to be viable. The cells containing the desired target sequence edit and PAM alteration will not be cut, as these edited cells no longer contain the necessary PAM site and will continue to grow and propagate.

As mentioned previously, the range of target sequences that nucleic acid-guided nucleases can recognize is constrained by the need for a specific PAM to be located near the desired target sequence. As a result, it often can be difficult to target edits with the precision that is necessary for genome editing. It has been found that nucleases can recognize some PAMs very well (e.g., canonical PAMs), and other PAMs less well or poorly (e.g., non-canonical PAMs). Because the mined MAD nucleases disclosed herein may recognize different PAMs, the mined MAD nucleases increase the number of target sequences that can be targeted for editing; that is, mined MAD nucleases decrease the regions of "PAM deserts" in the genome. Thus, the mined MAD nucleases expand the scope of target sequences that may be edited by increasing the number (variety) of PAM sequences recognized. Moreover, cocktails of mined MAD nucleases may be delivered to cells such that target sequences adjacent to several different PAMs may be edited in a single editing run.

Another component of the nucleic acid-guided nuclease system is the donor nucleic acid. In some embodiments, the donor nucleic acid is on the same polynucleotide (e.g., editing vector or editing cassette) as the guide nucleic acid and may be (but not necessarily) under the control of the same promoter as the guide nucleic acid (e.g., a single promoter driving the transcription of both the guide nucleic acid and the donor nucleic acid). For cassettes of this type, see U.S. Pat. Nos. 10,240,167; 10,266,849; 9,982,278; 10,351,877; 10,364,442; 10,435,715; and 10,465,207. The donor nucleic acid is designed to serve as a template for homologous recombination with a target sequence nicked or cleaved by the nucleic acid-guided nuclease as a part of the gRNA/nuclease complex. A donor nucleic acid polynucleotide may be of any suitable length, such as about or more than about 20, 25, 50, 75, 100, 150, 200, 500, or 1000 nucleotides in length. In certain preferred aspects, the donor nucleic acid can be provided as an oligonucleotide of between 20-300 nucleotides, more preferably between 50-250 nucleotides. The donor nucleic acid comprises a region that is complementary to a portion of the target sequence (e.g., a homology arm). When optimally aligned, the donor nucleic acid overlaps with (is complementary to) the target sequence by, e.g., about 20, 25, 30, 35, 40, 50, 60, 70, 80, 90 or more nucleotides. In many embodiments, the donor nucleic acid comprises two homology arms (regions complementary to the target sequence) flanking the mutation or difference between the donor nucleic acid and the target template. The donor nucleic acid comprises at least one mutation or alteration compared to the target sequence, such as an insertion, deletion, modification, or any combination thereof compared to the target sequence.

Often the donor nucleic acid is provided as an editing cassette, which is inserted into a vector backbone where the vector backbone may comprise a promoter driving transcription of the gRNA and the coding sequence of the gRNA, or the vector backbone may comprise a promoter driving the transcription of the gRNA but not the gRNA itself. Moreover, there may be more than one, e.g., two, three, four, or more guide nucleic acid/donor nucleic acid cassettes inserted into an engine vector, where each guide nucleic acid is under the control of separate different promoters, separate like promoters, or where all guide nucleic acid/donor nucleic acid pairs are under the control of a single promoter. In some embodiments the promoter driving transcription of the gRNA and the donor nucleic acid (or driving more than one gRNA/donor nucleic acid pair) is an inducible promoter. Inducible editing is advantageous in that isolated cells can be grown for several to many cell doublings to establish colonies before editing is initiated, which increases the likelihood that cells with edits will survive, as the double-strand cuts caused by active editing are largely toxic to the cells. This toxicity results both in cell death in the edited colonies, as well as a lag in growth for the edited cells that do survive but must repair and recover following editing. However, once the edited cells have a chance to recover, the size of the colonies of the edited cells will eventually catch up to the size of the colonies of unedited cells. See, e.g., U.S. Pat. Nos. 10,533,152; 10,550,363; 10,532,324; 10,550,363; 10,633,626; 10,633,627; 10,647,958; 10,760,043; 10,723,995; 10,801,008; and 10,851,339. Further, a guide nucleic acid may be efficacious directing the edit of more than one donor nucleic acid in an editing cassette; e.g., if the desired edits are close to one another in a target sequence.

In addition to the donor nucleic acid, an editing cassette may comprise one or more primer sites. The primer sites can be used to amplify the editing cassette by using oligonucleotide primers; for example, if the primer sites flank one or more of the other components of the editing cassette.

In addition, the editing cassette may comprise a barcode. A barcode is a unique DNA sequence that corresponds to the donor DNA sequence such that the barcode can identify the edit made to the corresponding target sequence. The barcode typically comprises four or more nucleotides. In some embodiments, the editing cassettes comprise a collection of donor nucleic acids representing, e.g., gene-wide or genome-wide libraries of donor nucleic acids. The library of editing cassettes is cloned into vector backbones where, e.g., each different donor nucleic acid is associated with a different barcode.

Additionally, in some embodiments, an expression vector or cassette encoding components of the nucleic acid-guided nuclease system further encodes one or more nuclear localization sequences (NLSs), such as about or more than about 1, 2, 3, 4, 5, 6, 7, 8, 9, 10, or more NLSs. In some embodiments, the nuclease comprises NLSs at or near the amino-terminus of the MADzyme, NLSs at or near the carboxy-terminus of the MADzyme, or a combination.

The engine and editing vectors comprise control sequences operably linked to the component sequences to be transcribed. As stated above, the promoters driving transcription of one or more components of the mined MAD nuclease editing system may be inducible, and an inducible system is likely employed if selection is to be performed. A number of gene regulation control systems have been developed for the controlled expression of genes in plant, microbe, and animal cells, including mammalian cells, including the pL promoter (induced by heat inactivation of the CI857 repressor), the pBAD promoter (induced by the addition of arabinose to the cell growth medium), and the rhamnose inducible promoter (induced by the addition of rhamnose to the cell growth medium). Other systems include the tetracycline-controlled transcriptional activation system (Tet-On/Tet-Off, Clontech, Inc. (Palo Alto, Calif.); Bujard and Gossen, PNAS, 89(12):5547-5551 (1992)), the Lac Switch Inducible system (Wyborski et al., Environ Mol Mutagen, 28(4):447-58 (1996); DuCoeur et al., Strategies 5(3):70-72 (1992); U.S. Pat. No. 4,833,080), the ecdysone-inducible gene expression system (No et al., PNAS, 93(8): 3346-3351 (1996)), the cumate gene-switch system (Mullick et al., BMC Biotechnology, 6:43 (2006)), and the tamoxifen-inducible gene expression (Zhang et al., Nucleic Acids Research, 24:543-548 (1996)) as well as others.

Typically, performing genome editing in live cells entails transforming cells with the components necessary to perform nucleic acid-guided nuclease editing. For example, the cells may be transformed simultaneously with separate engine and editing vectors; the cells may already be expressing the mined MAD nuclease (e.g., the cells may have already been transformed with an engine vector or the coding sequence for the mined MAD nuclease may be stably integrated into the cellular genome) such that only the editing vector needs to be transformed into the cells; or the cells may be transformed with a single vector comprising all components required to perform nucleic acid-guided nuclease genome editing.

A variety of delivery systems can be used to introduce (e.g., transform or transfect) nucleic acid-guided nuclease editing system components into a host cell. These delivery systems include the use of yeast systems, lipofection systems, microinjection systems, biolistic systems, virosomes, liposomes, immunoliposomes, polycations, lipid:nucleic acid conjugates, virions, artificial virions, viral vectors, electroporation, cell permeable peptides, nanoparticles, nanowires, exosomes. Alternatively, molecular trojan horse liposomes may be used to deliver nucleic acid-guided nuclease components across the blood brain barrier. Of particular interest is the use of electroporation, particularly flow-through electroporation (either as a stand-alone instrument or as a module in an automated multi-module system) as described in, e.g., U.S. Pat. Nos. 10,435,713; 10,443,074; 10,323,258; and 10,415,058.

After the cells are transformed with the components necessary to perform nucleic acid-guided nuclease editing, the cells are cultured under conditions that promote editing. For example, if constitutive promoters are used to drive transcription of the mined MAD nucleases and/or gRNA, the transformed cells need only be cultured in a typical culture medium under typical conditions (e.g., temperature, $CO_2$ atmosphere, etc.) Alternatively, if editing is inducible—by, e.g., activating inducible promoters that control transcription of one or more of the components needed for nucleic acid-guided nuclease editing, such as, e.g., transcription of the gRNA, donor DNA, nuclease, or, in the case of bacteria, a recombineering system—the cells are subjected to inducing conditions.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Exemplary Workflow Overview

Figure 2:
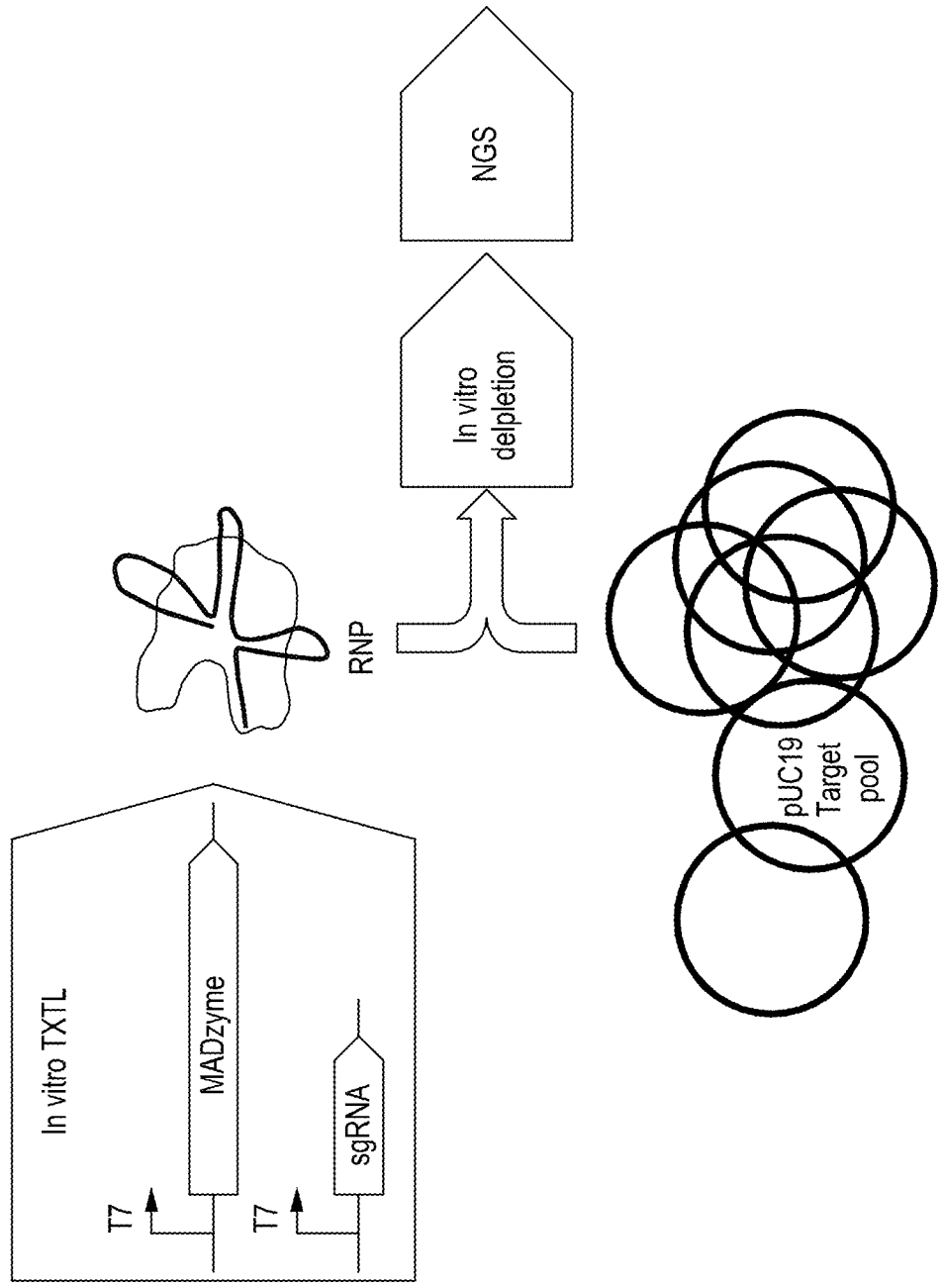
FIG. 2 is a simplified depiction of an in vitro test conducted on candidate enzymes.

The disclosed MADzyme Type II CRISPR enzymes were identified by the method depicted in FIG. 1. FIG. 1 shows an exemplary workflow for creating and for in vitro screening of MADzymes, including those in untapped clusters. In a first step, metagenome mining was performed to identify putative RGNs of interest based on, e.g., sequence (HM-MER profile) and a search for CRISPR arrays. Once putative RGNs of interest were identified in silico, candidate pools were created and each MADzyme was identified by cluster, the tracrRNA was identified, and the sgRNA structure was predicted. Final candidates were identified, then the genes were synthesized. An in vitro depletion test was performed (see FIG. 2), where a synthetic target library was constructed in which to test target depletion for each of the candidate MADzymes. After target depletion, amplicons were produced for analysis for in vivo analysis. FIG. 2 depicts the in vitro depletion test in more detail.

Example 2: Metagenome Mining

Figure 4:
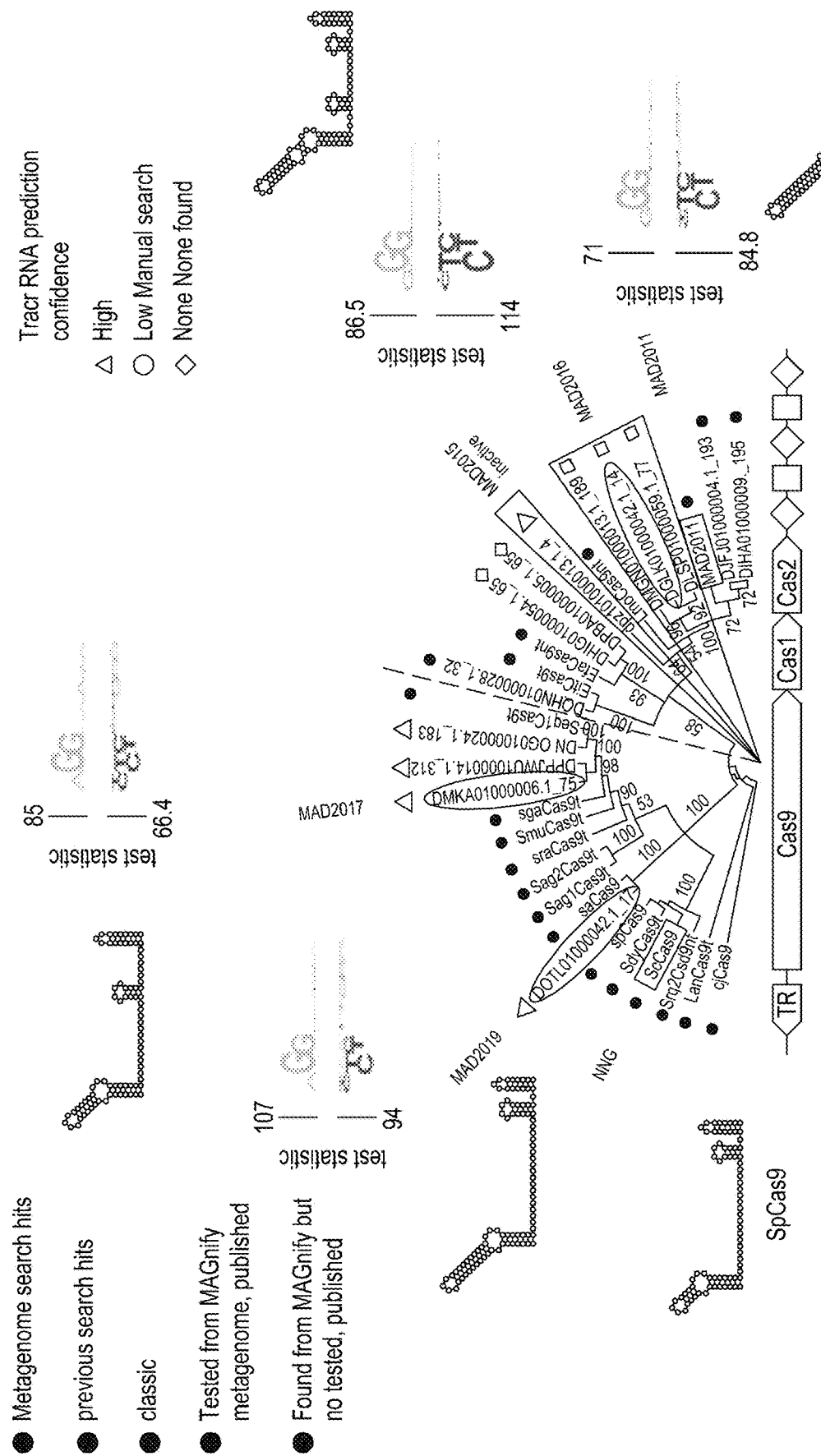
FIG. 4 is a map of Type II MADzymes in cluster 59.
Figure 5:
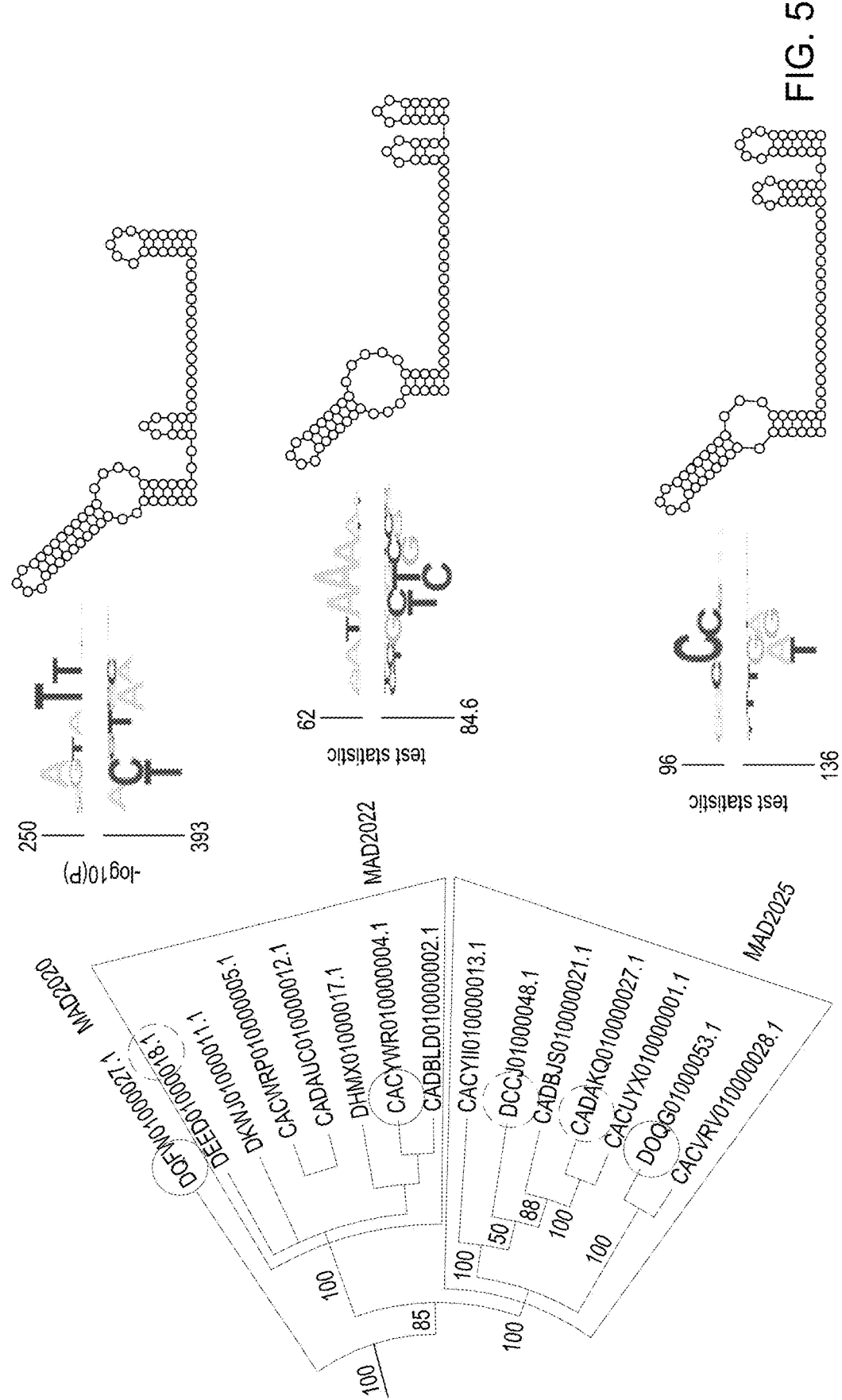
FIG. 5 is a map of Type II MADzymes in cluster 55, 56, 57 and 58.
Figure 6:
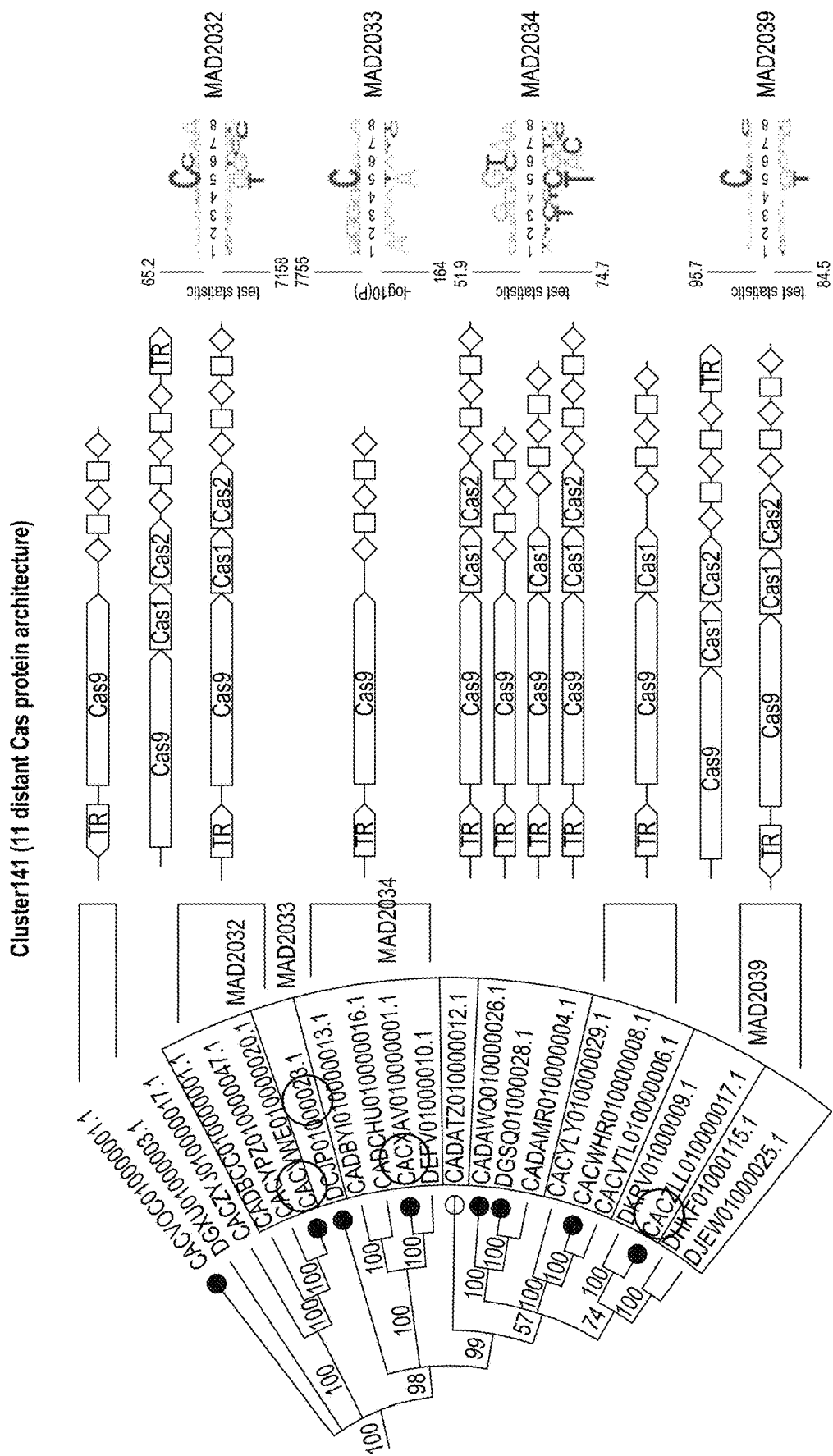
FIG. 6 is a map of Type II MADzymes in cluster 141.

The NCBI Metagenome database was used to search for novel, putative CRISPR nucleases using HMMER hidden Markov model searches. Hundreds of potential nucleases were identified. For each potential nuclease candidate, putative CRISPR arrays were identified and CRISPR repeat and anitirepeats were identified. Thirteen nucleases (FIG. 3) were chosen for in vitro validation and 11 active MADzymes were identified and assigned to clusters. There was less than 40% sequence identity between clusters. Cluster 59 shown in FIG. 4 presents two unique subclusters with distinct sgRNA architecture. Clusters 55-57 are shown in FIG. 5. These new MADzymes have diverse PAM preferences and distinct sgRNA structure. Cluster 141 (FIG. 6) is a distant cluster from 55, 56, 57 and 59 and shows diverse Cas protein structure and smaller-sized enzymes (e.g., approximately 200 amino acids shorter than the counterparts from the 55, 56, 57 and 59 clusters). Table 1 lists the identified MADzymes, including amino acid sequences, origin, and nucleic acid sequences of the CRISPR RNA and the trans-activating crispr RNA.

TABLE 1

| MAD name | Cluster | Contig_id | Organism (meta-genome) | Source | aa_seq | CRISPR repeat | tracrRNA |
|---|---|---|---|---|---|---|---|
| MAD 2015 | 59 | DPZI 01000013.1 | *Vagococcus* sp. | | MGKNYTIGLDIGTNSVGWSVVTENQQLVKKRMKIRGDS EKKQVKKNFWGVRLFDEGETAEATRLKRTTRRRYTRRRN RVVDLQNIFKDEINQKDSNFFNRLNESFLVVEDKKQPKQ MIFGTVEEEASYHESFPTIYHLRKELVDNKDQADIRLVYLA MAHMIKYRGHFLIEGQLSTENTSVEEKFHLFLKEYNSTFCK QEDGSLVNPVNEDINGEEILMGTLSRSKKAEQIMKSFEGE KSNGVFSQFLKMIVGNQGNFKKAFNLEEDAKIQFAKEEY DEDLTTLLSNIGDEYANVFSLAKETYEAIELSGILSTKDKETY AKLSSSMTERYEDHEKDLASLKSFFREHLPEKYAVMFKDV SKNGYAGYIENSNKISQEEFYKYTKKLIGQIEGADYFIKKME QEAFLRKQRTYDNGVIPYQVHLSELTHIINNQKKYYPFLLE KEEEIKSILTFKIPYYIGPLAKGNSDFAWLIRNSNDKITPSNF NEVLDIENSASQFIERMTNNDVYLPEEKVLPKNSMLYQKY IVFNELTKVRYINDRGTECNFSGEEKLQIFERFFKDSSTKVK KVSLENYLNKEYMIESPTIKGIEDDFNASFRTYHDFIKLGVS REMLDDIDNEEMFEDIVKILTIFEDRQMIKKQLEKYKDVFD SDILKKMVRRHYTGWGRLSKKLLHEMKDDNSGKTILDYLI EDDRLPKHINRNFMQLINDSNLSFKEKIEKAQLTDGTEDID SVVKNLIGSPAIKKGISQSLKIVEELVSIMGYQPTSIVVEMA RENQTTSKGKRQSIQRYKRLEAAINELGSDLLKVCPTDNH ALKDDRLYLYYLQNGRDMYTGLELDIHNLSQYDIDHIVPRS FITDNSIDNRVLVSSKKNRGKLDNVPSKEIVQKNKLLWMN LKKSKLMSEKKYANLIKGETGGLTEDDKAKFLNRQLVETR QITKNVAQILDQRFNTQKDEKGNIIREVKVITLKSALVSQF RQNFEFYKVREVNDFHHAHDAYLNAVVANTLLKVYPKLT PDFVYGEYRKGNPFKNTKATAKKHYYSNIMENLCHETTIID DETGEILWDKKCIGTIKQVLNYHQVNVVKKVETQTGRFSE ETLVPRGSTKNPIALKSHLDPQKYGGFKSPTIAYTIVIEYKK GKKDILIKELLGISIMNRGAFEKNNKEYLEKLNYKEPRVLM VLPKYSLFELENGRRRLLASDKESQKGNQMAVPSYLNNLL YHTNKSLSKNAKSLEYVNEHRQQFEELLEEIIDFANQFTLA EKNTLLIADLYESNKEADIELLASSFINLLRFNQMGAPAEFS FFEKPIPRKRYSSTFELLKGKVIHQSITGLYETHQKV [SEQ ID NO. 1] | GTTTT AGAGC TATGC TGTTTT GAATG CTTCC AAAAC [SEQ ID NO. 2] | TGTTGGT AGCATTC AAAACA ACATAGC AAGTTAA AATAAG GCTTTGT CCGTTCT CAACTTT TAGTGAC GCTGTTT CGGCG [SEQ ID NO. 3] |
| MAD 2016 | 59 | DGLK 01000042.1 | *Enterococcus faecalis* | New York City MTA subway | MKKDYVIGLDIGTNSVGWAVMTEDYQLVKKKMPIYGNT EKKKIKKNFWGVRLFEEGHTAEDRRLKRTARRIISRRRNRL RYLQAFFEEAMTDLDENFFARLQESFLVPEDKKWHRHPIF AKLEDEVAYHETYPTIYHLRKKLADSSEQADLRLIYLALAHI VKYRGHFLIEGKLSTENISVKEQFQQFMIIYNQTFVNGESR LVSAPLPESVLIEEELTEKASRTKKSEKVLQQFPQEKANGLF GQFLKLMVGNKADFKKVFGLEEEAKITYASESYEEDLEGIL AKVGDEYSDVFLAAKNVYDAVELSTILADSDKKSHAKLSSS MIVRFTEHQEDLKKFKRFIRENCPDEYDNLFKNEQKDGYA GYIAHAGKVSQLKFYQYVKKIIQDIAGAEYFLEKIAQENFLR KQRTFDNGVIPHQIHLAELQAIIHRQAAYYPFLKENQEKIE QLVTFRIPYYVGPLSKGDASTFAWLKRQSEEPIRPWNLQE TVDLDQSATAFIERMTNFDTYLPSEKVLPKHSLLYEKFMVF NELTKISYTDDRGIKANFSGKEKEKIFDYLFKTRRKVKKKDII QFYRNEYNTEIVTLSGLEEDQFNASFSTYQDLLKCGLTRAE LDHPDNAEKLEDIIKILTIFEDRQRIRTQLSTFKGQFSAEVLK KLERKHYTGWGRLSKKLINGIYDKESGKTILGYLIKDDGVSK | GTTTT AGAGT CATGT TGTTT AGAAT GGTAC CAAAA C [SEQ ID NO. 5] | TCTTTTG GGACTAT TCTAAAC AACATAG CAAGTTA AAATAA GGTTTTA ACCGTAA TCAACTG TAAAGTG GCGCTGT TTCGGCG C [SEQ ID NO. 6] |

TABLE 1-continued

| MAD name | Cluster | Contig_id | Organism (metagenome) | Source | aa_seq | CRISPR repeat | tracrRNA |
|---|---|---|---|---|---|---|---|
| | | | | | HYNRNFMQLINDSQLSFKNAIQKAQSSEHEETLSETVNEL AGSPAIKKGIYQSLKIVDELVAIMGYAPKRIVVEMARENQT TSTGKRRSIQRLKIVEKAMAEIGSNLLKEQPTTNEQLRDTR LFLYYMQNGKDMYTGDELSLHRLSHYDIDHIIPQSFMKD DSLDNLVLVGSTENRGKSDDVPSKEVVKDMKAYWEKLYA AGLISQRKFQRLTKGEQGGLTLEDKAHFIQRQLVETRQITK NVAGILDQRYNANSKEKKVQIITLKASLTSQFRSIFGLYKVR EVNDYHHGQDAYLNCVVATTLLKVYPNLAPEFVYGEYPKF QTFKENKATAKAIIYTNLLRFFTEDEPRFTKDGEILWSNSYL KTIKKELNYHQMNIVKKVEVQKGGFSKESIKPKGPSNKLIP VKNGLDPQKYGGFDSPIVAYTVLFTHEKGKKPLIKQEILGIT IMEKTRFEQNPILFLEEKGFLRPRVLMKLPKYTLYEFPEGRR RLLASAKEAQKGNQMVLPEHLLTLLYHAKQCLLPNQSESL TYVEQHQPEFQEILERVVDFAEVHTLAKSKVQQIVKLFEA NQTADVKEIAASFIQLMQFNAMGAPSTFKFFQKDIERAR YTSIKEIFDATIIYQSTTGLYETRRKVVD [SEQ ID NO. 4] | | |
| MAD 2017 | 59 | DMKA 01000006.1 | *Streptococcus* sp. (*firmicutes*) | | MKKPYSIGLDIGTNSVGWAVITDDYKVPAKKMKVLGNTD KKYIKKNLLGALLFDSGETAEVTRLKRTARRRYTRRKNRLR YLQEIFAKEMTKVDESFFQRLEESFLTDDDKTFDSHPIFGN KAEEDAYHQKFPTIYHLRKYLADSQEKADLRLVYLALAHMI KYRGHFLIEGELNAENTDVQKLFNVFVETYDKIVDESHLSEI EVDASSILTEKVSKSRRLENLIKQYPTEKKNTLFGNLIALALG LQPNFKTNFKLSEDAKLQFSKDTYEEDLEELLGKVGDDYA DLFISAKNLYDAILLSGILTVDDNSTKAPLSASMIKRYVEHH EDLEKLKEFIKINKLKLYHDIFKDKTKNGYAGYIDNGVKQDE FYKYLKTILTKIDDSDYFLDKIERDDFLRKQRTFDNGSIPHQI HLQEMHSILRRQGEYYPFLKENQAKIEKILTFRIPYYVGPLA RKDSRFAWANYHSDEPITPWNFDEVVDKEKSAEKFITRM TLNDLYLPEEKVLPKHSHVYETFTVYNELTKIKYVNEQGESF FFDANMKQEIFDHVFKENRKVTKAKLLSYLNNEFEEFRIN DLIGLDKDSKSFNASLGTYHDLKKILDKSFLDDKTNEQIIEDI VLTLTLFEDRDMIHERLQKYSDFFTSQQLKKLERRHYTGW GRLSYKLINGIRNKENNKTILDFLIDDGHANRNFMQLINDE SLSFKTIIQEAQVVGDVDDIEAVVHDLPGSPAIKKGILQSVK IVDELVKVMGDNPDNIVIEMARENQTTGYGRNKSNQRL KRLQDSLKEFGSDILSKKKPSYVDSKVENSHLQNDRLFLYYI QNGKDMYTGEELDIDRLSDYDIDHIIPQAFIKDNSIDNKVL TSSAKNRGKSDDVPSIEIVRNRRSYWYKLYKSGLISKRKFD NLTKAERGGLTEADKAGFIKRQLVETRQITKHVAQILDARF NTKRDENDKVIRDVKVITLKSNLVSQFRKEFKFYKVREIND YHHANDAYLNAVVGTALLKKYPKLTPEFVYGEYKKYDVRK LIAKSSDDYSEMGKATAKYFFYSNLMNFFKTEVKYADGRV FERPDIETNADGEVVWNKQKDFDIVRKVLSYPQVNIVKKV EAQTGGFSKESILSKGDSDKLIPRKTKKVYWNTKKYGGFDS PTVAYSVLVVADIEKGKAKKLKTVKELVGISIMERSFFEENP VSFLEKKGYHNVQEDKLIKLPKYSLFEFEGGRRRLLASATEL QKGNEVMLPAHLVELLYHAHRIDSFNSTEHLKYVSEHKKE FEKVLSCVENFSNLYVDVEKNLSKVRAAAESMTNFSLEEIS ASFINLLTLTALGAPADFNFLGEKIPRKRYTSTKECLSATLIH QSVTGLYETRIDLSKLGEE [SEQ ID NO. 7] | GTTTT AGAGC TGTGC TGTTT CGAAT GGTTC CAAAA C [SEQ ID NO. 8] | TGTTGGA ACTATTC GAAACA ACACAGC GAGTTAA AATAAG GCTTTGT CCGTACA CAACTTG TAAAAG GGGCAC CCGATTC GGGTGC A [SEQ ID NO. 9] |
| MAD 2019 | 59 | DOTL 01000042.1 | *Streptococcus* sp. (*firmicutes*) | | MTKPYSIGLDIGTNSVGWAVITDDYKVPSKKMKVLGNTS KKYIKKNLLGALLFDSGITAEGRRLKRTARRRYTRRRNRILY LQEIFSTEMATLDDAFFQRLDDSFLVPDDKRDSKYPIFGNL VEEKAYHDEFPTIYHLRKYLADSTKKADLRLVYLALAHMIK YRGHFLIEGEFNSKNNDIQKNFQDFLDTYNAIFESDLSLEN SKQLEEIVKDKISKLEKKDRILKLFPGEKNSGIFSEFLKLIVGN QADFKKYFNLDEKASLHFSKESYDEDLETLLGYIGDDYSDV FLKAKKLYDAILLSGILTVTDNGTETPLSSAMIMRYKEHEED LGLLKAYIRNISLKTYNEVFNDDTKNGYAGYIDGKTNQEDF YVYLKKLLAKFEGADYFLEKIDREDFLRKQRTFDNGSIPYQI HLQEMRAILDKQAKFYPFLAKNKERIEKILTFRIPYYVGPLA RGNSDFAWSIRKRNEKITPWNFEDVIDKESSAEAFINRMT SFDLYLPEEKVLPKHSLLYETFTVYNELTKVRFIAEGMSDYQ FLDSKQKKDIVRLYFKGKRKVKVTDKDIIEYLHAIDGYDGIE LKGIEKQFNSSLSTYHDLLNIINDKEFLDDSSNEAIIEEIIHTL TIFEDREMIKQRLSKFENIFDKSVLKKLSRRHYTGWGKLSA KLINGIRDEKSGNTILDYLIDDGISNRNFMQLIHDDALSFKK KIQKAQIIGDKDKDNIKEVVKSLPGSPAIKKGILQSIKIVDEL VKVMGRKPESIVVEMARENQYTNQGKSNSQQRLKRLEE SLEELGSKILKENIPAKLSKIDNNSLQNDRLYLYYLQNGKD MYTGDDLDIDRLSNYDIDHIIPQAFLKDNSIDNKVLVSSAS NRGKSDDVPSLEVVKKRKTLWYQLLKSKLISQRKFDNLTK AERGGLSPEDKAGFIQRQLVETRQITKHVARLLDEKFNNK KDENNRAVRTVKIITLKSTLVSQFRKDFELYKVREINDFHH | GTTTT AGAGC TGTGT TGTTT CGAAT GGTTC CAAAA C [SEQ ID NO. 11] | GGTTTGA AACCATT CGAAAC AATACAG CAAAGTT AAAATAA GGCTAGT CCGTATA CAACGTG AAAACAC GTGGCA CCGATTC GGTGC [SEQ ID NO. 12] |

TABLE 1-continued

| MAD name | Cluster | Contig_id | Organism (meta-genome) | Source | aa_seq | CRISPR repeat | tracrRNA |
|---|---|---|---|---|---|---|---|
| | | | | | AHDAYLNAVVASALLKKYPKLEPEFVYGDYPKYNSFRERKS ATEKVYFYSNIMNIFKKSISLADGRVIERPLIEVNEETGESV WNKESDLATVRRVLSYPQVNVVKKVEVQSGGFSKELVQP HGNSDKLIPRKTKKMIWDTKKYGGFDSPIVAYSVLVMAE REKGKSKKLKPVKELVRITIMEKESFKENTIDFLERRGLRNI QDENIILLPKFSLFELENGRRRLLASAKELQKGNEFILPNKLV KLLYHAKNIHNTLEPEHLEYVESHRADFGKILDVVSVFSEKY ILAEAKLEKIKEIYRKNMNTEIHEMATAFINLLTFTSIGAPAT FKFFGHNIERKRYSSVAEILNATLIHQSVTGLYETRIDLGKL GED [SEQ ID NO. 10] | | |
| MAD 2020 | 55 | DQFW 01000027.1 | Acholeplasmatales bacterium | human gut | MKNNEETLKKLRLGLDIGTNSVGYALLDENNKLIKKNGHT FWGVRMFDEAETAKDRGSYRKSRRRLLRRKERMEILRSFF TKEICDIDPTFFERLDDSFYYKEDKKNKNTYNLFTSEYTDKD FYLEYPTIYHLRKAMQEEDKKFDIRMVYLAIAHIIKYRGNFL YPGEEFSTSEYTSIKQFFLDFNDILDELSNELEDNEDYSAEYF DKIENINDDFLEKLKVILMEIKGISNKKKELLDLFNVNKKSIY NELVIPFISGSAKVNISSLSVIKNSKYPKTEISLGSEELEGQVE EAISVAPEIKSVLEMIIKIKEISDFYFINKILSDSKTISESMVK MYDEHNEDLKKLKGFFKKYAEDQYNEIFKIRDEKLANYVA YVGFNKLRKNKVERFKHASREEFYGYLKQKLNNIKYAEAQ EEIKYFIDKIDNNEFLLKQNSNQNGAFPMQLHLKELKTILN NQEKYYPFLSEGNDGYSIKEKIILTFKYKIPYYVGPLNKESKY SWVVREDEKIYPWNFDKVVKLDETAEKFILRMQNKCTYL KGDNDYCLPKNSLIFSEYSCLSYLNKLSINGKPIDPIMKSKIF NEVFLIKKQPTKKDIIEFIKTNYNADALTTTEKELPEATCNM ASYIKMKEIFGKDFNDNKEMIENIIKDITIFEDKSILGNRLKE LYKLNNDRIKQIKGLNYKGYSRLSKNLLVGLQIVDNQTGEI KGNVIEVMRKTNLNLQEILYLDGYRLIDAIDEYNRKNSLND SYLCARDYIAENLVISPSFKRALIQTCSIIQEIERIFHKKIDEFY VEVTRTNKDKNKGKTTSSRYDKIKKIYSSCQELAMAYNFD MKRLKNELESNKDNLKSDILYFYFTQLGKCMYSLEDIDISD LTNNYHYDIDHIYPQSIIKDDSLSNRVLVDKKKNAAKTDKF LFEAKVLNPKAQQFYKKLLSLELISKEKYRRLTQKEISKDELE GFVNRQLVSTNQSVMGLIKLLKEYYKVDEKNIIYSKGENVS DFRHTFDLVKSRTANNFHHANDAYLNVVVGGILNKYYTS RRFYQFSDIARIENEGESLNPSRIFTKRDILKANGKVIWDKK EDIKRIEKDLYHRFDITETIRTYNPNKMYSKVTILPKGEGES AVPFQTTTPRVDVEKYGGITSNKFSRYVIIEAHGKKGLDTIL EAIPKTACGDNNKIEKDIDNYIASLDEYQKYTSYKVVNYNIK ANVVIQEGSFKYIITGKSGNQYVLQNVQDRFFSKKAMITIK NIDKYLNNKKLGIIMAKDNEKIIVSPARGKNNEEIFFEKTEL VNLLKEIKTMYSKDIYSFSAIQNIVNNIDCSIDYSIDDFIIICN NLLQILKTNERKNADLRLIHLSGNSGTLYLGKKLKSGMKFI WQSITGYYEEILYEVK [SEQ ID NO. 13] | GTTTG CTAGT TATGT TATTT ATAGT ATTAA GCAAA C [SEQ ID NO. 14] | TGTAAAT AACATAA CGAGTG CAAATAA GCGTTTC GCGAAA ATTTACA GTGGCCC TGCTGTG GGGCCTT TTTTATTT ATCAAA [SEQ ID NO. 15] |
| MAD 2021 | 57 | DEED 01000018.1 | Lachnospiraceae bacterium | | MSEKYFVGLDMGTSSVGWAVTDEHYHLLRRKGKDLWG ARLFDEAETAAGRRTNRVSRRRLARQRARIGWLKELFRPY LEEKDAGFLQRLEESRFFLEDKTVKQPYALFSDKEFTDKDY YQKYPTIFHLRKELLESKAPHDVRLVFLAVLNMYAHRGHFL NPELQEGTLGDIHDLLSRLDAYIQDLFEDQGWSILENVEE QQKVLAEKNISNTVRLEKILSAIGTSPKDKEKKPLIEIYKLICG LKGSLSLAFSGVEMNETDAQMKFSFSDSNLEENEPEIERIL GERYFEMYSILKEIHAWGLLSEIMSDDSGKTYPYISYAKVD LYQKHHEQLRMLKKIIRTYAPDEYHRMFRSMEDNTYSAY VGSVNSKNKKQRRGAKSTDFFKEVKRIIEKIEKEHGELPEC EEILDLIARDSFLPKQLTTANGVIPNQVYATELRQIVTNAA AYLPFLNDKDDTGLTNAEKIVEMFKFHIPYYIGPLKNDGN GTAWVVRKQQGTVYPWNIDEKVDMAKTRDQFILNLVRK CSYLNDETVLPASSLLYEKFKVLNELNNLTINGQKISVELKQ DIFRDLFRATGKRVTTRKLMGYLRRKAVIDADADETCLEG FDKTQGGFVSTLSSYHKFMEIFSTDVLTDRQREIAEGAIYF ATVYGEDKSFLKKVLRDKFSPAELSQAQIDRLSGIRFKDWS HLSREFLLLEEADHSTGEIMTIIDRLWNTENLMQIIHSDE YTYKQAIEERTARLEKSLSEVSFEDIEDSYMSAPVRRMVW QTIRILQEIEEVMGSEPARVFVEMTRSEGEKGDKGRKDSR KKKLKELYKKCKDDDQGLLSDIEGRDERDFRIRKLYLYYMQ KGLCMYSGHPIDFGKLFDDSYYDIDHIYPRHYVKDDSIENN LVLVESKLNRDKKDTLLCPDIQERMHPVWEMLHRQGFM NDEKFKRLMRKEPFSEEEFAHFIERQLVETGQGTKEIARIL NDVLGNKDENNKVIYVKAGNVSSFRNDNKKNPEFVKCRV INDHHHAKDAYLNIVVGNTYYTKFTLHPANFIRELRNKSH PTLEDQYNMDKLFARRVERNGYTAWNPDTDFQTVKQVL RKNSVLISRRSFIEHGQIADLQLVSGRKISEVNGKGYLPIKA SDIRLSGPSGTMKYGGYNKASGAYFFLVEHELKGKLVRTIE PVYVYMMASIHGKEDLEKYCQEELGYIHPRICLKKIPMYSH | GTTTG AGAGC CTTGT AAAAC CGTAT ATCTC TCAAG C [SEQ ID NO. 17] | GATAATG TTTTACA AGGCGA GTTCAAA TAAGGAT TTATCCG AAATCGC TTGCGTG CATTGGC ACCATCT ATCTTTT AAGACTT TCTTTGA AAGTCTT [SEQ ID NO. 18] |

TABLE 1-continued

| MAD name | Cluster | Contig_id | Organism (metagenome) | Source | aa_seq | CRISPR repeat | tracrRNA |
|---|---|---|---|---|---|---|---|
| | | | | | IRINGFDYYLTGRSNDRLFICNAVQLTLSSEWSAYIKALSKA VDEKWDAAYIEQQASRIQDSLKSEEVFISKERNDQLYKVLL QKHLEGFFNNRINSIGTIMKEGYDSFRALPVNEQAETLME ILKISQLVNIGANLVSIGGKSRSGVATVSKKISDSKSFQLISD SVTGIFQRATDLLTI [SEQ ID NO. 16] | | |
| MAD 2022 | 57 | CACY WR01 0000004.1 | uncultured Lachnospiraceae bacterium | Cattle rumen | MEKEYYLGLDMGTSSVGWAVTDKEYRLLRAKGKDMWG IREFEEAQTAVERRTHRLSKRRRARQLVRIGLLKDYFHDEI MKIDPNFYIRLENSKYYLEDKDVRLASSNGIFDDKNYTDKD YYEQYKTIFHLRSELIHNSQKHDVRLVYLALLNMFKHRGHF LFEGDAYVQGNIGDIYKEFIQLLKNEYYEDENVKLTDQIDY FKLKEILSNSEFSRTAKAEKINSLVHIDKKNKLENTYIRLLCG LEIELKILFPEIDEKIKICFAKGYDEKLVEITEILTDNQLQILEN LKKIHDIAALDKIRKGKEYLSDARVAEYEKHREDLALLKKIY REYMTKQDYDRMFREGEDGSYSAYVNSYNTSKKQRRNMK HRKIDEFYGTIRKDLKLLLKQGIQDDNIERILEEIDGNNDNK FMPKQLSFANGVIPNSLHKAEMKAILRNAETYLPFLLETDE SGLTVSERILQLFSFHIPYYIGPVSVNSEKNNGNGWVVRRE DGEVLPWNIEQKIDYGETSKRFIEKMVRRCTYISGEQVLPK NSFIYEKYCVLNEINNIKIDGERITVELKQNIYNDLYLHGKR VTKKQLINYLNNRGMIEDENQVSGIDINLNNYLGSYGKFL PIFEEKLKEDNYIKIAEDIIYLASIYGDSKKMLKSQIKSKYGDI LDDKQIKRILGLKFKDWGRISRRFLELEGLDKETGEITTIIKA MWDYNLNFMEIIHSDAFDFKDKIEELHANSIKPLAEIEVED LDDMYFSAPVKRMIWQTFKVIKEIEKVMGCPPKKVFIEM TRINDKKSKGKRTNSRKEKFLSLYKNIHDELVDWKQLIISSD ESGKLNSKKMYLYLTQQGICMYTGRRINLEELFDDNKYDI DHIYPRHFVKDDNLENNLVLVEKQSNSRKSDTYPIDKSIRN NSQVYKHWKSLREGNFISKEKYDRLTGKNEFTDEQKAGFI ARQMVETSQGTKGVADIIKQALPQSRIIYSKASNVSEFRRK YDILKSRTVNEFHHAHDAYLNIVVGNVYDTKFTSNPLNFIK KQYNVDRKANNYNLDKMFVYDVKRGNEIAWIGWNPKK SEDSSEMSKRGTIVTVKKMLSKNTPLMTRMSFVGHGGIA EDNLSSHFVAKNKGYMPNGKESDVTKYGGYKKAKTAYFF VVEHGQTNNRIRTIETLPIYRRREVEKYEDGLIKYCEQSLSLL NPIIIYKKIKIQSLMKINGYYAYISGKSNEVYTFRNGVNMCL SQEWINYVKKLENYIEKDRQDRMITYEKNIELYEIILRKYST TILNKRLSKMDKKLINAKDRFCILNVKEQSQVLINVFVLSRI GDNQTDLSKIGIGKQSGQITQNKKITGCKEFKLVNQSVTG LYENEIDLLTV [SEQ ID NO. 19] | GTTTG AGAGT CTTGT TAATT CTTAA AGGTG TAAAA C [SEQ ID NO. 20] | GAGAATT AACAAG ACGAGT GCAAATA AGGTTTA TCCGGAA TCGTCAA TATGACC TGCATTG TGCAGA ATCTTTA AAATCAT ATGATTT CATATGG TTTTA [SEQ ID NO. 21] |
| MAD 2023 | 56 | DCGJ0 1000048.1 | Lachnoclostridium sp. | Feces of six-years old elephant | MEKNNYLLGLDIGTDSVGYAVTNDKYDILKFHGEPAWGV TIFDEASLSTEKRSFRVSRRRLDRRQQRVLLVQELFASEVA KVDKDFFKRIQESNLYRSDAENQAGLFIGEDYCDREYYGQ YPTIHHLISDLMNGTSPHDVRLVYLACAWLVAHRGHFLSN IDKDNLSGLKDFSSVYEGLMQYFSDNGYERPWNANVDV KALGDALKKKQGVTAKTKELLALLLDSAKAEKLPREEFPFS QDGIIKLLAGGTYKLSELFGNEEYKDFGSVKLSMDDEKLGE IMSNIGEDYELIASLRIVSDWAVLVDVLGESATISEAKVGIY NQHKADLEVLKKIIRKYTGKEGYKKVFRQVDSKENYVAYS QHESDGKAPKEKGIDIATFSKFILNIVRLLDVEPEDKEVYED MVARLELNSFLPKQVNTDNRVIPYQLYWFELHKILENASIY LPMLTEKDSNGISVMEKLESVFMFRIPYFVGPLNKHSKYA WLERKEGKIYPWNFENMVDLDASEANFIKRMTNTCTYLP GQNVLPKDSLRYHRFMVLNEINNLRINNERISVELKQKIYS ELFLNVKKVTRKRLVDFLISNGELRKGEESSLTGIDVEIKANL APQIAFKKLMESGQLTEEDVESIIERASYAEDKARLAHWLE AKYSKLSEIDRKYICGIKIKDFGRLSKMFLSELEGVDKTTGE MTTILGAMWNSQLNLMELINSELYSFREAICAYQTDYYST HSSSLEERMNEMYLSNAVKRPVYRTLDIVKDVKKAFGEPK KIFVEMTRGASEEQKGKRTKSRKEQILELYKQCKDEDVRIL QQQLEEMGDLADNKLQGDKLFLYYMQKGKCMYTGTPIV LEQLGSKAYDIDHIYPQAYVKDDSILNNRVLVLSEANGKKK DIYPIEKETRDKMHGFWTYLNDKGMITEEKYKRLTRTTGF TEEEKWSFINRQLTETSQATKAVATLLGELFPNAEIVYSKA RLTSEFRQEFNLLKCRSYNDLHHAVDAYLNIVCGNVYNM KFTKRWFNINKDYSIKTKTVFTHPVVCGGQVVWDGQEM LNKVIRNAKKNTAHFTKYAYIRKGGFFDQMPVKAAEGLTP LKKDMPTAVYGGYNKPSVAFLIPTRYKAGKKTEIIILSVEHL FGERFLRDEAYAKEYAAERLKKILGKQVDEVSFPMGMRP WKINTVLSLDGFLICISGIGSGGKCLRAQSIMQFSSDYRWT IYLKRLERLVEKITVNAKYVYSEEFDKVSTIENIELYDLYIEKY KATIFSKRVNSPEEIIESGRDKFVKLDVLSQARALLCIHQTF GRIVGGCDLGLIGGKKNSAATGNFSSTISNWAKYYKDVRII DQSTSGLWVRKSENLLELV [SEQ ID NO. 22] | GTTTG AGAGT AGTGT AAATC CATAG GGGTC TCAAA C [SEQ ID NO. 23] | AGACCCC TATGGAT TTACATT GCGAGTT CAAATAA AAGTTTA CTCAAAT CGTTGGC TTGACCA ACCGCAC AGCGTGT GCTTAAA GATCTCT TCAGTGA GGTC [SEQ ID NO. 24] |

TABLE 1-continued

| MAD name | Cluster | Contig_id | Organism (metagenome) | Source | aa_seq | CRISPR repeat | tracrRNA |
|---|---|---|---|---|---|---|---|
| MAD 2024 | 56 | CADA KQ01 0000027.1 | uncultured Lachnospiraceae bacterium | Cattle rumen | MNFDGEYFLGLDIGTDSVGYAVTDQRYNLVKFKGEPMW GSHLFDAANQCAERRGFRTARRRLDRRQQRVKLVDEIFA PEVAKVDPNFYIRKMESALYPEDKSNKGDLYLYFNKQEYD EKHYYKDYPTIHHLICALMNDEKTKFDIRLINIAIDWLVAH RGHFLSEVGTDSVDKVLDFRKIYDEFMALFSDEDDAVSSK PWENINPDELGKVLKIHGKNAKRNELKKLLYGGKIPTDED SFIDRKLLIDFIAGTSVQCNKLFRNSEYEDDLKITISNSDERE VVLPQLEDFHADIIAKLSSMYDWSVLSDILSGSTYISESKVK VYEQHKKDLKELKEFVRKYAPEKYNDIFRLASKETYNYTAY SYNLKSVKDEKDLPKGKASKEDFYSYLKKTLKLDKAENYNF VNDADTRFFDDMVERISSGTFLPKQVNSDNRVIPYQVYYI ELKKILENAKKHYAFFEEKDEDGYSNVEKIMSVFTFRIPYYV GPLRNDDKSPYAWIRRKADGKIYPWDFEEKVDLDASENA FIDRMTNSCTYIPGADVLPKWSLLYTKYMVLNEINNIKVN NIGISVEAKQGIYNELFCKKAKVSLKAIREYLISNGFMQKD DEMSGIDITVKSSLKSRYDFRHLLEKNELTTDDVEAIISRSTY AEDKARFKKWLKKEFPQLSDEDYKYVSKLKYKDFGRLSRSL LNGLEGASKETGEIGTIMHFLWETNDNLMQLLSDRYTFM EEINKKRQDYYIEHKLTLNEQMEELGISNAVKRPVTRTLAV VKDVVSAIGYAPQKIFVEMARQEDEKKKRSVTRKEQILELY KNVEEDTKELERQLKKMGDTANNELQSDALFLYYLQLGK CMYSGKPIDLTQIKTTKKYDIDHIWPQSMVKDDSLLNNRV LVLSEINGDKKDVYPIDESIRSKMHSYWKMLLDKNLITKEK YSRLTRPTPFTESEKLGFINRQLVETRQSMKAVTQLLNNM YPDSEIVYVKAKLAADFKQDFKLAPKSRIINDLHHAKDTYL NVVAGNVYNERFTKKWFNVNEKYSMKTKVLFGHDVKIG DRLIWDSKKDLQTVKNTYEKNNIHLTRYAYCQKGGLFDQ MPVKKGQGQIQLKKGMDIDRYGGYNKATASFFIIARYLR GGKKEVSFVPVELMVSEKFLNDDNFAIEYITNVLTGMNTK KIENVELPLGKRVIKIKTVLLLDGYKVWVNGKASGGTRVM LTSAESLRMPKEYVEYLKKMENYSEKKKSNRNFMHDSEN DGLSEEKNILLYDKLLEKLDENHFKKMPGNQCETMKSGRV KFIELDFDVQISTLLNCIDLLKSGRTGGCDLKNIGGKSASGV VYISANLSACKYNDVHIIDISPAGLHENISCNLMELFE [SEQ ID NO. 25] | GTTTG AGAGT AGTGT AAATC CAGAG GGCTC CAAAA C [SEQ ID NO. 26] | GAGCCCT CTGGATT TACACTA CGAGTTC AAATAAA AATTATT TCAAATC GCCGCTA TGTCGGC CGCACA GTGTGTG CATTAAG AAAAGTC CGAAAG GGC [SEQ ID NO. 27] |
| MAD 2025 | 56 | DOQG 01000053.1 | Ruminococcaceae bacterium | human gut | MSFKENSKFYFGLDIGTDSVGWAVTDNLYKLYKYKNNLM WGVSLFEAASPAEDRRNHRTARRRLDRRQQRVALLRELF AKEILKTDPDFFLRLKESSLYPEDRTNKNVNTYFDDADFKD SDYFKMYPTVHHLIKELSESDKPHDVRLVYLACAFIVAHRG HFLNGADENNVQEVLDFNSSYCEFTDWFKSNDIEDNPFS ESTENEFSVILRKKIGITAKEKEIKNLLFGTTKTPDCYKDEEY PIDIDVLIKFISGGKTNLAKLFRNPAYDELDIQTVEVGKADF ADTIDLLASSMEDTDVPLLSAVKAMYDWSLLIDVLKGQKT ISDAKVCEYEQHKSDLKALKHIVRKYLDKAQYDEIFRTAGE KPNYVSYSYNVTDVKLKQLPSNFKKKYSEEFCKYINSKLEKI KPEPDDEAVYNELIEKCNSKTLCPKQVTDENRVIPYQLYYH ELSMILDKASAYLDFLNETEDGISVKQKILTLMKFRIPYFVG PSVKRNETDNVWIVRKAEGRIYPWNFENMVDYDKSEDG FIRRMTCKCTYLAGEDVLPKYSLLYSRYTVLNEINNIKVKDV KISPELKQDIFNELFMKTSRVTVKKITELLKRKGAFSEENGD SLSGVDINIKSSLKSYLDFRRLLENGSLSESDVERIIERITVTT DKPRLISWLKTEYPALPAEDIRYISRLSYKDYGRLSAKMLTG CYELDMDTGEIGGRSIIDLMWAENINLMQIMSDSYGYKS FIEEENKKYYAINPTGSIAQTLREMYVSPSASRAIIRTMDIV KELRKIIKRDPDKIFVEMARGSKPEDKGKRTSSRREQIEKLF ASAKEFVSDEEISHLRSQLGSLSDEQLRSEKYYLYFTQFGKC VYSGEAIDFSRLGDNHCYDIDHIYPQSKVKDDSLHNKVLV KSQLNGEKSDDYPIKEQIRNKMHPIWKNLFYRDPKNPTD KIKYERLTRSTPFTEDELAGFIERQLVETRQSTKAVATLLKE MFPDSKIVYVKAGQVSKFRHDFDMLKCREINDLHHAKDA YLNVVVGNVHDVKFTSNPLNFVKNADKHYTIKIKETLKHK VARNGETAWNPETDFDTVKRMMSKNSVRYVRYCYKRK GELFKQQPKKAGNPDLAWLKKNLDPVKYGGYNSKSISCFS LIKCTGVGVVIIPVELLCEKRYFSDDSFASEYAYSVLKNALPA KNIAKISIDDISFPLKRRPIKINTLFEFDGYRVNIRSKDSYSVF RISSAMAAIYSKDTSDYIKAISSYIDKSDKGSKFKPGEAFDVL SNLKAYDEIAKKCISEPFCKISKLAEAGKKMEEGRNKFAELS IIEQMKTLLLLVDVLKTGRVDKCNLKPVGGVDNFHTERMS AILKNTKYSDIRIIDQSPTGLYENKSDNLLEL [SEQ ID NO. 28] | GTTTG AGAGT AGTGT AAATT TATAG GGTAG TAAAA C [SEQ ID NO. 29] | TTTTACT ACCCTAT AAATTTA CACTACG AGTTCAA ATAAAAA TTATTTC AAATCGT ACTTTTT AGTACCT TCACAAG TGTTGTG AATATTA ACTCACC TTCGGGT GAG [SEQ ID NO. 30] |
| MAD 2026 | 65 | CADB QN01 0000053.1 | uncultured Firmicutes bacterium | Cattle rumen | MEQKDYYIGLDIGTNSVGWAVVDEGYQLCRFKKYDMW GVRLFDSAETAAERRMNRVNRRRNRRKKQRIDLLQGLFA EEIAKIDRTFFVRLNESRLHPEDKSTAFRHPLFNDPNYTDV DYYKEYPTIYHLRKELMDSAEPHDIRLVYLALHHILKNRGH FLIEGGFEDSKKFEPTFRQLLEVLTEELGLKMDGADAALAE SVLKDRGMKKTEKVKRLKNVFTLNTTDMDQESQKKQKA | GTTTG AGAGT AGTGT AATTT CATAT GGTAG | GACTACC ATATGAG ATTACAC TACACGG TTCAAAT AAAGAA |

TABLE 1-continued

| MAD name | Cluster | Contig_id | Organism (metagenome) | Source | aa_seq | CRISPR repeat | tracrRNA |
|---|---|---|---|---|---|---|---|
| | | | | | QIDAVCKFLAGSKGDFKKLVADEALNELKLDTFALGTSKAE DIGLEIEKSAPQYCVVFESVKSVFDWKIMTQILGDESTFSS AKVKEYEKHHENLIILRELIRKYCDKETYRHFFNNVNGGYS RYIGSLKKNGKKYYVAGCTQEEFYKELKGLLKSIDQRVDPE DRPVYQRVLAETEDETFLPLLRSKANSAIPRQIHQKELDDIL QNASVYLPFLNDVDEDGLSAAEKIRSIFTFRIPYYVGPLSLR HKDKGAHVWIKRKEEGYIYPWNYEKKIDREKSNEEFIRRLI NQCTYLKDEKVLPKKSLLYSEFMVLNELNNLRIRGKRLSEE QVELKQRIYRDLFMTKTRVTKKTLLNYLRKEDSDLTEEDLS GFDNDFKASLSSCLELKNKVFGDRIEEDRVRKIAEDLIRWL TIYDDDKKMIKEVIRAEYPNEFTNEQLDVICRLKFSGWGN LSEAFLCGVEGADKDTGEVFTIIEALRNTNHNLMELLSGNY TFTEKIREHNAALSSEIKAKDYESLVRDLYVSPACKRGIWQ TIRITEEIKKIMGHEPKKIFVEMTREHRDSGRTTSRKDQLLA LYQKCEEDARDWVKEIEDREERDFSSIKLFLYYLQQGKCM YSGEAIDLDELMSKNSRWDRDHIYPQSKIKDDSLDNLVLV KKELNAVKDNGEIAPDIQKRMKGFWLSLLRQGFLSKKKFD RLTRTGPFTSEELAGFISRQLVETSQMSKAVAELLNQLYED SRVVYVKAGLVSQFRQKDLGVLKSRSVNDYHHAKDAYLN VVVGDMFDRKFTSDPARWFKKNKKVNYSINQVFRRDYE ENGKLIWKGIDRGEDGKPLFRDGLIHGGTIDLVRAIAKRNT NIRYTEYTYCETGQLYNLTLLPKTDTAITIPLKKELPAAKYGG FKGAGTSYFSLIEFDDKKGHHHKQIVGVPIYVANMLEHNE NAFIEYLETVCSFRNITVLCEKIKKNALISVNGYPMRIRGEN EILNMLKNNLQLVLSQEGEETLRHIEKYFNKKPGFEPDKEH DGIDRDAMAALYDEMTEKLCTVYKKRPTNQGELLKNNR GLFLNLEKRSEMAKVLSETAKMFGTTAQTTADLSLIKGSKY AGKIVINKNTLGAAKLILIHQSVTGLFETRVEL [SEQ ID NO. 31] | TCAAAC [SEQ ID NO. 32] | TGTTCGA AACCGCC CTTTGGG GCCCGCT TGTTGCG GATTTAC AGACTTG ATATCAA GTCTG [SEQ ID NO. 33] |
| MAD 2027 | 65 | CACW RN01 0000001.1 | uncultured Succinic- lasticum sp. | Cattle rumen | MSKKFAGEYYLGLDIGTDSVGWAVTDNQYNVLKFNGKS MWGIRLFDAAQTAAERRMFRTARRRVERRRWRLELLQE LFQNEIEKKDPDFFQRMKDSALYPEDSKTGKPFALFCDKD LNDKLYYKQYPTIYHLRKALLTENSKFDIRLVYLAIHHILKHR GHFLFNGDFSNVTRFSFAFEQLQTCLCNELDMDFECNNV QKLSEILKDTHMSKNDKVKASVALFENSGDKKQLQAVIGL FCGAKKKLADVFLDETLNDTEMPSISIADKPYEELRPELESI LAEKCCVIDYIKAVYDWAILADMLDGGEYGNRTYISVARV RQYEKHHDDLKKLKKLVRRYCKSEYKSFFSVAGTDNYCAYI GDDIETDDRKSVKKCKQEDFYKRIKGLLKKAIENGCPKDEV VEIIKDIDAQVFLPLQVTKDNGVIPHQVHEMELKQILKNAE KYYPFLCKKDEEGIVTSNKILQLFKFRIPYYVGPLNSRIGKNS WIVRRAEGKIYPWNFEEKVDFDKSEEGFIRRMTNPCTYM AGADVLPKYSLLYSEFMVLNELNNVRICGDKLSVEIKQTIIK DLFQRTRRVTVRKLCDKLKAEGVISRNSNQKDIDIKGIDQD LKSSMVSYVDFKNIFGKEIEKYSVQQMCERIIFLLTIHHDDK RRLQKRIRAEFTEAQITDDQLQKVLRLNYQGWGRFSAEFL KELKGVDTETGEVFSIINALRETDDNLMQLLSNRYTFAEEL EKYNSNKRKKIEALTYDNIMEGIVASPAIKRSAWQAISIVM ELSKIMGREPKRIFVEMARGPEEKKHTISRKNQLLELYKSV KDESRDWKTELETKTESDFRSIKLFLYYTQMGRCMYTGEPI DLDQLANTTIYDRDHIYPQSLTKDDSLNNLVLVKKVENAN KGNGLISADIQKKMRGFWAELKKKGLISDEKFSRLTRTTPL SDDELAGFINRQLVETRQSSKIVADLFHQLYPTTQVVYVKA KIVSDFRHETLDMVKVRSLNDLHHAKDAYLNIVTGNVYYE KFSGNPLTWLRKNPDRNYSLNQMFNYDIVKKTKEGTSYV WKKKGKDGSIAVVRRTMERNDILYTRQATENKNGGLFDQ NIVSSKNKPFIPVKKGLDVNKYGGYKGITPAYFALIEFTDKK GSRQRLLEAVPLYLRADIDNDSNVLRDFYKNVLGLENPVVI LNRIKKNSLLKINGFLIHLRGTTGFSASQLKVQNAVEFSLPH HMEDYVKKLENYEKHIIAERGSTKNSQIKITEWDGISKEKN LQLYDMFINKMENTIYKFRPANQVSNLKENREVFNSLAVE DQCSVLNQVLMLFVCKPVTANLSLIKGSKNAGNMALSKII SNMRSAYLIHQSVTGLFEQKIDLLKVSSQKD [SEQ ID NO. 34] | GTTTG AGAGT AATGT AAATT CATAG GATGG TAAAA C [SEQ ID NO. 35] | TTTACCA TCCAGTG AGTTTAC ATTACAA GTTCAAA TAAAAAT TTATTCA ACCCGTT CTTCGGA ACCTCCA CCGTGTG GAACATT AAGGTCT GCTTTGC AGGCC [SEQ ID NO. 36] |
| MAD 2028 | 66 | DHKP 01000031.1 | Bacillales bacterium | gut meta- genome | MANKLFIGLDVGSDSVGWAATDENFHLYRLKGKTAWGA RIFSEASDAKGRRGFRVAGRRLARRKERIRLLNTLFDPLLKE KDPTFLLRLENSAIQNDDPNKPAQAVTDCLLFANKQEEKG FYKRYPTIWHLRKALMDNEDCAFSDIRFLYLAIHHIIKYRG NFLRDGEIKIGQFDYSVFDKLNETLSVLFDLQSEDEDSQEG HFVGLPKSQYEAFITTANDRNLPKQTKKTKLLSMFEKDEES KSFLEMFCTLCAGGEFSTKKLNKKGEETFDDTKISFNASYD QNEPNYQEILGDAFDLVDIAKAVFDYCDLSDILNGNDNLS NAFVELYDSHKSQLSALKAICKQIDNQSNLKGDASVYVKLF NDPNDKSNYPAFTHNKTLVDKRCDIHTFDKYVIDTVLPYE PLLMGQDATNWQMLKSLAEQDRLLQTIALRSTSVIPMQL HQKELKIILKNAISRNVKGIAEIEEKILKLFQYKIPYYCGPLTT | GTTTG AGAGC AGTGT TGTCT TATAT AGCTC GAAAA C [SEQ ID NO. 38] | GCATTGT AAGACA ACACTGC TACGTTC AAATAA GCATATT GCTACAA GGTTCTC CCTCGGA GAATGA CCATTAG GTCACTT |

TABLE 1-continued

| MAD name | Cluster | Contig_id | Organism (metagenome) | Source | aa_seq | CRISPR repeat | tracrRNA |
|---|---|---|---|---|---|---|---|
| | | | | | KSAYSNVVFKNNEYRPLKPWDYEEAIDWDETKKKFMEGL TNKCTYLKDKNVLPKQSILYQDFDAWNKLNNLKVNGSKP SLKELKDLFSFVSQRPKTTMKDIQRHFKSDTNSKDKDVVV SGWNPEDYICCSSRASFGKNGVFDLNNPDSSDPKDLSKCE RMIFLKTIYADSPKDADVAILKEFPDLTNDQKSLLKTIKCKE WSPLSKEFLELRYADKYGEIRESIINLLRSGEGNLMQILAKY DYQERIDAYNADSFQTKSKSQIVSDLIEEMPPKMRRPVIQ AVRIVHEVVKVAKKEPDQISIEVTRENNNKEKKQQLTKKA KSRSAQIQTFLKNLVKIDTFEEKRVDEVLEELKKYSDRSING KHLYLYFLQNGKDAYTGKPINIDDVLSGNKYDTDHVIPQS KMKDDSIDNLVLVERSINQHRSNEYPLPESIRKNPANVAF WSKLKKAGMMSEKKFNNLTRANPLTEEELSAFVAAQINV VNRSNIVIRDVLKVLYPNAKLIFSKAQYPSQIRKELNIPKLR DLNDTHHAVDAYLNIVSGVSLTERYGNLSFIKAAQKNENQ TDYSLNMERYISSLIQTKEGEKTSLGKLIDQTSRRHDFLLTY RFSYQDSAFYNQTIYKKNAGLIPVHEKLPPERYGGYNSMS TEVNCVVTIKGKKERRYLVGVPHLLLEKGNKVADINKEIAN SVPHKENETIAVSLKDIIQLDSMVKKDGLVYLCTTQNKDLV KLKPFGPIFLSRESEVYLSNLNKFVEKYPNIADGNENYSLKT NRYGEKSIDFLQEKTGNVLKELVDLSNQKRFDYCPMICKL RTIDYRKGVEGKTLTEQLILIRSFVGVFTRKSEALSNGSNFR KARGLVLQDGLVLCSDSITGLYHTERKL [SEQ ID NO. 37] | | AGATAG CCGGTTC TTCTGGC TA [SEQ ID NO. 39] |
| MAD 2029 | 66 | DBKT 01000013.1 | Bacillales bacterium | gut metagenome | MADKLFIGLDVGSESVGWAATDENFHLYRLKGKTAWGA RIFSEANDAKTRRGFRVAGRRLARRKERIRLLNTLFDPLLKK DPAFLLRLENSAIQNDDPNKPIQAIADCPLLVNKQEEKDYY KRYPTIWHLRKALMENDDHAFSDIRFLYLAIHHIIKYRGNF LREGDIKIGQFDYSIFDKLNETLAVLFDLQNEDGENEEGRFI GLPKSQYEAFITCANDRNLPKQPKKAKLLSMFEKTEESKAF LEMFCTLCSGGEFSTKKLNAKGEETYQDAKISFNSSYDENE GAYQEILGDFFDLVDIAKAVFDYCDLSDILNGNDNLSSAFV ELYDSHKSQLSALKSICKRIDNQNGFIGEKSIYVKLFNDPND KSNYPAFTNNKTLVDKRCDIHTFDKYVKETILPYESSLTGR DAVNWQMLKSLAEQDRLLQTIALRSTSVIPMQLHQKELKI ILKNAVSRNIKGVAEIEEKILKLFQYKIPYYCGPLTTKSDYSN VVFKNNEYRPLKPWDYEEAIDWDGTKQKFMEGLTNKCT YLKDKNVLPKQSVLYQDFDTWNKLNNLKVNGNKPSLEDL NDLFSFVSQRSKTTMRDIQRYLKSKTNSKENDVVVSGWN SEDYICCSSRASFNKNGIFNLNNSEVLKECERIIFLKTIYTDS PKDADAAVLKEFPDLTNNQKTLLLKTIKCKEWSPLSKEFLEL RYSDKYGEIRQSIIDLLRNGEGNLMQILAKYDYQEVIDACN AASFQTKSKSQIVSDLIEEMPPKMRRPVIQAVRIVQEVAK VAKKEPDEISIEVTRENNDKEKKQQLTKKAKSRSTQIQNFL KNLVKIDASEKKQANEVLEELKKYSDQSINGKHLYLYFLQN GKDAYTGKPINIDDVLSGNKYDTDHIIPQSKMKDDSIDNL VLVEREINQHRSNEYPLPESIRKNPANVAFWRKLKKAGM MSEKKFNNLTRSNPLTEEELGAFVAAQINVVNRSNVVIRD VLKILYPNAKLIFSKAQYPSQIRKELNIPKLRDLNDTHHAVD AYLNIVSGVTLTDRYGNMRFIKASQDEEKHSLNMERYISSL IQTKEGQRTELGELIDQTSRRHDFLLTYRFSYQDSAFYKQTI YKKNAGLIPAHDNLPPERYGGYDSMSTEVNCVATIIGKKT TRYLVGVPHLLIKKAKDGIDVNDELIKLVPHKENEVVKVDL NTTLQLDCTVKKDGFMYLCTSNNIALVKLKPFSPIFLSRESE IYLSNLMKYVEKYPNISDENSEYEFKINRENVDPIKFTEKQSI EVVQDLIIKAKQDRFSYCSMISKLRDINAEEMIHSKSLTEQL KIIKSLIGVFTRKSEILSDKNNFRKSRGAILQEDLFLCSDSITG LYHTERKL [SEQ ID NO. 40] | GTTTG AGAGC AGTGT TGTCT TATAT AGCTC GAAAA C [SEQ ID NO. 41] | GCATTGT AAGACA ACACTGC TACGTTC AAATAA GCATATT GCTACAA GGTTCTC CATTGGA GAATGA CCATTAG GTCGCTT AGATAG CCAGTTC TTCTGGC TA [SEQ ID NO. 42] |
| MAD 2030 | 66 | DBLD 01000015.1 | Bacillales bacterium | gut metagenome | MEQNTKKLFIGLDVGTDSVGWAATDEYFNLYRLKGKTA WGARLFLDAANAKDRRQHRVSGRRLARRKERIRLLNALF DPLLKKVDPTFLLRLESSTLQNDDPNKDQRAVSDALLFGN KKHEKAYYAAFPTIWHLRKALIENDDKAFSDIRYLYLAIHHII KYRGNFLRQGEIKIGEFDFSCFDKLNQFFDIYFSKEDEEEVE FIGLPNENYQRFIDCAADKNLGKGKKKGDLLKLMSFSEDE KPFCEMFCSLCAGLAFSTKKLNKKDETVFEDIKVEFNGKFD DKQEEIKSVLGDAYDLVELAKIFDYCDLKDILGASTNRLSE AFAGIYDSHKEELKALKGICREIDRSLGNESKNSLYREVFND KGIPNNYAAFIHHETNSSRCGIADFNNYVLQKIEPLENLLS KQNYKNWIQLKQLASQGRLLQTIAIRSTSIIPMQLHLKDLK LILANAEKRDIPGIKDIKEKILLLFQFKVPYYCGPLTDRSQYS NVVLKAGTREKITPWNFADQVDLEETKKKFMEGLTNKCT YLKDCNVLPRQSLMFQEYDAWNKLNNLSINGNKPSPEE MNALFDFASKRRKTTMSDIKKFEKRATMSKENDVTVSG WNENDFIDLSSFVSLSGFFDLGEIHSADYMACEEAILLKTIF TDAPQDADPIIAEKFPNLKPNQLAALKKMSCKGWATLSR EFLTLKAVDADGEVMNETLLGLMKEGKGNLMQLLHSSLY NFQDVIDSHNRAVFGDKSPKQIANDLIEEMPPQMRRPVI | GTTTG AGAGC AGTGT TGTCT TAAAT AGCTC GAAAA C [SEQ ID NO. 44] | GCATTGT AAGACA ACACTGC ACGTTCA AATAAGC AGATTGC TACAAG GTTCCCG TAAGGG AATGACC ATCTGGT CACATGA ATAGCCC CCGGCA ACGGTG GCTG [SEQ ID NO. 45] |

TABLE 1-continued

| MAD name | Cluster | Contig_id | Organism (metagenome) | Source | aa_seq | CRISPR repeat | tracrRNA |
|---|---|---|---|---|---|---|---|
| | | | | | QALRIVREVSKVAKKQPDVISIEVTRESNDKKKKEEWSKKA TDRKKQIDLFLKNLKKTEDVKQTESELDGQAINDIDSIRGK HLYLYFLQNGKDAYTGLPIDINDVLNGTKYDTDHIIPQSLM KDDSIDNLVLVNREKNQHKSNEFPLRDIQTKANIERWRA LKKAGGMSEKKFNNLTRTTPLTEEELSAFVAAQINVVNRS NVVIRDVLKILYPNAKLIFSKAQYPSQIRRDLEIPKLRDLNDT HHAVDAFLNIVSGVELTKQFGRMDVIKAAAKGDKDHSLN MTRYLERLLKKVDENKNETMTELGNHVFVTSQRHDFLLT YRFDYQDSAFYNATIYSPDKNLIPMHDGMDPERYGGYSS LNIEYNCIATIKGKKKTTRYLLGVPHLLALKFKNDGIDITSDLI KLVPHKGDEEVSIDWKNPIPLRITVKKDGVEYLLAPFNAQ VMELKPVSPVFLPREAAEYLARLKKAVDQKKQFIYQNSAEI FQSKDKNNALQFGPEQSKNVALKIYALADAKKYDYCAMIS KLRDAALRAEMLDSLSSEALFKQYNDLISLLSQLTRRSKKIS SKYFSKSRGALLQDGLKIVSKSITGLYETERNL [SEQ ID NO. 43] | | |
| MAD 2031 | 141 | CACV OG01 0000001.1 | uncultured Selenomonadaceae bacterium | Cattle rumen | MNYILGLDIGIASVGWAAVALDANDEPCKILDLNARIFEA AEQPKTGASLAAPRREARGSRRRTRRRRHRMERLRHLFA REELISAENIAALFEAPADVYRLRAEGLSRRLDEGEWARVL YHIAKRRGFKSNRKGAASDADEGKVLEAVKENEALLKNYK TVGEMMFRDEKFQTAKRNKGGSYTFCVSRGMLAEEIGEL FAAQREQGNPHASETFETAYSKIFADQRSFDDGPDANSR SPYAGNQIEKMIGTCSLETDPPEKRAAKASYSFMRFSLLQK INHLRLKDAKGEERPLTDEERAAVEALAWKSPSLTYGAIRK ALPLPDELRFTDLYYRWDKKPEEIEKKKLPFAAPYHEIRKAL DKREKGRIQSLTPDALDAVGYAFTVFKNDAKIEAALSAAGI DGEDAVALMAAGLTFRGFGHISVKACRKLIPHLEKGMTY DKACKEAGYDLQKTGGEKTKLLSGNLDEIREIPNPVVRRAI AQTVKVVNAVIRRYGSPVAVNVELAREMGRTFQERRDM MKSMEDNNAENEKRKEELKGYGVVHPSGLDIVKLKLYKE QGGVCAYSLAAMPIEKVLKDHDYAEVDHILPYSRSFDDSY ANKVLVLSKENRDKGNRTPMEYMANMPGRRHDFITWV KSAVRNPRKRDNLLLEKFGEDKEAAWKERHLTDTKYIGSFI ANLLRDHLEFAPWLNGKKKQHVLAVNGAVTDYTRKRLGI RKIREDGDLHHAVDAAVIATVTQGNIQKLTDYSKQIERAF VKNRDGRYVNPDTGEVLKDEWIVQRSRHFPEPWPGFR HELEARVSDHPKEMIESLRLPTYTPEEIDGLKPPFVSRMPT RKVRGAAHLETVVSPRLKDEGMIVKKVSLDALKLTKDKDA IENYYAPESDHLLYEALLHRLQAFGGDGEKAFAESFHKPKA DGTPGPVVKKVKIAEKSTLSVPVHHGRGLAANGGMVRV DVFFIPEGKDRGYYLVPVYTSDVVRGELPMRAVVQGKSY AEWKLMREEDFIFSLYPNDLVYIEHEKGVKVKIQKKLREIST LPREKTMTSGLFYYRTMGIAVASIHIYAPDGVYVQESLGV KTLKEFKKWTIDILGGEPHPVQKEKRQDFASVKRDPHAAK STSSG [SEQ ID NO. 46] | ATTGT ACCAT AGCGA GTTAA ATTAG GGAAT TACAA C [SEQ ID NO. 47] | TTGTAAT AACCTAT TTTACCT CGCTATG GCACAAT TTGTTAT TACATGG ACATTAT ACTAAAC ATTTCCT AAAAAA GCAACG AAAAAC GTGCTG GCAGCA A [SEQ ID NO. 48] |
| MAD 2032 | 141 | CACV WE01 0000020.1 | uncultured Ruminococcus sp. | Cattle rumen | MKYIIGLDMGITSVGFATMMLDDKDEPCRIIRMGSRIFEA AEHPKDGSSLAAPRRINRGMRRRLRRKSHRKERIKDLIIKN ELMTADEISAIYSTGKQLSDIYQIRAEALDRKLNTEEFVRLLI HLSQRRGFKSNRKVDAKEKGSDAGKLLSAVNSNKELMIEK NYRTIGEMLYKDEKFSEYKRNKADDYSNTFARSEYEDEIRQ IFSAQQEHGNPYATDELKESYLDIYLSQRSFDEGPGGSSPY GGNQIEKMIGNCTLEPEEKRAAKATFSFEYFNLLSKVNSIKI VSSSGKRALNNDERQSVIRLAFAKNAISYTSLRKELNMEYS ERFNISYSQSDKSIEEIEKKTKFTYLTAYHTFKKAYGSVFVE WSADKKNSLAYALTAYKNDTKIIEYLTQKGFDAAETDIALT LPSFSKWGNLSEKALNNIIPYLEQGMLYHDACTAAGYNFK ADDTDKRMYLPAHEKEAPELDDITNPVVRRAISQTIKVIN ALIREMGESPCFVNIELARELSKNKAERSKIEKGQKENQVR NDRIMERLRNEFGLLSPTGQDLIKLKLWEEQDGICPYSLKP IKIEKLFDVGYTDIDHIIPYSLSFDDTYNNKVLVMSSENRQK GNRIPMQYLEGKRQDDFWLWVDNSNLSRRKKQNLTKET LSEDDLSGFKKRNLQDTQYLSRFMMNYLKKYLALAPNTT GRKNTIQAVNGAVTSYLRKRWGIQKVRENGDTHHAVDA VVISCVTAGMTKRVSEYAKYKETEFQNPQTGEFFDVDIRT GEVINRFPLPYARFRNELLMRCSENPSRILHEMPLPTYAAD EKVAPIFVSRMPKHKVKGSAHKETIRRAFEEDGKKYTVSK VPLTDLKLKNGEIENYYNPESDGLLYNALKEQLIAFGGDAA KAFEQPFYKPKSDGSEGPLVKKVKLINKATLTVPVLNNTAV ADNGSMVRVDVFFVEGEGYYLVPIYVADTVKKELPNKAII ANKPYEEWKEMREENFVFSLYPNDLIKISSRKDMKFNLVN KESTLAPNCQSKEALVYYKGSDISTAAVTAINHDNTYKLRG LGVKTLLKIEKYQVDVLGNVFKVGKEKRVRFK [SEQ ID NO. 49] | GTTGT AGTTC CCTAA TTATTC TTGGT ATGGT ATAAT [SEQ ID NO. 50] | ATTGTAT CATACCA AGAACA ATTAGGT TACTATG ATAAGGT AGTATAC CGCAAA GCTCTAA CACCTCA TCTTCGG ATGAGG TGTTATC T [SEQ ID NO. 51] |

TABLE 1-continued

| MAD name | Cluster | Contig_id | Organism (metagenome) | Source | aa_seq | CRISPR repeat | tracrRNA |
|---|---|---|---|---|---|---|---|
| MAD 2033 | 141 | DCJP0 1000021.1 | uncultivated *Faecalibacterium* sp. | Feces of three-weeks old elephant | MKNTLYGIGLDIGVASVGWAVVGLNGTGEPVGLHRLGV RIFDKAEQPKTGESLAAPRRMARGMRRRLRRKALRRADV YALLERSGLSTREALAQMFEAGGLEDIYALRTRALDEPVGK AEFSRILLHLAQRRGFKSNRRTASDGEDGRLLAAVNENRR RMAQGGWRTVGEMLYRHEAFALRKRNKADEYLSTVGR DMVAEEASLLFQRQRELGCAWATPELQAEYLSILLRQRSF DEGPGGNSPYGGNQVEKMVGRCTFEPDEPRAAKAAYSF EYFSLLQKLNHIRLAENGETRPLTQPQRQQLLSLAHKTPDV SLARIRKELALPETVQFNGVRCRANETLEESEKKEKFACLP AYHKMRKALDGVVKGRISSLSISQRDAAATALSLYKNEDT LRAKLTEAGFQAPEIDALAGLTGFSKFGHLSLKACRKLIPHL EQGLTYDQACSAAGYDFKGHGAGERAFTLPAAAPEMEQI TSPVVRRAVAQTIKVVNGIIREMDASPAWVRIELARELSKT FGERQEMDRSMRENAAQNERLMQELRDTFHLLSPTGQ DLVKYRLWKEQDGVCAYSLRRLDVERLFEPGYVDVDHIVP YSLSFDDRRSNKVLVLSSENRQKGNRLPLQYLQGKRREDFI VWTNSSVRDYRKRQNLLREKFSGDEAEGFRQRNLQDTQ HMARFLYNYISDHLAFAQSEALGKKRVFAVSGAVTSHLRK RWGLSKVRADGDLHHALDAAVIACTTDGMIRRISGYYGH IEGEYLQDADGAGSQHARTKERFPAPWPRFRDELIVRLSE QPGEHLLDINPAFYCEYGTEHICPVFVSRMPRRKVTGPGH KETIKGAAAADEGLLTVRKALTELKLDKDGEIKDYYMPSSD TLLYEALKAQLRRFGGDGKKAFAEPFYKPKADGTPGPLVR KVKTIEKATLTVPHGGAASNDTMVRVDVFLVPGDGYY WVPVYVADTLKPELPNRAVVAFKPYSEWKEMREEDFIFSL YPNDLVYVEHKSGLKFTLQNADSTLEKTWVPKASFAYFVG GDISTAAISLRTHDNAYGLRGLGIKTLKVLKKYQVDVLGNIS PVHRETRQRFR [SEQ ID NO. 52] | GTTGT AGTTC CCTAA CAGTT CTTGG TATGG TATAA T [SEQ ID NO. 53] | TTATACC ATACCAA GAACTGT TATGGTT GCTATGA TAAGGTC TTAGCAC CGTAAA GCTCTGA CGCCTCG CTTTCAG CGGGGC GTCATCT TTTTTGC CCAAAA GACACG GATATTT TT [SEQ ID NO. 54] |
| MAD 2034 | 141 | CACX AV01 0000001.1 | uncultured *Clostridiales bacterium* | Cattle rumen | MAYGIGLDIGIASVGFATVALNEQDEPCGILRMGSRIFDA AEHPKNGASLAAPRREARSARRRLRRHRHRLERIRNLLVE SCLISQDGLGSLFEGRLEDIYALRTRALDERLTDAELCRVLIH LAQRRGFRSNRKADAADKEAGKLLKAVSENDRRMEENG YRTVGEMLYKDPLFAEHRRNKGEAYLSTVTRTAVEQEARL VLSTQREKGNAAITEDFVEKYLDILLSQRPFDVGPGGNSPY GGNMIEKMIGRCTFEPDELRAPKASYSFEYFQLLQKVNHI RLLRDGRSEPLSEEQRRAIIDLALASADVTFAKIRKALSLPDS VRFNDVYYRESAEEAEKKKKLGCMDAYHEMRKALDKVAK GRICAIPVEQRNAIAYVLTVHKTDERILTELQNINLERSDID QLMQMKGFSKFGHLSIKACDRIIPYLEQGMTYSDACTAA GYAFRGHEGGEHSLYLPAQTPEMDEITSPVVRRAVSQTIK VVNALIREQGESPTFVNIELAREMSKDFAERNDIRRENEK NAKANEAVMNELRRTFGLVNPSGQDLVKYKLFLEQGGVC PYTQRPMEPGRLFEAGYADVDHIVPYSISFDDRYCNKVLT FASVNRKEKGNRLPLQFLKGERRESFIVYVKANVRDYRKQ RLLLKETVTEEDRKGFRDRNLQDTKHMAAFLHSYINDHLQ FAPFQTDRKRHVTAVNGAVTAYLRKRWGIRKVRAEGDLH HASDALVIACTTPGMIQRLSRYAELREAEYMQTEDGAVRF DPATGEVLEKFPYPWPCFRQEWTARVSDDPQAMLQDM KLTDYRGLPLEQVKPVFVSRMPKHKVTGAAHKDTVKSAK ALDRGVVLVKRALTDLKLKDGEIENYYDPASDRLLYEALKE RLIAFGGDAQKAFAEPFHKPKRDGTPGPLVKKVKLMEKSS LTVPVHDGKGVADNDSMVRIDVFFVAGEGYYFVPIYVAD TVKPELPNRAVVANKPYAEWKEMKDEDFLFSLYPSDLMR VTQKKGIKLSLINKESTLKKEEMAQSILLYYVKGSISTGSITA ENHDRTYAINSLGIKTLEKLEKYQVDVLGNVSPVGKEKRLT FC [SEQ ID NO. 55] | GTTGT AGTTC CCTAA CGGTT CTTGG TATGG TATAA T [SEQ ID NO. 56] | TTATACC ATACCAA GAACTGT TGGGTTA CTACAAT AAGGTA GTAAACC GAAAAG CTCTGAC GTCTTGT TTGCGCA GGACGT CATCTTT ATATCAG ACGGAT G [SEQ ID NO. 57] |
| MAD 2035 | 141 | CADA TZ010 000012.1 | uncultured *Chloroflexi bacterium* | Cattle rumen | MLPYAIGLDIGIASVGWAVVGLDTNERPFCILGMGSRIFD KAEQPKTGASLALPRREARSLRRRLRRHRHRNERIRNLLLR EKIISESELQDLFSGTLSDIYQLRVEALDRKLDDKEFSRVLIHI AQRRGFKSNRKNAAASQEDGKLLSAVTENQQRMNDKG YRTVSEMLLRDDKFKDHKRNKGGEYLTTVTRTMVEDVH KIFSAQRTHGNLKADNQLESEYLEILLSQRSFDEGPGGDSP YGGSQIEKMIGKCTFPPEEKRAAKATYTFEYFNLLEKINHIR LVSKDNLPEPLSDFQRRSLIELAYKVENLTYDRIRKELHISPE LKFNTIRYESDDLPENEKKQKLNCLKAYHEIRKALDKLGKG TINTLSKEQLNTIGTVLSMYKTSEIIKNKMEQIPAEIVDKLD EEGINFSKFGHLSIKACELIIPGLEKGLNYNDACEEAGLNFK AHNNEEKSFLLHPTEDDYADITSPVVKRAASQTIKVINAIIR KQGCSPTYINIEVARELSKDFYERDKINKRNEANRAENERS LEQIRKEYGKSNASGLDLVKFKLYQKQDGVCAYSQKQISFE RLFEPNYVEVDHIIPYSKCFDDRESNKVLVFAKENREKGNR LPLEYLDGKKRESFIVWVNSKVKDYRKKQNLLKESLSEEEE KQFKERNLQDTKTVSKFLMNYINDNLIFSSSNKRKKHVTA VSGGVTSYMRKRWGISKVREDGDQHHAVDALVIVCTTD | GTTGT AGTCC CCTGA TGGTT TCTGG AATGG TATAA T [SEQ ID NO. 59] | TTATACC ATTCCAG AAACTAT TATGGTC ACTACAA TAAGGTA TTAGACC GTAGAG CACTAAC ACCCCAT TGGGGT GTTATCT CTTTAAA CTGTCCA AAATTTA GTATTGC AATTATT GA |

TABLE 1-continued

| MAD name | Cluster | Contig_id | Organism (metagenome) | Source | aa_seq | CRISPR repeat | tracrRNA |
|---|---|---|---|---|---|---|---|
| | | | | | GMIQQVSKYVEYKECQYIQTDAGSLAVDPYTGEVLRSFPY PWARFHEDAVTWTEKIFVSRMPMRKVTGPAHKETIKSPK ALGEGLLIVRKPLTELKLKNGEIENYYKPEADLLLYNGLKERL MEFGGDAKKAFAEPFPKPGNPQKIVKKVRLTEKSTLNVPV LKGEGRADNDSMVRVDVFLKDGKYYLVPIYVADTLKPELP NKACIAHKPYDEWATMDDGDFLFSLYPNDLIYIKHKKGIKL TKINKNSTLADSIEGKEFFLFYKTMGISSAVLTCTNHDNTYY IESLGVKTLESLEKCVVGVLGEIHKVRKEKRTGFSGN [SEQ ID NO. 58] | | [SEQ ID NO. 60] |
| MAD 2036 | 141 | CADA WQ01 0000026.1 | Ruminococcaceae bacterium | Cattle rumen | MLPYAIGLDIGISSVGWASVALDEEDKPCGIIGMGSRIFDA AEQPKTGDSLAAPRRAARSARRRLRRRRHRNERIRALML REGLLSEAELAALFDGRLEDICALRVRALDEAVTNDELARIL LHLSQRRGFRSNRKTAATQEDGELLAAVSANRALMQERG YRTVAEMLLRDERYRDHRRNKGGAYIATVGRDMVEDEV RQIFAAQRALGSTAASETLETAYLEILLSQRSFDAGPGEPSP YAGGQIERMIGRCTFEPDEPRAARATYSFEYFSLLEAVNHI RLTEAGESVPLTKEQREKLIALAHRTADLSYAKIRKELGVPE SQRFNMVTYGKTDSADEAEKKTKLKQLRAYHQMRAAFE KAAKGSFVLLTKEQRNAVGQTLSIYKTSDNIRPRLREAGLT EAEIDVAEGLSFSKFGHLSVKACDKIIPFLEQGMKYSEACV AAGYAFRGHEGQDKQRLLPPLDNDAKDTITSPVVLRAVS QTIKVVNAIIRERGGSPTFINIELAREMAKDFSERSQIKREQ DSNRARNERMMERIKTEYGKSSPTGLDLVKLKLYEEQAG VCAYSLKQMSLEHLFDPNYAEIDHIIPYSISFDDGYKNKVLV LAKENRDKGNRLPLEYLNGKRREDFIVWVNSSVRDWRKK QNLLKEHVTPEDEAKFKERNLQDTKTASRFLLNYIADNLAF APFQTERKKRVTAVNGSVTAYLRKRWGIAKVRANGDLHH AVDALVIACTTDGLIQKVSRYACYQENRYSEAGGVIVDSA TGEVVAQFPEPWPRFRHELEARLSDDPARAVLGLGLAHY MTGEIRPRPLFVSRMPRRKVTGAAHKETVKSPRALDEGQ LVTKTPLSALKLGKDGEIPGYYKPESDRLLYEALKARLRQFG GDGKKAFAEPFHKPKHDGTPGPVVTKVKLCEPATLSVPV HGGLGAANNDSMVRIDVFHVEGDGYYFVPIYIADTLKLEL PNKACVKIKKISEWKHMKPQDFMFSLYPNDLFRIVSKKGI TLNLVSKESTLPTSVNVSDTLLYFVSAGIASACLTCRNHDN TYQIESLGIKTLEKLEKYTVDVLGNVHRVEKEPRMSFSQKG D [SEQ ID NO. 61] | GTTAT AGTTC CCTGT TCGTT CTTGG TATGG TATAA T [SEQ ID NO. 62] | TTATACC ATACCAA GAACGA AGCAGG TTACTAT GATAAG GTAGTAT ACCGCA GAGCTCC AACGCCT CGCTTTT GCGGGG CGTTGTC TCT [SEQ ID NO. 63] |
| MAD 2037 | 141 | DGSQ 01000028.1 | Clostridiales bacterium | low methane producing sheep | MLPYGIGLDIGITSVGWATVALDENDRPYGIIGMGSRIFD AAEQPKTGESLAAPRRAARSARRRLRRHRNERIRALILR ENLLSEGQLLHLYDGQLSDVYSLRVKALDERVSNEEFARILI HISQRRGFKSNRKGASSKEDSELLAAISANQVRMQQQGY RTVAEMYLKDPIYQEHRRNKGGNYIATVSRAMVEDEVH QIFTGQRACGNPAATKELEEAYVEILLSQRSFDDGPGDGS PYAGSQIERMIGKCQLEKEAGEPRAAKATYSFEYFSLLAAI NNISIISNGQLSPLTKEQREMLIALAHKTSELNYARIRKELG LSEAQRFNTVSYGKMEIAEAEKKTKFEHLKAYHKMRREFE RIAKGHFASITIEQRNAIGDVLSKYKTDAKIRPALREAGLTE LDIDAAEALNFSKFGHISIKACKKIIPWLEQGMKYSEACNA AGYNFKGHDGQEKSHLLPPLDEESRNVITSPVALRAISQTI KVVNAIIRERGCSPTFINIELAREMSKDFYERIEIKKEQDGN RAKNERMMERIRTEYGKASPTGQDLVKFKLYEEQGGVCA YSLKQMSLAHLFEPDYAEVDHIVPYSISFDDGYKNKVLVLA KENRDKGNRLPLQYLQGKRREDFIAWVNSCVRDYKKRQR LLKESISEDDLRAFKERNLQDTKTASRFLLNYISDHLEFTQF ATERKKHVTAVNGSVTAYLRKRWGITKIRENGDLHHAVD ALVIACTTDGMIQQVSRFAQHRENQYSLAEDSRFIIDPET GEVIKEFPYPWPRFRQELEARLSSNPGLAVRDRGFLLYMA ESIPVHPLFVSRMPRRKVTGAAHKETIKSGKAQKDGLLIVK KPLTDLKLDKEGEIANYYNPMSDRLLYEALKKRLTAFNGD GKKAFADPFYKPKSDGTQGPLVNKVKLCEPSTLNVSVIGG KGVAENDSMVRIDVFRVEGDGYYFVPVYVADTVKPELPN KACVANKPYTDWKEMRESDFLFSLYPNDLLKVTHKKALIL TKAQKDSDLPDCKETKSEMLYFVSASISTASLACRTHDNSY RINSLGIKTLEALEKYTVDVLGEYHPVRRETRQTFTGRESSG HSGIS [SEQ ID NO. 64] | GTTAT AGTTC CCTGA TAGTT CTTGG TATGG TATAA T [SEQ ID NO. 65] | TTATACC ATACCAA GAACTAT GAGGTT GCTATAA TAAGGTA GTAAACC GCAGAG CTCTAAC GCCTCAC ATTTGTG GGGCGT TATCTCT [SEQ ID NO. 66] |
| MAD 2038 | 141 | CACW HR01 0000008.1 | Ruminococcaceae bacterium | Cattle rumen | MRPYGIGLDIGISSVGWAAIALDHQDSPCGILDMGARIFD AAENPKDGASLAAPRREKRSQRRRLRRHRNERIRRML LKEGLLTEAELTGLFDGALEDIYALRTRALDEALTKQEFARV LLHLSQRRGFRSNRRATAAQEDGKLLDAVSENAKRMADC GYRTVGEMLCRDATFAKHKRNKGGEYLTTVSRAMIEDEV KLVFASQRRLGSAFASEALEQGYLDILLSQRSFDEGPGGNS PYGGAQIERMIGKCTFYPEEPRAARACYSFEYFSLLQKVN HIRLQKDGESTPLTSEQRLQLIELAHKTENLDYARIRRALQI PDAYRFNTVSYRIESDPAAAEKKEKFQYLRAYHTMRKAID [SEQ ID | GTTGT AGTTC CCTGA TCGTT CTTGG TATGG TATAA T [SEQ ID | TTATACC ATACCAA GAACGA TCAGGTT GCTACAA TAAGGTA GTAAACC GAAGAG CTCTAAC |

TABLE 1-continued

| MAD name | Cluster | Contig_id | Organism (metagenome) | Source | aa_seq | CRISPR repeat | tracrRNA |
|---|---|---|---|---|---|---|---|
| | | | | | GASKGRFALLSQEQRDQIGTVLTLYKSQERISEKLTEAGIEP CDIAALESVSGFSKTGHISLRACKELIPYLEQGMNYNEACA AAGIEFHGHSGTERTVVLHPTPDDLADITSPVVRRAVAQT VKVINAVIRRYGSPVFVNIELARELAKDFTERKKLEKDNKT NRAENERLMRRIREEYGKMNPTGLDLVKLRLYEEQAGVC PYSQKQMSLQRLFEPNYAEVDHIIPYSISFDDSRRNKVLVL AEENRNKGNRLPLQYLTGERRDNFIVWVNSSVRDYRKKQ KLLKPTVTDEDKQQFKERNLQDTKTMSRFLMNYINDHLQ FGVSAKERKKRVTAVNGIVTSYLRKRWGITKIRGDGDLHH AVDALVIACATDGMIRQITRYAQYRECRYMQTDTGSAAI DEATGEVLRIFPYPWEHFRKELEARLSSDPARAVNALRLPF YLDSGEPLPKPLFVSRMPRRKVSGAAHKDTVKSPKAMAE GKVIVRRALTDLKLKNGEIENYFDPGSDRLLYDALKARLAA FGGDGAKAFREPFYKPRHDGTPGPLVKKVKLCEPTTLNVA VHGGKGVADNDSMVRIDVFRVEGDGYYFVPIYADTLKP VLPNKACVAFKPYSEWRTMDDRDFIFSLYPNDLIRVTHKS ALKLSRVSKESTLPESIESKTALLYYVSAGISGAAVSCRNHD NSYEIKSMGIKTLEKLEKYTVDVLGEYHKVEKERRMPFTGK RS [SEQ ID NO. 67] | NO. 68] | GCCCCGT TTCTTTA CGGGGC GTTATCT CT [SEQ ID NO. 69] |
| MAD 2039 | 141 | CACZL L0100 00017.1 | Ruminococcaceae bacterium | Cattle rumen | MRPYAIGLDIGITSVGWATVALDADESPCGIIGLGSRIFDA AEQPKTGESLAAPRRAARGSRRRLRRHRHRNERIRSLMLE ERLISQDELETLFDGRLEDIYALRVKALDEIVSRTDFARILLHI SQRRGFKSNRKNPTTKEDGVLLAAVNENKQRMSEHGYR TVGEMFLLDETFKDHKRNKGGNYITTVARDMVADEVRAI FSAQRELGASFASEEFEERYLEILLSQRSFDEGPGGNSPYG GSQIERMVGRCTFFPDEPRAAKATYSFEYFTLLQKVNHIRI VENGVASKLTDEQRRIIIELAHTTKDVSYAKIRKVLKLSDKQ LFNIRYSDNSPAEDSEKKEKLGIMKAYHQMRSALDRVSKG RFAMMPRAQRNAIGTALSLYKTSDKIRKYLTDAGLDEIDIN SADSIGSFSKFGHISVKACDMLIPFLEQGMNYNEACAAAG LNFKGHDAGEKSKLLHPKEEDYEDITSPVVRRAIAQTIKVIN AIIRREGCSPTFINIELAREMAKDFRERNRIKKENDDNRAK NERLLERIRTEYGKNNPTGLDLVKLRLYEEQSGVCMYSLK QMSLEKLFEPNYAEVDHIVPYSISFDDSRKNKVLVLTEENR NKGNRLPLQYLKGRRREDFIVWVNNNVKDYRKRRLLLKE ELTAEDESGFKERNLQDTKTMSRFLLNYIADNLEFAESTRG RKKKVTAVNGAVTAYMRKRWGITKIREDGDCHHAVDAV VIACTTDAMIRQVSRYAQFRECEYMQTESGSVAVDTGTG EVLRTFPYPWPDFRKELEARLANDPAKVINDLHLPFYMSA GRPLPEPVFVSRMPRRKVTGAAHKDTIKSARELDNGYLIV KRPLTDLKLKNGEIENYYNPQSDKCLYDALKNALIEHGGD AKKAFAGEFRKPKRDGTPGPIVKKVKLLEPTTMCVPVHGG KGAADNDSMVRVDVFLSGGKYYLVPIYADTLKPELPNK AVTRGKKYSEWLEMADEDFIFSLYPNDLICATSKNGITLSV CRKDSTLPPTVESKSFMLYYRGTDISTGSISCITHDNAYKLR GLGVKTLEKLEKYTVDVLGEYHKVGKEVRQPFNIKRRKAC PSEML [SEQ ID NO. 70] | GTTAT AGTTC CCTGA TAGTT CTTGG TATGG TATAA T [SEQ ID NO. 71] | TTATACC ATACCAA GAACTAT TTAGGTT ACTATGA TAAGGTT TAGTACA CCTTAGA GCTCTGA CGCCTCG CTTTTGC GAGGCG TTATCTC TTTATAT TGCCAAA AATGCAA ATATATC GTACAAT GGTGGC [SEQ ID NO. 72] |
| MAD 2040 | 141 | DHKF 01000115.1 | Clostridiales bacterium UBA4701 | Feces | MHRYAIGLDIGITSVGWAAIALDAEENPCGMLDFGSRIFT GAEHPKTGASLAAPRREARGARRRLRRHRHRNERIRRLM VSGGLISQEQLESLFAGQLEDIYALRTRALDEQVAREELARI MLHLSQRRGFRSNRKGGADAEDGKLLEAVGDNKRRMD EKGYRTAGEMFFKDEAFAAHKRNKGGNYIATVTRAMTE DEVHRIFAAQRGFGAEYANEKLEAAYLDILLSQRSFDEGP GGDSPYGGSQIERMIGTCAFEPDQPRAAKAAYSFEYFSLL EKLNHIRLVSGGKSEPLTDAQRKKLIELAHKQDTLSYAKIRK ELELNEAVRFNSVRYTDDATFEEQEKKEKIVCMKAYHAM RKAVDKNAKGRFAYLTIPQRNEIGRVLSTYKTSAKIEPALA AAGIEPCDIAALEGLSFSKFGHLSIKACDKLIPFLEKAMNYN DACAAAGYDFRGHSRDGRQMYLPPLGGDCTEITSPVVRR AVSQTIKVINAIIRRYGTSPVYVNIELAREMSKDFAERNKIK KQNDDNRSKNEKIKEQVAEYKHGAATGLDIVKMKLFNEQ GGICAYSQRQMSLERLFDPNYAEVDHIVPYSISFDDRYKN KVLVLTEENRNKGNRLPLQYLTGERRDRFIVWVNNSVRD FQKRKLLLKEALTPEEENDWKERNLQDTKFVSSFLLNYIND NLLFAPSVRRKKRVTAVNGAVTDYMRKRWGISKVREDG DRHHAVDAVVIACTNDALIQKVSRYESWHERHYMPTEN GSILVDPATGEIKQTFPYPWAMFRKELEARLSNDPSRAVA DLKLPFYMDADAPPVKPLFVSRMPTRKVTGAAHKDTVKS ARALADGLAIVRRPLTALKLDKDGEIAGYYNKDSDRLLYDA LKARLTEYGGNAAKAFAEPFYKPKSDGTPGPVVNKVKLTE PTTLSVPVQDGTGIADNDSMVRIDVFRVGDGYYFVPVY VADTLKQELPDRAVVAFKAHSEWKVMSDGDFVFSLYPN | GTTGT AGTTC CCTGA TGGTT CTTGG TATGG TATAA T [SEQ ID NO. 74] | TTATACC ATACCAA GAACTGC TCAGGTT ACTATGA TAAGGTA GTAAACC GAAGAG CTCTAAT GCCCCGT CTCGCAC GGGGCA TTATCTC TAACAGC GAAAAG GCAAA [SEQ ID NO. 75] |

TABLE 1-continued

| MAD name | Cluster | Contig_id | Organism (metagenome) | Source | aa_seq | CRISPR repeat | tracrRNA |
|---|---|---|---|---|---|---|---|
| | | | | | DLVKVTRKKDVILKRSFDNSTLPETIASNECLLYYAGADIST GAISCVTNDNAYSIRGLGIKTLVSMEKYTVDILGEYHPVRK EERQRFNTKR [SEQ ID NO. 73] | | |

Example 3: Vector Cloning, MADZYME Library Construction and PCR

The MADzyme coding sequences were cloned into a pUC57 vector with T7-promoter sequence attached to the 5'-end of the coding sequence and a T7-terminator sequence attached to the 3'-end of the coding sequence.

First, Q5 Hot Start 2× master mix reagent (NEB, Ipswich, Mass.) was used to amplify the MADzyme sequences cloned in the pUC57 vector. The forward primer 5'-TTGGGTAACGCCAGGGTTTT [SEQ ID No. 172] and reverse primer 5'-TGTGTGGAATTGTGAGCGGA [SEQ ID No. 173] amplified the sequences flanking the MADzyme in the pUC57 vector including the T7-promoter and T7-terminator components at the 5'- and 3'-end of the MADzymes, respectively. 1 µM primers were used in a 10 µL PCR reaction using 3.3 µL boiled cell samples as templates in 96 well PCR plates. The PCR conditions shown in Table 2 were used:

| STEP | TEMPERATURE | TIME |
|---|---|---|
| DENATURATION | 98° C. | 30 SEC |
| 30 CYCLES | 98° C. | 10 SEC |
| | 66° C. | 30 SEC |
| | 72° C. | 3 MIN |
| FINAL EXTENSION | 72° C. | 2 MIN |
| HOLD | 12° C. | |

Example 4: gRNA Construction

Several functional gRNAs associated with each MADzyme was designed by truncating the 5' region, the 3' region and the repeat/anti-repeat duplex (see Table 3).

TABLE 3

| gRNA name | sgRNAv1 | sgRNAv2 | sgRNAv3 | sgRNAv4 | sgRNAv5 |
|---|---|---|---|---|---|
| sgM 2015 | GTTTTAGAGCTATGC TGTTTTGAATGCTTC CAAAACGAAATGTT GGTAGCATTCAAAA CAACATAGCAAGTT AAAATAAGGCTTTG TCCGTTCTCAACTTT TAGTGACGCTGTTTC GGCG [SEQ ID NO. 76] | GTTTTAGAGCTATGC TGTTTTGAATGCTTC GTAGCATTCAAAAC AACATAGCAAGTTA AAATAAGGCTTTGTC CGTTCTCAACTTTTA GTGACGCTGTTTCG GCG [SEQ ID NO. 77] | GTTTTAGAGCTATGC TGTTAACAACATAGC AAGTTAAAATAAGG CTTTGTCCGTTCTCA ACTTTTAGTGACGCT GTTTCGGCG [SEQ ID NO. 78] | GTTTTAGAGCT ATGCAAACAT AGCAAGTTAA AATAAGGCTTT GTCCGTTCTCA ACTTTTAGTGA CGCTGTTTCGG CG [SEQ ID NO. 79] | NONE |
| sgM 2016 | GTTTTAGAGTCATGT TGTTTAGAATGGTA CCAAAACATCTTTTG GGACTATTCTAAAC AACATAGCAAGTTA AAATAAGGTTTTAA CCGTAATCAACTGTA AAGTGGCGCTGTTT CGGCGC [SEQ ID NO. 80] | GTTTTAGAGTCATGT TGTAAAAACAACATA GCAAGTTAAAATAA GGTTTTAACCGTAAT CAACTGTAAAGTGG CGCTGTTTCGGCGC [SEQ ID NO. 81] | GTTTTAGAGTCATGT TGTAAAAACAACATA GCAAGTTAAAATAA GCGTAATCAACTGTA AAGTGGCGCTGTTTC GGCGC [SEQ ID NO. 82] | NONE | NONE |
| sgM 2017 | GTTTTAGAGCTGTG CTGTTTCGAATGGTT CCAAAACGAAATGT TGGAACTATTCGAA ACAACACAGCGAGT TAAAATAAGGCTTT GTCCGTACACAACTT GTAAAAGGGGCACC CGATTCGGGTGCA [SEQ ID NO. 83] | GTTTTAGAGCTGTGC TGTTTCGAAAAATCG AAACAACACAGCGA GTTAAAATAAGGCTT TGTCCGTACACAACT TGTAAAAGGGGCAC CCGATTCGGGTGC [SEQ ID NO. 84] | GTTTTAGAGCTGTGC TGTAAAAACAACAC AGCGAGTTAAAATA AGGCTTTGTCCGTAC ACAACTTGTAAAAG GGGCACCCGATTCG GGTGC [SEQ ID NO. 85] | GTTTTAGAGCT GTGCAAACAC AGCGAGTTAA AATAAGGCTTT GTCCGTACACA ACTTGTAAAA GGGGCACCCG ATTCGGGTGC [SEQ ID NO. 86] | NONE |
| sgM 2019 | GTTTTAGAGCTGTGT TGTTTCGAATGGTTC CAAAACGGTTTGAA ACCATTCGAAACAA TACAGCAAAGTTAA AATAAGGCTAGTCC GTATACAACGTGAA AACACGTGGCACCG ATTCGGTGC [SEQ ID NO. 87] | GTTTTAGAGCTGTGT TGTAAAAACAATACA GCAAAGTTAAAATA AGGCTAGTCCGTAT ACAACGTGAAAACA CGTGGCACCGATTC GGTGC [SEQ ID NO. 88] | GTTTTAGAGCTGTGT TGTAAAAACAATACA GCAAGTTAAAATAA GGCTAGTCCGTATAC AACGTGAAAACACG TGGCACCGATTCGG TGC [SEQ ID NO. 89 | NONE | NONE |

TABLE 3-continued

| gRNA name | sgRNAv1 | sgRNAv2 | sgRNAv3 | sgRNAv4 | sgRNAv5 |
|---|---|---|---|---|---|
| sgM 2020 | GTTTGCTAGTTATGT TATTTATAGTATTAA GCAAACTGTAAATA ACATAACGAGTGCA AATAAGCGTTTCGC GAAAATTTACAGTG GCCCTGCTGTGGGG CCTTTTTTATTTATCA AA [SEQ ID NO. 90] | GTTTGCTAGTTATGT TATAAAAATAACATA ACGAGTGCAAATAA GCGTTTCGCGAAAA TTTACAGTGGCCCTG CTGTGGGGCCTTTTT TATTTATCAAA [SEQ ID NO. 91] | GTTTGCTAGTTATGT TATAAAAATAACATA ACGAGTGCAAATAA GCGTTTCGCGAAAA TTTACAGTGGCCCTG CTGTGGGGCC [SEQ ID NO. 92] | NONE | NONE |
| sgM 2021 | GTTTGAGAGCCTTG TAAAACCGTATATCT CTCAAGCGAAAGAT AATGTTTTACAAGG CGAGTTCAAATAAG GATTTATCCGAAATC GCTTGCGTGCATTG GCACCATCTATCTTT TAAGACTTTCTTTGA AAGTCTT [SEQ ID NO. 93] | NONE | NONE | NONE | NONE |
| sgM 2022 | GTTTGAGAGTCTTGT TAATTCTTAAAGGTG TAAAACGAGAATTA ACAAGACGAGTGCA AATAAGGTTTATCC GGAATCGTCAATAT GACCTGCATTGTGC AGAATCTTTAAAATC ATATGATTTCATATG GTTTTA [SEQ ID NO. 94] | GTTTGAGAGTCTTGT AAAAACAAGACGAG TGCAAATAAGGTTTA TCCGGAATCGTCAAT ATGACCTGCATTGTG CAGAATCTTTAAAAT CATATGATTTCATAT GGTTTTA [SEQ ID NO. 95] | GTTTGAGAGTCTTGT AAAAACAAGACGAG TGCAAATAAGGTTTA TCCGGAATCGTCAAT ATGACCTGCATTGTG CAG [SEQ ID NO. 96] | GTTTGAGAGT CTTGTTAATTC AAAAGAATTA ACAAGACGAG TGCAAATAAG GTTTATCCGGA ATCGTCAATAT GACCTGCATTG TGCAGAATCTT TAAAATCATAT GATTTCATATG GTTTTA [SEQ ID NO. 97] | NONE |
| sgM 2023 | GTTTGAGAGTAGTG TAAATCCATAGGGG TCTCAAACGAAAAG ACCCCTATGGATTTA CATTGCGAGTTCAA ATAAAAGTTTACTCA AATCGTTGGCTTGA CCAACCGCACAGCG TGTGCTAAAGATCT CTTCAGTGAGGTC [SEQ ID NO. 98] | NONE | NONE | NONE | NONE |
| sgM 2024 | GTTTGAGAGTAGTG TAAATCCAGAGGGC TCCAAAACGAGCCC TCTGGATTTACACTA CGAGTTCAAATAAA AATTATTTCAAATCG CCGCTATGTCGGCC GCACAGTGTGTGCA TTAAGAAAAGTCCG AAAGGGC [SEQ ID NO. 99] | NONE | NONE | NONE | NONE |
| sgM 2025 | GTTTGAGAGTAGTG TAAATTTATAGGGT AGTAAAACAAATTTT ACTACCCTATAAATT TACACTACGAGTTCA AATAAAAATTATTTC AAATCGTACTTTTA GTACCTTCACAAGT GTTGTGAATATTAAC TCACCTTCGGGTGA G [SEQ ID NO. 100] | GTTTGAGAGTAGTG TAAAAATACACTACG AGTTCAAATAAAAT TATTTCAAATCGTAC TTTTTAGTACCTTCA CAAGTGTTGTGAAT ATTAACTCACCTTCG GGTGAG [SEQ ID NO. 101] | GTTTGAGAGTAGTG TAAAAATACACTACG AGTTCAAATAAAAT TATTTCAAATCGTAC TTTTTAGTACCTTCA CAAGTGTTGTGAA [SEQ ID NO. 102] | GTTTGAGAGT AGTGTAAATTT ATAGGAAAAC CTATAAATTTA CACTACGAGTT CAAATAAAAA TTATTTCAAAT CGTACTTTTTA GTACCTTCACA AGTGTTGTGA ATATTAACTCA CCTTCGGGTG AG [SEQ ID NO. 103] | NONE |
| sgM 2026 | GTTTGAGAGTAGTG TAATTTCATATGGTA GTCAAACGACTACC ATATGAGATTACACT ACACGGTTCAAATA | NONE | NONE | NONE | NONE |

TABLE 3-continued

| gRNA name | sgRNAv1 | sgRNAv2 | sgRNAv3 | sgRNAv4 | sgRNAv5 |
|---|---|---|---|---|---|
| | AAGAATGTTCGAAA CCGCCCTTTGGGGC CCGCTGTTGCGGA TTTACAGACTTGATA TCAAGTCTG [SEQ ID NO. 104] | | | | |
| sgM 2027 | GTTTGAGAGTAATG TAAATTCATAGGAT GGTAAAACGAAATT TACCATCCAGTGAG TTTACATTACAAGTT CAAATAAAAATTTAT TCAACCCGTTCTTCG GAACCTCCACCGTG TGGAAC [SEQ ID NO. 105] | GTTTGAGAGTAATG TAAAAATACATTACA AGTTCAAATAAAAAT TTATTCAACCCGTTC TTCGGAACCTCCACC GTGTGGAACATTAA GGTCTGCTTTGCAG GCC [SEQ ID NO. 106] | GTTTGAGAGTAATG TAAAAATACATTACA AGTTCAAATAAAAAT TTATTCAACCCGTTC TTCGGAACCTCCACC GTGTGGA [SEQ ID NO. 107] | GTTTGAGAGT AATGTAAATTC ATAAAAGTGA GTTTACATTAC AAGTTCAAATA AAAATTTATTC AACCCGTTCTT CGGAACCTCC ACCGTGTGGA ACATTAAG [SEQ ID NO. 108] | NONE |
| sgM 2028 | GTTTGAGAGCAGTG TTGTCTTATATAGCT CGAAAACGCATTGT AAGACAACACTGCT ACGTTCAAATAAGC ATATTGCTACAAGG TTCTCCCTCGGAGAA TGACCATTAGGTCA CTTAGATAGCCGGT TCTTCTGGCTA [SEQ ID NO. 109] | NONE | NONE | NONE | NONE |
| sgM 2029 | GTTTGAGAGCAGTG TTGTCTTATATAGCT CGAAAACGCATTGT AAGACAACACTGCT ACGTTCAAATAAGC ATATTGCTACAAGG TTCTCCATTGGAGAA TGACCATTAGGTCG CTTAGATAGCCAGTT CTTCTGGCTA [SEQ ID NO. 110] | GTTTGAGAGCAGTG TAAAAACACTGCTAC GTTCAAATAAGCATA TTGCTACAAGGTTCT CCATTGGAGAATGA CCATTAGGTCGCTTA GATAGCCAGTTCTTC TGGCTA [SEQ ID NO. 111] | GTTTGAGAGCAGTG TAAAAACACTGCTAC GTTCAAATAAGCATA TTGCTACAAGGTTCT CCATTGGAGAATGA CCATTAGGTC [SEQ ID NO. 112] | GTTTGAGAGC AGTGTTGTCAA AAGACAACAC TGCTACGTTCA AATAAGCATAT TGCTACAAGG TTCTCCATTGG AGAATGACCA TTAGGTCGCTT AGATAGCCAG TTCTTCTGGCT A [SEQ ID NO. 113] | NONE |
| sgM 2030 | GTTTGAGAGCAGTG TTGTCTTAAATAGCT CGAAAACGCATTGT AAGACAACACTGCA CGTTCAAATAAGCA GATTGCTACAAGGT TCCCGTAAGGGAAT GACCATCTGGTCAC ATGAATAGCCCCG GCAACGGTGGCTG [SEQ ID NO. 114] | NONE | NONE | NONE | NONE |
| sgM 2031 | ATTGTACCATAGCG AGTTAAATTAGGGA ATTACAACGAAATT GTAATAACCTATTTT ACCTCGCTATGGCA CAATTTGTTATTACA TGGACATTATACTAA ACATTTCCTAAAAAA GCAACGAAAAACGT GCT [SEQ ID NO. 115] | NONE | NONE | NONE | NONE |
| sgM 2032 | GTTGTAGTTCCCTAA TTATTCTTGGTATGG TATAATGAAAATTGT ATCATACCAAGAAC AATTAGGTTACTATG ATAAGGTAGTATAC CGCAAAGCTCTAAC ACCTCATCTTCGGAT | GTTGTAGTTCCCTAA TTATTCTTGGTAAAA ACCAAGAACAATTA GGTTACTATGATAA GGTAGTATACCGCA AAGCTCTAACACCTC ATCTTCGGATGAGG TGTTA | GTTGTAGTTCCCTAA TTATTCTTGGTAAAA ACCAAGAACAATTA GGTTACTATGATAA GGTAGTATACCGCA AAGCTCTAACACCTC ATCTTCGGATGAG [SEQ ID NO. 118] | GTTGTAGTTCC CTAATTATTCT TGGTATGGTA AAAATATCATA CCAAGAACAA TAGGTTACTA TGATAAGGTA GTATACCGCA | NONE |

TABLE 3-continued

| gRNA name | sgRNAv1 | sgRNAv2 | sgRNAv3 | sgRNAv4 | sgRNAv5 |
|---|---|---|---|---|---|
| | GAGGTGTTATCT [SEQ ID NO. 116] | [SEQ ID NO. 117] | | AAGCTCTAACA CCTCATCTTCG GATGAGGTGT TATCT [SEQ ID NO. 119] | |
| sgM 2033 | GTTGTAGTTCCCTAA CAGTTCTTGGTATG GTATAATAAAAATT ATACCATACCAAGA ACTGTTATGGTTGCT ATGATAAGGTCTTA GCACCGTAAAGCTC TGACGCCTCGCTTTC AGCGGGGCGTCATC TTTTTTGCCCAAAAG ACACGGATATTTT [SEQ ID NO. 120] | GTTGTAGTTCCCTAA CAGTTCTAAAAAGA ACTGTTATGGTTGCT ATGATAAGGTCTTA GCACCGTAAAGCTCT GACGCCTCGCTTTCA GCGGGGCGTCA [SEQ ID NO. 121] | GTTGTAGTTCCCTAA CAGTTCTAAAAAGA ACTGTTATGGTTGCT ATGATAAGGTCTTA GCACCGTAAAGCTCT GACGCCTCGCTTTCA GCGGGG [SEQ ID NO. 122] | GTTGTAGTTCC CTAACAGTAA AAACTGTTATG GTTGCTATGAT AAGGTCTTAG CACCGTAAAG CTCTGACGCCT CGCTTTCAGCG GGGCGTCA [SEQ ID NO. 123] | NONE |
| sgM 2034 | GTTGTAGTTCCCTAA CGGTTCTTGGTATG GTATAATGAATTATA CCATACCAAGAACT GTTGGGTTACTACA ATAAGGTAGTAAAC CGAAAAGCTCTGAC GTCTTGTTTGCGCAG GACGTCATCTTTATA TCAGACGGATG [SEQ ID NO. 124] | GTTGTAGTTCCCTAA CGGTACTGTTGGGTT ACTACAATAAGGTA GTAAACCGAAAAGC TCTGACGTCTTGTTT GCGCAGGACGTCAT CTTTATATCAGACGG ATG [SEQ ID NO. 125] | GTTGTAGTTCCCTAA CGGTACTGTTGGGTT ACTACAATAAGGTA GTAAACCGAAAAGC TCTGACGTCTTGTTT GCGCAGGACGTCAT CTTT [SEQ ID NO. 126] | GTTGTAGTTCC CTAACGGTTCT TGAAAACAAG AACTGTTATG TTACTACAATA AGGTAGTAAA CCGAAAAGCT CTGACGTCTTG TTTGCGCAGG ACGTCATCTTT ATATCAGACG GATG [SEQ ID NO. 127] | NONE |
| sgM 2035 | GTTGTAGTCCCCTGA TGGTTTCTGGAATG GTATAATGAAATTAT ACCATTCCAGAAACT ATTATGGTCACTACA ATAAGGTATTAGAC CGTAGAGCACTAAC ACCCCATTTGGGGT GTTATCTCTTTAAAC TGTCCAAAATTTAGT ATTGCAATTATTGA [SEQ ID NO. 128] | NONE | NONE | NONE | NONE |
| sgM 2036 | GTTATAGTTCCCTGT TCGTTCTTGGTATGG TATAATGAAATTATA CCATACCAAGAACG AAGCAGGTTACTAT GATAAGGTAGTATA CCGCAGAGCTCCAA CGCCTCGCTTTTGCG GGGCGTTGTCTCT [SEQ ID NO. 128] | NONE | NONE | NONE | NONE |
| sgM 2037 | GTTATAGTTCCCTGA TAGTTCTTGGTATGG TATAATGAAATTATA CCATACCAAGAACT ATGAGGTTGCTATA ATAAGGTAGTAAAC CGCAGAGCTCTAAC GCCTCACATTTGTGG GGCGTTATCTCT [SEQ ID NO. 129] | NONE | NONE | NONE | NONE |
| sgM 2038 | GTTGTAGTTCCCTGA TCGTTCTTGGTATGG TATAATGAAATTATA CCATACCAAGAACG ATCAGGTTGCTACA ATAAGGTAGTAAAC CGAAGAGCTCTAAC GCCCCGTTTCTTTAC GGGGCGTTATCTCT [SEQ ID NO. 130] | NONE | NONE | NONE | NONE |

TABLE 3-continued

| gRNA name | sgRNAv1 | sgRNAv2 | sgRNAv3 | sgRNAv4 | sgRNAv5 |
|---|---|---|---|---|---|
| sgM 2039 | GTTATAGTTCCCTGA TAGTTCTTGGTATGG TATAATGAATTATAC CATACCAAGAACTA TTTAGGTTACTATGA TAAGGTTTAGTACA CCTTAGAGCTCTGAC GCCTCGCTTTTGCGA GGCGTTATCTCTTTA TATTGCCAAAAATG CAAATATATCGTACA ATGGTGGC [SEQ ID NO. 131] | GTTATAGTTCCCTGA TAGTTCTTGGTATGG TATAATGAATTATAC CATACCAAGAACTAT TTAGGTTACTATGAT AAGGTTTAGTACACC TTAGAGCTCTGACGC CTCGCTTTTGCGAGG CGTTATCTCT [SEQ ID NO. 132] | GTTATAGTTCCCTGA TAGTTCTTAACCAAG AACTATTTAGGTTAC TATGATAAGGTTTAG TACACCTTAGAGCTC TGACGCCTCGCTTTT GCGAGGCGTTATCT CT [SEQ ID NO. 133] | GTTATAGTTCC CTGATAGTTCT TGCAAGAACT ATTTAGGTTAC TATGATAAGG TTTAGTACACC TTAGAGCTCTG ACGCCTCGCTT TTGCGAGGCG TTATCTCT [SEQ ID NO. 134] | GTTATAGTTC CCTGATAGTT CTGCAAGAA CTATTTAGGT TACTATGATA AGGTTTAGTA CACCTTAGAG CTCTGACGCC AAAAGGCGT TATCTCT [SEQ ID NO. 135] |
| sgM 2040 | GTTGTAGTTCCCTGA TGGTTCTTGGTATG GTATAATAAATTATA CCATACCAAGAACT GCTCAGGTTACTAT GATAAGGTAGTAAA CCGAAGAGCTCTAA TGCCCCGTCTCGCAC GGGGCATTATCTCT [SEQ ID NO. 136] | NONE | GTTGTAGTTCCCTGA TGGTTCTTGAAAAA GAACTGCTCAGGTT ACTATGATAAGGTA GTAAACCGAAGAGC TCTAATGCCCCGTCT CGCACGGGGCATTA TCTCT [SEQ ID NO. 137] | GTTGTAGTTCC CTGATGGTTCT TGAAAAAGAA CTGCTCAGGTT ACTATGATAA GGTAGTAAAC CGAAGAGCTC TAATGCCAAA GGGCATTATCT CT [SEQ ID NO. 138] | NONE |

To find the optimal gRNA length, different lengths of spacer, repeat:anti-repeat duplex and 3' end of the tracrRNA were included. These gRNAs were then synthesized as a single stranded DNA downstream of the T7 promoter (see Table 4). These sgRNAs were amplified using two primers (5'-AAACCCCTCCGTTTAGAGAG [SEQ ID NO. 174] and 5'-AAGCTAATACGACTCACTATAGGCCAGTC [SEQ ID NO. 175]) and 1 uL of 10 uM diluted single stranded DNA as a template in 25 uL PCR reactions for each sgRNA according to the conditions of Table 5.

TABLE 4

| Name | Sequence |
|---|---|
| sgM2016v1 | AAACCCCTCCGTTTAGAGAGGGGTTATGCTAGTTAGCGCCGAAACAGCGCCACTTTACAGTTGATTACGGT TAAAACCTTATTTTAACTTGCTATGTTGTTTAGAATAGTCCCAAAAGATGTTTTGGTACCATTCTAAACAACA TGACTCTAAAACCCAGTAACATTACTGACTGGCCTATAGTGAGTCGTATTA [SEQ ID NO. 139] |
| sgM2016v2 | AAACCCCTCCGTTTAGAGAGGGGTTATGCTAGTTAGCGCCGAAACAGCGCCACTTTACAGTTGATTACGGT TAAAACCTTATTTTAACTTGCTATGTTGTTTTTACAACATGACTCTAAAACCCAGTAACATTACTGACTGGCC TATAGTGAGTCGTATTA [SEQ ID NO. 140] |
| sgM2016v3 | AAACCCCTCCGTTTAGAGAGGGGTTATGCTAGTTAGCGCCGAAACAGCGCCACTTTACAGTTGATTACGCT TATTTTAACTTGCTATGTTGTTTTTACAACATGACTCTAAAACCCAGTAACATTACTGACTGGCCTATAGTGA GTCGTATTA [SEQ ID NO. 141] |
| sgM2019v1 | AAACCCCTCCGTTTAGAGAGGGGTTATGCTAGTTAGCACCGAATCGGTGCCACGTGTTTTCACGTTGTATA CGGACTAGCCTTATTTTAACTTTGCTGTATTGTTTCGAATGGTTTCAAACCGTTTTGGAACCATTCGAAACAA CACAGCTCTAAAACCCAGTAACATTACTGACTGGCCTATAGTGAGTCGTATTA [SEQ ID NO. 142] |
| sgM2019v2 | AAACCCCTCCGTTTAGAGAGGGGTTATGCTAGTTAGCACCGAATCGGTGCCACGTGTTTTCACGTTGTATA CGGACTAGCCTTATTTTAACTTTGCTGTATTGTTTTTACAACACAGCTCTAAAACCCAGTAACATTACTGACT GGCCTATAGTGAGTCGTATTA [SEQ ID NO. 143] |
| sgM2019v3 | AAACCCCTCCGTTTAGAGAGGGGTTATGCTAGTTAGCACCGAATCGGTGCCACGTGTTTTCACGTTGTATA CGGACTAGCCTTATTTTAACTTGCTGTATTGTTTTTACAACACAGCTCTAAAACCCAGTAACATTACTGACTG GCCTATAGTGAGTCGTATTA [SEQ ID NO. 144] |
| sgM2020v1 | AAACCCCTCCGTTTAGAGAGGGGTTATGCTAGTTATTTGATAAATAAAAAAGGCCCCACAGCAGGGCCACT GTAAATTTTCGCGAAACGCTTATTTGCACTCGTTATGTTATTTTACAGTTTGCTTAATACTATAAATAACATAA CTAGCAAACCCAGTAACATTACTGACTGGCCTATAGTGAGTCGTATTA [SEQ ID NO. 145] |
| sgM2020v2 | AAACCCCTCCGTTTAGAGAGGGGTTATGCTAGTTATTTGATAAATAAAAAAGGCCCCACAGCAGGGCCACT GTAAATTTTCGCGAAACGCTTATTTGCACTCGTTATGTTATTTTTATAACATAACTAGCAAACCCAGTAACAT TACTGACTGGCCTATAGTGAGTCGTATTA [SEQ ID NO. 146] |
| sgM2020v3 | AAACCCCTCCGTTTAGAGAGGGGTTATGCTAGTTAGGCCCCACAGCAGGGCCACTGTAAATTTTCGCGAAA CGCTTATTTGCACTCGTTATGTTATTTTTATAACATAACTAGCAAACCCAGTAACATTACTGACTGGCCTATA GTGAGTCGTATTA [SEQ ID NO. 147] |
| sgM2022v1 | AAACCCCTCCGTTTAGAGAGGGGTTATGCTAGTTATAAAACCATATGAAATCATATGATTTTAAAGATTCTG CACAATGCAGGTCATATTGACGATTCCGGATAAACCTTATTTGCACTCGTCTTGTTAATTCTTTTGAATTAAC AAGACTCTCAAACCCAGTAACATTACTGACTGGCCTATAGTGAGTCGTATTA [SEQ ID NO. 148] |
| sgM2022v2 | AAACCCCTCCGTTTAGAGAGGGGTTATGCTAGTTATAAAACCATATGAAATCATATGATTTTAAAGATTCTG CACAATGCAGGTCATATTGACGATTCCGGATAAACCTTATTTGCACTCGTCTTGTTTTTACAAGACTCTCAAA CCCAGTAACATTACTGACTGGCCTATAGTGAGTCGTATTA [SEQ ID NO. 149] |
| sgM2022v3 | AAACCCCTCCGTTTAGAGAGGGGTTATGCTAGTTACTGCACAATGCAGGTCATATTGACGATTCCGGATAA ACCTTATTTGCACTCGTCTTGTTTTTACAAGACTCTCAAACCCAGTAACATTACTGACTGGCCTATAGTGAGT CGTATTA [SEQ ID NO. 150] |

TABLE 4-continued

| Name | Sequence |
|---|---|
| sgM202 5v1 | AAACCCCTCCGTTTAGAGAGGGGTTATGCTAGCTCACCCGAAGGTGAGTTAATATTCACAACACTTGTGAAGGTACTAAAAAGTACGATTTGAAATAATTTTTATTTGAACTCGTAGTGTAAATTTATAGGTTTTCCTATAAATTTACACTACTCTCAAACCCAGTAACATTACTGACTGGCCTATAGTGAGTCGTATTA [SEQ ID NO. 151] |
| sgM202 5v2 | AAACCCCTCCGTTTAGAGAGGGGTTATGCTAGTTACTCACCCGAAGGTGAGTTAATATTCACAACACTTGTGAAGGTACTAAAAAGTACGATTTGAAATAATTTTTATTTGAACTCGTAGTGTATTTTTACACTACTCTCAAACCCAGTAACATTACTGACTGGCCTATAGTGAGTCGTATTA [SEQ ID NO. 152] |
| sgM202 5v3 | AAACCCCTCCGTTTAGAGAGGGGTTATGCTAGTTATTCACAACACTTGTGAAGGTACTAAAAAGTACGATTTGAAATAATTTTTATTTGAACTCGTAGTGTATTTTTACACTACTCTCAAACCCAGTAACATTACTGACTGGCCTATAGTGAGTCGTATTA [SEQ ID NO. 153] |
| sgM202 7v1 | AAACCCCTCCGTTTAGAGAGGGGTTATGCTAGTTAGGCCTGCAAAGCAGACCTTAATGTTCCACACGGTGGAGGTTCCGAAGAACGGGTTGAATAAATTTTTATTTGAACTTGTAATGTAAACTCACTTTTATGAATTTACATTACTCTCAAACCCAGTAACATTACTGACTGGCCTATAGTGAGTCGTATTA [SEQ ID NO. 154] |
| sgM202 7v2 | AAACCCCTCCGTTTAGAGAGGGGTTATGCTAGTTAGGCCTGCAAAGCAGACCTTAATGTTCCACACGGTGGAGGTTCCGAAGAACGGGTTGAATAAATTTTTATTTGAACTTGTAATGTATTTTTACATTACTCTCAAACCCAGTAACATTACTGACTGGCCTATAGTGAGTCGTATTA [SEQ ID NO. 155] |
| sgM202 7v3 | AAACCCCTCCGTTTAGAGAGGGGTTATGCTAGTTATCCACACGGTGGAGGTTCCGAAGAACGGGTTGAATAAATTTTTATTTGAACTTGTAATGTATTTTTACATTACTCTCAAACCCAGTAACATTACTGACTGGCCTATAGTGAGTCGTATTA [SEQ ID NO. 156] |
| sgM202 9v1 | AAACCCCTCCGTTTAGAGAGGGGTTATGCTAGTTATAGCCAGAAGAACTGGCTATCTAAGCGACCTAATGGTCATTCTCCAATGGAGAACCTTGTAGCAATATGCTTATTTGAACGTAGCAGTGTTGTCTTTTGACAACACTGCTCTCAAACCCAGTAACATTACTGACTGGCCTATAGTGAGTCGTATTA [SEQ ID NO. 157] |
| sgM202 9v2 | AAACCCCTCCGTTTAGAGAGGGGTTATGCTAGTTATAGCCAGAAGAACTGGCTATCTAAGCGACCTAATGGTCATTCTCCAATGGAGAACCTTGTAGCAATATGCTTATTTGAACGTAGCAGTGTTTTTACACTGCTCTCAAACCCAGTAACATTACTGACTGGCCTATAGTGAGTCGTATTA [SEQ ID NO. 158] |
| sgM202 9v3 | AAACCCCTCCGTTTAGAGAGGGGTTATGCTAGTTAGACCTAATGGTCATTCTCCAATGGAGAACCTTGTAGCAATATGCTTATTTGAACGTAGCAGTGTTTTTACACTGCTCTCAAACCCAGTAACATTACTGACTGGCCTATAGTGAGTCGTATTA [SEQ ID NO. 159] |
| sgM203 2v1 | AAACCCCTCCGTTTAGAGAGGGGTTATGCTAGTTAAGATAACACCTCATCCGAAGATGAGGTGTTAGAGCTTTGCGGTATACTACCTTATCATAGTAACCTAATTGTTCTTGGTATGATATTTTTACCATACCAAGAATAATTAGGGAACTACAACCCAGTAACATTACTGACTGGCCTATAGTGAGTCGTATTA [SEQ ID NO. 160] |
| sgM203 2v2 | AAACCCCTCCGTTTAGAGAGGGGTTATGCTAGTTATAACACCTCATCCGAAGATGAGGTGTTAGAGCTTTGCGGTATACTACCTTATCATAGTAACCTAATTGTTCTTGGTTTTTACCAAGAATAATTAGGGAACTACAACCCAGTAACATTACTGACTGGCCTATAGTGAGTCGTATTA [SEQ ID NO. 161] |
| sgM203 2v3 | AAACCCCTCCGTTTAGAGAGGGGTTATGCTAGTTACTCATCCGAAGATGAGGTGTTAGAGCTTTGCGGTATACTACCTTATCATAGTAACCTAATTGTTCTTGGTTTTTACCAAGAATAATTAGGGAACTACAACCCAGTAACATTACTGACTGGCCTATAGTGAGTCGTATTA [SEQ ID NO. 162] |
| sgM203 3v1 | AAACCCCTCCGTTTAGAGAGGGGTTATGCTAGTTATGACGCCCGCTGAAAGCGAGGCGTCAGAGCTTTACGGTGCTAAGACCTTATCATAGCAACCATAACAGTTTTTACTGTTAGGGAACTACAACCCAGTAACATTACTGACTGGCCTATAGTGAGTCGTATTA [SEQ ID NO. 163] |
| sgM203 3v2 | AAACCCCTCCGTTTAGAGAGGGGTTATGCTAGTTATGACGCCCGCTGAAAGCGAGGCGTCAGAGCTTTACGGTGCTAAGACCTTATCATAGCAACCATAACAGTTCTTTTTAGAACTGTTAGGGAACTACAACCCAGTAACATTACTGACTGGCCTATAGTGAGTCGTATTA [SEQ ID NO. 164] |
| sgM203 3v3 | AAACCCCTCCGTTTAGAGAGGGGTTATGCTAGTTACCCCGCTGAAAGCGAGGCGTCAGAGCTTTACGGTGCTAAGACCTTATCATAGCAACCATAACAGTTCTTTTTAGAACTGTTAGGGAACTACAACCCAGTAACATTACTGACTGGCCTATAGTGAGTCGTATTA [SEQ ID NO. 165] |
| sgM203 4v1 | AAACCCCTCCGTTTAGAGAGGGGTTATGCTAGTTACATCCGTCTGATATAAAGATGACGTCCTGCGCAAACAAGACGTCAGAGCTTTTCGGTTTACTACCTTATTGTAGTAACCCAACAGTTCTTGTTTTCAAGAACCGTTAGGGAACTACAACCCAGTAACATTACTGACTGGCCTATAGTGAGTCGTATTA [SEQ ID NO. 166] |
| sgM203 4v2 | AAACCCCTCCGTTTAGAGAGGGGTTATGCTAGTTACATCCGTCTGATATAAAGATGACGTCCTGCGCAAACAAGACGTCAGAGCTTTTCGGTTTACTACCTTATTGTAGTAACCCAACAGTACCGTTAGGGAACTACAACCCAGTAACATTACTGACTGGCCTATAGTGAGTCGTATTA [SEQ ID NO. 167] |
| sgM203 4v3 | AAACCCCTCCGTTTAGAGAGGGGTTATGCTAGTTAAAAGATGACGTCCTGCGCAAACAAGACGTCAGAGCTTTTCGGTTTACTACCTTATTGTAGTAACCCAACAGTACCGTTAGGGAACTACAACCCAGTAACATTACTGACTGGCCTATAGTGAGTCGTATTA [SEQ ID NO. 168] |
| sgM203 9v1 | AAACCCCTCCGTTTAGAGAGGGGTTATGCTAGTTAAGAGATAACGCCTCGCAAAAGCGAGGCGTCAGAGCTCTAAGGTGTACTAAACCTTATCATAGTAACCTAAATAGTTCTTGCAAGAACTATCAGGGAACTATAACCCAGTAACATTACTGACTGGCCTATAGTGAGTCGTATTA [SEQ ID NO. 169] |
| sgM203 9v2 | AAACCCCTCCGTTTAGAGAGGGGTTATGCTAGTTAAGAGATAACGCCTTTTGGCGTCAGAGCTCTAAGGTGTACTAAACCTTATCATAGTAACCTAAATAGTTCTTGCAAGAACTATCAGGGAACTATAACCCAGTAACATTACTGACTGGCCTATAGTGAGTCGTATTA [SEQ ID NO. 170] |
| sgM203 9v3 | AAACCCCTCCGTTTAGAGAGGGGTTATGCTAGTTAAGAGATAACGCCTCGCAAAAGCGAGGCGTCAGAGCTCTAAGGTGTACTAAACCTTATCATAGTAACCTAAATAGTTCTTGGTTAAGAACTATCAGGGAACTATAACCCAGTAACATTACTGACTGGCCTATAGTGAGTCGTATTA [SEQ ID NO. 171] |

TABLE 5

| STEP | TEMPERATURE | TIME |
|---|---|---|
| DENATURATION | 98° C. | 30 SEC |
| 12 CYCLES | 98° C. | 10 SEC |
| | 66° C. | 30 SEC |
| | 72° C. | 2 MIN |
| FINAL EXTENSION | 72° C. | 2 MIN |
| HOLD | 12° C. | |

The target library was designed based on an assumption that the eight randomized NNNNNNNN [SEQ ID NO. 176] PAMs of these nucleases reside on the 3' end of the target sequence (5'-CCAGTCAGTAATGTTACTGG [SEQ ID NO. 177]).

Example 5: In Vitro Transcription and Translation for Production of MAD Nucleases and gRNAs The MADZYMEs were tested for activity by in vitro transcription and translation (txtl). Both the gRNA plasmid and nuclease plasmid were included in each txtl reaction. A PURExpress® In Vitro Protein Synthesis Kit (NEB, Ipswich, Mass.) was used to produce MADzymes from the PCR-amplified MADZYME library and also to produce the gRNA libraries. In each well in a 96-well plate, the reagents listed in Table 6 were mixed to start the production of MADzymes and gRNAs:

TABLE 6

| | REAGENTS | VOLUME (µL) |
|---|---|---|
| 1 | SolA (NEB kit) | 10 |
| 2 | SolB (NEB kit) | 7.5 |
| 3 | PCR amplified gRNA | 0.4 |
| 4 | Murine RNase inhibitor (NEB) | 0.5 |
| 5 | Water | 3.0 |
| 6 | PCR amplified T7 MADZYMEs | 3.6 |

A master mix with all reagents was mixed on ice with the exception of the PCR-amplified T7-MADZYMEs to cover enough 96-well plates for the assay. After 21 µL of the master mix was distributed in each well in 96 well plates, 4 µL of the mixture of PCR amplified MADZYMEs and gRNA under the control of T7 promoter was added. The 96-well plates were sealed and incubated for 4 hrs at 37° C. in a thermal cycler. The plates were kept at room temperature until the target pool was added to perform the target depletion reaction.

After 4 hours incubation to allow production of the MADzymes and gRNAs, 4 µL of the target library pool (10 ng/µL) was added to the 10 µL aliquots of in vitro transcription/translation reaction mixture and allowed to deplete for 30 min, 3 hrs or overnight at 37° C. and 48° C. The target depletion reaction mixtures were diluted into PCR-grade water that contains RNAse A incubated for 5 min at room temperature. Proteinase K was then added and the mixtures were incubated for 5 min at 55° C. RNAseA/Proteinase K treated samples were purified with DNA purification kits and the purified DNA samples were then amplified and sequenced. The PCR conditions are shown in Table 7:

TABLE 7

| STEP | TEMPERATURE | TIME |
|---|---|---|
| DENATURATION | 98° C. | 30 SEC |
| 4 CYCLES | 98° C. | 10 SEC |
| | 66° C. | 30 SEC |
| | 72° C. | 20 SEC |
| 12 CYCLES | 98° C. | 10 SEC |
| | 72° C. | 20 SEC |
| FINAL EXTENSION | 72° C. | 2 MINUTES |
| HOLD | 12° C. | |

Example 6: Measurement of Nicked Plasmid with Nickase RNP Complexes

Figure 7:
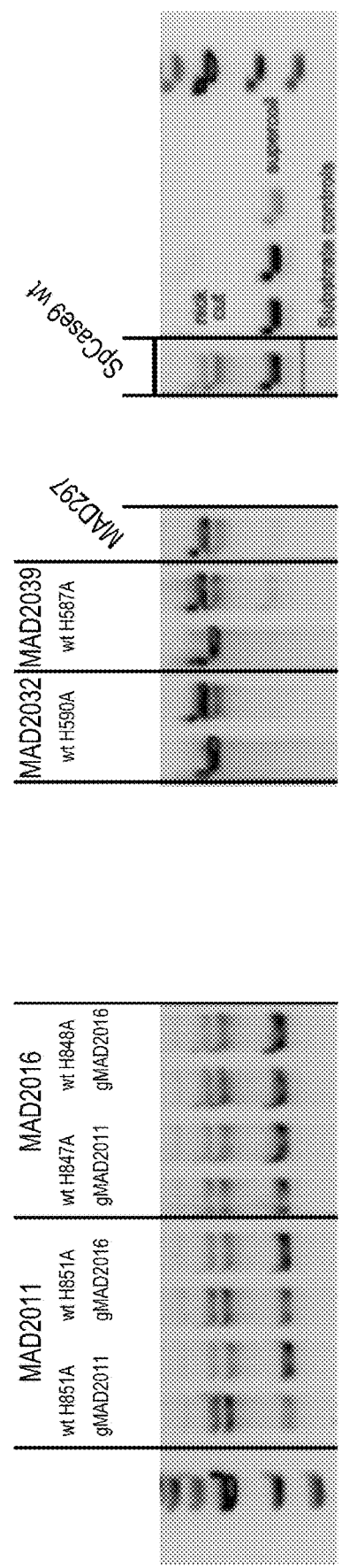
FIG. 7 is a reproduction of a gel showing nicked plasmid formation with different MADzyme nickases compared to corresponding MADzyme nucleases.

Proteins were produced in vitro under a PURExpress® In Vitro Protein Synthesis Kit (NEB, Ipswich, Mass.). Guide RNAs that target the target plasmid were also produced under a T7 promoter in the same mixture. The MADzyme Nickase or Nuclease and guide complexes (RNP complex) formed as they were produced in the in vitro transcription and translation reagent. Supercoiled plasmid target was diluted into the digestion buffer, then the RNP complex was added to the same digestion buffer to initiate the plasmid digestion. After incubation at 37° C. to allow digestion of the plasmid, the resulting mixtures were treated with RNAase and Proteinase K, then the target plasmid was purified with a PCR cleanup kit, and run on TAE-agarose gel to observe the formation of nicked or double stand cut plasmid. The results are shown in FIG. 7. Table 8 lists the identified MADzyme nickases, including the variations from the nuclease sequence in Table 1 and the amino acid sequence.

TABLE 8

| MADzyme Nickase Name | SEQ ID NO | Amino Acid Sequence |
|---|---|---|
| MAD2016-H851A | 177 | MKKDYVIGLDIGTNSVGWAVMTEDYQLVKKKMPIYGNTEKKKIKKNFWGVRLFEEGHTAEDRR LKRTARRIISRRRNRLRYLQAFFEEAMTDLDENFFARLQESFLVPEDKKWHRHPIFAKLEDEVAYH ETYPTIYHLRKKLADSSEQADLRLIYLALAHIVKYRGHFLIEGKLSTENISVKEQFQQFMIIYNQTFVN GESRLVSAPLPESVLIEEELTEKASRTKKSEKVLQQFPQEKANGLFGQFLKLMVGNKADFKKVFGL EEEAKITYASESYEEDLEGILAKVGDEYSDVFLAAKNVYDAVELSTILADSDKKSHAKLSSSMIVRFT EHQEDLKKFKRFIRENCPDEYDNLFKNEQKDGYAGYIAHAGKVSQLKFYQYVKKIIQDIAGAEYFL EKIAQENFLRKQRTFDNGVIPHQIHLAELQAIIHRQAAYYPFLKENQEKIEQLVTFRIPYYVGPLSKG DASTFAWLKRQSEEPIRPWNLQETVDLDQSATAFIERMTNFDTYLPSEKVLPKHSLLYEKFMVFN ELTKISYTDDRGIKANFSGKEKEKIFDYLFKTRRKVKKKDIIQFYRNEYNTEIVTLSGLEEDQFNASFS TYQDLLKCGLTRAELDHPDNAEKLEDIIKILTIFEDRQRIRTQLSTFKGQFSAEVLKKLERKHYTGW GRLSKKLINGIYDKESGKTILGYLIKDDGVSKHYNRNFMQLINDSQLSFKNAIQKAQSSEHEETLSE TVNELAGSPAIKKGIYQSLKIVDELVAIMGYAPKRIVVEMARENQTTSTGKRRSIQRLKIVEKAMA EIGSNLLKEQPTTNEQLRDTRLFLYYMQNGKDMYTGDELSLHRLSHYDIDAIIPQSFMKDDSLDN LVLVGSTENRGKSDDVPSKEVVKDMKAYWEKLYAAGLISQRKFQRLTKGEQGGLTLEDKAHFIQ RQLVETRQITKNVAGILDQRYNANSKEKKVQIITLKASLTSQFRSIFGLYKVREVNDYHHGQDAYL NCVVATTLLKVYPNLAPEFVYGEYPKFQTFKENKATAKAIIYTNLLRFFTEDEPRFTKDGEILWSNS YLKTIKKELNYHQMNIVKKVEVQKGGFSKESIKPKGPSNKLIPVKNGLDPQKYGGFDSPIVAYTVLF THEKGKKPLIKQEILGITIMEKTRFEQNPILFLEEKGFLRPRVLMKLPKYTLYEFPEGRRRLLASAKEA QKGNQMVLPEHLLTLLYHAKQCLLPNQSESLTYVEQHQPEFQEILERVVDFAEVHTLAKSKVQQI VKLFEANQTADVKEIAASFIQLMQFNAMGAPSTFKFFQKDIERARYTSIKEIFDATIIYQSTTGLYET RRKVVD |
| MAD2016-N874A | 178 | MKKDYVIGLDIGTNSVGWAVMTEDYQLVKKKMPIYGNTEKKKIKKNFWGVRLFEEGHTAEDRR LKRTARRIISRRRNRLRYLQAFFEEAMTDLDENFFARLQESFLVPEDKKWHRHPIFAKLEDEVAYH ETYPTIYHLRKKLADSSEQADLRLIYLALAHIVKYRGHFLIEGKLSTENISVKEQFQQFMIIYNQTFVN GESRLVSAPLPESVLIEEELTEKASRTKKSEKVLQQFPQEKANGLFGQFLKLMVGNKADFKKVFGL EEEAKITYASESYEEDLEGILAKVGDEYSDVFLAAKNVYDAVELSTILADSDKKSHAKLSSSMIVRFT EHQEDLKKFKRFIRENCPDEYDNLFKNEQKDGYAGYIAHAGKVSQLKFYQYVKKIIQDIAGAEYFL EKIAQENFLRKQRTFDNGVIPHQIHLAELQAIIHRQAAYYPFLKENQEKIEQLVTFRIPYYVGPLSKG DASTFAWLKRQSEEPIRPWNLQETVDLDQSATAFIERMTNFDTYLPSEKVLPKHSLLYEKFMVFN ELTKISYTDDRGIKANFSGKEKEKIFDYLFKTRRKVKKKDIIQFYRNEYNTEIVTLSGLEEDQFNASFS TYQDLLKCGLTRAELDHPDNAEKLEDIIKILTIFEDRQRIRTQLSTFKGQFSAEVLKKLERKHYTGW |

TABLE 8-continued

| MADzyme Nickase Name | SEQ ID NO | Amino Acid Sequence |
|---|---|---|
| | | GRLSKKLINGIYDKESGKTILGYLIKDDGVSKHYNRNFMQLINDSQLSFKNAIQKAQSSEHEETLSE TVNELAGSPAIKKGIYQSLKIVDELVAIMGYAPKRIVVEMARENQTTSTGKRRSIQRLKIVEKAMA EIGSNLLKEQPTTNEQLRDTRLFLYYMQNGKDMYTGDELSLHRLSHYDIDHIIPQSFMKDDSLDN LVLVGSTEARGKSDDVPSKEVVKDMKAYWEKLYAAGLISQRKFQRLTKGEQGGLTLEDKAHFIQ RQLVETRQITKNVAGILDQRYNANSKEKKVQIITLKASLTSQFRSIFGLYKVREVNDYHHGQDAYL NCVVATTLLKVYPNLAPEFVYGEYPKFQTFKENKATAKAIIYTNLLRFFTEDEPRFTKDGEILWSNS YLKTIKKELNYHQMNIVKKVEVQKGGFSKESIKPKGPSNKLIPVKNGLDPQKYGGFDSPIVAYTVLF THEKGKKPLIKQEILGITIMEKTRFEQNPILFLEEKGFLRPRVLMKLPKYTLYEFPEGRRRLLASAKEA QKGNQMVLPEHLLTLLYHAKQCLLPNQSESLTYVEQHQPEFQEILERVVDFAEVHTLAKSKVQQI VKLFEANQTADVKEIAASFIQLMQFNAMGAPSTFKFFQKDIERARYTSIKEIFDATIIYQSTTGLYET RRKVVD |
| MAD2032-H590A | 179 | MKYIIGLDMGITSVGFATMMLDDKDEPCRIIRMGSRIFEAAEHPKDGSSLAAPRRINRGMRRRL RRKSHRKERIKDLIIKNELMTADEISAIYSTGKQLSDIYQIRAEALDRKLNTEEFVRLLIHLSQRRGFK SNRKVDAKEKGSDAGKLLSAVNSNKELMIEKNYRTIGEMLYKDEKFSEYKRNKADDYSNTFARSE YEDEIRQIFSAQQEHGNPYATDELKESYLDIYLSQRSFDEGPGGSSPYGGNQIEKMIGNCTLEPEE KRAAKATFSFEYFNLLSKVNSIKIVSSSGKRALNNDERQSVIRLAFAKNAISYTSLRKELNMEYSERF NISYSQSDKSIEEIEKKTKFTYLTAYHTFKKAYGSVFVEWSADKKNSLAYALTAYKNDTKIIEYLTQK GFDAAETDIALTLPSFSKWGNLSEKALNNIIPYLEQGMLYHDACTAAGYNFKADDTDKRMYLPA HEKEAPELDDITNPVVRRAISQTIKVINALIREMGESPCFVNIELARELSKNKAERSKIEKGQKENQ VRNDRIMERLRNEFGLLSPTGQDLIKLKLWEEQDGICPYSLKPIKIEKLFDVGYTDIDAIIPYSLSFDD TYNNKVLVMSSENRQKGNRIPMQYLEGKRQDDFWLWVDNSNLSRRKKQNLTKETLSEDDLSG FKKRNLQDTQYLSRFMMNYLKKYLALAPNTTGRKNTIQAVNGAVTSYLRKRWGIQKVRENGDT HHAVDAVVISCVTAGMTKRVSEYAKYKETEFQNPQTGEFFDVDIRTGEVINRFPLPYARFRNELL MRCSENPSRILHEMPLPTYAADEKVAPIFVSRMPKHKVKGSAHKETIRRAFEEDGKKYTVSKVPLT DLKLKNGEIENYYNPESDGLLYNALKEQUAFGGDAAKAFEQPFYKPKSDGSEGPLVKKVKLINKA TLTVPVLNNTAVADNGSMVRVDVFFVEGEGYYLVPIYVADTVKKELPNKAIIANKPYEEWKEMR EENFVFSLYPNDLIKISSRKDMKFNLVNKESTLAPNCQSKEALVYYKGSDISTAAVTAINHDNTYKL RGLGVKTLLKIEKYQVDVLGNVFKVGKEKRVRFK |
| MAD2039-H587A | 180 | MRPYAIGLDIGITSVGWATVALDADESPCGIIGLGSRIFDAAEQPKTGESLAAPRRAARGSRRRLR RHRHRNERIRSLMLEERLISQDELETLFDGRLEDIYALRVKALDEIVSRTDFARILLHISQRRGFKSN RKNPTTKEDGVLLAAVNENKQRMSEHGYRTVGEMFLLDETFKDHKRNKGGNYITTVARDMVA DEVRAIFSAQRELGASFASEEFEERYLEILLSQRSFDEGPGGNSPYGGSQIERMVGRCTFFPDEPR AAKATYSFEYFTLLQKVNHIRIVENGVASKLTDEQRRIIIELAHTTKDVSYAKIRKVLKLSDKQLFNIR YSDNSPAEDSEKKEKLGIMKAYHQMRSAIDRVSKGRFAMMPRAQRNAIGTALSLYKTSDKIRKYL TDAGLDEIDINSADSIGSFSKFGHISVKACDMLIPFLEQGMNYNEACAAAGLNFKGHDAGEKSKL LHPKEEDYEDITSPVVRRAIAQTIKVINAIIRREGCSPTFINIELAREMAKDFRERNRIKKENDDNRA KNERLLERIRTEYGKNNPTGLDLVKLRLYEEQSGVCMYSLKQMSLEKLFEPNYAEVDAIVPYSISFD DSRKNKVLVLTEENRNKGNRLPLQYLKGRRREDFIVWVNNNVKDYRKRRLLLKEELTAEDESGFK ERNLQDTKTMSRFLLNYIADNLEFAESTRGRKKKVTAVNGAVTAYMRKRWGITKIREDGDCHHA VDAVVIACTTDAMIRQVSRYAQFRECEYMQTESGSVAVDTGTGEVLRTFPYPWPDFRKELEARL ANDPAKVINDLHLPFYMSAGRPLPEPVFVSRMPRRKVTGAAHKDTIKSARELDNGYLIVKRPLTD LKLKNGEIENYYNPQSDKCLYDALKNALIEHGGDAKKAFAGEFRKPKRDGTPGPIVKKVKLLEPTT MCVPVHGGKGAADNDSMVRVDVFLSGGKYYLVPIYVADTLKPELPNKAVTRGKKYSEWLEMA DEDFIFSLYPNDLICATSKNGITLSVCRKDSTLPPTVESKSFMLYYRGTDISTGSISCITHDNAYKLRG LGVKTLEKLEKYTVDVLGEYHKVGKEVRQPFNIKRRKACPSEML |
| MAD2039-N610A | 181 | MRPYAIGLDIGITSVGWATVALDADESPCGIIGLGSRIFDAAEQPKTGESLAAPRRAARGSRRRLR RHRHRNERIRSLMLEERLISQDELETLFDGRLEDIYALRVKALDEIVSRTDFARILLHISQRRGFKSN RKNPTTKEDGVLLAAVNENKQRMSEHGYRTVGEMFLLDETFKDHKRNKGGNYITTVARDMVA DEVRAIFSAQRELGASFASEEFEERYLEILLSQRSFDEGPGGNSPYGGSQIERMVGRCTFFPDEPR AAKATYSFEYFTLLQKVNHIRIVENGVASKLTDEQRRIIIELAHTTKDVSYAKIRKVLKLSDKQLFNIR YSDNSPAEDSEKKEKLGIMKAYHQMRSAIDRVSKGRFAMMPRAQRNAIGTALSLYKTSDKIRKYL TDAGLDEIDINSADSIGSFSKFGHISVKACDMLIPFLEQGMNYNEACAAAGLNFKGHDAGEKSKL LHPKEEDYEDITSPVVRRAIAQTIKVINAIIRREGCSPTFINIELAREMAKDFRERNRIKKENDDNRA KNERLLERIRTEYGKNNPTGLDLVKLRLYEEQSGVCMYSLKQMSLEKLFEPNYAEVDHIVPYSISFD DSRKNKVLVLTEENRNKGNRLPLQYLKGRRREDFIVWVNNNVKDYRKRRLLLLKEELTAEDESGFK ERNLQDTKTMSRFLLNYIADNLEFAESTRGRKKKVTAVNGAVTAYMRKRWGITKIREDGDCHHA VDAVVIACTTDAMIRQVSRYAQFRECEYMQTESGSVAVDTGTGEVLRTFPYPWPDFRKELEARL ANDPAKVINDLHLPFYMSAGRPLPEPVFVSRMPRRKVTGAAHKDTIKSARELDNGYLIVKRPLTD LKLKNGEIENYYNPQSDKCLYDALKNALIEHGGDAKKAFAGEFRKPKRDGTPGPIVKKVKLLEPTT MCVPVHGGKGAADNDSMVRVDVFLSGGKYYLVPIYVADTLKPELPAKAVTRGKKYSEWLEMA DEDFIFSLYPNDLICATSKNGITLSVCRKDSTLPPTVESKSFMLYYRGTDISTGSISCITHDNAYKLRG LGVKTLEKLEKYTVDVLGEYHKVGKEVRQPFNIKRRKACPSEML |

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A nickase selected from the following nickases: MAD2016-H851A [SEQ ID NO: 177]; MAD2016-N874A [SEQ ID NO: 178]; MAD2032-H590A [SEQ ID NO: 179]; MAD-2039-H587A [SEQ ID NO: 180]; MAD2039-N610A [SEQ ID NO: 181].

2. The nickase of claim 1 having the amino acid sequence of SEQ ID NO: 177.

3. The nickase of claim 1 having the amino acid sequence of SEQ ID NO: 178.

4. The nickase of claim 1 having the amino acid sequence of SEQ ID NO: 179.

5. The nickase of claim 1 having the amino acid sequence of SEQ ID NO: 180.

6. The nickase of claim 1 having the amino acid sequence of SEQ ID NO: 181.

* * * * *